US008552196B2

(12) United States Patent
Corkey et al.

(10) Patent No.: US 8,552,196 B2
(45) Date of Patent: Oct. 8, 2013

(54) APOPTOSIS SIGNAL-REGULATING KINASE INHIBITORS

(75) Inventors: Britton Corkey, Redwood, CA (US); Michael Graupe, Pacifica, CA (US); Keith Koch, Erie, CO (US); Lawrence S. Melvin, Jr., Longmont, CO (US); Gregory Notte, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/615,259

(22) Filed: Sep. 13, 2012

(65) Prior Publication Data

US 2013/0035339 A1 Feb. 7, 2013

Related U.S. Application Data

(62) Division of application No. 12/834,673, filed on Jul. 12, 2010, now Pat. No. 8,378,108.

(60) Provisional application No. 61/225,076, filed on Jul. 13, 2009, provisional application No. 61/225,079, filed on Jul. 13, 2009, provisional application No. 61/289,263, filed on Dec. 22, 2009.

(51) Int. Cl.
| | |
|---|---|
| *A61K 31/4439* | (2006.01) |
| *A61K 31/444* | (2006.01) |
| *A61K 31/496* | (2006.01) |
| *A61K 31/506* | (2006.01) |
| *A61K 31/5377* | (2006.01) |
| *A61P 1/16* | (2006.01) |
| *A61P 25/28* | (2006.01) |
| *A61P 29/00* | (2006.01) |
| *A61P 37/06* | (2006.01) |
| *A61P 13/12* | (2006.01) |
| *A61P 9/00* | (2006.01) |
| *A61P 3/10* | (2006.01) |
| *A61P 11/00* | (2006.01) |

(52) U.S. Cl.
USPC ........ 546/256; 546/167; 546/272.4; 546/113; 544/364; 544/331; 544/333; 544/131; 544/316

(58) Field of Classification Search
None
See application file for complete search history.

(56) References Cited

U.S. PATENT DOCUMENTS

| | | | |
|---|---|---|---|
| 2006/0223996 A1* | 10/2006 | Sun et al. ....................... 544/81 |
| 2007/0167386 A1 | 7/2007 | Otsu et al. | |
| 2007/0276050 A1 | 11/2007 | Koch et al. | |
| 2009/0318425 A1 | 12/2009 | Chang et al. | |

FOREIGN PATENT DOCUMENTS

| | | |
|---|---|---|
| EP | 2058309 A1 | 5/2009 |
| WO | WO-2008016131 A1 | 2/2008 |
| WO | WO-2008042867 A2 | 4/2008 |
| WO | WO-2009011850 A2 | 1/2009 |
| WO | WO-2009027283 A1 | 3/2009 |
| WO | WO-2009123986 A1 | 10/2009 |
| WO | WO-2010111464 A1 | 9/2010 |

OTHER PUBLICATIONS

Guo, X. et al. (2010), "Regulation of the severity of neuroinflammation and demyelination by TLR-ASK1-p38 pathway", *EMBO Molecular Medicine*, vol. 1, pp. 1-12.
Hattori, K. et al. (2009) "The roles of ASK family proteins in stress responses and diseases", *Cell Comunication and Signaling*, 7:9 pp. 1-10.
Ichijo, H. et al. (1997) "Induction of Apoptosis by ASK1, a Mammalian MAPKKK that Activates SAPK/JNK and p38 Signaling Pathways", *Science*, vol. 275, pp. 90-94.
International Search Report for PCT/US2010/041739, International Filing Date Jul. 12, 2010, mailed Sep. 16, 2010.
Iriyama, T. et al. (2009), "ASK1 and ASK2 differently regulate the counteracting roles of apoptosis and inflammation in tumorigensis", *The European Molecular Biology Organization Journal*, pp. 1-11.
Kumar, S. et al. (2003) "P38 Map Kinases: Key Singalling Molecules as Therapeutic Targets for Inflammatory Diseases", *Nature Reviews*, vol. 2, pp. 717-726.
Nagai, H. et al. (2007) "Pathophysiological Roles of ASK-1 MAP Kinase Signaling Pathways", *Journal of Biochemistry and Molecular Biology*, vol. 40, pp. 1-6.
Pimienta, G. et al. (2007) "Canonical and Alternative MAPK Signaling", *Cell Cycle*, vol. 6(21), pp. 2628-2632. Ii.
Saitoh, M. et al. (1998), "Mammalian thioredoxin is a direct inhibitor of apoptosis signal-regulating kinase (ASK) 1", *The European Molecular Biology Organization Journal*, vol. 17(9), pp. 2596-2606.
Takeda, K. (2008) "Apoptosis Signal-Regulating Kinase 1 in Stress and Immune Response", *Annu. Rev. Pharmacol. Toxicol.*, 48:8.1-8. 27.
Takeda, K. et al. (2007), "Apoptosis Signal-regulating Kinase (ASK) 2 Functions as a Mitogen-activated Protein Kinase Kinase Kinase in a Heteromeric Complex with ASK1", *Journal of Biological Chemistry*, vol. 282(10), pp. 7522-7531.

(Continued)

*Primary Examiner* — Dennis Heyer
(74) *Attorney, Agent, or Firm* — Francis O. Ginah; J. Elin Hartrum

(57) ABSTRACT

The present invention relates to compounds of Formula (I):

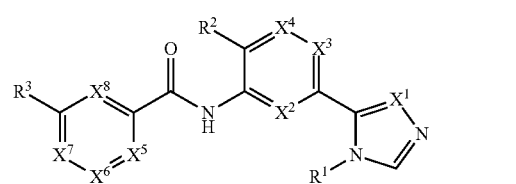

(I)

wherein $X^1, X^2, X^3, X^4, X^5, X^6, X^7, X^8, R^1, R^2, R^3$ are defined above. The compounds have apoptosis signal-regulating kinase ("ASK1") inhibitory activity, and are thus useful in the treatment of ASK1-mediated conditions, including autoimmune disorders, inflammatory diseases, cardiovascular diseases and neurodegenerative diseases. The invention also relates to pharmaceutical compositions comprising one or more of the compounds of Formula (I), and to methods of preparing the compounds of Formula (I).

10 Claims, No Drawings

(56) References Cited

OTHER PUBLICATIONS

Terada, Y. et al (2007) "Important role of apoptosis signal-regulating kinase 1 in ischemic aute kidney injury" *BBRC* 364:1042-1049.

Wang, Z.S. et al. (1998), "MAPKKK6, a Novel Mitogen-Activiated Protein Kinase Kinase Kinase, That Associates with MAPKKK5", *Biochemical and Biophysical Research Communications*, vol. 253, pp. 33-37.

Written Opinion for International Application No. PCT/US2010/041739, International Filing Date, Jul. 12, 2010, mailed Sep. 16, 2010.

Zhang, L. et al. (1999), "Suppression of apoptosis signal-regulating kinase 1-induced cell death by 14-3-3 proteins", *Proc. Natl. Acad. Sci*, vol. 96, pp. 8511-8515.

* cited by examiner

APOPTOSIS SIGNAL-REGULATING KINASE INHIBITORS

CROSS-REFERENCE TO RELATED APPLICATIONS

This application is a divisional application of U.S. patent application U.S. Ser. No. 12/834,673 filed Jul. 12, 2010, now pending, which claims the benefit under 35 U.S.C. 119(E) of U.S. Provisional Patent Applications Ser. No. 61/225,076 and 61/225,079, both filed Jul. 13, 2009, and U.S. Provisional Patent Application Ser. No. 61/289,263, filed Dec. 22, 2009, the entireties of each of which is herein incorporated by reference.

FIELD OF THE INVENTION

The present invention relates to novel compounds having enzyme inhibitory activity, and to their use in the treatment of ASK1-mediated conditions, including autoimmune disorders, inflammatory diseases, including chronic kidney disease, cardiovascular diseases and neurodegenerative diseases. The invention also relates to methods for their preparation, and to pharmaceutical compositions containing such compounds.

BACKGROUND

Mitogen-activated protein kinase (MAPK) signaling cascades couple diverse extracellular and intracellular queues to appropriate cellular stress responses, including cell growth, differentiation, inflammation, and apoptosis (Kumar, S., Boehm, J., and Lee., J. C. (2003) Nat. Rev. Drug Dis. 2:717-726; Pimienta, G., and Pascual, J. (2007) Cell Cycle, 6: 2826-2632). MAPKs exist in three groups, MAP3Ks, MAP2Ks, and MAPKs, which are sequentially activated. MAPK3s directly respond to environmental signals and phosphorylate MAP2Ks, which in turn phosphorylate specific MAPKs. MAPKs then mediated the appropriate cellular response by phosphorylating cellular substrates, including transcription factors that regulate gene expression.

Apoptosis signal-regulating kinase 1 (ASK1) is a member of the mitogen-activated protein kinase kinase kinase ("MAP3K") family that activates the c-Jun N-terminal protein kinase ("JNK.") and p38 MAP kinase (Ichijo, H., Nishida, E, Irie, K., Dijke, P. T., Saitoh, M., Moriguchi, T., Matsumoto, K., Miyazono, K., and Gotoh,Y. (1997) Science, 275, 90-94). ASK1 is activated by a variety of stimuli including oxidative stress, reactive oxygen species (ROS), LPS, TNF-α, FasL, ER stress, and increased intracellular calcium concentrations (Hattori, K., Naguro, I., Runchel, C., and Ichijo, H. (2009) Cell Comm. Signal. 7:1-10; Takeda, K., Noguchi, T., Naguro, I., and Ichijo, H. (2007) Annu. Rev. Pharmacol. Toxicol. 48: 1-8.27; Nagai, H., Noguchi, T., Takeda, K., and Ichijo, I. (2007) J. Biochem. Mol. Biol. 40:1-6). ASK1 undergoes activation via autophosphorylation at Thr838 in response to these signals and in turn phosphorylates MAP2Ks, such as MKK3/6 and MKK4/7, which then phosphorylate and activate p38 and JNK MAPKs, respectively. ASK2 is a related MAP3K that shares 45% sequence homology with ASK1 (Wang, X. S., Diener, K., Tan, T-H., and Yao, Z. (1998) Biochem. Biophys. Res. Commun. 253, 33-37. Although ASK2 tissue distribution is restricted, in some cell types ASK1 and ASK2 have been reported to interact and function together in a protein complex (Takeda, K., Shimozono, R., Noguchi, T., Umeda, T., Morimoto, Y., Naguro, I., Tobiume, K., Saitoh, M., Matsuzawa, A., and Ichijo, H. (2007) J. Biol. Chem. 282: 7522-7531; Iriyarna, T., et al. (2009) Embo J. 28: 843-853) In non stressed conditions, A SK1 is kept in an inactive state through binding to its repressor Thioredoxin (Trx) (Saitoh, M., Nishitoh, H., Fuji, M., Takeda, K., Tobiume, K., Sawada, Y., Kawabata, M., Miyazono, K., and Ichijo, H. (1998) Embo J. 17:2596-2606), and through association with AKT (Zhang, L., Chen, J. and Fu, H. (1999) Proc. Natl. Acad. Sci. U.S.A 96:8511-8515).

Phosphorylation of ASK1 protein can lead to apoptosis or other cellular responses depending on the cell type. ASK1 activation and signaling have been reported to play an important role in a broad range of diseases including neurodegenerative, cardiovascular, inflammatory, autoimmunity, and metabolic disorders. In addition, ASK1 has been implicated in mediating organ damage following ischemia and reperfusion of the heart, brain, and kidney (Watanabe et al. (2005) BBRC 333, 562-567; Zhang et al., (2003) Life Sci 74-37-43; Terada et al. (2007) BBRC 364: 1043-49). Emerging evidence suggests that ASK2, either alone or in a complex with ASK1, may play important roles in human diseases as well. Therefore, therapeutic agents that function as inhibitors of ASK1 and ASK2 signaling complexes have the potential to remedy or improve the lives of patients suffering from such conditions.

U.S. Publication No. 2007/0276050 describes methods for identifying ASK1 inhibitors useful for preventing and/or treating cardiovascular disease and methods for preventing and/or treating cardiovascular disease in an animal. The methods comprise administering to the animal an ASK1 inhibitor and, optionally, a hypertensive compound.

U.S. Publication No. 2007/0167386 reports a drug for at least one of prevention and treatment of cardiac failure containing a compound that inhibits a functional expression of ASK1 protein in a cardiomyocyte, and a method for screening the drug.

WO2009027283 discloses triazolopyridine compounds, methods for preparation thereof and methods for treating autoimmune disorders, inflammatory diseases, cardiovascular diseases and neurodegenerative diseases.

SUMMARY OF THE INVENTION

Accordingly, the present invention provides novel compounds that function as ASK1 inhibitors. In a first aspect, the invention relates to compounds of Formula I:

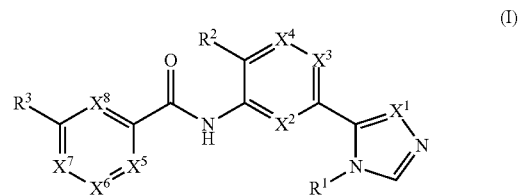

wherein:
$R^1$ is alkyl, alkenyl, alkynyl, cycloalkyl, aryl, heteroaryl, or heterocyclyl, all of which are optionally substituted with 1, 2, or 3 substituents selected from halo, oxo, alkyl, cycloalkyl, heterocyclyl, aryl, aryloxy, —NO$_2$, $R^6$, —C(O)—$R^6$, —OC(O)—$R^6$—C(O)—O—$R^6$, —C(O)—N($R^6$)($R^7$), —OC(O)—N($R^6$)($R^7$), —S—$R^6$, —S(═O)—$R^6$, —S(═O)$_2R^6$, —S(═O)$_2$—N($R^6$)($R^7$), —S(═O)$_2$—O—$R^6$, —N($R^6$)($R^7$), —N($R^6$)—C(O)—$R^7$, —N($R^6$)—C(O)—O—$R^7$, —N($R^6$)—C(O)—N($R^6$)($R^7$), —N($R^6$)—S(═O)$_2$—$R^6$, —CN, and —O—$R^6$, wherein alkyl, cycloalkyl, heterocyclyl, phenyl, and phenoxy are optionally substituted by 1, 2, or 3 substituents selected from alkyl, cycloalkyl, alkoxy, hydroxyl, and halo;

wherein $R^6$ and $R^7$ are independently selected from the group consisting of hydrogen, $C_1$-$C_{15}$ alkyl, cycloalkyl, heterocyclyl, aryl, and heteroaryl, all of which are optionally substituted with 1-3 substituents selected from halo, alkyl, mono- or dialkylamino, alkyl or aryl or heteroaryl amide, —CN, lower alkoxy, —$CF_3$, aryl, and heteroaryl; or $R^6$ and $R^7$ when taken together with the nitrogen to which they are attached form a heterocycle;

$R^2$ is hydrogen, halo, cyano, alkoxy, or alkyl optionally substituted by halo;

$R^3$ is aryl, heteroaryl, or heterocyclyl, all of which are optionally substituted with one or more substituents selected from alkyl, alkoxy, cycloalkyl, cycloalkylalkyl, aryl, arylalkyl, heteroaryl, heteroarylalkyl, heterocyclyl, heterocyclylalkyl, halo, oxo, —$NO_2$, haloalkyl, haloalkoxy, —CN, —O—$R^6$, —O—C(O)—$R^6$, —O—C(O)—N($R^6$)($R^7$), —S—$R^6$, —N($R^6$)($R^7$), —S(=O)—$R^6$, —S(=O)$_2R^6$, —S(=O)$_2$—N($R^6$)($R^7$), S(=O)$_2$—O—$R^6$, —N($R^6$)—C(O)—$R^7$, —N($R^6$)—C(O)—O—$R^7$, —N($R^6$)—C(O)—N($R^6$)($R^7$), —C(O)—$R^6$, —C(O)—O—$R^6$, —C(O)—N($R^6$)($R^7$), and —N($R^6$)—S(=O)$_2$—$R^7$, wherein the alkyl, alkoxy, cycloalkyl, aryl, heteroaryl or heterocyclyl is further optionally substituted with one or more substituents selected from halo, oxo, —$NO_2$, alkyl, haloalkyl, haloalkoxy, —N($R^6$)($R^7$), —C(O)—$R^6$, —C(O)—O—$R^6$, —C(O)—N($R^6$)($R^7$), —CN, —O—$R^6$, cycloalkyl, aryl, heteroaryl and heterocyclyl;

with the proviso that the heteroaryl or heterocyclyl moiety includes at least one ring nitrogen atom;

$X^1$, $X^2$, $X^3$, $X^4$, $X^5$, $X^6$, $X^7$ and $X^8$ are independently C($R^4$) or N, in which each $R^4$ is independently hydrogen, alkyl, alkoxy, cycloalkyl, aryl, heteroaryl, heterocyclyl, halo, —$NO_2$, haloalkyl, haloalkoxy, —CN, —O—$R^6$, —S—$R^6$, —N($R^6$)($R^7$), —S(=O)—$R^6$, —S(=O)$_2R^6$, —S(=O)$_2$—N($R^6$)($R^7$), —S(=O)$_2$—O—$R^6$, —N($R^6$)—C(O)—$R^6$, —N($R^6$)—C(O)—O—$R^7$, —N($R^6$)—C(O)—N($R^6$)($R^7$), —C(O)—$R^6$, —C(O)—O—$R^6$, —C(O)—N($R^6$)($R^7$), or —N($R^6$)—S(=O)$_2$—$R^7$, wherein the alkyl, cycloalkyl, aryl, heteroaryl, and heterocyclyl is further optionally substituted with one or more substituents selected from halo, oxo, —$NO_2$, —$CF_3$, —O—$CF_3$, —N($R^6$)($R^7$), —C(O)—$R^6$, —C(O)—O—$R^7$, —C(O)—N($R^6$)($R^7$), —CN, —O—$R^6$; or $X^5$ and $X^6$ or $X^6$ and $X^7$ are joined to provide optionally substituted fused aryl or optionally substituted fused heteroaryl; and with the proviso that at least one of $X^2$, $X^3$, and $X^4$ is C($R^4$); at least two of $X^5$, $X^6$, $X^7$, and $X^8$ are C($R^4$); and at least one of $X^2$, $X^3$, $X^4$, $X^5$, $X^6$, $X^7$ and $X^8$ is N.

In a second aspect, the invention relates to a method of using the compounds of Formula (I) in the treatment of a disease or condition in a mammal that is amenable to treatment by an ASK1 inhibitor. Such diseases include autoimmune disorders, inflammatory diseases, cardiovascular diseases and neurodegenerative diseases.

In a third aspect, the invention relates to pharmaceutical formulations comprising a therapeutically effective amount of a compound of the invention and at least one pharmaceutically acceptable excipient.

In a fourth aspect, the invention relates to methods of preparing the compounds of Formula (I).

Non-limiting examples of $R^3$ are shown below:

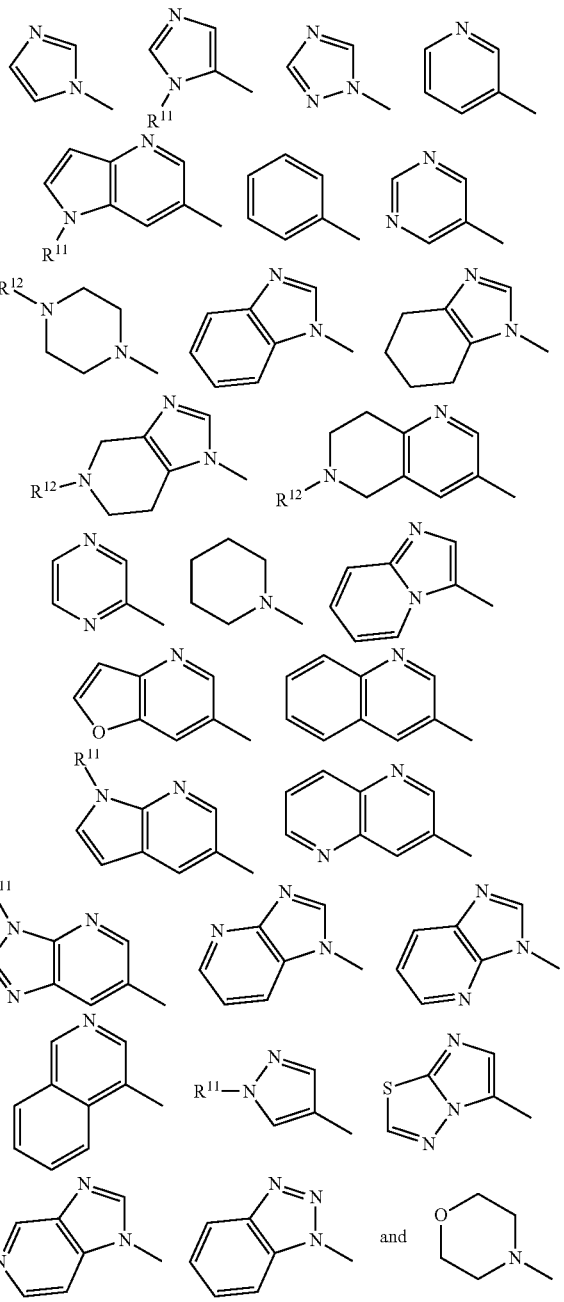

in which:
$R^{11}$ is hydrogen, alkyl, or cycloalkyl, wherein alkyl and cycloalkyl are optionally substituted by hydroxyl or halo;
$R^{12}$ is hydrogen, alkyl, cycloalkyl, —S(=O)—$R^6$ or —S(=O)$_2R^6$, wherein alkyl and cycloalkyl are optionally substituted by hydroxyl or halo.

One embodiment of the invention includes those compounds of Formula (I) in which $X^1$, $X^2$, and $X^5$ are all N, and $X^3$, $X^4$, $X^6$, $X^7$, and $X^8$ are C($R^4$). This group includes compounds in which $R^1$ is optionally substituted alkyl, optionally substituted cycloalkyl, or optionally substituted heterocyclyl, particularly where the optional substitutions are 1, 2, or 3 substituents chosen from hydroxyl, halo, or cycloalkyl. Within this group, a subgroup includes compounds in which R³ is optionally substituted aryl, optionally substituted heteroaryl or optionally substituted heterocyclyl, wherein the heteroaryl or heterocyclyl moieties contain 1, 2 or 3 ring nitrogen atoms, and the aryl, heteroaryl, and heterocyclyl moieties are optionally substituted by alkyl, cycloalkyl, halo, cyano,—or OR⁶, in which alkyl and cycloalkyl are optionally substituted by hydroxyl or halo. A preferred group of R³ moieties includes those non-limiting examples described above.

Another embodiment of the invention includes those compounds of Formula (I) in which X¹ and X⁵ are N, and X², X³, X⁴, X⁶, X⁷, and X⁸ are C(R⁴). This group includes compounds in which R¹ is optionally substituted alkyl, optionally substituted cycloalkyl, or optionally substituted heterocyclyl., particularly where the optional substitutions are 1, 2, or 3 substituents chosen from hydroxyl, halo, or cycloalkyl. Within this group, a subgroup includes compounds in which R³ is optionally substituted aryl, optionally substituted heteroaryl or optionally substituted heterocyclyl, wherein the heteroaryl or heterocyclyl moieties contain 1, 2 or 3 ring nitrogen atoms, and the aryl, heteroaryl, and heterocyclyl moieties are optionally substituted by alkyl, cycloalkyl, halo, cyano,—or OR⁶, in which alkyl and cycloalkyl are optionally substituted by hydroxyl or halo. A preferred group of R³ moieties includes: those non-limiting examples described above.

Another embodiment of the invention includes those compounds of Formula (I) in which X¹ and X² are N, and X³, X⁴, X⁵, X⁶, X⁷, and X⁸ are C(R⁴). This group includes compounds in which R¹ is optionally substituted alkyl, optionally substituted cycloalkyl, or optionally substituted heterocyclyl., particularly where the optional substitutions are 1, 2, or 3 substituents chosen from hydroxyl, halo, or cycloalkyl. Within this group, a subgroup includes compounds in which R³ is optionally substituted aryl, optionally substituted heteroaryl or optionally substituted heterocyclyl, wherein the heteroaryl or heterocyclyl moieties contain 1, 2 or 3 ring nitrogen atoms, and the aryl, heteroaryl, and heterocyclyl moieties are optionally substituted by alkyl, cycloalkyl, halo, cyano,—or OR⁶, in which alkyl and cycloalkyl are optionally substituted by hydroxyl or halo. A preferred group of R³ moieties includes: those non-limiting examples described above.

Another embodiment of the invention includes those compounds of Formula (I) in which X¹ is C(R⁴). This group includes compounds in which R¹ is optionally substituted alkyl, optionally substituted cycloalkyl, or optionally substituted heterocyclyl., particularly where the optional substitutions are 1, 2, or 3 substituents chosen from hydroxyl, halo, or cycloalkyl. Within this group, a subgroup includes compounds in which R³ is optionally substituted aryl, optionally substituted heteroaryl or optionally substituted heterocyclyl, wherein the heteroaryl or heterocyclyl moieties contain 1, 2 or 3 ring nitrogen atoms, and the aryl, heteroaryl, and heterocyclyl moieties are optionally substituted by alkyl, cycloalkyl, halo, cyano,—or OR⁶, in which alkyl and cycloalkyl are optionally substituted by hydroxyl or halo. A preferred group of R³ moieties includes: those non-limiting examples described above.

The compounds of the invention include, but are not limited to, those compounds named below:

5-(2,5-difluorophenyl)-N-(3-(4-methyl-4H-1,2,4-triazol-3-yl)phenyl)nicotinamide;
4-(imidazo[1,2-a]pyridin-3-yl)-N-(3-(4-methyl-4H-1,2,4-triazol-3-yl)phenyl)-picolinamide;
4-(2-aminopyrimidin-5-yl)-N-(3-(4-cyclopropyl-4H-1,2,4-thiazol-3-yl)phenyl)picolinamide;
N-(3-(4-methyl-4H-1,2,4-triazol-3-yl)phenyl)-5-phenylnicotinamide;
N-(3-(4-cyclopropyl-4H-1,2,4-triazol-3-yl)phenyl)-4-phenylpicolinamide;
N-(3-(4-(tetrahydro-2H-pyran-4-yl)-4H-1,2,4-triazol-3-yl)phenyl)-3,4'-bipyridine 2'-carboxamide;
2-hydroxy-N-(3-(4-methyl-4H-1,2,4-triazol-3-yl)phenyl)-6-phenylpyrimidine-4-carboxamide;
N-(3-(4-cyclopropyl-4H-1,2,4-triazol-3-yl)phenyl)-3,4'-bipyridine-2'-carboxamide;
N-(3-(4-cyclopropyl-4H-1,2,4-triazol-3-yl)phenyl)-4-(1H-imidazol-1-yl)picolinamide;
N-(3-(4-methyl-4H-1,2,4-triazol-3-yl)phenyl)-4-phenylpicolinamide
N-(3-(4-(3-amino-3-oxopropyl)-4H-1,2,4-triazol-3-yl)phenyl)-3,4'-bipyridine-2'-carboxamide;
N-(3-(4-cyclopropyl-4H-1,2,4-triazol-3-yl)phenyl)-4-(1H-1,2,4-triazol-1-yl)picolinamide;
N-(3-(4-methyl-4H-1,2,4-triazol-3-yl)phenyl)-6-phenylpicolinamide;
N-(3-(4-(2-acetamidoethyl)-4H-1,2,4-triazol-3-yl)phenyl)-3,4'-bipyridine-2'-carboxamide;
N-(3-(4-methyl-4H-1,2,4-triazol-3-yl)phenyl)-4-(4-methylpiperazin-1-yl)picolinamide;
N-(3-(4-methyl-4H-1,2,4-triazol-3-yl)phenyl)-2,3'-bipyridine-6-carboxamide;
N-(3-(4-methyl-4H-1,2,4-triazol-3-yl)phenyl)-4-morpholinopicolinamide;
N-(3-(4-methyl-4H-1,2,4-triazol-3-yl)phenyl)-6-(quinolin-6-yl)picolinamide;
(R)—N-(3-(4-(1-hydroxypropan-2-yl)-4H-1,2,4-triazol-3-yl)phenyl)-3,4'-bipyridine-2'-carboxamide;
N-(3-(4-cyclopropyl-4H-1,2,4-triazol-3-yl)phenyl)-6-hydroxy-3,4'-bipyridine-2'-carboxamide;
N-(3-(4-methyl-4H-1,2,4-triazol-3-yl)phenyl)-3,3'-bipyridine-5-carboxamide;
(S)—N-(3-(4-(1-hydroxypropan-2-yl)-4H-1,2,4-triazol-3-yl)phenyl)-3,4'-bipyridine-2'-carboxamide;
N-(3-(4-methyl-4H-1,2,4-triazol-3-yl)phenyl)-4-(3-oxopiperazin-1-yl)picolinamide;
N-(3-(4-methyl-4H-1,2,4-triazol-3-yl)phenyl)-3,4'-bipyridine-2'-carboxamide;
N-(3-(4-cyclopropyl-4H-1,2,4-triazol-3-yl)phenyl)-6-methoxy-3,4'-bipyridine-2'-carboxamide;
4-(3-aminopyrrolidin-1-yl)-N-(3-(4-methyl-4H-1,2,4-triazol-3-yl)phenyl)picolinamide;
N-(3-(4-methyl-4H-1,2,4-triazol-3-yl)phenyl)-2-phenylisonicotinamide;
6-amino-N-(3-(4-cyclopropyl-4H-1,2,4-triazol-3-yl)phenyl)-3,4'-bipyridine-2'-carboxamide;
(R)—N-(3-(4-(2-hydroxypropyl)-4H-1,2,4-triazol-3-yl)phenyl)-3,4'-bipyridine-2'-carboxamide;
5-methoxy-N-(3-(4-methyl-4H-1,2,4-triazol-3-yl)phenyl)-3,4'-bipyridine-2'-carboxamide;
methyl 2'-(3-(4-cyclopropyl-4H-1,2,4-triazol-3-yl)phenylcarbamoyl)-3,4'-bipyridin-6-ylcarbamate;
5-methoxy-N-(3-(4-methyl-4H-1,2,4-triazol-3-yl)phenyl)-3,4'-bipyridine-2'-carboxamide;
methyl 2'-(3-(4-cyclopropyl-4H-1,2,4-triazol-3-yl)phenylcarbamoyl)-3,4'-bipyridin-6-yl carbamate;
(S)—N-(3-(4-(2-hydroxypropyl)-4H-1,2,4-triazol-3-yl)phenyl)-3,4'-bipyridine-2'-carboxamide;
4-(1-methyl-1H-imidazol-5-yl)-N-(3-(4-methyl-4H-1,2,4-triazol-3-yl)phenyl)picolinamide;
N-(3-(4-cyclopropyl-4H-1,2,4-triazol-3-yl)phenyl)-4-(1-methyl-1H-imidazol-5-yl)picolinamide;
4-(1H-benzo[d]imidazol-1-A-N-(3-(4-cyclopropyl-4H-1,2,4-triazol-3-yl)phenyl)picolinamide;

N-(3-(4-cyclopropyl-4H-1,2,4-triazol-3-yl)phenyl)-4-(2,4-dimethoxypyrimidin-5-yl)picolinamide;
N-(3-(4-((1-hydroxycyclopropyl)methyl)-4H-1,2,4-triazol-3-yl)phenyl)-3,4'-bipyridine-2'-carboxamide;
N-(3-(4-cyclopropyl-4H-1,2,4-triazol-3-yl)phenyl)-4-(4-phenyl-1H-imidazol-1-yl)picolinamide;
6-cyclopropyl-N-(3-(4-cyclopropyl-4H-1,2,4-triazol-3-yl)phenyl)-3,4'-bipyridine-2'-carboxamide;
(S)—N-(3-(4-(2-hydroxypropyl)-4H-1,2,4-triazol-3-yl)phenyl)-3,4'-bipyridine-2'-carboxamide;
N-(3-(4-cyclobutyl-4H-1,2,4-triazol-3-yl)phenyl)-3,4'-bipyridine-2'-carboxamide;
N2'-(3-(4-cyclopropyl-4H-1,2,4-triazol-3-yl)phenyl)-3,4'-bipyridine-2',6-dicarboxamide;
(S)—N-(3-(4-(1,1,1-trifluoropropan-2-yl)-4H-1,2,4-triazol-3-yl)phenyl)-3,4'-bipyridine-2'-carboxamide;
N-(3-(4-cyclopentyl-4H-1,2,4-triazol-3-yl)phenyl)-3,4'-bipyridine-2'-carboxamide;
N-(3-(4-cyclopropyl-4H-1,2,4-triazol-3-yl)phenyl)-6-(trifluoromethyl)-3,4'-bipyridine-2'-carboxamide;
N2'-(3-(4-cyclopropyl-4H-1,2,4-triazol-3-yl)phenyl)-3,4'-bipyridine-2',5-dicarboxamide;
N-(3-(4-cyclopropyl-4H-1,2,4-triazol-3-yl)phenyl)-4-(2-methyl-1H-imidazol-1-yl)picolinamide;
N-(3-(4-cyclopropyl-4H-1,2,4-triazol-3-yl)phenyl)-6-methyl-3,4'-bipyridine-2'-carboxamide;
5-cyano-N-(3-(4-cyclopropyl-4H-1,2,4-triazol-3-yl)phenyl)-3,4'-bipyridine-2'-carboxamide;
N-(3-(4-cyclopropyl-4H-1,2,4-triazol-3-yl)phenyl)-4-(4-methyl-1H-imidazol-1-yl)picolinamide;
N-(6-(4-cyclopropyl-4H-1,2,4-triazol-3-yl)pyridin-2-yl)-3,4'-bipyridine-2'-carboxamide;
2-amino-N-(3-(4-cyclopropyl-4H-1,2,4-triazol-3-yl)phenyl)-3,4'-bipyridine-2'-carboxamide;
N-(3-(4-cyclopropyl-4H-1,2,4-triazol-3-yl)phenyl)-4-(4,5-dimethyl-1H-imidazol-1-yl)picolinamide;
N-(3-(4-((1S,2S)-2-methylcyclopropyl)-4H-1,2,4-triazol-3-yl)phenyl)-3,4)-bipyridine-2'-carboxamide;
N-(3-(4-cyclopropyl-4H-1,2,4-triazol-3-yl)phenyl)-2-methoxy-3,4'-bipyridine-2'-carboxamide;
N-(3-(4-cyclopropyl-4H-1,2,4-triazol-3-yl)phenyl)-4-(4-(trifluoromethyl)-1H-imidazol-1-yl)picolinamide;
N-(3-(4-cyclopropyl-4H-1,2,4-triazol-3-yl)phenyl)-6-(2,2,2-trifluoroethoxy)-3,4'-bipyridine-2'-carboxamide;
N-(3-(4-cyclopropyl-4H-1,2,4-triazol-3-yl)phenyl)-4-(1-methyl-1H-pyrazol-4-yl)picolinamide;
N-(3-(4-cyclopropyl-4H-1,2,4-triazol-3-yl)phenyl)-4-(2-methoxypyrimidin-5-yl)picolinamide;
N-(3-(4-cyclopropyl-4H-1,2,4-triazol-3-yl)phenyl)-4-methyl-3,4'-bipyridine-2'-carboxamide;
N-(3-(4-cyclopropyl-4H-1,2,4-triazol-3-yl)phenyl)-4-(imidazo[1,2-a]pyridin-3-yl)picolinamide;
ethyl-N-(3-(4-methyl-4H-1,2,4-triazol-3-yl)phenyl)-3,4'-bipyridine-2'-carboxamide;
N-(3-(4-(2,2,2-trifluoroethyl)-4H-1,2,4-triazol-3-yl)phenyl)-3,4'-bipyridine-2'-carboxamide;
6-chloro-[3,2',5',4''']terpyridine-2''-carboxylic acid[3-(4-cyclopropyl-4H-[1,2,4]triazol-3-yl)-phenyl]amide
N-(3-(4-cyclopropyl-4H-1,2,4-triazol-3-yl)phenyl)-6-(pyrrolidin-1-yl)-3,4'-bipyridine-2'-carboxamide;
N-(3-(4-cyclopropyl-4H-1,2,4-triazol-3-yl)phenyl)-5-(trifluoromethyl)-3,4'-bipyridine-2'-carboxamide;
N-(3-(1-cyclopropyl-1H-imidazol-5-yl)phenyl)-3,4'-bipyridine-2'-carboxamide;
N-(3-(4-cyclopropyl-4H-1,2,4-triazol-3-yl)phenyl)-4-(1,2-dimethyl-1H-imidazol-5-yl)picolinamide;
4-(1H-benzo[d][1,2,3]triazol-yl)-N-(3-(4-cyclopropyl-4H-1,2,4-triazol-3-yl)phenyl)picolinamide;
N-(3-(4-cyclopropyl-4H-1,2,4-triazol-3-yl)phenyl)-4-(4-sulfamoylphenyl)picolinamide;
N-(3-(4-cyclopropyl-4H-1,2,4-triazol-3-yl)phenyl)-5-methoxy-3,4'-bipyridine-2'-carboxamide;
N-(3-(4-cyclopropyl-4H-1,2,4-triazol-3)phenyl)-6-fluoro-5-methyl-3,4'-bipyridine-2'-carboxamide;
N-(3-(4-cyclopropyl-4H-1,2,4-triazol-3-yl)phenyl)-5-fluoro-3,4'-bipyridine-2'-carboxamide;
N-(3-(4-cyclopropyl-4H-1,2,4-triazol-3-yl)phenyl)-2-methyl-3,4'-bipyridine-2'-carboxamide;
N-(3-(4-cyclopropyl-4H-1,2,4-triazol-3-yl)phenyl)-4-(4,5,6,7-tetrahydro-1H-benzo[d]imidazol-1-yl)picolinamide;
N-(3-(4-cyclopropyl-4H-1,2,4-triazol-3-yl)phenyl)-4-(4-(N-methylsulfamoyl)phenyl)picolinamide;
N5-tert-butyl-N2'-(3 (4-cyclopropyl-4H-1,2,4-triazol-3-yl)phenyl)-3,4'-bipyridine-2',5-dicarboxamide;
N-(3-(4-cyclopropyl-4H-1,2,4-triazol-3-yl)phenyl)-4-(pyrazin-2-yl)picolinamide;
N-(3-(4-cyclopropyl-4H-1,2,4-triazol-3-yl)phenyl)-4-(4-(N-isopropylsulfamoyl)phenyl)picolinamide;
chloro-N-(3-(4-cyclopropyl-4H-1,2,4-triazol-3-yl)phenyl)-3,4'-bipyridine-2'-carboxamide;
4-(1H-benzo[d]imidazol-1-yl)-N-(3-(1-cyclopropyl-1H-imidazol-5-yl)phenyl)picolinamide;
6-cyclopropyl-N-(6-(4-cyclopropyl-4H-1,2,4-triazol-3-yl)pyridin-2-yl)-3,4'-bipyridine-2'-carboxamide;
N-(3-(4-cyclopropyl-4H-1,2,4-triazol-3-yl)phenyl)-4-(3-(methylsulfonyl)phenyl)picolinamide;
N-(3-(4-cyclopropyl-4H-1,2,4-triazol-3-yl)phenyl)-4-(isoquinolin-4-yl)picolinamide;
N-(6-(4-cyclopropyl-4H-1,2,4-triazol-3-yl)pyridin-2-yl)-4-(4-(methylsulfonyl)phenyl)picolinamide;
N-(3-(4-cyclopropyl-4H-1,2,4-triazol-3-yl)phenyl)-4-(2-(methylsulfonyl)phenyl)picolinamide;
N-(3-(4-cyclopropyl-4H-1,2,4-triazol-3-yl)phenyl)-4-(1,5-dimethyl-1H-pyrazol-4-yl)picolinamide;
6-cyclobutyl-N-(3-(4-cyclopropyl-4H-1,2,4-triazol-3-yl)phenyl)-3,4'-bipyridine-2'-carboxamide;
N-(3-(4-cyclopropyl-4H-1,2,4-triazol-3-yl)phenyl)-6-isopropyl-3,4'-bipyridine-2'-carboxamide;
N-(3-(4-cyclopropyl-5H-1,2,4-triazol-3-yl)phenyl)-4-(4-(methylsulfonyl)phenyl)picolinamide;
N-(3-(4-cyclopropyl-4H-1,2,4-triazol-3-yl)phenyl)-6-(dimethylamino)-3,4'-bipyridine-2'-carboxamide;
N-(3-(4-cyclopropyl-4H-1,2,4-triazol-3-yl)phenyl)-4-(pyridin-3-yl)quinoline-2-carboxamide;
N-(3-(4-cyclopropyl-4H-1,2,4-triazol-3-yl)phenyl)-4-(1H-pyrrolo[2,3-b]pyridin-5-yl)picolinamide;
6-cyclopropoxy-N-(3-(4-cyclopropyl-4H-1,2,4-triazol-3-yl)phenyl)-3,4'-bipyridine-2'-carboxamide;
N-(3-(4-cyclopropyl-4H-1,2,4-triazol-3-yl)phenyl)-4-(1H-imidazo[4,5-b]pyridin-1-yl)picolinamide;
N-(3-(4-cyclopropyl-4H-1,2,4-triazol-3-yl)phenyl)-6-fluoro-3,4'-bipyridine-2'-carboxamide;
N-(3-(4-cyclopropyl-4H-1,2,4-triazol-3-yl)phenyl)-4-(4-(2-oxoimidazolidin-1-yl)phenyl)picolinamide;
N-(3-(4-cyclopropyl-4H-1,2,4-triazol-3-yl)phenyl)-4-(3H-imidazo[4, 5-1)]pyridin-3-yl)picolinamide;
N-(3-(4-cyclopropyl-4H-1,2,4-triazol-3-yl)phenyl)-6-isopropoxy-3,4'-bipyridine-2'-carboxamide;
N-(3-(4-cyclopropyl-4H-1,2,4-triazol-3-yl)phenyl)-6-ethyl-3,4'-bipyridine-2'-carboxamide;
N-(3-(4-cyclopropyl-4H-1,2,4-triazol-3-yl)phenyl)-4-(1H-imidazo[4,5-c]pyridin-1-yl)picolinamide;

6-cyclobutoxy-N-(3-(4-cyclopropyl-4H-1,2,4-triazol-3-yl) phenyl)-3,4'-bipyridine-2'-carboxamide;

6-cyclopropyl-N-(3-(1-cyclopropyl-1H-imidazol-5-yl)phenyl)-3,4'-bipyridine-2'-carboxamide;

N-(3-(4-cyclopropyl-4H-1,2,4-triazol-3-yl)phenyl)-4-(quinolin-3-yl)picolinamide;

N-(3-(4-cyclopropyl-4H-1,2,4-triazol-3-yl)phenyl)-4-(4-(N-cyclopropylsulfamoyl) phenyl)picolinamide;

N-(3-(1-cyclopropyl-1H-imidazol-5-yl)phenyl)-4-(quinolin-3-yl)picolinamide;

6-cyclopentyl-N-(3-(4-cyclopropyl-4H-1,2,4-triazol-3-yl) phenyl)-3,4'-bipyridine-2'-carboxamide;

N-(3-(4-cyclopropyl-4H-1,2,4-triazol-3-yl)phenyl)-4-(imidazo[2,1-b][1,3,4]thiadiazol-5-yl)picolinamide;

N-(3-(4-cyclopropyl-4H-1,2,4-triazol-3-yl)phenyl)-4-(5-cyclopropylpyrazin-2-yl)picolinamide;

N-(3-(4-cyclopropyl-4H-1,2,4-triazol-3-yl)phenyl)-6-(1-methyl-2-oxopyrrolidin-3-yl)-3,4'-bipyridine-2'-carboxamide;

4-(4-chloro-1H-imidazol-1-yl)-N-(3-(4-cyclopropyl-4H-1,2,4-triazol-3-yl)phenyl)picolinamide;

6-cyclopropyl-N-(3-(4-cyclopropyl-4H-1,2,4-triazol-3-yl) phenyl)-5-fluoro-3,4'-bipyridine-2'-carboxamide;

(S)-4-(4-cyclopropyl-1H-imidazol-1-yl)-N-(3-(4-(3-methylbutan-2-yl)-4H-1,2,4-triazol-3-yl)phenyl)picolinamide;

6'-cyclopropyl-N-(3-(4-cyclopropyl-4H-1,2,4-triazol-3-yl) phenyl)-2,3'-bipyridine-6-carboxamide;

6'-cyclopropyl-N-(3-(4-cyclopropyl-4H-1,2,4-triazol-3-yl) phenyl)-2,3'-bipyridine-4-carboxamide;

N-(6-(4-cyclopropyl-4H-1,2,4-triazol-3-yl)pyridin-2-yl)-5-(6-cyclopropylpyridin-3-yl)-2,4-difluorobenzamide;

6'-cyclopropyl-N-(6-(4-cyclopropyl-4H-1,2,4-triazol-3-yl) pyridin-2-yl)-2,3'-bipyridine-4-carboxamide;

6'-cyclopropyl-N-(6-(4-cyclopropyl-4H-1,2,4-triazol-3-yl) pyridin-2-yl)-3,3'-bipyridine-5-carboxamide;

6'-cyclopropyl-N-(6-(4-cyclopropyl-4H-1,2,4-triazol-3-yl) pyridin-2-yl)-2,3'-bipyridine-6-carboxamide;

N-(3-(4-cyclopropyl-4H-1,2,4-triazol-3-yl)phenyl)-4-(5-methyl-4-(trifluoromethyl)-4,5,6,7-tetrahydro-1H-imidazo[4,5-c]pyridin-1-yl)picolinamide;

N-(6-(4-cyclopropyl-4H-1,2,4-triazol-3-yl)pyridin-2-yl)-4-(5-methyl-4-(trifluoromethyl)-4,5,6,7-tetrahydro-1H-imidazo[4,5-c]pyridin-1-yl)picolinamide;

4-(5-cyclopropyl-4-methyl-4H-1,2,4-triazol-3-yl)-N-(3-(4-cyclopropyl-4H-1,2,4-triazol-3-yl)phenyl)picolinamide;

4-(3-cyclopropyl-1,2,4-oxadiazol-5-yl)-N-(3-(4-cyclopropyl-4H-1,2,4-triazol-3-yl)phenyl)picolinamide;

N-(3-(4-cyclopropyl-4H-1,2,4-triazol-3-yl)phenyl)-4-(3-methyl-1,2,4-oxadiazol-5-yl)picolinamide;

6-cyclopropyl-N-(3-(4-(3-hydroxybutan-2-yl)-4H-1,2,4-triazol-3-yl)phenyl)-3,4'-bipyridine-2'-carboxamide;

4-chloro-N-(6-(4-cyclopropyl-4H-1,2,4-triazol-3-yl)pyridin-2-yl)-5-(6-cyclopropylpyridin-3-yl)-2-fluorobenzamide;

N-(3-(4-cyclopropyl-4H-1,2,4-triazol-3-yl)phenyl)-4-(5-(1-hydroxyethyl)-1,3,4-oxadiazol-2-yl)picolinamide;

N-(3-(4-cyclopropyl-4H-1,2,4-triazol-3-yl)phenyl)-4-(6-methoxyquinolin-3-yl)picolinamide;

6-cyclopropyl-N-(3-(4-cyclopropyl-4H-1,2,4-triazol-3-yl) phenyl)-5'-methyl-3,4'-bipyridine-2'-carboxamide;

6-cyclopropyl-N-(3-(4-cyclopropyl-4H-1,2,4-triazol-3-yl) phenyl)-6'-methyl-3,4'-bipyridine-2'-carboxamide;

6-cyclopropyl-N-(6-(4-((2R)-3-hydroxybutan-2-yl)-4H-1,2,4-triazol-3-yl)pyridin-2-yl)-3,4'-bipyridine-2'-carboxamide;

6-cyclopropyl-N-(6-(4-((2S,3R)-3-hydroxybutan-2-yl)-4H-1,2,4-triazol-3-yl)pyridin-2-yl)-3,4'-bipyridine-2'-carboxamide;

6-cyclopropyl-N-(6-(4-((2S,3S)-3-hydroxybutan-2-yl)-4H-1,2,4-triazol-3-yl)pyridin-2-yl)-3,4'-bipyridine-2'-carboxamide;

6-cyclopropyl-N-(6-(4-(1-(pyrrolidin-1-yl)propan-2-yl)-4H-1,2,4-triazol-3-yl)pyridin-2-yl)-3,4'-bipyridine-2'-carboxamide;

N-(3-(4-cyclopropyl-4H-1,2,4-triazol-3-yl)phenyl)-4-(1-(2,2,2-trifluoroethyl)-1H-pyrrolo[3,2-b]pyridin-6-yl)picolinamide;

N-(3-(4-cyclopropyl-4H-1,2,4-triazol-3-yl)phenyl)-4-(isopropyl-1-pyrrolo[3,2-b]pyridin-6-yl)picolinamide;

(S)-6-cyclopropyl-N-(3-(4-(3,3-dimethylbutan-2-yl)-4H-1,2,4-triazol-3-yl)phenyl)-3,4'-bipyridine-2'-carboxamide;

6-cyclopropyl-N-(6-(4-(1-methylpiperidin-4-yl)-4H-1,2,4-triazol-3-yl)pyridin-2-yl)-3,4'-bipyridine-2'-carboxamide;

N-(3-(4-sec-butyl-4H-1,2,4-triazol-3-yl)phenyl)-6-cyclopropyl-3,4'-bipyridine-2'-carboxamide;

(S)-6-cyclopropyl-N-(3-(4-(1-cyclopropylethyl)-4H-1,2,4-triazol-3-yl)phenyl)-3,4'-bipyridine-2'-carboxamide;

6-cyclopropyl-N-(3-(4-(pentan-3-yl)-4H-1,2,4-triazol-3-yl) phenyl)-3,4'-bipyridine-2'-carboxamide;

(S)-6-cyclopropyl-N-(3-(4-(1-methoxypropan-2-yl)-4H-1,2,4-triazol-3-yl)phenyl)-3,4'-bipyridine-2'-carboxamide;

6-cyclopropyl-N-(6-(4-cyclopropyl-4H-1,2,4-triazol-3-yl) pyridin-2-yl)-6'-methyl-3,4'-bipyridine-2'-carboxamide;

(S)-6-cyclopropyl-N-(6-(4-(1-methoxypropan-2-yl)-4H-1,2,4-triazol-3-yl)pyridin-2-yl)-dine-2'-carboxamide;

(S)—N-(3-(4-sec-butyl-4H-1,2,4-triazol-3-yl)phenyl)-6-cyclopropyl-3,4'-bipyridine-2'-carboxamide;

N-(6-(4-cyclopropyl-4H-1,2,4-triazol-3-yl)pyridin-2-yl)-3-(4-(2,2,2-trifluoro-1-methoxyethyl)-1H-imidazol-1-yl) benzamide;

N-(6-(4-cyclopropyl-4H-1,2,4-triazol-3-yl)pyridin-2-yl)-4-(6-cyclopropylpyridin-3-yl)-7,8-dimethyl quinoline-2-carboxamide;

(S)-6-cyclopropyl-N-(3-(4-(3-methylbutan-2-yl)-4H-1,2,4-triazol-3-yl)phenyl)-3,4'-bipyridine-2'-carboxamide;

(R)-6-cyclopropyl-N-(3-(4-(1-(2,6-dimethylphenoxy)propan-2-yl)-4H-1,2,4-triazol-3-yl)phenyl)-3,4'-bipyridine-2'-carboxamide;

N-(3-(4-cyclopropyl-4H-1,2,4-triazol-3-yl)phenyl)-4-(6-cyclopropylpyridin-3-yl)-7,8-dimethylquinoline-2-carboxamide;

3-(4-cyclopropyl-1H-imidazol-1-yl)-N-(6-(4-cyclopropyl-4H-1,2,4-triazol-3-yl)pyridin-2-yl)-4-methoxybenzamide;

4-chloro-3-(4-cyclopropyl-1H-imidazol-1-yl)-N-(6-(4-cyclopropyl-4H-1,2,4-triazol-3-yl)pyridin-2-yl)benzamide;

4-(4-cyclopropyl-1H-imidazol-1-yl)-N-(6-(4-cyclopropyl-4H-1,2,4-triazol-3-yl)pyridin-2-yl)quinoline-2-carboxamide;

N-(6-(4-cyclopropyl-4H-1,2,4-triazol-3-yl)pyridin-2-yl)-4-(6-cyclopropylpyridin-3-yl)quinoline-2-carboxamide;

N-(6-(4-cyclopropyl-4H-1,2,4-triazol-3-yl)pyridin-2-yl)-5-(6-cyclopropylpyridin-3-yl)-2-fluorobenzamide;

(S)-6-cyclopropyl-N-(3-(4-(1,1,1-trifluoropropan-2-yl)-4H-1,2,4-triazol-3-yl)phenyl)-3,4'-bipyridine-2'-carboxamide;

(S)-tert-butyl 2-(3-(3-(6-cyclopropyl-3,4'-bipyridine-2'-carboxamido)phenyl)-4H-1,2,4-triazol-4-yl)propanoate;

N-(3-(4-cyclobutyl-4H-1,2,4-triazol-3-yl)phenyl)-6-cyclopropyl-3,4'-bipyridine-2'-carboxamide;

(S)-6-cyclopropyl-N-(3-(4-(1-phenylethyl)-4H-1,2,4-triazol-3-yl)phenyl)-3,4'-bipyridine-2'-carboxamide;

6-cyclopropyl-N-(3-(4-isopropyl-4H-1,2,4-triazol-3-yl)phenyl)-3,4'-bipyridine-2'-carboxamide;
3-(4-cyclopropyl-1H-imidazol-1-yl)-N-(6-(4-isopropyl-4H-1,2,4-triazol-3-yl)pyridin-2-yl)benzamide;
(S)-3-(4-cyclopropyl-1H-imidazol-1-yl)-N-(6-(4-(1-phenylethyl)-4H-1,2,4-triazol-3-yl)pyridin-2-yl)benzamide;
N-(6-(1-cyclopropyl-1H-imidazol-5-yl)pyridin-2-yl)-4-(4,5-dimethyl-1H-imidazol-1-yl)picolinamide;
N-(6-(1-cyclopropyl-1H-imidazol-5-yl)pyridin-2-yl)-6-(2-hydroxypropan-2-yl)-3,4'-bipyridine-2'-carboxamide;
N-(3-(4-(cyclopropylmethyl)-4H-1,2,4-triazol-3-yl)phenyl)-3,4'-bipyridin carboxamide;
4-(4-cyclopropyl-2-methyl-1H-imidazol-1-yl)-N-(3-(4-cyclopropyl-4H-1,2,4-triazol-3-yl)phenyl)picolinamide;
4-(4-cyclopropyl-2-methyl-1H-imidazol-1-yl)-N-(6-(4-cyclopropyl-4H-1,2,4-triazol-3-yl)pyridin-2-yl)picolinamide;
4-(4-cyclopropyl-1H-imidazol-1-yl)-N-(3-(4-isopropyl-4H-1,2,4-triazol-3-yl)phenyl)picolinamide;
4-(4-cyclopropyl-1H-imidazol-1-yl)-N-(3-(4-(cyclopropylmethyl)-4H-1,2,4-triazol-3-yl)phenyl)picolinamide;
4-(4-cyclopropyl-1-imidazol-1-yl)-N-(3-(4-(1-phenylethyl)-4H-1,2,4-triazol-3-yl)phenyl)picolinamide;
N-(6-(4-cyclopropyl-4H-1,2,4-triazol-3-yl)pyridin-2-yl)-4-(4,5,6,7-tetrahydro-1H-benzo[d]imidazol-1-yl)picolinamide;
N-(6-(4-cyclopropyl-4H-1,2,4-triazol-3-yl)pyridin-2-yl)-4-(4-(trifluoromethyl)-1H-imidazol-1-yl)picolinamide;
(R)-4-(4-cyclopropyl-1H-imidazol-1-yl)-N-(3-(4-(1,1,1-trifluoropropan-2-yl)-4H-1,2,4-triazol-3-yl)phenyl)picolinamide;
N-(3-(4-cyclopropyl-4H-1,2,4-triazol-3-yl)phenyl)-4-(1,5-naphthyridin-3-yl)picolinamide;
N-(6-(4-cyclopropyl-4H-1,2,4-triazol-3-yl)pyridin-2-yl)-3-(1,5-naphthyridin-3-yl)benzamide;
3-(4-cyclopropyl-1H-imidazol-1-yl)-N-(6-(4-cyclopropyl-4H-1,2,4-triazol-3-yl)pyridin-2-yl)benzamide;
N-(6-(4-cyclopropyl-4H-1,2,4-triazol-3-yl)pyridin-2-yl)-3-(4-isopropyl-1H-imidazol-1-yl)benzamide;
3-(4-cyclopropyl-1H-imidazol-1-yl)-N-(6-(4-cyclopropyl-4H-1,2,4-triazol-3-yl)pyridin-2-yl)-2-methylbenzamide;
N-(6-(4-cyclopropyl-4H-1,2,4-triazol-3-yl)pyridin-2-yl)-4-(4-(trifluoromethyl)-4,5,6,7-tetrahydro-1H-imidazo[4,5-c]pyridin-1-yl)picolinamide;
N-(3-(4-cyclopropyl-4H-1,2,4-triazol-3-yl)phenyl)-4-(4-(trifluoromethyl)-4,5,6,7-tetrahydro-1H-imidazo[4,5-c]pyridin-1-yl)picolinamide;
5-(4-cyclopropyl-1H-imidazol-1-yl)-N-(6-(4-cyclopropyl-4H-1,2,4-triazol-3-yl)pyridin-2-yl)-2-methylbenzamide;
N-(3-(4-cyclopropyl-4H-1,2,4-triazol-3-yl)phenyl)-4-(4-(perfluoroethyl)-1H-imidazol-1-yl)picolinamide;
N-(6-(4-cyclopropyl-4H-1,2,4-triazol-3-yl)pyridin-2-yl)-4-(4-(perfluoroethyl)-1H-imidazol-1-yl)picolinamide;
3-(4-cyclopropyl-1H-imidazol-1-yl)-N-(6-(4-cyclopropyl-4H-1,2,4-triazol-3-yl)pyridin-2-yl)-4-methylbenzamide;
4-(3-cyclopropyl-1H-1,2,4-triazol-1-yl)-N-(6-(4-cyclopropyl-4H-1,2,4-triazol-3-yl)pyridin-2-yl)picolinamide;
4-(3-cyclopropyl-1H-1,2,4-triazol-1-yl)-N-(3-(4-cyclopropyl-4H-1,2,4-triazol-3-yl)phenyl)picolinamide;
4-(5-cyclopropyl-1H-1,2,4-triazol-1-yl)-N-(3-(4-cyclopropyl-4H-1,2,4-triazol-3-yl)phenyl)picolinamide;
N-(6-(4-cyclopropyl-4-H-1,2,4-triazol-3-yl)pyridin-2-yl)-3-(6-(2-hydroxypropan-2-yl)pyridin-3-yl)benzamide;
3-(4-cyclopropyl-1H-imidazol-1-yl)-N-(6-(4-cyclopropyl-4H-1,2,4-triazol-3-yl)pyridin-2-yl)-5-fluorobenzamide;
N-(6-(4-cyclopropyl-4H-1,2,4-triazol-3-yl)pyridin-2-yl)-4-(4-(2,2,2-trifluoro-1-hydroxyethyl)-1H-imidazol-1-yl)picolinamide;
N-(3-(4-cyclopropyl-4H-1,2,4-triazol-3-yl)phenyl)-4-(4-(2,2,2-trifluoro-1-hydroxyethyl)-1H-imidazol-1-yl)picolinamide;
N-(6-(4-cyclopropyl-4H-1,2,4-triazol-3-yl)pyridin-2-yl)-3-(4-(2,2,2-trifluoro-1-hydroxyethyl)-1H-imidazol-1-yl)benzamide;
3-(4-cyclopropyl-1H-imidazol-1-yl)-N-(6-(4-cyclopropyl-4H-1,2,4-triazol-3-yl)pyridin-2-yl)-5-methylbenzamide;
N-(6-(4-cyclopropyl-4H-1,2,4-triazol-3-yl)pyridin-2-yl)-3-(4,5-dimethyl-1H-imidazol-1-yl)benzamide;
N-(6-(4-cyclopropyl-4H-1,2,4-triazol-3-yl)pyridin-2-yl)-3-(4,5,6,7-tetrahydro-1-benzo[d]imidazol-1-yl)benzamide;
1-(3-(6-(4-cyclopropyl-4H-1,2,4-triazol-3-yl)pyridin-2-ylcarbamoyl)phenyl)-5-methyl-1H-imidazole-4-carboxylic acid;
(S)-3-(4-cyclopropyl-1H-imidazol-1-yl)-N-(6-(4-(1-phenylethyl)-4H-1,2,4-triazol-3-yl)pyridin-2-yl)benzamide;
6-cyclopropyl-N-(6-(4-cyclopropyl-4H-1,2,4-triazol-3-yl)pyridin-2-yl)-5'-methyl-3,4'-bipyridine-2'-carboxamide;
(S)-3-(4,5-dimethyl-1H-imidazol-1-yl)-N-(6-(4-(1,1,1-trifluoropropan-2-yl)-4H-1,2,4-triazol-3-yl)pyridin-2-yl)benzamide;
N-(3-(4-cyclopropyl-4H-1,2,4-triazol-3-yl)phenyl)-4-(2-ethylpyrimidin-5-yl)picolinamide;
N-(3-(4-cyclopropyl-4H-1,2,4-triazol-3-yl)phenyl)-5-ethyl-3,4'-bipyridine-2'-carboxamide;
6-cyclopropyl-N-(3-(4-cyclopropyl-4H-1,2,4-triazol-3-yl)-4-fluorophenyl)-3,4'-bipyridine-2'-carboxamide;
N-(3-(4-cyclopropyl-4H-1,2,4-triazol-3-yl)-4-fluorophenyl)-6-ethyl-3,4'-bipyridin carboxamide;
6-tert-butyl-N-(3-(4-cyclopropyl-4H-1,2,4-triazol-3-yl)phenyl)-3,4'-bipyridine-2'-carboxamide;
N-(6-(4-cyclopropyl-4H-1,2,4-triazol-3-yl)pyridin-2-yl)-3-(quinolin-3-yl)benzamide;
N-(6-(4-cyclopropyl-4H-1,2,4-triazol-3-yl)pyridin-2-yl)-3-(6-cyclopropylpyridin-3-yl)benzamide;
6-cyclopropyl-N-(2-(4-cyclopropyl-4H-1,2,4-triazol-3-yl)pyridin-4-yl)-3,4'-bipyridine-2'-carboxamide;
N-(2-(4-cyclopropyl-4H-1,2,4-triazol-3-yl)pyridin-4-yl)-4-(quinolin-3-yl)picolinamide;
N-(3-(4-cyclopropyl-4H-1,2,4-triazol-3-yl)phenyl)-4-(5,6,7,8-tetrahydro-1,6-naphthyridin-3-yl)picolinamide;
6-cyclopropyl-N-(3-(4-cyclopropyl-4H-1,2,4-triazol-3-yl)-2-fluorophenyl)-3,4'-bipyridine-2'-carboxamide;
5-cyclopropyl-N-(3-(4-cyclopropyl-4H-1,2,4-triazol-3-yl)phenyl)-3,4'-bipyridine-2'-carboxamide;
N-(3-(4-cyclopropyl-4H-1,2,4-triazol-3-yl)-2-fluorophenyl)-3,4'-bipyridine-2'-carboxamide;
N-(3-(4-cyclopropyl-4H-1,2,4-triazol-3-yl)phenyl)-4-(4-ethyl-1H-imidazol-1-yl)picolinamide;
N-(6-(4-cyclopropyl-4H-1,2,4-triazol-3-yl)pyridin-2-yl)-4-(4-methyl-1H-imidazol-1-yl)picolinamide;
N-(6-(4-cyclopropyl-4H-1,2,4-triazol-3-yl)pyridin-2-yl)-4-(4,5-dimethyl-1H-imidazol-1-yl)picolinamide;
N-(3-(4-cyclopropyl-4H-1,2,4-triazol-3-yl)phenyl)-4-(6-(2,2,2-trifluoroethyl)-5,6,7,8-tetrahydro-1,6-naphthyridin-3-yl)picolinamide;
N-(3-(4-cyclopropyl-4H-1,2,4-triazol-3-yl)phenyl)-4-(4-isopropyl-1H-imidazol-1-yl)picolinamide;
N-(3-(4-cyclopropyl-4H-1,2,4-triazol-3-yl)phenyl)-6-(2-hydroxypropan-2-yl)-3,4'-bipyridine-2'-carboxamide;
N-(6-(4-cyclopropyl-4H-1,2,4-triazol-3-yl)pyridin-2-yl)-6-(2-hydroxypropan-2-yl)-3,4'-bipyridine-2'-carboxamide;

N-(6-(4-cyclopropyl-4H-1,2,4-triazole-3-yl)pyridin-2-yl)-4-(4-isopropyl-1H-imidazol-1-yl)picolinamide;
6-cyclopropyl-N-(3-(4-cyclopropyl-4H-1,2,4-triazol-3-yl)-5-fluorophenyl)-3,4'-bipyridine-2'-carboxamide;
N-(3-(4-cyclopropyl-4H-1,2,4-triazol-3-yl)-5-fluorophenyl)-3,4'-bipyridine-2'-carboxamide;
4-(4-cyclopropyl-1H-imidazol-1-yl)-N-(6-(4-cyclopropyl-4H-1,2,4-triazol-3-yl)pyridin-2-yl)picolinamide;
N-(3-(4-cyclopropyl-4H-1,2,4-triazol-3-yl)phenyl)-6-(2,2,2-trifluoroethyl)-3,4'-bipyridine-2'-carboxamide;
N-(3-(4-cyclopropyl-4H-1,2,4-triazol-3-yl)phenyl)-4-(6-isopropyl-5,6,7,8-tetrahydro-1,6-naphthyridin-3-yl)picolinamide;
N-(3-(4-cyclopropyl-4H-1,2,4-triazol-3-yl)phenyl)-4-(6-methyl-5,6,7,8-tetrahydro-1,6-naphthyridin-3-yl)picolinamide;
N-(3-(4-cyclopropyl-4H-1,2,4-triazol-3-yl)phenyl)-4-(3-hydroxypiperidin-1-yl)picolinamide;
N-(6-(4-cyclopropyl-4H-1,2,4-triazol-3-yl)pyridin-2-yl)-4-(3-hydroxypiperidin-1-yl)picolinamide;
6-cyclopropyl-N-(6-(4-isopropyl-4H-1,2,4-triazol-3-yl)pyridin-2-yl)-3,4'-bipyridine-2'-carboxamide;
N-(3-(4-cyclopropyl-4H-1,2,4-triazol-3-yl)phenyl)-4-(4-ethyl-3-oxopiperazin-1-yl)picolinamide;
N-(6-(4-cyclopropyl-4H-1,2,4-triazol-3-yl)pyridin-2-yl)-4-(4-ethyl-3-oxopiperazin-1-yl)picolinamide;
(R)-6-cyclopropyl-N-(6-(4-(1,1,1-trifluoropropan-2-yl)-4H-1,2,4-triazol-3-yl)pyridin-2-yl)-3,4'-bipyridine-2'-carboxamide;
N-(3-(4-isopropyl-4H-1,2,4-triazol-3-yl)phenyl)-3,4'-bipyridine-2'-carboxamide;
6-cyclopentyl-N-(3-(4-cyclopropyl-4H-1,2,4-triazol-3-yl)phenyl)-3,4'-bipyridine-2'-carboxamide;
N-(3-(4-cyclopropyl-4H-1,2,4-triazol-3-yl)phenyl)-6-(1-methyl-2-oxopyrrolidin-3-yl)-3,4'-bipyridine-2'-carboxamide;
N-(6-(4-cyclopropyl-4H-1,2,4-triazol-3-yl)pyridin-2-yl)-4-(N-methyl sulfamoyl)phenyl)picolinamide;
N-(6-(4-cyclopropyl-4H-1,2,4-triazol-3-yl)pyridin-2-yl)-4-(quinolin-3-yl)picolinamide;
N-(6-(4-cyclopropyl-4H-1,2,4-triazol-3-yl)pyridin-2-yl)-4-(4-phenyl-1H-imidazol-1-yl)picolinamide;
N-(3-(4-cyclopropyl-4H-1,2,4-triazol-3-yl)phenyl)-6-propyl-3,4'-bipyridine-2'-carboxamide;
N-(3-(4-cyclopropyl-4H-1,2,4-triazol-3-yl)phenyl)-6-neopentyl-3,4'-bipyridine-2'-carboxamide;
N-(3-(4-cyclopropyl-4H-1,2,4-triazol-3-yl)phenyl)-4-(1-methyl-2-phenyl-1H-imidazol-5-yl)picolinamide;
N-(3-(4-cyclopropyl-4H-1,2,4-triazol-3-yl)phenyl)-4-(4-(ethylsulfonyl)phenyl)-picolinamide;
N-(3-(4-cyclopropyl-4H-1,2,4-triazol-3-yl)phenyl)-4-(4-(isopropylsulfonyl)phenyl)picolinamide;
N-(3-(4-cyclopropyl-4H-1,2,4-triazol-3-yl)phenyl)-6-(ethylamino)-3,4'-bipyridine-2'-carboxamide;
N-(3-(4-cyclopropyl-4H-1,2,4-triazol-3-yl)phenyl)-6-(cyclopropylamino)-3,4'-bipyridine-2'-carboxamide;
N-(3-(4-cyclopropyl-4H-1,2,4-triazol-3-yl)phenyl)-4-(imidazo[2,1-b][1,3,4]thiadiazol-5-yl)picolinamide;
4-(4-chloro-1H-imidazol-1-yl)-N-(3-(4-cyclopropyl-4H-1,2,4-triazol-3-yl)phenyl)picolinamide;
N-(3-(4-cyclopropyl-4H-1,2,4-triazol-3-yl)phenyl)-4-(2-cyclopropylpyrimidin-5-yl)picolinamide;
N-(3-(4-cyclopropyl-4H-1,2,4-triazol-3-yl)phenyl)-6'-(trifluoromethyl)-3,4'-bipyridine-2'-carboxamide;
N-(3-(4-cyclopropyl-4H-1,2,4-triazol-3-yl)phenyl)-4-(quinolin-3-yl)-6-(trifluoromethyl)picolinamide;
N-(6-(1-cyclopropyl-1H-imidazol-5-yl)pyridin-2-yl)-4-(quinolin-3-yl)picolinamide;
6-cyclopropyl-N-(6-(1-cyclopropyl-1H-imidazol-5-yl)pyridin-2-yl)-3,4'-bipyridine-2'-carboxamide;
N-(3-(4-cyclopropyl-4H-1,2,4-triazol-3-yl)phenyl)-4-(1H-pyrrolo[3,2-b]pyridin-6-yl)picolinamide;
N-(3-(4-cyclopropyl-4H-1,2,4-triazol-3-yl)phenyl)-4-(4-cyclopropylphenyl)picolinamide;
N-(6-(4-cyclopropyl-4H-1,2,4-triazol-3-yl)pyridin-2-yl)-3-(pyridin-3-yl)benzamide;
N-(3-(4-cyclopropyl-4H-1,2,4-triazol-3-yl)phenyl)-6-(methylthio)-3,4'-bipyridine-2'-carboxamide;
N-(3-(4-cyclopropyl-4H-1,2,4-triazol-3-yl)phenyl)-6-(isobutylthio)-3,4'-bipyridine-2'-carboxamide;
N-(3-(4-cyclopropyl-4H-1,2,4-triazol-3-yl)phenyl)-4-(5-cyclopropylpyrazin-2-yl)picolinamide;
6-cyclopropyl-N-(3-(4-cyclopropyl-4H-1,2,4-triazol-3-yl)phenyl)-5-fluoro-3,4'-bipyridine-2'-carboxamide;
5-chloro-6-cyclopropyl-N-(3-(4-cyclopropyl-4H-1,2,4-triazol-3-yl)phenyl)-3,4'-bipyridine-2'-carboxamide;
N-(3-(4-cyclopropyl-4H-1,2,4-triazol-3-yl)phenyl)-6-(2-methoxyethylamino)-3,4'-bipyridine-2'-carboxamide;
N-(3-(4-cyclopropyl-4H-1,2,4-triazol-3-yl)phenyl)-4-(4-(methylsulfonyl)piperazin-1-yl)picolinamide;
N-(3-(4-cyclopropyl-4H-1,2,4-triazol-3-yl)phenyl)-6-ethyl-5-fluoro-3,4'-bipyridine-2'-carboxamide;
5-chloro-N-(3-(4-cyclopropyl-4H-1,2,4-triazol-3-yl)phenyl)-6-ethyl-3,4'-bipyridine-2'-carboxamide;
4-(4-cyclopropyl-1H-imidazol-1-yl)-N-(3-(4-cyclopropyl-4H-1,2,4-triazol-3-yl)phenyl)picolinamide;
N-(3-(4-cyclopropyl-4H-1,2,4-triazol-3-yl)phenyl)-5,6-diethyl-3,4'-bipyridine-2'-carboxamide;
N-(3-(4-cyclopropyl-4H-1,2,4-triazol-3-yl)phenyl)-4-(furo[3,2-b]pyridin-6-yl)picolinamide;
N-(4-cyclopropyl-4H-1,2,4-triazol-3-yl)phenyl)-4-(3-methyl-3H-imidazo[4,5-b]pyridin-6-yl)picolinamide;
N-(3-(4-cyclopropyl-4H-1,2,4-triazol-3-yl)phenyl)-6-(6-cyclopropylpyridin-3-yl)pyrimidine-4-carboxamide.
6-cyclopropyl-N-(3-(4-cyclopropyl-4H-1,2,4-triazol-3-yl)phenyl)-6'-methyl-3,4'-bipyridine-2'-carboxamide;
6-cyclopropyl-N-(3-(4-cyclopropyl-4H-1,2,4-triazol-3-yl)phenyl)-5'-methyl-3,4'-bipyridine-2'-carboxamide;
N-(6-(4-cyclopropyl-4H-1,2,4-triazol-3-yl)pyridin-2-yl)-4-(5-methyl-4-(trifluoromethyl)-4,5,6,7-tetrahydro-1H-imidazo[4,5-c]pyridin-1-yl)picolinamide;
N-(3-(4-cyclopropyl-4H-1,2,4-triazol-3-yl)phenyl)-4-(5-methyl-4-(trifluoromethyl)-4,5,6,7-tetrahydro-1H-imidazo[4,5-c]pyridin-1-yl)picolinamide;
6'-cyclopropyl-N-(6-(4-cyclopropyl-4H-1,2,4-triazol-3-yl)pyridin-2-yl)-2,3'-bipyridine-6-carboxamide;
6'-cyclopropyl-N-(6-(4-cyclopropyl-4H-1,2,4-triazol-3-yl)pyridin-2-yl)-3,3'-bipyridine-5-carboxamide;
6'-cyclopropyl-N-(6-(4-cyclopropyl-4H-1,2,4-triazol-3-yl)pyridin-2-yl)-2,3'-bipyridine-4-carboxamide;
N-(6-(4-cyclopropyl-4H-1,2,4-triazol-3-yl)pyridin-2-yl)-5-(6-cyclopropylpyridin-3-yl)-2,4-difluorobenzamide;
6'-cyclopropyl-N-(3-(4-cyclopropyl-4H-1,2,4-triazol-3-yl)phenyl)-2,3'-bipyridine-6-carboxamide;
(S)-4-(4-cyclopropyl-1H-imidazol-1-yl)-N-(3-(4-(3-methylbutan-2-yl)-4H-1,2,4-triazol-3-yl)phenyl)picolinamide;
4-chloro-N-(6-(4-cyclopropyl-4H-1,2,4-triazol-3-yl)pyridin-2-yl)-5-(6-cyclopropylpyridin-3-yl)-2-fluorobenzamide;
6-cyclopropyl-N-(3-(4-(2-phenylcyclopropyl)-4H-1,2,4-triazol-3-yl)phenyl)-3,4'-bipyridine-2'-carboxamide;
N-(3-(4-cyclopropyl-4H-1,2,4-triazol-3-yl)phenyl)-6-(cyclopropylmethyl)-3,4'-bipyridine-2'-carboxamide;

3-(4-cyclopropyl-1H-1,2,3-triazol-1-yl)-N-(6-(4-cyclopropyl-4H-1,2,4-triazol-3-yl)pyridin-2-yl)benzamide;
4-(5-cyclopropyl-1,3,4-thiadiazol-2-yl)-N-(3-(4-cyclopropyl-4H-1,2,4-triazol-3-yl)phenyl)picolinamide;
6-cyclopropyl-N-(3-(4-phenyl-4H-1,2,4-triazol-3-yl)phenyl)-3,4'-bipyridine-2'-carboxamide;
6-cyclopropyl-N-(3-(4-(pyridin-2-yl)-4H-1,2,4-triazol-3-yl)phenyl)-3,4'-bipyridine-2'-carboxamide;
6-cyclopropyl-N-(3-(4-(pyridin-3-yl)-4H-1,2,4-triazol-3-yl)phenyl)-3,4'-bipyridine-2'-carboxamide;
6-cyclopropyl-N-(3-(4-(pyridin-4-yl)-4H-1,2,4-triazol-3-yl)phenyl)-3,4'-bipyridine-2'-carboxamide;
6-cyclopropyl-N-(3-(4-(pyrimidin-5-yl)-4H-1,2,4-triazol-3-yl)phenyl)-3,4'-bipyridine-2'-carboxamide;
N-(3-(4-(but-2-ynyl)-4H-1,2,4-triazol-3-yl)phenyl)-6-cyclopropyl-3,4'-bipyridine-2'-carboxamide;
6-cyclopropyl-N-(3-(4-(1-(pyridin-3-yloxy)propan-2-yl)-4H-1,2,4-triazol-3-yl)phenyl)-3,4'-bipyridine-2'-carboxamide;
6-cyclopropyl-N-(3-(4-(1-(2,2,2-trifluoroethoxy)propan-2-yl)-4H-1,2,4-triazol-3-yl)phenyl)-3,4'-bipyridine-2'-carboxamide;
4-(4-cyclopropyl-1H-imidazol-1-yl)-N-(3-(4-phenyl-4H-1,2,4-triazol-3-yl)phenyl)picolinamide
4-(4-cyclopropyl-1H-imidazol-1-yl)-N-(3-(4-(pyridin-2-yl)-4H-1,2,4-triazol-3-yl)phenyl)picolinamide;
4-(4-cyclopropyl-1H-imidazol-1-yl)-N-(3-(4-(pyridin-3-yl)-4H-1,2,4-triazol-3-yl)phenyl)picolinamide;
4-(4-cyclopropyl-1H-imidazol-1-yl)-N-(3-(4-(pyridin-4-yl)-4H-1,2,4-triazol-3-yl)phenyl)picolinamide;
4-(4-cyclopropyl-1H-imidazol-1-yl)-N-(3-(4-(pyrimidin-5-yl)-4H-1,2,4-triazol-3-yl)phenyl)picolinamide;
N-(3-(4-(but-2-ynyl)-4H-1,2,4-triazol-3-yl)phenyl)-4-(4-cyclopropyl-1H-imidazol-1-yl)picolinamide;
4-(4-cyclopropyl-1H-imidazol-1-yl)-N-(3-(4-(1-(pyridin-3-yloxy)propan-2-yl)-4H-1,2,4-triazol-3-yl)phenyl)picolinamide and
4-(4-cyclopropyl-1H-imidazol-1-yl)-N-(3-(4-(1-(2,2,2-trifluoroethoxy)propan-2-yl)-4H-1,2,4-triazol-3-yl)phenyl)picolinamide.

DETAILED DESCRIPTION OF THE INVENTION

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:

1) an alkyl group as defined above, having 1, 2, 3, 4 or 5 substituents, (typically 1, 2, or 3 substituents) selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkyl thio, aryl, aryloxy, heteroaryl, aminosulfonyl, aminocarbonylamino, heteroaryloxy, heterocyclyl heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF), amino, substituted amino, cyano, and —S(O)$_n$R, where R is alkyl, aryl, or heteroaryl and n is 0, 1 or 2; or 2) an alkyl group as defined above that is interrupted by 1-10 atoms (e.g. 1, 2, 3, 4, or 5 atoms) independently chosen from oxygen, sulfur and NRa—, where Ra is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2; or 3) an alkyl group as defined above that has both 1, 2, 3, 4 or 5 substituents as defined above and is also interrupted by 1-10 atoms (e.g. 1, 2, 3, 4, or 5 atoms) as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents (typically 1, 2, or 3 substituents), as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, typically having from 1 to 20 carbon atoms (e.g. 1-10 carbon atoms, or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "lower alkylene" refers to a diradical of a branched or unbranched saturated hydrocarbon chain, typically having 1, 2, 3, 4, 5, or 6 carbon atoms.

The term "substituted alkylene" refers to:

(1) an alkylene group as defined above having 1, 2, 3, 4, or 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2; or (2) an alkylene group as defined above that is interrupted by 1-10 groups (e.g. 1, 2, 3, 4, or 5 groups) independently chosen from —O—, —S—, sulfonyl, —C(O)—, —C(O)O—, —C(O)N—, and —NRa—, where Ra is chosen from hydrogen, optionally substituted alkyl, cycloalkyl, cycloalkenyl, aryl, heteroaryl and heterocyclyl; or (3) an alkylene group as defined above that has both 1, 2, 3, 4 or 5 substituents as defined above and is also interrupted by 1-10 groups as defined above. Examples of substituted alkylenes are chloromethylene (—CH(Cl)—), aminoethylene (—CH(NH$_2$)CH$_2$—), methylaminoethylene (—CH(NHMe)

CH$_2$—), 2-carboxypropylene isomers (—CH$_2$CH(CO$_2$H) CH$_2$—), ethoxyethyl (—CH$_2$CH$_2$O—CH$_2$CH$_2$—), ethylmethylaminoethyl (—CH$_2$CH$_2$—N(CH$_3$)—CH$_2$CH$_2$—), 1-ethoxy-2-(2-ethoxy-ethoxy)ethane (—CH$_2$CH$_2$O—CH$_2$CH$_2$—OCH$_2$CH—OCH$_2$CH$_2$—), and the like.

The term "aralkyl" or "arylalkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are alkyl-O— and include, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "lower alkoxy" refers to the group R—O— in which R is optionally substituted lower alkyl as defined above. This term is exemplified by groups such as methoxy, ethoxy, n-propoxy, iso-propoxy, n-butoxy, iso-butoxy, t-butoxy, n-hexyloxy, and the like.

The term "alkylthio" refers to the group R—S—, where R is as defined for alkoxy.

The term "alkenyl" refers to a monoradical of a branched or unbranched unsaturated hydrocarbon group typically having from 2 to 20 carbon atoms (more typically from 2 to 10 carbon atoms, e.g. 2 to 6 carbon atoms) and having from 1 to 6 carbon-carbon double bonds, e.g. 1, 2, or 3 carbon-carbon double bonds. Typical alkenyl groups include ethenyl (or vinyl, i.e. —CH═CH$_2$), 1-propylene (or allyl, —CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl, —SO-heteroaryl, SO$_2$-aryl and —SO$_4$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon, typically having from 2 to 20 carbon atoms (more typically from 2 to 6 carbon atoms) and having e.g. 1, 2, or 3 carbon-carbon triple bonds. Typical alkynyl groups include ethynyl (—C≡CH), propargyl (or propynyl, —C≡CCH3), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$Ra, in which Ra is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —OC(O)-alkyl, —OC(O)-cycloalkyl, —OC(O)-aryl, —OC(O)-heteroaryl, and —OC(O)-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl, fluorenyl, and anthryl). Typical aryls include phenyl, fluorenyl, naphthyl, anthryl, 1,2,3,4-tetrahydronaphthalene, and the like.

Unless otherwise constrained by the definition for the aryl substituent, such aryl groups can optionally be substituted with 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, aryloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocylooxy, hydroxyamino, alkoxyamino, nitro, —SO-alkyl, —SO-aryl, —SO-heteroaryl, —SO$_2$-alkyl, SO$_2$-aryl and —SO-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "aryloxy" refers to the group aryl-O— wherein the aryl group is as defined above, and includes optionally substituted aryl groups as also defined above.

The term "arylthio" refers to the group R—S—, where R is as defined for aryl.

The term "amino" refers to the group —$NH_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl are as defined herein, and may be optionally further substituted by alkyl, alkenyl, alkynyl, alkoxy, halogen, $CF_3$, amino, substituted amino, cyano, or —$S(O)_nR$, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed or bridged rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1] heptane, or cyclic alkyl groups to which is fused an aryl group, for example indan, and the like.

The term "substituted cycloalkyl" refers to cycloalkyl groups having 1, 2, 3, 4 or 5 substituents (typically 1, 2, or 3 substituents), selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. The term "substituted cycloalkyl" also includes cycloalkyl groups wherein one or more of the annular carbon atoms of the cycloalkyl group is a carbonyl group (i.e. an oxygen atom is oxo to the ring). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2.

The term "halogen" or "halo" refers to fluoro, bromo, chloro, and iodo.

The term "haloalkyl" refers to alkyl of 1-6 carbon atoms substituted by 1, 2, 3, 4, 5, or 6 halo atoms.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to a group comprising 1 to 15 carbon atoms and 1 to 4 heteroatoms selected from oxygen, nitrogen, and sulfur within at least one ring.

The term "heteroaryl" is generic to the terms "aromatic heteroaryl" and "partially saturated heteroaryl".

The term "aromatic heteroaryl" refers to a heteroaryl in which at least one ring is aromatic. Examples of aromatic heteroaryls include pyridyl, thienyl, furanyl, pyrimidyl, imidazolyl, imidazopyridyl, pyranyl, pyrazolyl, pyrzolopyridyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl.

The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, 4,5,6,7-tetrahydro-1H-imidazo[4,5-c]pyridine, and the like.

Unless otherwise constrained by the definition for the heteroaryl substituent, such heteroaryl groups can be optionally substituted with 1 to 5 substituents (typically 1, 2, or 3 substituents) selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkyl thio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed or bridged rings, having from 1 to 40 carbon atoms and from 1 to 10 hetero atoms, preferably 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, 4,5,6,7-tetrahydro-1H-benzo[d]imidazole, benzo[d]imidazole, 4,5,6,7-tetrahydro-1H-imidazo[4,5-c]pyridine, and the like.

Unless otherwise constrained by the definition for the heterocyclic substituent, such heterocyclic groups can be optionally substituted with 1, 2, 3, 4 or 5, and preferably 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "thiol" refers to the group —SH.

The term "substituted alkylthio" refers to the group —S-substituted alkyl.

The term "heteroarylthio" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH. The term "oxo" refers to =O.

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

A compound of a given Formula (e.g. the "compound of Formula (I)") is intended to encompass the compounds of the invention as disclosed, and the pharmaceutically acceptable salts, pharmaceutically acceptable esters, hydrates, polymorphs, and prodrugs of such compounds. Additionally, the compounds of the invention may possess one or more asymmetric centers, and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis, or by resolution of the compound by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

The invention also included compounds of Formula I in which from 1 to n hydrogens attached to a carbon atom is/are replaced by deuterium, in which n is the number of hydrogens in the molecule. Such compounds exhibit increased resistance to metabolism, and are thus useful for increasing the half life of any compound of Formula I when administered to a mammal. See, for example, Foster, "Deuterium Isotope Effects in Studies of Drug Metabolism", Trends Pharmacol. Sci. 5(12):524-527 (1984). Such compounds are synthesized by means well known in the art, for example by employing starting materials in which one or more hydrogens have been replaced by deuterium.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

The term "therapeutically effective amount" refers to an amount that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diary amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardiovasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes, and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs, or calves when walking, climbing stairs, or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, and the ventricular tachycardias (VTs), including idiopathic ventricular tachycardia, ventricular fibrillation, pre-excitation syndrome, and Torsade de Pointes (TdP).

Where a given group (moiety) is described herein as being attached to a second group and the site of attachment is not explicit, the given group may be attached at any available site of the given group to any available site of the second group. For example, a "lower alkyl-substituted phenyl", where the attachment sites are not explicit, may have any available site of the lower alkyl group attached to any available site of the phenyl group. In this regard, an "available site" is a site of the group at which a hydrogen of the group may be replaced with a substituent.

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable carrier" refers to a diluent, adjuvant, excipient, or carrier, other ingredient, or combination of ingredients that alone or together provide a carrier or vehicle with which a compound or compounds of the invention is formulated and/or administered, and in which every ingredient or the carrier as a whole is pharmaceutically acceptable.

"Pharmaceutically-acceptable salt" refers to a salt which may enhance desired pharmacological activity. Examples of pharmaceutically-acceptable salts include acid addition salts formed with inorganic or organic acids, metal salts and amine salts.

Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, laurylsulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

"Prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

"Polymorph" refers to the different crystal forms of a compound, resulting from the possibility of at least two different arrangements of the molecules of the compound in the solid state. Polymorphs of a given compound will be different in crystal structure but identical in liquid or vapor states. Different polymorphic forms of a given substance may differ from each other with respect to one or more physical properties, such as solubility and dissociation, true density, crystal shape, compaction behavior, flow properties, and/or solid state stability.

Nomenclature

Names of compounds of the present invention are provided using ChemBioDraw Ultra 11. Other compounds or radicals may be named with common names, or systematic or non-systematic names. The naming and numbering of the compounds of the invention is illustrated with a representative compound of Formula (I)

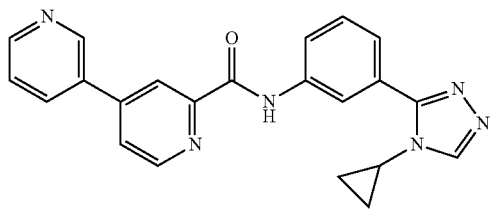 [SMILES: O=C(Nc1cccc(-c2nncn2C2CC2)c1)c1cc(-c2cccnc2)ccn1]

which is named:
N-(3-(4-cyclopropyl-4H-1,2,4-triazol-3-yl)phenyl)-3,4'-bipyridine-2'-carboxamide.

Combination Therapy

Coronary patients being treated for an acute cardiovascular disease event by administration of ASK1 inhibitors often exhibit diseases or conditions that benefit from treatment with other therapeutic agents. These diseases or conditions can be of the cardiovascular nature or can be related to pulmonary disorders, metabolic disorders, gastrointestinal disorders and the like. Additionally, some coronary patients being treated for an acute cardiovascular disease event by administration of an ASK1 inhibitor exhibit conditions that can benefit from treatment with therapeutic agents that are antibiotics, analgesics, and/or antidepressants and anti-anxiety agents.

Cardiovascular related diseases or conditions that can benefit from a combination treatment of ASK1 inhibitors with other therapeutic agents include, without limitation, angina, including stable angina, unstable angina (UA), exercised-induced angina, variant angina, arrhythmias, intermittent claudication, myocardial infaretion including non-STE myocardial infaretion (NSTEMI), heart failure including congestive (or chronic) heart failure, acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of ASK1 inhibitors with therapeutic agents suitable for treating cardiovascular related conditions allows enhancement in the standard of care therapy the patient is currently receiving.

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include accbutolol (Sectral), atenolol (Tenormin), betaxolol (Kerlone), bisoprolol/hydrochlorothiazide (Ziac), bisoprolol (Zebeta), carteolol (Cartrol), esmolol (Brevibloe), labetalol (Noiniodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calciumin to the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplercnonc (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNI), and tissue plasminogen activator (t-PA).

Antiarrhythmic agents are used to treat disorders of the heart rate and rhythm. Examples of antiarrhythmic agents include amiodarone, quinidine, procainamide, lidocaine, and propafenone. Cardiac glycosides and beta blockers are also used as antiarrhythmic agents.

Antihypertensive agents are used to treat hypertension, a condition in which the blood pressure is consistently higher than normal. Hypertension is associated with many aspects of cardiovascular disease, including congestive heart failure, atherosclerosis, and clot formation.

Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (Ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient in need of the ASK1 inhibitor often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient the compounds of the invention in combination with at least one therapeutic agent.

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solo-Medrol, Medrol), magnesium, and potassium.

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Patients presenting with an acute coronary disease event may exhibit conditions that benefit from administration of therapeutic agent or agents that are antibiotics, analgesics, antidepressant and anti-anxiety agents in combination with ranolazine.

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef), cephalexin (Keflex), cephradine (Velosef), cefaclor (Ceder), cefuroxime axtel (Ceftin), cefprozil (Cefzil), loracarbef (Lorabid), cefixime (Suprax), cefpodoxime proxetil (Vantin), ceflibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics are therapeutic agents that are used to relieve pain. Examples of analgesics include opiates and morphinomimetics, such as fentanyl and morphine; paracetamol; NSAIDs, and COX-2 inhibitors.

Antidepressant and anti-anxiety agents include those agents used to treat anxiety disorders, depression, and those used as sedatives and tranquillers. Examples of antidepressant and anti-anxiety agents include benzodiazepines, such as diazepam, lorazepam, and midazolam; enzodiazepines; barbiturates; glutethitnide; chloral hydrate; meprobamate; sertraline (Zoloft, Lustral, Apo-Sertral, Asentra, Gladern, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban).

Pharmaceutical Compositions and Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Marcel Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Synthesis of Compounds of Formula I

The compounds of the invention may be prepared using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by one or more of Formula (I), may be accomplished as described in the following examples. If available, reagents may be purchased commercially, e.g. from Sigma Aldrich or other chemical suppliers.

General Syntheses:

Typical embodiments of compounds in accordance with the present invention may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present invention, inspection of the structure of the compound to be synthesized will provide the identity of each substituent group. The identity of the final product will generally render apparent the identity of the necessary starting materials by a simple process of inspection, given the examples herein Synthetic Reaction Parameters The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present invention are inert organic solvents, and the reactions are carried out under an inert gas, preferably nitrogen.

One method of preparing compounds of Formula (I) is shown in Reaction Scheme I.

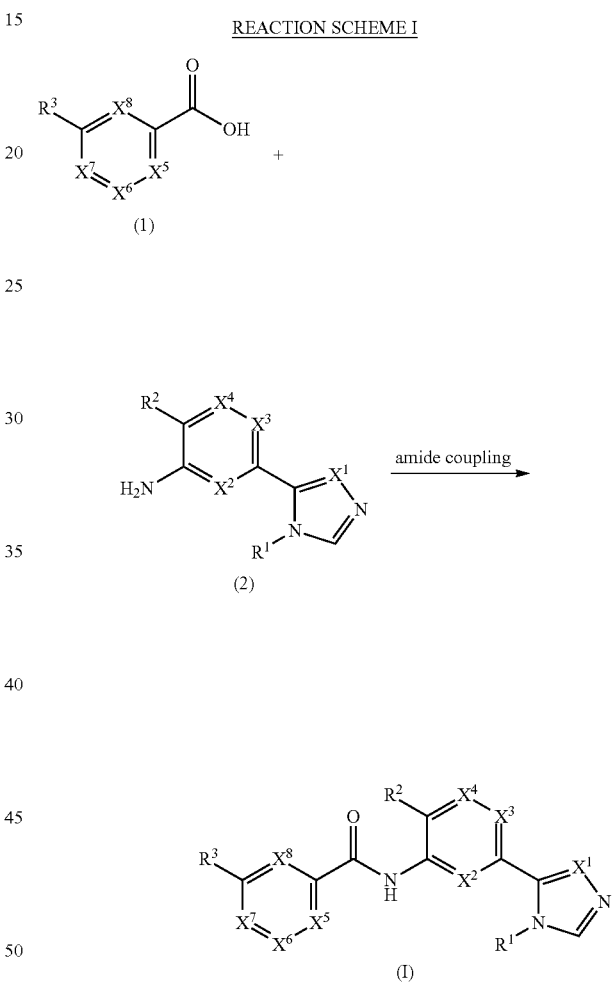

A carboxylic acid of formula (1) is reacted with an amine of formula (2) under conditions suitable for the formation of an amide. For example, to a mixture of the compound of formula (1) and formula (2) in an inert solvent, for example N,N-dimethylformamide, is added (2-(7-Aza-1H-benzotriazole-1-yl)-1,1,3,3-tetramethyluronium hexafluorophosphate (HATU) and a base, typically N-methyl morpholine, and the mixture is maintained at about room temperature for about 1-12 hours. When the reaction is substantially complete, the product of Formula (I) is isolated by conventional means, for example by filtration.

The compound of formula (2) is either commercially available or is prepared by means well know in the art. One example of the preparation of a compound of formula (2) in which $X^1$ is nitrogen is shown in Reaction Scheme IA.

REACTION SCHEME IA

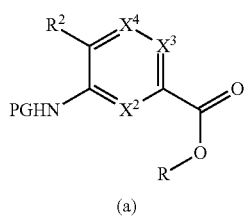

(a)
where R is methyl or ethyl
and PG is a protecting group

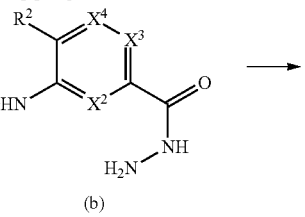

(b)

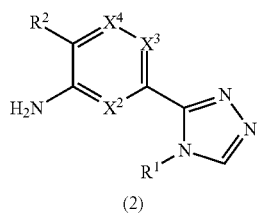

(2)

where $X^1$ is nitrogen

Step 1—Preparation of a Compound of Formula (b)

In general, a protected amino ester of formula (a) is reacted with hydrazine hydrate in a protic solvent, for example ethanol. The reaction is carried out at a temperature of about 50-90° C., for about 1-5 hours. When the reaction is substantially complete, the product of formula (b) is isolated by conventional means.

Step 2—Preparation of a Compound of Formula (2)

The compound of formula (b) is then placed in a sealable flask with an amine of formula $R^1NH_2$ together with a formamide of formula $R^1NHCHO$ in an inert solvent, for example toluene, in the presence of an acid, for example trifluoroacetic acid. The sealed flask is heated at about 100° C. for about 24 hours. When the reaction is substantially complete, the product is isolated by conventional means, for example by flash chromatography.

The product is then reduced under an atmosphere of hydrogen with a palladium catalyst. The reaction is carried out in a protic solvent, for example ethanol, for about 1-2 hours. When the reaction is substantially complete, the product of formula (2) is isolated by conventional means.

Another example of the preparation of a compound of formula (2) in which $X^1$ is nitrogen is shown in Reaction Scheme IB.

REACTION SCHEME IB

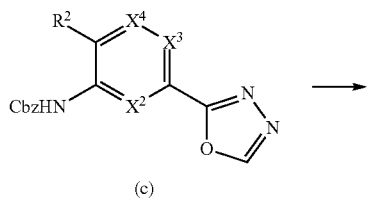

(c)

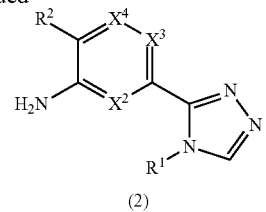

(2)

where $X^1$ is nitrogen

Step 1

A mixture of a compound of formula (c) and an amine of formula $R^1NH_2$ in the presence of a strong acid, for example trifluoroacetic acid, is placed in a sealed tube and heated at about 70-110° C. for about 12-36 hours. When the reaction is substantially complete, the product is isolated by conventional means.

The protecting group is then removed by conventional treatment with an acid, for example hydrobromic acid in acetic acid, to provide a compound of formula (2) in which $X^1$ is nitrogen.

The preparation of compounds of formula (2) in which $X^1$ is carbon is shown in Reaction Scheme IC.

REACTION SCHEME IC

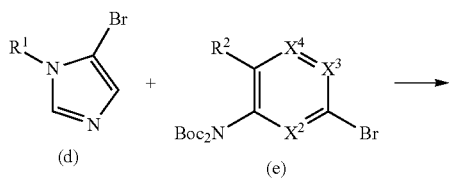

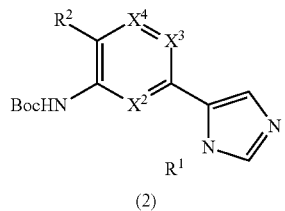

(2)

To a solution of the imidazole derivative of formula (d) in an inert solvent, for example tetrahydrofuran, at about −50° C. to −80° C., is added an alkyl derivative, for example n-butyl lithium. The reaction is maintained at this temperature for about 10-60 minutes, then a solution of zinc bromide in an inert solvent, for example tetrahydrofuran, is added, and the mixture allowed to warm to about room temperature for about 2-3 hours. A solution of the compound of formula (e) in an inert solvent, for example tetrahydrofuran, is added, and the mixture stirred for about 10-24 hours. When the reaction is substantially complete, the product of formula (2) is isolated by conventional means and purified, for example by chromatography.

An alternative preparation of a compound of Formula (I) is shown in Reaction Scheme II.

REACTION SCHEME II

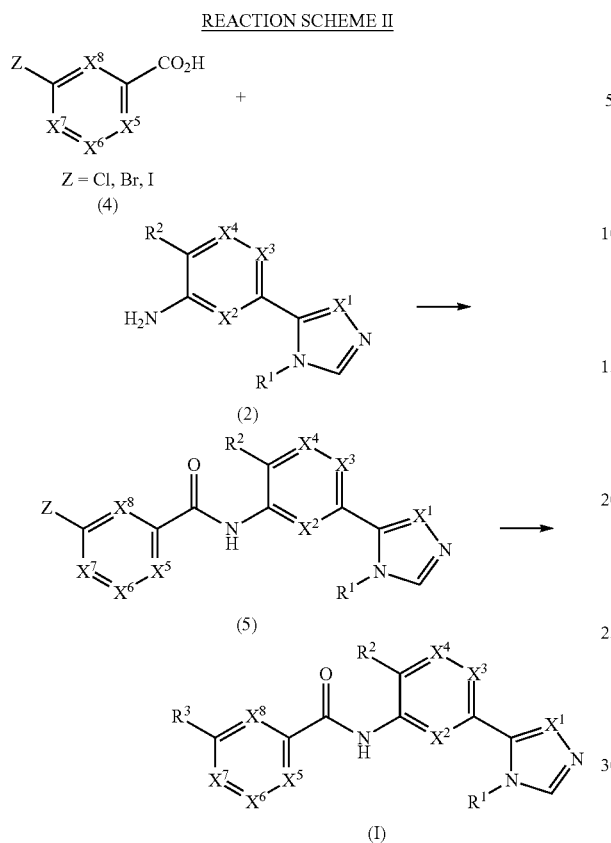

REACTION SCHEME IIIA

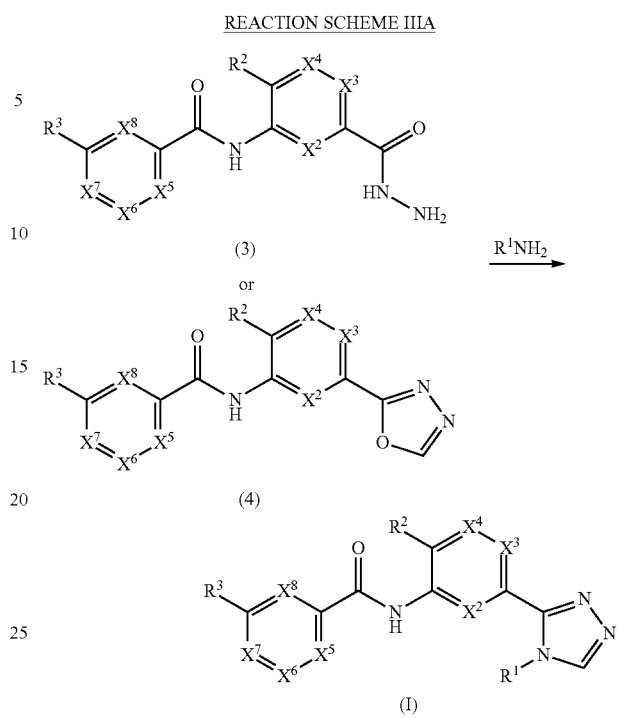

A carboxylic acid of formula (4) in which Z is a halogen, for example chloro, bromo, or iodo, is reacted with an amine of formula (2) in the same manner as described in Reaction Scheme I. The compound of formula (5) thus prepared is then reacted with a boronic acid derivative of $R^3$, for example 3-pyridine boronic acid, in the presence of a phosphine ligand of a palladium halide derivative, for example dppf(Pd)Cl$_2$ (diphenylphosphineferrocenepalladium chloride) and a mild base, for example potassium carbonate. The reaction is typically conducted in a mixture of inert solvents, for example a mixture of toluene, water, and ethanol, for about 60-100° C. for about 1-4 hours. When the reaction is substantially complete, the product of Formula (I) is isolated by conventional means, for example by reverse-phase HPLC.

A compound of Formula (I) in which $R^3$ is a non-aromatic ring can be prepared by displacement of Z with a nucleophile, for example an amine, particularly a cyclic amine, or with an alcohol or thiol derivative. Typically, if the nucleophile is an amine, the reaction is carried out using the amine as a solvent if possible, or the reaction is carried out in a polar aprotic solvent, such as N,N-dimethylformamide, dimethylsulfoxide, or N-methylpyrrolidine, for example. The reaction mixture is maintained at about 80-119° C. for about 1-10 hours. When the reaction is substantially complete, the product of Formula (I) is isolated by conventional means, for example by reverse-phase HPLC.

The construction of the triazole (i.e., where $X^1$ is N) or imidazole (i.e., where $X^1$ is C($R^4$)) moiety of compounds of Formula (I) can be accomplished as a last step. Reaction Scheme IIIA shows the preparation of a compound of Formula (I) in which $X^1$ is nitrogen.

Conversion of Compound (3) to a Compound of Formula (I)

The compound of formula (3) is placed in a sealable flask with an amine of formula $R^1NH_2$ together with a formamide of formula $R^1NHCHO$ in an inert solvent, for example toluene, in the presence of an acid, for example trifluoroacetic acid. The scaled flask is heated at about 100° C. for about 12-48 hours. When the reaction is substantially complete, the product is isolated by conventional means, for example by flash chromatography.

Conversion of Compound (4) to a Compound of Formula (I)

To a suspension of a compound of formula (4) in an inert solvent, for example toluene, is added N,N-dimethylformamide/N,N-dimethylacetamide complex. To this mixture is added a compound of formula $R^1NH_2$ and a carboxylic acid, for example acetic acid. The mixture is heated at about 100-160° C. in a microwave reactor for about 10-60 minutes. When the reaction is substantially complete, the product of Formula (I) is isolated by conventional means, for example by filtration of the precipitated solid.

Reaction Scheme IIIB shows the preparation of a compound of Formula (I) in which $X^1$ is carbon.

REACTION SCHEME IIIB

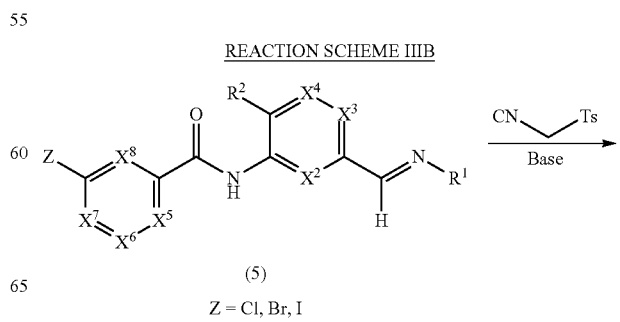

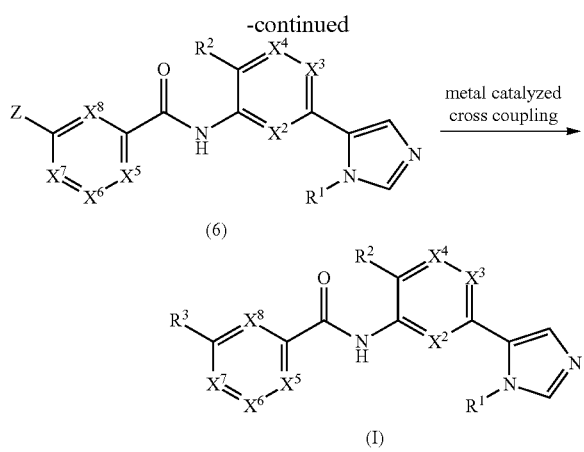

(6)

(I)

Step 1
To a solution of an imine of formula (5) in an inert solvent, or a mixture of inert solvents, for example a mixture of dimethoxyethane and methanol, is added toluenesulfonylmethyl isocyanide and an amine of formula $R^1NH_2$. The mixture is maintained at about 40-60° C. for about 6-24 hours, optionally adding a further amount of the isocyanide. When the reaction is substantially complete, the product of formula (6) is isolated by conventional means, for example by chromatography.

Step 2
The compound of formula (6) is then converted to a compound of Formula (I) in which $X^1$ is carbon in the same manner as described in Reaction Scheme II.

The following synthetic schemes represent a summary of specific reaction conditions used in the preparation of intermediates and compounds of Formula (I) of the present invention.

REACTION SCHEME IV
Alternative preparation of Compounds of Formula (2) where $X^1$ is N

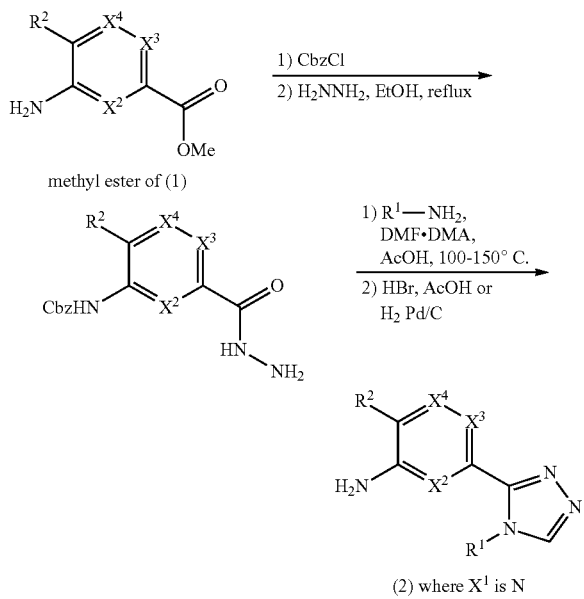

Step 1
The amino moiety of the compound of formula (1) as an alkyl ester, for example a methyl ester, is first protected, for example as a benzyloxycarbonyl derivative. In general, the aminoester is dissolved in an inert solvent, for example a mixture of acetone and water, at about 0° C., and an amino protecting agent added, for example benzyloxycarbonyl chloride. The reaction mixture is allowed to warm to about room temperature for about 12-30 hours. When the reaction is substantially complete, the protected amine is isolated by conventional means, for example by addition of water and filtration of the resultant precipitate.

The protected amine is then dissolved in an inert solvent, for example ethanol, and hydrazine hydrate added, and the mixture maintained at about 60-80° C. for about 1-6 hours. When the reaction is substantially complete, the hydrazide is isolated by conventional means.

Step 2
The hydrazide from Step 1 is treated with a compound of the formula $R^1NHCHO$ and an amine of formula $R^1NH_2$ in an inert solvent, for example toluene, in the presence of a strong acid, for example trifluoroacetic acid. The reaction is conducted in a sealed flask, heating to about 80-120° C., for about 12-48 hours. When the reaction is substantially complete, the product is isolated by conventional means. The benzyloxycarbonyl protecting group is removed conventionally, for example by contact with hydrogen in the preseance of a metal catalyst, for example palladium on carbon. The product is isolated and purified by conventional means.

REACTION SCHEME V
Alternative preparation of Compounds of Formula (2) where $X^1$ is N

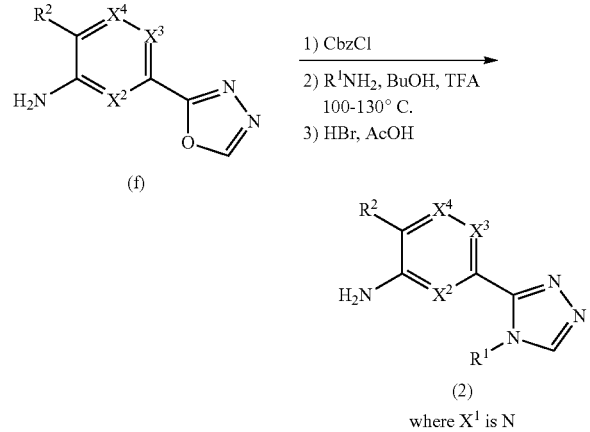

Step 1
To a solution of an amino 1,3,4-oxadiazol-2-yl derivative of formula (f) and a mild base, for example sodium bicarbonate, in a mixture of water and an inert solvent, for example a mixture of acetone and water at about 0° C. is added benzylchloroformate, and the mixture maintained at about room temperature for about 10-60 minutes. When the reaction is substantially complete, the protected product is isolated by conventional means, for example by addition of water and filtering off the precipitate.

Step 2
To the product of step 1 in an inert protic solvent, for example butanol, is added an amine of formula $R^1NH_2$ and a strong acid, for example trifluoroacetic acid. The mixture is maintained at about 90-120° C. in a sealed tube for about 10-24 hours. When the reaction is substantially complete, the protected product is isolated by conventional means, for example by chromatography on silica gel.

Step 3

The product of step 2 is deprotected by conventional means, for example by treatment with a solution of hydrobromic acid in acetic acid. The mixture is maintained at about room temperature for about 12-24 hours. When the reaction is substantially complete, the compound of formula (2) in which $X^1$ is N is isolated by conventional means.

REACTION SCHEME VI
Alternative Preparation of a Compound of Formula (1)

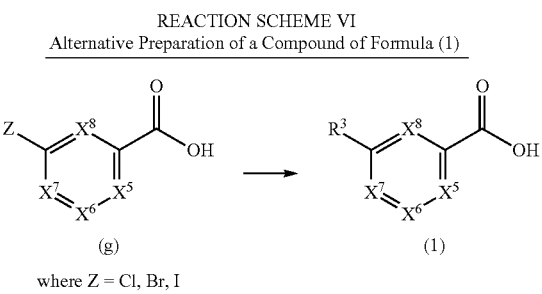

where Z = Cl, Br, I

Step 1

To a suspension of a carboxylic acid of formula (g) in oxalyl chloride is added N,N-dimethylformamide. The mixture is maintained at about room temperature for about 1 hour, then the reaction quenched by addition of an alcohol, for example isopropanol. The ester thus produced is separated conventionally, for example by chromatography.

Step 2

To this ester in an inert aqueous solvent mixture, for example toluene/water/isopropanol, is added a 4,4,5,5-tetramethyl-2-aryl-1,3,2-dioxaborolane derivative and a base, for example potassium carbonate, and dppf(Pd)Cl$_2$. The mixture is maintained at about 40-80° C. for about 30 minutes to 4 hours. When the reaction is substantially complete, the product is isolated by conventional means. This ester is converted to a carboxylic acid by conventional means, for example by heating in aqueous hydrochloric acid, to provide a compound of formula (1)

Alternatively, the halide of the compound of formula (g) as an alkyl ester can first be converted to a boronic acid derivative, for example by treatment with 4,4,4',4',5,5,5',5'-octamethyl-2,2'-bi(1,3,2-dioxaborolane) in the presence of dppf(Pd)Cl$_2$, then reacting the boronic acid derivative thus obtained with an aryl bromide in the presence of dppf(Pd)Cl$_2$ in an inert aqueous solvent mixture, for example toluene/water/isopropanol and a mild base, for example potassium acetate (the Suzuki Reaction).

REACTION SCHEME VII
Alternative Preparation of a Hydrazide precursor to Compounds of Formula (I)

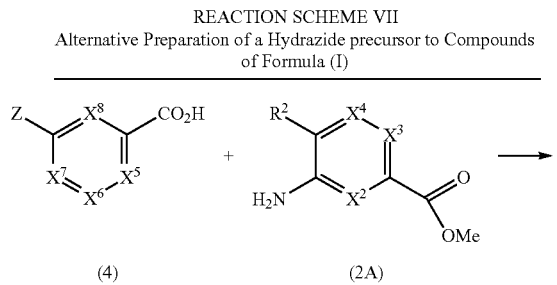

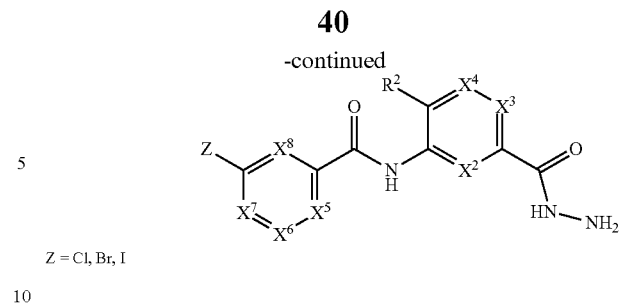

Z = Cl, Br, I

A carboxylic acid of formula (4) is reacted with an amine of formula (2A) under conditions suitable for the formation of an amide. For example, to a mixture of the compound of formula (4) and formula (2A) in an inert solvent, for example N,N-dimethylformamide, is added (2-(7-Aza-1H-benzotriazole-1-yl)-1,1,3,3-tetramethyluronium hexafluorophosphate (HATU) and a base, typically N-methyl morpholine, and the mixture is maintained at about room temperature for about 1-24 hours. When the reaction is substantially complete, the hydrazide product is isolated by conventional means, for example by filtration.

REACTION SCHEME VIII
Alternative Preparation of an Oxadiazole precursor to Compounds of Formula (I)

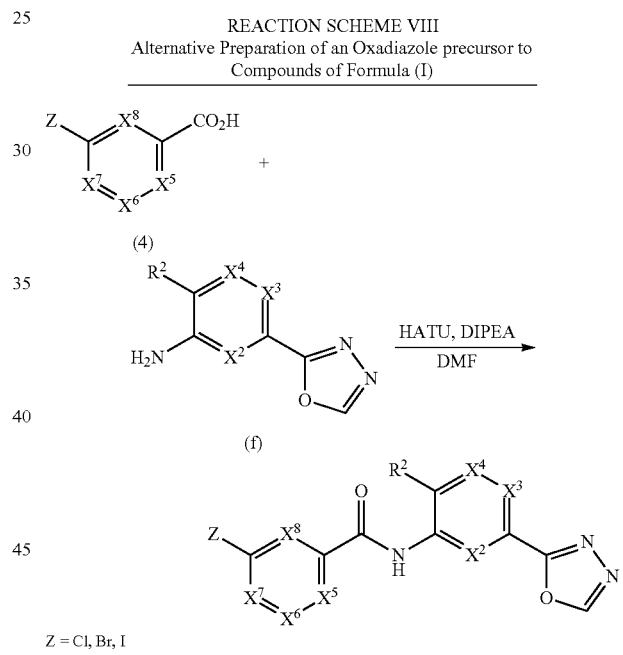

Z = Cl, Br, I

A compound of formula (4) is coupled to the compound of formula (f) using standard conditions suitable for the formation of an amide, for example as shown above in Reaction Scheme VII.

REACTION SCHEME IX
Alternative Preparation of a Precursor to a Compound of Formula (I)

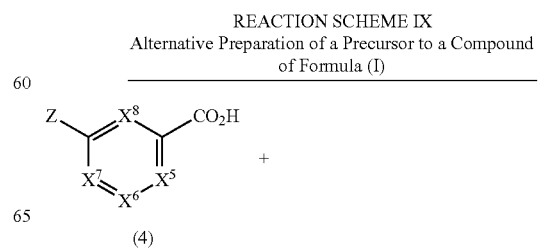

-continued

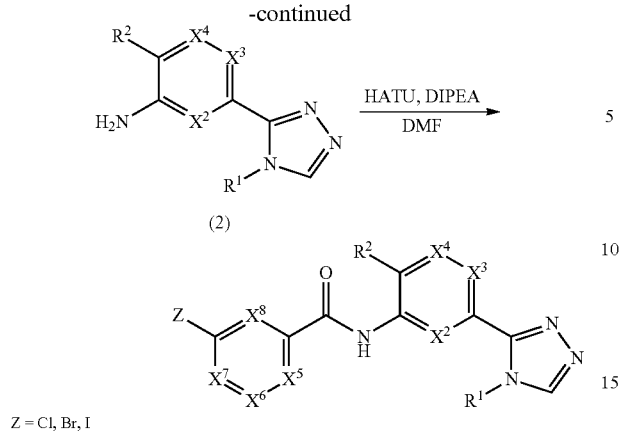

(2)

Z = Cl, Br, I

A compound of formula (4) is coupled to the compound of formula (2) using standard conditions suitable for the formation of an amide, for example as shown above in Reaction Scheme VII.

REACTION SCHEME X
Alternative Preparation of a Precursor to a Compound of Formula (I)

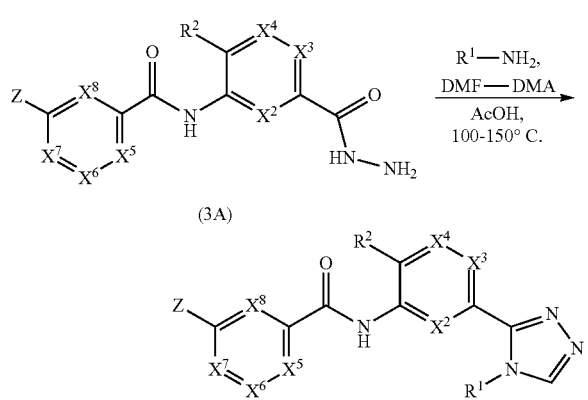

(3A)

The hydrazide of formula (3A) is converted to a triazole using the conditions described in Reaction Scheme IIIA.

REACTION SCHEME XI
Alternative Preparation of a Precursor to a Compound of Formula (I)

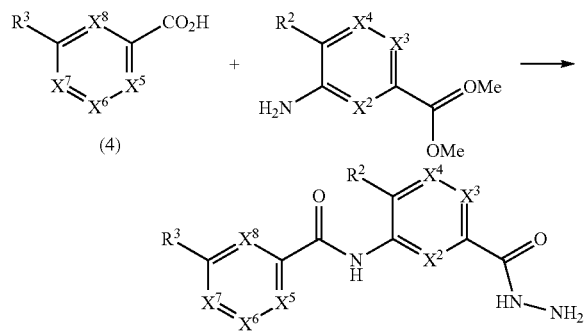

(4)

A compound of formula (4) is coupled to an amino ester using standard conditions suitable for the formation of an amide, for example as shown above in Reaction Scheme VII.

REACTION SCHEME XII
Alternative Preparation of an Oxadiazole Precursor to a Compound of Formula (I)

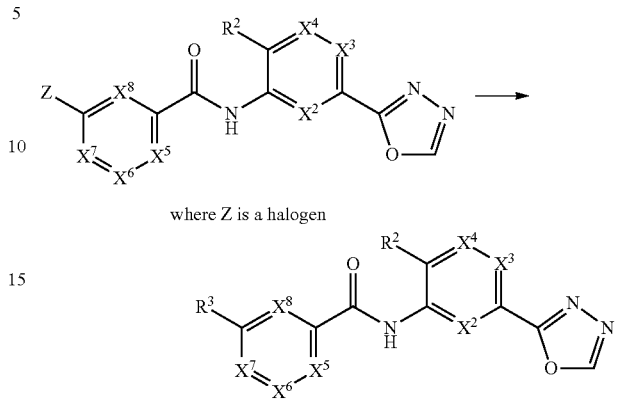

where Z is a halogen

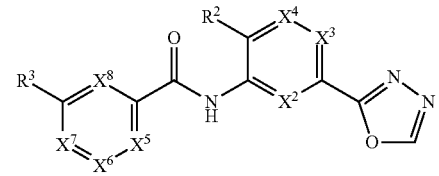

The halide of the compound of the starting oxadiazole compound is first converted to a boronic acid derivative, for example by treatment with 4,4,4',4',5,5,5',5'-octamethyl-2,2'-bi(1,3,2-dioxaborolane) in the presence of dppf(Pd)Cl$_2$, then reacting the boronic acid derivative thus obtained with an aryl bromide in the presence of dppf(Pd)Cl$_2$ in an inert aqueous solvent mixture, for example toluene/water/isopropanol and a mild base, for example potassium acetate (the Suzuki Reaction).

REACTION SCHEME XIII
Synthesis of heterocyclic building blocks
A. Preparation of a Compound of Formula (d)

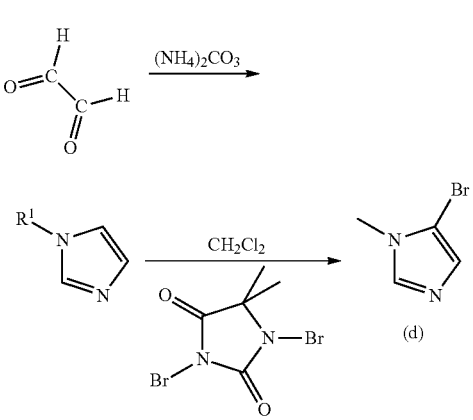

Step 1

A mixture of paraformaldehyde and an inert solvent, for example methanol, is maintained at a temperature of about 0-15° C., and an amine of formula R$^1$NH$_2$ is added along with ammonium carbonate, and trimeric glyoxal dihydrate. The reaction is maintained at about room temperature for about 12-36 hours. When the reaction is substantially complete, the imidazole derivative is isolated by conventional means, for example by distillation/chromatography.

Step 2

The product form Step 1 is dissolved in an inert solvent, for example methylene chloride, and a mild brominating agent added, for example. The temperature is maintained at about 5-10° C. for about 1-10 hours. When the reaction is substantially complete, the product of formula (c) is isolated by conventional means, for example by column chromatography.

B. Preparation of 4-Substituted Imidazoles

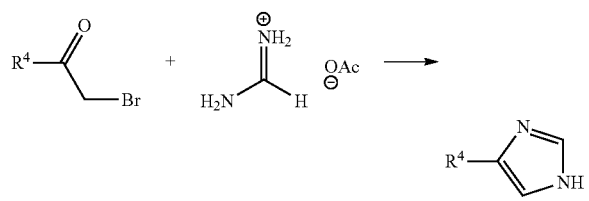

Ammonia is condensed into a pressure vessel containing formamidine acetate, and a compound of formula $R^4$—C(O)CH$_2$Br added. The pressure vessel is sealed and maintained at about room temperature for about 2-24 typically 12 hours. When the reaction is substantially complete, the product of formula (c) is isolated by conventional means.

The following examples are provided to illustrate the preparation of the compounds of the invention, and do not limit this disclosure in any way.

Example 1

Preparation of a Compound of Formula (2)

A. Preparation of a Compound of Formula (2) in which $R^1$ is Cyclopropyl, $R^2$ is Hydrogen, $X^2$ is N, and $X^3$ and $X^4$ are (CR$^4$)

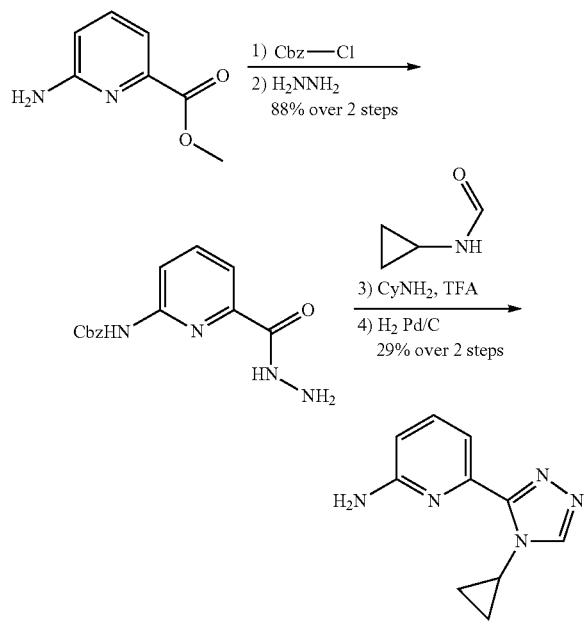

Step 1: Preparation of Methyl 6-(benzyloxycarbonylamino)picolinate

A solution of methyl 6-aminopicolinate (10.65 g, 70 mmol, 1 eq) and sodium bicarbonate (13 g, 154 mmol, 2.2 eq) was dissolved in a mixture of acetone/water (2:1, 1M), and the solution cooled to 0° C. Benzyloxycarbonyl chloride (Cbz-Cl, 11.3 ml, 80.5 mmol, 1.15 eq) was added dropwise, and the reaction was warmed to room temperature and stirred for 18 hours. Water (200 mL) was added, and the resultant suspension was filtered to give a white solid. This solid was dissolved in methylene chloride, dried over magnesium sulfate, filtered, and concentrated under reduced pressure to provide methyl 6-(benzyloxycarbonylamino)picolinate (17.5 g).

Step 2: Preparation of Benzyl 6-(hydrazinocarbonyl) pyridin-2-ylcarbamate

The methyl 6-(benzyloxycarbonylamino)picolinate from step 1 was dissolved in ethanol (0.5 M), and hydrazine hydrate (15 mL, 310 mmol, 5.0 eq) was added. The solution was heated to reflux and stirred for 2 hours, then cooled to room temperature. The solvent was removed under reduced pressure to provide a yellow solid, which was suspended in acetonitrile, filtered, and the solid washed with acetonitrile to yield benzyl 6-(hydrazinocarbonyl)pyridin-2-ylcarbamate (17.5 g) as a white solid. The filtrate was concentrated and the precipitated solid filtered off and washed with acetonitrile to provide more benzyl 6-(hydrazinecarbonyl)pyridin-2-ylcarbamate. A total of 17.5 g of pure material was obtained.

Step 3: Preparation of benzyl 6-(4-cyclopropyl-4H-1, 2,4-triazol-3-yl)pyridin-2-ylcarbamate To a sealable flask containing benzyl 6-(hydrazinecarbonyl)pyridin-2-ylcarbamate (1.97 g, 6.89 mmol, 1.0 eq) was added N-cyclopropyl formamide (1.8 mL, 20.7 mmol, 3.0 eq), cyclopropylamine (1.4 mL, 20.7 mmol, 3.0 eq), toluene (0.2 M), and trifluoracetic acid (0.511 mL, 6.89 mmol, 1.0 eq). The flask was sealed and heated to 100° C. for 24 hours. The reaction mixture was concentrated under reduced pressure to provide a yellow oil, which was purified by flash chromatography (Rf=0.44 in 10% methanol/ethyl acetate, gradient flash: 3%→10% methanol in ethyl acetate). The product, which consisted of a mixture of the desired compound with cyclopropyl formamide, was suspended in acetonitrile, sonicated, and the resultant suspension filtered to provide benzyl 6-(4-cyclopropyl-4H-1,2,4-triazol-3-yl)pyridin-2-ylcarbamate (680 mg).

Step 4: Preparation of 6-(4-Cyclopropyl-4H-[1,2,4] triazol-3-yl)pyridin-2-ylamine A mixture of benzyl 6-(4-cyclopropyl-4H-1,2,4-triazol-3-yl)pyridin-2-ylcarbamate (660 mg, 1.96 mmol, 1.0 eq) and Pd/C (80 mg 10% Pd loading, 40 mg/mmol) was loaded into a flask and purged with nitrogen. Ethanol (0.4 M) was added and the flask was charged with hydrogen (1 atm balloon pressure). The reaction was stirred at room temperature for 90 minutes, and judged to be complete by TLC. The reaction mixture was filtered through celite, and concentrated under reduced pressure to give 395 mg (95%) of 6-(4-cyclopropyl-4H-[1,2,4]triazol-3-yl)-pyridin-2-ylamine. $C_{10}H_{11}N_5$. 202.1 (M+1). $^1$H NMR (DMSO) d 8.14 (s, 1H), 7.54 (t, J=8 Hz, 1H), 7.46 (d, J=7 Hz, 1H), 6.60 (d, J=8 Hz, 1H), 4.70 (br s, 2H), 3.85-3.88 (m, 1H), 1.04-1.07 (m, 2H), 0.85-0.88 (m, 2H).

B. Preparation of other Compounds of Formula (2)

Similarly, optionally replacing methyl 6-aminopicolinate in Example 1A, step 1, and/or optionally replacing cyclopropylamine in Example 1, step 3, and following the procedures of Example 1, other compounds of formula (2) are prepared.

Example 2

Alternative Preparation of a Compound of Formula (2)

A. Alternative Preparation of a Compound of Formula (2) in which $R^1$ is Cyclopropyl, $R^2$ is Hydrogen and $X^2$, $X^3$ and $X^4$ are ($CR^4$)

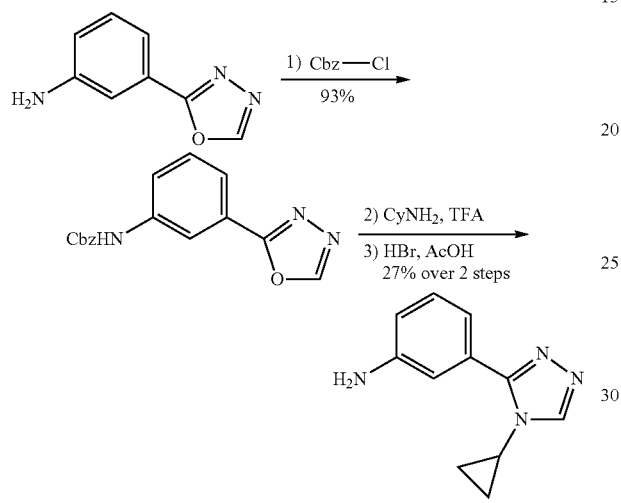

Step 1: Preparation of benzyl 3-(1,3,4-oxadiazol-2-yl)phenylcarbamate

A solution of 3-(1,3,4-oxadiazol-2-yl)aniline (1 g, 6.2 mmol) and sodium bicarbonate (1.1 g, 13 mmol) in a 2:1 mixture of acetone/water (10 mL) was cooled to 0° C. Benzylchloroformate (0.92 mL, 6.5 mmol) was added dropwise over 5 minutes. The reaction mixture was brought to room temperature and stirred for 30 minutes at which point LCMS indicated completion of the reaction. The reaction mixture was diluted with water and filtered on a glass frit to give (3-[1,3,4]Oxadiazol-2-yl-phenyl)-carbamic acid benzyl ester as a white powder (1.7 g, 93%). M+1=296.4

Step 2: Preparation of benzyl 3-(4-cyclopropyl-4H-1,2,4-triazol-3-yl)phenylcarbamate A mixture of (3-[1,3,4]Oxadiazol-2-yl-phenyl)-carbamic acid benzyl ester (200 mg, 0.68 mmol), cyclopropylamine (0.5 mL, 7.2 mmol), trifluoroacetic acid (0.05 mL, 0.65 mmol) in anhydrous 1-butanol (3 mL) was heated at 110° C. overnight in a sealed tube. The reaction mixture was cooled to room temperature and the solvent was removed. The residue was partitioned between ethyl acetate and saturated sodium bicarbonate solution, and the aqueous phase was extracted with ethyl acetate. Solvent was removed after drying with sodium sulfate and purified by silica gel chromatography (rf=0.26 in 20:1 ethyl acetate/methanol) to obtain [3-(4-Cyclopropyl-4H-[1,2,4]triazol-3-yl)-phenyl]-carbamic acid benzyl ester as a white powder (70 mg, 31%). M+1=335.1

Step 3: Preparation of 3-(4-cyclopropyl-4H-[1,2,4]triazol-3-yl)-phenylamine

[3-(4-Cyclopropyl-4H-[1,2,4]triazol-3-yl)-phenyl]-carbamic acid benzyl ester (60 mg, 0.17 mmol) was dissolved in HBr solution (1 mL, 33% in acetic acid) and the reaction mixture was stirred overnight. The solvent was removed and the residue was neutralized with saturated sodium bicarbonate solution before being poured into brine. The aqueous phase was extracted 5 times with ethyl acetate. The organic phase was dried with sodium sulfate and the solvent was removed to obtain 3-(4-cyclopropyl-4H-[1,2,4]triazol-3-yl)-phenylamine as an off-white powder (30 mg, 88%). 201.1 (M+1). $^1$H NMR of HBr salt (DMSO) d 9.24 (s, 1H), 7.50-7.63 (m, 3H), 6.6-8.0 (br, 4H+$H_2O$), 3.65 ppm (m, 1H), 1.05 (m, 4H).

B. Preparation of other Compounds of Formula (2)

Similarly, optionally replacing 3-(1,3,4-oxadiazol-2-yl) aniline in Example 2, step 1, and/or optionally replacing cyclopropylamine in Example 2, step 2, and following the procedures of Example 2, other compounds of formula (2) are prepared.

Example 3

Preparation of Compounds of Formula (1)

A. Preparation of a Compound of Formula (I) in which $R^3$ is 4-(1-isopropyl-1H-pyrrolo[3,2-b]pyridin-6-yl, $X^5$ is N, and $X^6$, $X^7$, and $X^8$ are ($CR^4$)

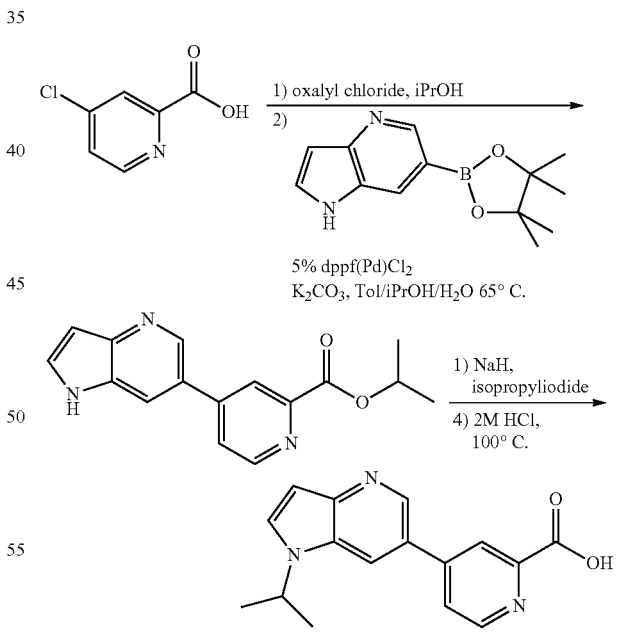

Step 1: Preparation of isopropyl 4-(1H-pyrrolo[3,2-b]pyridin-6-yl)picolinate N,N-Dimethylformamide (0.3 mL) was added dropwise to a suspension of oxalyl chloride (6.6 mL, 76 mmol) and 4-chloropicolinic acid (10.0 g, 63.5 mmol) in dichloromethane (200 mL). The reaction mixture was stirred for 1 hour and additional oxalyl chloride (4 mL) and N,N-dimethylformamide (0.2 mL) was added. After a further 30 minutes, isopropanol (100 mL) was slowly added, followed by, after a further 15 minutes, solid sodium bicarbonate (12 g). The reaction mixture was diluted with 1:1 saturated sodium bicarbonate solution and water, the aqueous phase extracted with dichloromethane (3×100 mL), and solvent removed from the extract under reduced pressure. The residue was purified by flash chromatography (rf: 0.48 in 2:1 hexanes:ethyl acetate) to give 4-chloropicolinic acid isopropyl ester (11.0 g, 87% yield). 200.1 (MH+1).

A mixture of 4-chloropicolinic acid isopropyl ester (1.5 g, 7.5 mmol), 6-(4,4,5,5-tetramethyl-1,3,2-dioxaborolan-2-yl)-1H-pyrrolo[3,2-b]pyridine (1.83 g, 7.5 mmol), dppf(Pd)Cl$_2$ (270 mg, 5 mol %), and potassium carbonate (2.0 g, 15 mmol) in degassed toluene (8 mL), degassed water (4 mL) and degassed isopropanol (4 mL) was heated at 65° C. for 2 hours. The aqueous phase was discarded and the solvent removed under reduced pressure. The residue was purified by flash chromatography (rf: 0.41 in 20:1 ethyl acetate:methanol) to provide isopropyl 4-(1H-pyrrolo[3,2-b]pyridin-6-yl)picolinate (1.20 g, 57%) as a yellow powder. 282.1 (M+1).

Step 2: Preparation of 4-(1-isopropyl-1H-pyrrolo[3,2-b]pyridin-6-yl)picolinic acid Sodium hydride (55 mg, 60% in mineral oil, 1.4 mmol) was added to a solution of isopropyl 4-(1H-pyrrolo[3,2-b]pyridin-6-yl)picolinate (250 mg, 0.89 mmol) in N,N-dimethylformamide (3 mL). After stirring for 10 minutes, isopropyl iodide was added and the reaction was stirred for 3 hours at room temperature. Solvent was removed from the reaction mixture under reduced pressure, and the residue dissolved in 2M HCl (3 mL) and heated at 100° C. overnight. The crude reaction mixture was purified by reverse-phase HPLC to give 4-(1-isopropyl-1H-pyrrolo[3,2-b]pyridin-6-yl)picolinic acid (50 mg, 20%). 282.1 (M+1).

B. Preparation of other Compounds of Formula (I)

Similarly, optionally replacing 4-chloropicolinic acid in Example 3, step 1 with other aromatic carboxylic acids, and/or optionally replacing 6-(4,4,5,5-tetramethyl-1,3,2-dioxaborolan-2-yl)-1H-pyrrolo[3,2-b]pyridine in Example 3, step 1 with similar boron complexes, and optionally replacing isopropyl iodide with other alkyl halides in Example 3, step 2, and following the procedures of Example 3, other compounds of formula (1) are prepared.

Example 4

Preparation of Compounds of Formula (1)

A. Preparation of a Compound of Formula (1) in which $R^3$ is (2-hydroxypropan-2-yl)pyridine, $X^5$ is N, and $X^6$, $X^7$, and $X^8$ are (CR$^4$)

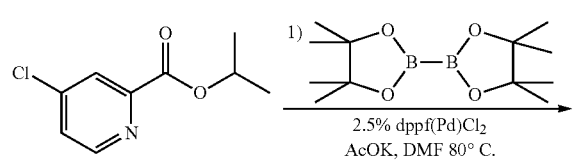

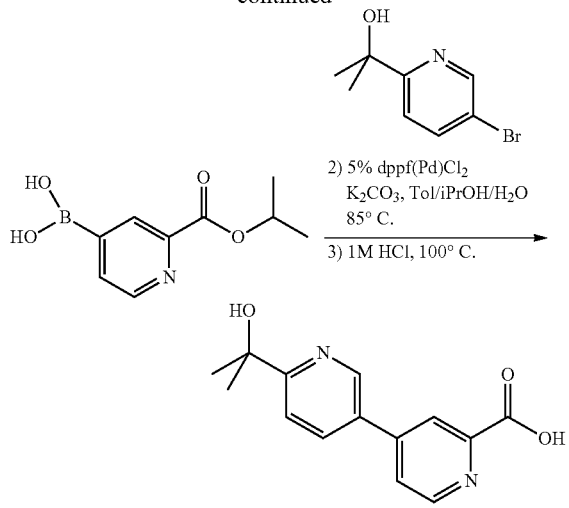

Step 1: Preparation of 2-isopropoxycarbonyl)pyridin-4-ylboronic acid

A suspension of 4-chloropicolinic acid isopropyl ester (2.0 g, 10 mmol), bis-pinacolatodiboron (3.05 g, 12 mmol), dppf(Pd)Cl$_2$ (150 mg, 2.5 mol %), potassium acetate (1.5 g, 15 mmol) in degassed N,N-dimethylformamide (10 mL) was heated at 80° C. for 4 hours. The solvent was removed under reduced pressure, and the crude mixture thus obtained was used in Step 2 without purification. 210.1 (M+1).

Step 2: Preparation of isopropyl 6-(2-hydroxypropan-2-yl)-3,4'-bipyridine-2'-carboxylate A mixture of crude 2-(isopropoxycarbonyl)pyridin-4-ylboronic acid (700 mg, 1.0 mmol), dppf(Pd)Cl$_2$ (40 mg, 5 mol %), potassium carbonate (280 mg, 2.0 mmol) and 2-(5-bromopyridin-2-yl)propan-2-ol (216 mg, 1.0 mmol) in degassed toluene (3 mL), degassed water (1 mL) and degassed isopropanol (1 mL) was heated at 85° C. for 1 hour. The aqueous layer was discarded and the solvent removed under reduced pressure. The residue was purified by flash chromatography (rf: 0.53 in 20:1 ethyl acetate:methanol) to give isopropyl 6-(2-hydroxypropan-2-yl)-3,4'-bipyridine-2'-carboxylate (140 mg, 47% yield). 301.1 (M+1).

Step 3: Preparation of 6-(2-hydroxypropan-2-yl)-3,4'-bipyridine-2'-carboxylic acid A solution of isopropyl 6-(2-hydroxypropan-2-yl)-3,4'-bipyridine-2'-carboxylate (140 mg, 0.47 mmol) in 1 M hydrochloric acid (2 mL) was heated at 100° C. overnight. The solvent was removed under reduced pressure to give 6-(2-hydroxypropan-2-yl)-3,4'-bipyridine-2'-carboxylic acid hydrochloride salt as a white powder (106 mg, 87%). 259.1 (M+1).

B. Preparation of other Compounds of Formula (1)

Similarly, optionally replacing 4-chloropicolinic acid isopropyl ester in Example 4, step 1 with other aromatic carboxylic esters, and/or optionally replacing bis-pinacolatodiboron in Example 4, step 1 with similar boron complexes, and optionally replacing 2-(5-bromopyridin-2-yl)propan-2-ol with other haloaryl derivatives in Example 4, step 2, and following the procedures of Example 4, other compounds of formula (1) are prepared.

Example 5

Preparation of Compounds of Formula (3)

A. Preparation of a Compound of Formula (3) in which $X^2$ and $X^5$ are N, $X^3$, $X^4$, $X^6$, $X^7$, and $X^8$ are $(CR^4)$, and $R^2$ is Hydrogen, and $R^3$ is Chloro

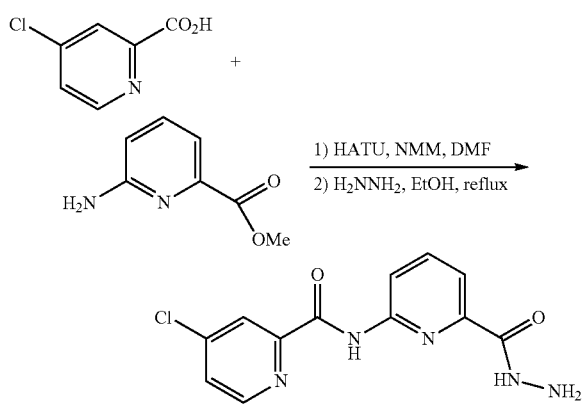

Step 1: Preparation of methyl 6-(4-chloropicolinamide)picolinate

A solution of 4-chloro-pyridine-2-carboxylic acid (16.3 g, 103 mmol), methyl 6-aminopicolinate (3.0 g, 18.6 mmol), (2-(7-Aza-1H-benzotriazole-1-yl)-1,1,3,3-tetramethyluminium hexafluorophosphate (HATU, 41.1 g, 108 mmol), and N-methyl morpholine (12.5 mL, 108 mmol) in N,N-dimethylformamide was stirred at room temperature for 12 hours. The solvent was removed under reduced pressure, and the residue suspended in acetonitrile. The solid thus obtained was isolated by filtration, washed with water (80 mL), acetonitrile (80 mL) and diethyl ether (80 m L) and dried under reduced pressure to afford 6-[(4-chloro-pyridine-2-carbonyl)-amino]-pyridine-2-carboxylic acid methyl ester as a white powder (25.6, 93% yield).

Step 2: Preparation of 4-chloro-N-(6-(hydrazinecarbonyl)pyridin-2-yl)picolinamide The crude 6-[(4-chloro-pyridine-2-carbonyl)-amino]-pyridine-2-carboxylic acid methyl ester from the previous step (25.3 g, 87.8 mmol) was suspended in ethanol (200 mL), and hydrazine hydrate (21.3 mL, 439 mmol) was added. The reaction mixture was refluxed for 4 hours, solvent removed under reduced pressure, and the residue suspended in acetonitrile and collected by filtration. The solids were washed with acetonitrile (2×100 mL) and diethylether (2×100 mL), and dried under reduced pressure to afford 25.3 g (92% yield) of 4-chloro-N-(6-(hydrazinecarbonyl)pyridin-2-yl)picolinamide as a white solid.

B. Preparation of other Compounds of Formula (3)

Similarly, optionally replacing 4-chloro-pyridine-2-carboxylic acid in Example 5 step 1, with other aromatic carboxylic esters, and/or optionally replacing methyl 6-aminopicolinate in Example 5, step 1, with other aromatic aminoesters, and following the procedures of Example 5, other compounds of formula (3) are prepared.

Example 6

Preparation of Compounds of Formula (4)

Preparation of a Compound of Formula (4) in which $X^2$, $X^3$, $X^4$, $X^6$, $X^7$, and $X^8$ are $(CR^4)$, $X^5$ is N, $R^2$ is Hydrogen, and $R^3$ is Bromo A. Preparation of N-(3-(1,3,4-oxadiazol-2-yl)phenyl)-4-bromopicolinamide

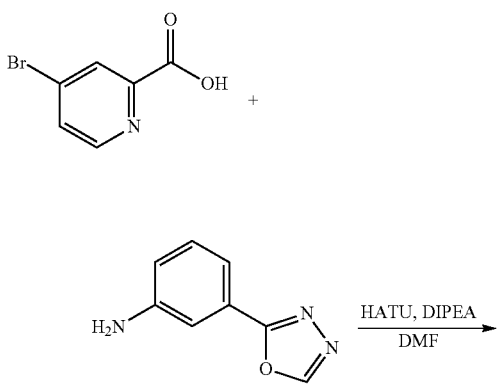

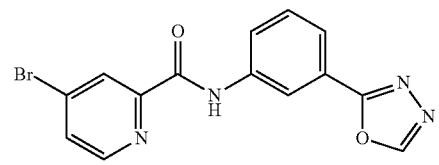

A solution of 4-bromopyridine-2-carboxylic acid (3.76 g, 18.6 mmol), 3-[1,3,4]oxadiazol-2-yl-phenylamine (3.0 g, 18.6 mmol), (2-(7-Aza-1H-benzotriazole-1-yl)-1,1,3,3-tetramethyluronium hexafluorophosphate (HATU) (7.1 g, 18.7 mmol), and diisopropylethylamine (15 mL) in N,N-dimethylformamide was stirred at room temperature for 1 hour. The solvent was removed under reduced pressure, and the residue was stirred with acetonitrile (40 mL) and water (40 mL). The solid thus obtained was isolated by filtration, washed with water (20 mL), acetonitrile (20 mL) and diethyl ether (40 mL), and dried under reduced pressure to give N-(3-(1,3,4-oxadiazol-2-yl)phenyl)-4-bromopicolinamide as a white powder (5.2 g, 15.0 mmol, 81% yield).

B. Preparation of other Compounds of Formula (4)

Similarly, optionally replacing 4-bromopyridine-2-carboxylic acid with other haloaromatic carboxylic acids, and/or optionally replacing 3-[1,3,4]oxadiazol-2-yl-phenylamine with other 3-[1,3,4]oxadiazol-2-yl-aromatic amines, and following the procedures of Example 6, other compounds of formula (4) are prepared.

Example 7

Preparation of Compounds of Formula (5)

Preparation of a Compound of Formula (5) in which $R^1$ is Cyclopropyl, $R^2$ is Hydrogen, $X^1$, $X^2$, and $X^5$ are N, $X^3$, $X^4$, $X^6$, and $X^8$ are (CR$^4$), $X^7$ is C(CH$_3$), and Z is Chloro A. Preparation of 4-Chloro-N-(6-(4-cyclopropyl-4H-1,2,4-triazol-3-yl)pyridin-2-yl)-5-methylpicolinamide

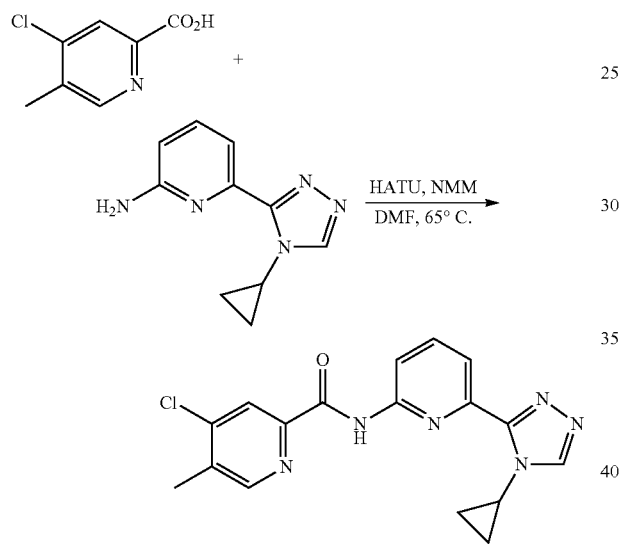

A solution of 4-chloro-5-methylpicolinic acid (159 mg, 0.924 mmol), 6-(4-Cyclopropyl-4H-[1,2,4]triazol-3-yl)-pyridin-2-ylamine (169 mg, 0.840 mmol), (2-(7-Aza-1H-benzotriazole-1-yl)-1,1,3,3-tetramethyluronium hexafluorophosphate (HATU) (383 mg, 1.01 mmol), and N-methylmorpholine (11 μL, 1.01 mmol) in N,N-dimethylformamide was stirred at 65° C. for 1.2 hours. The solvent was removed under reduced pressure, the residue was suspended in acetonitrile, and the solid product was isolated by filtration, washed with water (80 mL), acetonitrile (80 mL), diethyl ether (80 mL), and dried under vacuum to afford 4-chloro-N-(6-(4-cyclopropyl-4H-1,2,4-triazol-3-yl)pyridin-2-yl)-5-methylpicolinamide as a white powder (140 mg, 47% yield).

B. Preparation of other Compounds of Formula (5)

Similarly, optionally replacing 4-chloro-5-methylpicolinic acid with other halo aromatic carboxylic acids of formula (4), and/or optionally replacing 6-(4-cyclopropyl-4H-[1,2,4]triazol-3-yl)-pyridin-2-ylamine with other compounds of formula (2), and following the procedures of Example 7, other compounds of formula (5) are prepared.

Example 8

Alternative Preparation of Compounds of Formula (5)

Preparation of a Compound of Formula (5) in which $R^1$ is Cyclopropyl, $R^2$ is Hydrogen, $X^1$, $X^2$, and $X^5$ are N, $X^3$, $X^4$, $X^6$, $X^7$, and $X^8$ are (CR$^4$), and Z is Chloro A. Preparation 4-chloro-N-(6-(4-cyclopropyl-4H-1,2,4-triazol-3-yl)pyridin-2-yl)picolinamide

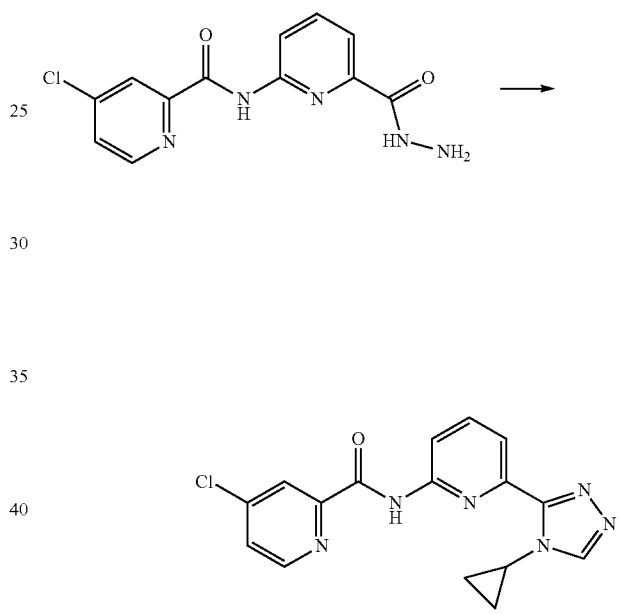

To a suspension of 4-chloro-N-(6-(hydrazinecarbonyl)pyridin-2-yl)picolinamide (1.00 g, 3.43 mmol) in toluene (0.20 M) was added a mixture of N,N-dimethylformamide•N-dimethylacetamide (1.14 mL, 8.56 mmol), cyclopropylamine (873 μL, 13.7 mmol), and acetic acid (194 μL, 3.43 mmol). The reaction mixture was heated to 150° C. for 30 minutes in a microwave reactor. The reaction product was concentrated under reduced pressure, and the residue was suspended in acetonitrile/diethylether (1.5 mL, 1:1 ratio), filtered, and the solid washed with acetonitrile/diethylether (2×10 mL). The filtrate was concentrated and the solid thus obtained was purified as above. The combined solids were dried under reduced pressure to afford 842 mg (72% yield) of 4-chloro-N-(6-(4-cyclopropyl-4H-1,2,4-triazol-3-yl)pyridin-2-yl)picolinamide as a white solid.

B. Preparation of other Compounds of Formula (5)

Similarly, optionally replacing 4-chloro-N-(6-(hydrazinecarbonyl)pyridin-2-yl)picolinamide with other compounds of formula (3), and/or optionally replacing cyclopropylamine with other amines of formula R¹NH₂, and following the procedures of Example 8, other compounds of formula (5) are prepared.

Example 9

Alternative Preparation of Compounds of Formula (3)

Preparation of a Compound of Formula (3) in which $X^2$ and $X^5$ are N, $X^3$, $X^4$, $X^6$, $X^7$, and $X^8$ are $(CR^4)$, and $R^3$ is 2-cyclopropylpyridine A. Preparation of 6-cyclopropyl-N-(6-(hydrazinecarbonyl)pyridin-2-yl)-3,4'-bipyridine-2'-carboxamide

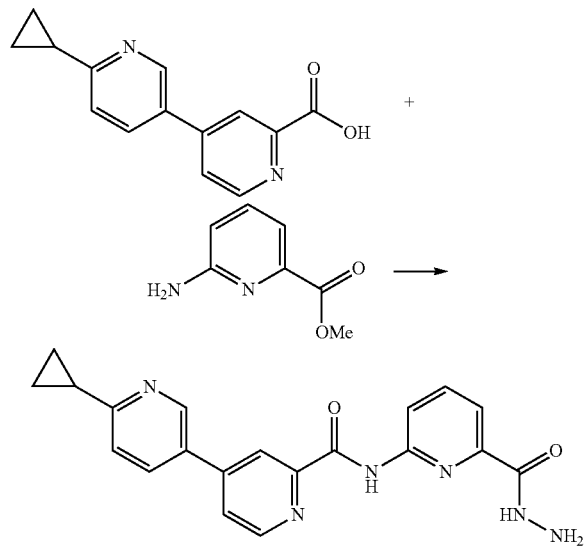

Step 1

A solution of 6-cyclopropyl-3,4'-bipyridine-2'-carboxylic acid hydrochloride salt (1.73 g, 6.25 mmol), 6-aminopicolinate methyl ester (1.05 g, 6.87 mmol), (2-(7-Aza-1H-benzotriazole-1-yl)-1,1,3,3-tetramethyluronium hexafluorophosphate (HATU, 2.85 g, 7.50 mmol), and N-methylmorpholine (1.51 mL, 13.8 mmol) in N,N-dimethylformamide was stirred at room temperature for 4 hours. The solvent was removed under reduced pressure, and the residue suspended in acetonitrile. The solid thus obtained was isolated by filtration, washed with water (80 mL), acetonitrile (80 mL) and diethyl ether (80 mL) and dried under reduced pressure to afford methyl 6-(6-cyclopropyl-3,4'-bipyridine-2'-carboxamido)picolinate as a white powder, which was used directly in the next step.

Step 2

The methyl 6-(6-cyclopropyl-3,4'-bipyridine-2'-carboxamido)picolinate from the previous step were suspended in ethanol (20 mL), hydrazine hydrate (700 μL, 14.4 mmol) was added, and the reaction was heated to reflux for 4 hours. The reaction mixture was concentrated and the resultant solids were suspended in acetonitrile and collected by filtration. The solids were washed with acetonitrile (2×100 mL) and diethyl ether (2×100 mL), and dried under reduced pressure to afford 1.21 g (47% yield) of 6-cyclopropyl-N-(6-(hydrazinecarbonyl)pyridin-2-yl)-3,4'-bipyridine-2'-carboxamide as a white solid.

B. Preparation of other Compounds of Formula (3)

Similarly, optionally replacing 6-cyclopropyl-3,4'-bipyridine-2'-carboxylic acid hydrochloride in Step 1 with other equivalent carboxylic acids, and/or optionally replacing 6-aminopicolinate methyl ester in step 1 with other amino esters, and following the procedures of Example 9, other compounds of formula (3) are prepared.

Example 10

Alternative Preparation of Compounds of Formula (4)

Preparation of a Compound of Formula (4) in which $X^2$, $X^3$, $X^4$, $X^6$, $X^7$ and $X^8$ are $(CR^4)$, $X^5$ is N, $R^2$ is Hydrogen, and $R^3$ is 2-cyclopropylpyridine A. Preparation of N-(3-(1,3,4-oxadiazol-2-yl)phenyl)-6-cyclopropyl-3,4'-bipyridine-2'-carboxamide

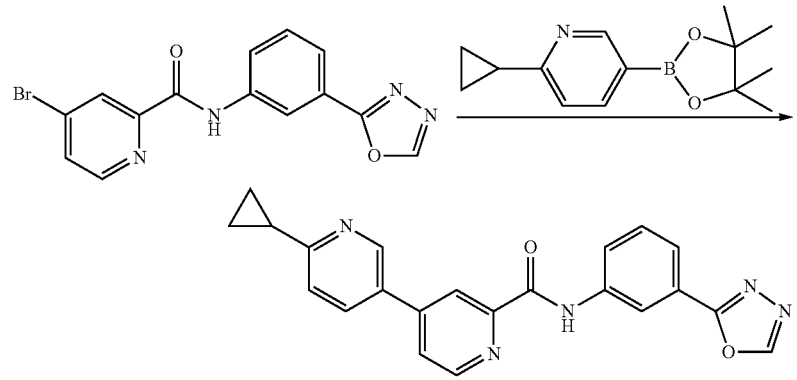

A suspension of N-(3-(1,3,4-oxadiazol-2-yl)phenyl)-4-bromopicolinamide (3.0 g, 8.7 mmol), 2-cyclopropyl-5-(4,4,5,5-tetramethyl-1,3,2-dioxaborolan-2-yl)pyridine (2.25 g, 9.2 mmol), dppf(Pd)Cl₂ (320 mg, 5 mol %), potassium carbonate (2.4 g, 17 mmol) in degassed toluene (10 mL), degassed water (10 mL) and degassed isopropanol (10 mL) was heated at 85° C. for 4 hours. The solvent was removed under reduced pressure and the residue was suspended and sonicated in methanol (40 mL) before being filtered and washed with methanol (10 mL). The grey powder was then suspended and sonicated in water (40 mL) before being filtered and washed with water (10 mL), methanol (10 mL) and diethyl ether (10 mL) to give 6-cyclopropyl-[3,4']bipyridinyl-2'-carboxylic acid (3-[1,3,4]oxadiazol-2-yl-phenyl)-amide (3.0 g, 90%). 384.1 (M+1).

B. Preparation of other Compounds of Formula (4)

Similarly, optionally replacing N-(3-(1,3,4-oxadiazol-2-yl)phenyl)-4-bromopicolinamide with other equivalent aromatic halo derivatives, and/or optionally replacing 2-cyclopropyl-5-(4,4,5,5-tetramethyl-1,3,2-dioxaborolan-2-yl)pyridine with other boron complexes, and following the procedures of Example 10, other compounds of formula (4) are prepared.

Example 11

Preparation of Compounds of Formula (d)

Preparation of a Compound of Formula (d) in which $R^1$ is Cyclopropyl

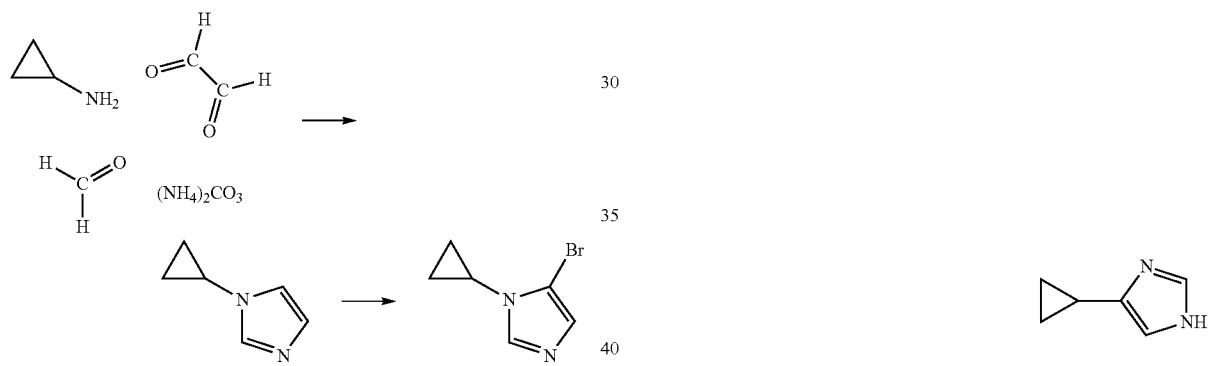

Step 1

To a 200 ml round bottomed flask was added 4.08 g (136 mmol) of paraformaldehyde and 20 mL of methanol. After cooling the mixture to 0-5° C., the following were added in order, 7.36 g (129 mmol) cyclopropyl amine, 10 mL methanol, 6.20 g (65 mmol) ammonium carbonate, 10 mL methanol, 9.07 g (43.1 mmol) trimeric glyoxal dihydrate and 25 mL methanol. The reaction was stirred overnight at room temperature. The volatiles were removed by rotary evaporation, with special care not to heat the mixture as the product is volatile. The mixture was then distilled at 15-20 torr and the product co-distilled with another impurity at 90-95° C. This mixture was chromatographed on silica gel (1:1 hexanes/ethyl acetate, then 7% methanol in methylene chloride) to afford 1.76 g (25% yield) of 1-cyclopropyl-1H-imidazole as a yellow oil.

Step 2

Cyclopropyl-1H-imidazole (1.18 g, 10.9 mmol) was dissolved in methylene chloride (0.1 M), cooled to 5-10° C., and 1,3-dibromo-5,5-dimethylhydantoin (1.59 g, 5.57 mmol) was added. The temperature was maintained between 5-10° C. and the reaction was stirred for 2 hours. Solvent was removed from the reaction mixture under reduced pressure, and the residue was purified by column chromatography (eluting with 1%-7% methanol in methylene chloride, 5% methanol/methylene chloride) to afford 620 mg (37% yield) of 5-bromo-1-cyclopropyl-1H-imidazole.

B. Preparation of other Compounds of Formula (d)

Similarly, replacing cyclopropylamine with other amines of formula $R^1NH_2$, and following the procedures of Example 11, other compounds of formula (d) are prepared.

Example 12

Preparation of 4-alkyl Substituted Imidazoles

A. Preparation of 4-cyclopropyl-1H-imidazole

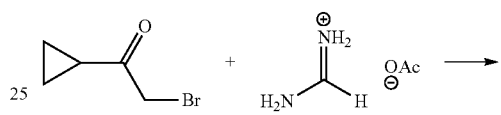

Ammonia (~75 mL) was condensed into a pressure vessel containing formamidine acetate (60 g, 0.58 mol) and a stir bar at −78° C. 2-bromo-1-cyclopropyl-ethanone (10.2 g, 0.063 mol) was added dropwise and the pressure vessel was sealed and warmed to room temperature and stilled for 12 hours. The reaction mixture was then cooled to −78° C. before being carefully opened. The cooling bath was removed and the ammonia was allowed to evaporate. The residue was dissolved in 100 mL of water and 20 mL saturated sodium bicarbonate solution, and then solid sodium chloride was added until the solution was saturated. This mixture was extracted with ethyl acetate (4×100 mL) and the organic phase was dried with sodium sulfate before being evaporated to yield 4-cyclopropyl-1H-imidazole as a yellow oil (70-80% purity, 5.3 g, 78% yield, M+1=109.1) which was used without further purification. Reverse-phase HPLC (0.1% HCl H₂0, MeCN) of the crude compound gave an analytically pure sample (1.0 g). $^1$H NMR of HCl salt (DMSO) d 8.96 (s, 1H), 7.38 (s, 1H), 1.96 (m, 1H), 0.97 (m, 2H), 0.79 (m, 2H).

B. Preparation of other Compounds of Formula (d)

Similarly, replacing 2-bromo-1-cyclopropyl-ethanone with other haloethanones of formula RC(O)CH₂X, where R is alkyl and X is halo, and following the procedures of Example 12, other 4-alkylimidazoles are prepared.

Example 13

Preparation of Compounds of Formula (I) via the Suzuki Reaction

A. Preparation of a Compound of Formula (I) in which $X^2$, $X^3$, $X^4$, $X^6$, $X^7$ and $X^8$ are (CR$^4$), $X^1$ and $X^5$ are N, $R^1$ is Cyclopropyl, $R^2$ is Hydrogen, and $R^3$ is Pyridin-3-yl

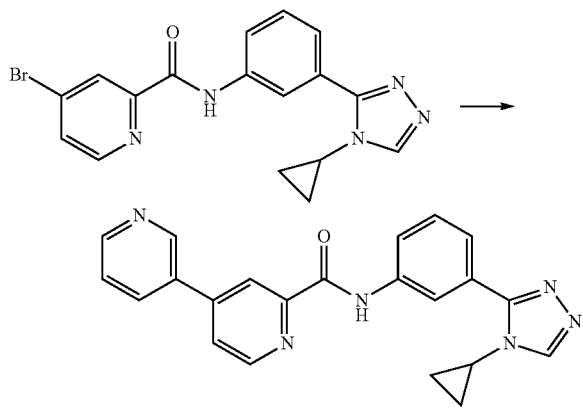

A suspension of 4-bromo-N-(3-(4-cyclopropyl-4H-1,2,4-triazol-3-yl)phenyl)picolinamide (120 mg, 0.31 mmol), 3-pyridine boronic acid (77 mg, 0.62 mmol), dppf(Pd)Cl$_2$ (23 mg, 0.03 mmol), potassium carbonate (86 mg, 0.62 mmol) in degassed toluene (2 mL), degassed water (1 mL) and degassed ethanol (1 mL) was heated at 100° C. for 1 hour. The solvent was removed under reduced pressure and the residue purified by reverse-phase HPLC, to give N-(3-(4-cyclopropyl-4H-1,2,4-triazol-3-yl)phenyl)-3,4'-bipyridine-2'-carboxamide as a white powder (58 mg, 0.15 mmol, 48% yield). $C_{22}H_{18}N_6O$. 383.1 (M+1). $^1$H NMR (DMSO) d 10.98 (s, 1H), 9.12 (d, J=1.6 Hz, 1H), 8.87 (d, J=4.8 Hz, 1H), 8.72 (dd, J=4.8, 1.2 Hz, 1H), 8.63 (s, 1H), 8.60 (s, 1H), 8.48 (d, J=1.2 Hz, 1H), 8.34 (m, 1H), 8.11 (m, 2H), 7.69 (d, J=8.0 Hz, 1H), 7.59 (m, 2H), 3.66 (m, 1H), 1.09 (m, 2H), 0.94 (m, 2H).

B. Similarly, following the procedures as described in Examples 1-13 where appropriate, the following compounds of Formula (I) were prepared:

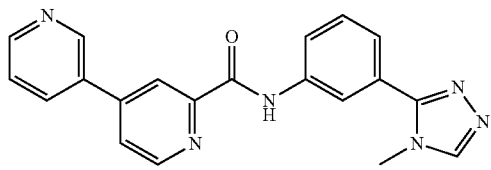 [SMILES: Cn1cnnc1-c1cccc(NC(=O)c2cc(-c3cccnc3)ccn2)c1]

N-(3-(4-methyl-4H-1,2,4-triazol-3-yl)phenyl)-3,4'-bipyridine-2'-carboxamide $C_{20}H_{16}N_6O$. 357.1 (M+1). $^1$H NMR (DMSO) d 10.98 (s, 1H), 9.11 (d, J=1.6 Hz, 1H), 8.87 (d, J=5.2 Hz, 1H), 8.73 (dd, J=4.8, 1.6 Hz, 1H), 8.59 (s, 1H), 8.49 (d, J=1.2 Hz, 1H), 8.34 (m, 2H), 8.11 (m, 2H), 7.58 (m, 3H), 3.81 (s, 3H).

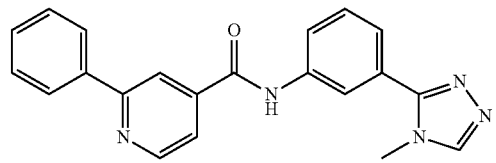 [SMILES: Cn1cnnc1-c1cccc(NC(=O)c2ccnc(-c3ccccc3)c2)c1]

N-(3-(4-methyl-4H-1,2,4-triazol-3-yl)phenyl)-2-phenylisonicotinamide $C_{21}H_{17}N_5O$. 356.1 (M+1). $^1$H NMR (DMSO) d 10.76 (s, 1H), 8.88 (d, J=5.2 Hz, 1H), 8.60 (s, 1H), 8.43 (s, 1H), 8.18-8.22 (m, 3H), 7.98 (d, J=7.6 Hz, 1H), 7.83 (d, J=7.6 Hz, 1H), 7.46-7.62 (m, 5H), 3.79 (s, 3H).

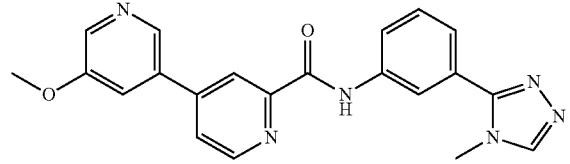 [SMILES: COc1cncc(-c2ccnc(C(=O)Nc3cccc(-c4nncn4C)c3)c2)c1]

5-methoxy-N-(3-(4-methyl-4H-1,2,4-triazol-3-yl)phenyl)-3,4'-bipyridine-2'-carboxamide $C_{21}H_{18}N_6O_2$. 387.2 (M+1). $^1$H NMR (DMSO) d 10.98 (s, 1H), 8.86 (d, J=4.8 Hz, 1H), 8.68 (d, J=1.6 Hz, 1H), 8.59 (s, 1H), 8.51 (d, J=1.2 Hz, 1H), 8.44 (d, J=2.4 Hz, 1H), 8.35 (s, 1H), 8.12 (m, 2H), 7.88 (t, J=2.2 Hz, 1H), 7.55 (m, 2H), 3.96 (s, 3H), 3.81 (s, 3H).

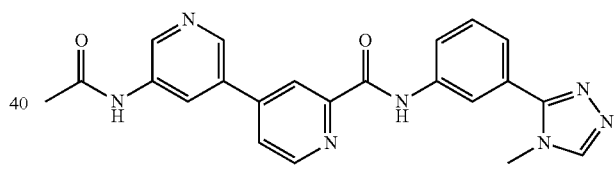

5-acetamido-N-(3-(4-methyl-4H-1,2,4-triazol-3-yl)phenyl)-3,4'-bipyridine-2'-carboxamide $C_{22}H_{19}N_7O_2$. 414.1 (M+1). $^1$H NMR (DMSO) d 10.99 (s, 1H), 10.39 (s, 1H), 8.87 (d, J=5.2 Hz, 1H), 8.84 (d, J=2.4 Hz, 1H), 8.79 (d, J=2.0 Hz, 1H), 8.59 (s, 1H), 8.53 (s, 1H), 8.41 (s, 1H), 8.36 (s, 1H), 8.12 (d, J=7.6 Hz, 1H), 8.06 (dd, J=5.4, 1.8 Hz, 1H), 7.56 (m, 2H), 3.81 (s, 3H), 2.13 (s, 3H).

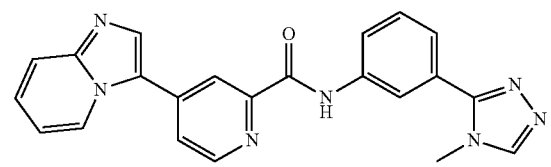 [SMILES: Cn1cnnc1-c1cccc(NC(=O)c2cc(-c3cnc4ccccn34)ccn2)c1]

4-(imidazo[1,2-a]pyridin-3-yl)-N-(3-(4-methyl-4H-1,2,4-triazol-3-yl)phenyl)-picolinamide $C_{22}H_{17}N_7O$. 396.1 (M+1). $^1$H NMR (DMSO) d 10.98 (s, 1H), 8.84 (m, 2H), 8.59 (s, 1H), 8.42 (d, J=0.8 Hz, 1H), 8.35

(s, 1H), 8.20 (s, 1H), 8.14 (m, 1H), 8.04 (dd, J=5.2, 1.6 Hz, 1H), 7.76 (d, J=9.2 Hz, 1H), 7.54 (m, 2H), 7.44 (m, 1H), 7.12 (dt, J=7.2, 0.8 Hz, 1H), 3.81 (s, 3H).

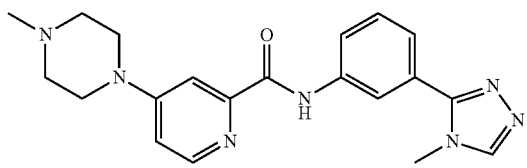 [SMILES: CN1CCN(c2ccnc(C(=O)Nc3cccc(-c4nncn4C)c3)c2)CC1]

N-(3-(4-methyl-4H-1,2,4-triazol-3-yl)phenyl)-4-(4-methylpiperazin-1-yl)picolinamide $C_{20}H_{13}N_7O$. 378.1 (M+1). $^1$H NMR (DMSO) d 10.80 (s, 1H), 8.58 (s, 1H), 8.30-8.32 (m, 2H), 8.02-8.09 (m, 1H), 7.57 (d, J=2.4 Hz, 1H), 7.48-7.56 (m, 2H), 7.08 (dd, J=2.4, 6 Hz, 1H), 3.79 (s, 3H), 3.42 (t, J=4.8 Hz, 4H), 2.44 (t, J=4.8 Hz, 4H), 2.23 (s, 3H).

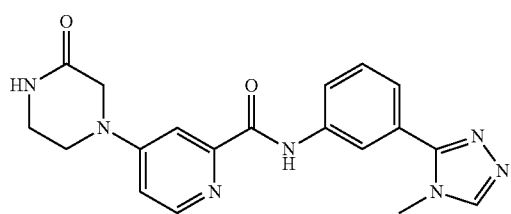 [SMILES: Cn1cnnc1-c1cccc(NC(=O)c2cc(N3CCNC(=O)C3)ccn2)c1]

N-(3-(4-methyl-4H-1,2,4-triazol-3-yl)phenyl)-4-(3-oxopiperazin-1-yl)picolinamide;

$C_{19}H_{19}N_7O_2$. 378.1 (M+1). $^1$H NMR (DMSO) d 10.81 (s, 1H), 8.59 (s, 1H), 8.33 (d, J=6 Hz, 1H), 8.27-8.32 (m, 2H), 8.15 (br s, 1H), 8.05-8.09 (m, 1H), 7.48-7.56 (m, 3H), 7.03 (dd, J=2.8, 5.6 Hz, 1H), 3.96 (s, 2H), 3.79 (s, 3H), 3.63 (t, J=4.8 Hz, 2H), 3.33-3.35 (m, 2H).

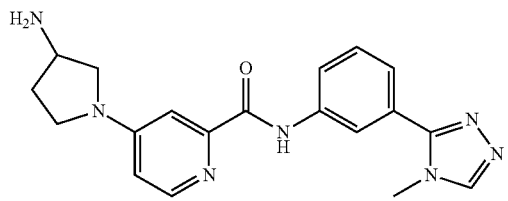 [SMILES: Cn1cnnc1-c1cccc(NC(=O)c2cc(N3CCC(N)C3)ccn2)c1]

4-(3-aminopyrrolidin-1-yl)-N-(3-(4-methyl-4H-1,2,4-triazol-3-yl)phenyl)picolinamide $C_{19}H_{21}H_7O$. 364.1 (M+1). $^1$H NMR (CD$_3$OD) d 8.59 (s, 1H), 8.49 (s, 1H), 8.30 (d, J=6 Hz, 1H), 8.23-8.25 (m, 1H), 7.60 (t, J=8 Hz, 1H), 7.51 (d, J=7.6 Hz, 1H), 7.60 (t, J=8 Hz, 1H), 7.51 (d, J=7.6 Hz, 1H), 7.40 (d, J=2.4 Hz, 1H), 6.73 (dd, J=2.4, 6 Hz, 1H), 4.04-4.09 (m, 1H), 3.86 (s, 3H), 3.78 (dd, J=2, 7.2 Hz, 1H), 3.63-3.72 (m, 1H) 3.47-3.60 (m, 2H), 2.45-2.56 (m, 1H), 2.17-2.25 (m, 1H).

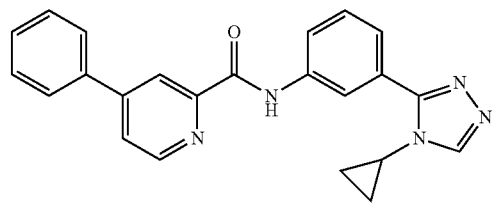 [SMILES: O=C(Nc1cccc(-c2nncn2C2CC2)c1)c1cc(-c2ccccc2)ccn1]

N-(3-(4-cyclopropyl-4H-1,2,4-triazol-3-yl)phenyl)-4-phenylpicolinamide $C_{23}H_{19}N_5O$. 382.2 (M+1). $^1$H NMR (CD$_3$OD) d 8.71 (d, J=4.8 Hz, 1H), 8.60 (s, 1H), 8.44 (d, J=1.2 Hz, 1H), 7.92-7.95 (m, 1H), 7.84 (dd, J=2, 5.2 Hz, 1H), 7.78 (d, J=7.2 Hz, 1H), 7.66 (d, J=7.2 Hz, 2H), 7.66 (d, J=7.2 Hz, 1H), 7.56 (t, J=8 Hz, 1H), 7.45-7.53 (m, 3H), 3.64 (m, 1H), 1.14-1.19 (m, 2H), 0.95-1.00 (m, 2H).

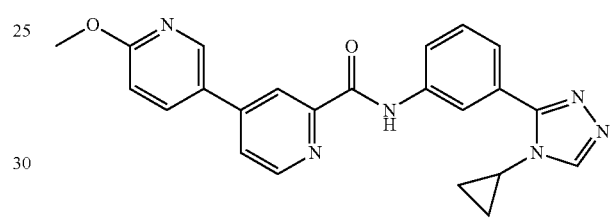

N-(3-(4-cyclopropyl-4H-1,2,4-triazol-3-yl)phenyl)-6-methoxy-3,4'-bipyridine-2'-carboxamide $C_{23}H_{20}N_6O_2$. 413.4 (M+1). $^1$H NMR (DMSO) d 10.93 (s, 1H), 8.80 (d, J=4.8 Hz, 1H), 8.76 (d, J=2.0 Hz, 1H), 8.63 (s, 1H), 8.58 (s, 1H), 8.43 (d, J=1.2 Hz, 1H), 8.28 (dd, J=4.8, 2.8 Hz, 1H), 8.05 (m, 2H), 7.68 (d, J=8.0 Hz, 1H), 7.55 (t, J=8.0 Hz, 1H), 7.01 (d, J=8.0 Hz, 1H), 3.94 (s, 3H), 3.67 (m, 1H), 1.09 (m, 2H), 0.95 (m, 2H).

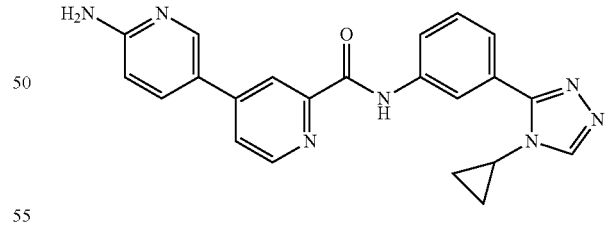

6-amino-N-(3-(4-cyclopropyl-4H-1,2,4-triazol-3-yl)phenyl)-3,4'-bipyridine-2'-carboxamide $C_{22}H_{19}N_7O$. 398.1 (M+1). $^1$H NMR (DMSO) d 10.88 (s, 1H), 8.69 (d, J=5.2 Hz, 1H), 8.62 (s, 1H), 8.58 (s, 1H), 8.53 (d, J=2.0 Hz, 1H), 8.33 (d, J=1.2 Hz, 1H), 8.06 (d, J=8.8 Hz, 1H), 7.94 (m, 2H), 7.68 (d, J=8.0 Hz, 1H), 7.54 (t, J=8.0 Hz, 1H), 6.58 (d, 8.8 Hz, 1H), 6.47 (s, 2H), 3.66 (m, 1H), 1.08 (m, 2H), 0.95 (m, 2H).

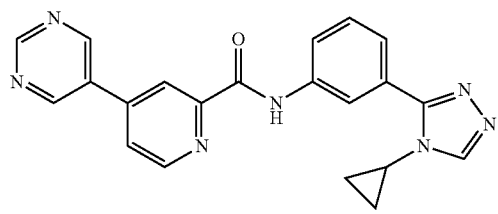 [SMILES: O=C(Nc1cccc(-c2nncn2C2CC2)c1)c1cc(-c2cncnc2)ccn1]

N-(3-(4-cyclopropyl-4H-1,2,4-triazol-3-yl)phenyl)-4-(pyrimidin-5-yl)picolinamide $C_{21}H_{17}N_7O$. 384.1 (M+1). $^1$H NMR (DMSO) d 10.99 (s, 1H), 9.37 (s, 2H), 9.33 (s, 1H), 8.91 (d, J=5.2 Hz, 1H), 8.63 (s, 1H), 8.58 (m, 2H), 8.18 (dd, J=4.8, 1.6 Hz, 1H), 8.08 (d, J=4.8 Hz, 1H), 7.69 (d, J=8.0 Hz, 1H), 7.56 (t, J=8.0 Hz, 1H), 3.67 (m, 1H), 1.09 (m, 2H), 0.95 (m, 2H).

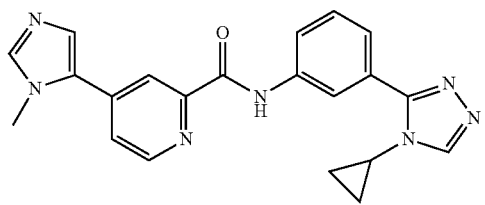

N-(3-(4-cyclopropyl-4H-1,2,4-triazol-3-yl)phenyl)-4-(1-methyl-1H-imidazol-5-yl)picolinamide $C_{21}H_{19}N_7O$. 386.1 (M+1). $^1$H NMR (DMSO) d 10.92 (s, 1H), 8.78 (d, J=5.2 Hz, 1H), 8.62 (s, 1H), 8.57 (s, 1H), 8.26 (s, 1H), 8.07 (d, J=8.0 Hz, 1H), 7.86 (m, 2H), 7.69 (d, J=8.0 Hz, 1H), 7.54 (m, 2H), 3.86 (s, 3H), 3.66 (m, 1H), 1.08 (m, 2H), 0.94 (m, 2H).

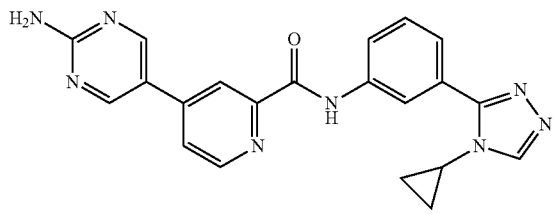 [SMILES: Nc1ncc(-c2ccnc(C(=O)Nc3cccc(-c4nncn4C4CC4)c3)c2)cn1]

4-(2-aminopyrimidin-5-yl)-N-(3-(4-cyclopropyl-4H-1,2,4-triazol-3-yl)phenyl)picolinamide $C_{21}H_{18}N_8O$. 399.1 (M+1). $^1$H NMR (DMSO) d 10.91 (s, 1H), 8.85 (s, 2H), 8.74 (d, J=4.8 Hz, 1H), 8.63 (s, 1H), 8.58 (s, 1H), 8.40 (d, J=1.2 Hz, 1H), 8.06 (d, J=9.2 Hz, 1H), 8.00 (dd, J=5.0, 1.8 Hz, 1H), 7.68 (d, J=7.6 Hz, 1H), 7.54 (t, J=8.0 Hz, 1H), 7.17 (s, 2H), 3.66 (m, 1H), 1.08 (m, 2H), 0.95 (m, 2H).

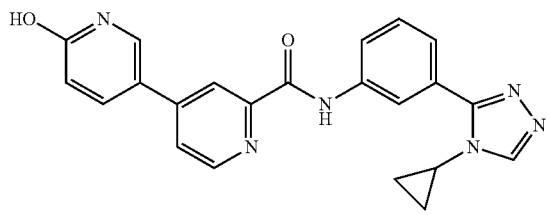 [SMILES: O=C(Nc1cccc(-c2nncn2C2CC2)c1)c1cc(-c2ccc(O)nc2)ccn1]

N-(3-(4-cyclopropyl-4H-1,2,4-triazol-3-yl)phenyl)-4-(2-methoxypyrimidin-5-yl)picolinamide $C_{22}H_{19}N_7O_2$. 414.8 (M+1). $^1$H NMR (DMSO) d 10.99 (s, 1H), 9.19 (s, 2H), 8.84 (d, J=5.2 Hz, 1H), 8.63 (s, 1H), 8.59 (s, 1H), 8.51 (d, J=0.8 Hz, 1H), 8.05-8.12 (m, 2H), 7.69 (d, J=7.6 Hz, 1H), 7.55 (t, J=8 Hz, 1H), 4.01 (s, 3H), 3.64-3.68 (m, 1H), 1.06-1.11 (m, 2H), 0.92-0.97 (m, 2H).

N-(3-(4-cyclopropyl-4H-1,2,4-triazol-3-yl)phenyl)-6-hydroxy-3,4'-bipyridine-2'-carboxamide $C_{22}H_{18}N_6O_2$. 399.2 (M+1). $^1$H NMR (DMSO) d 12.18 (br, 1H), 10.91 (s, 1H), 8.71 (d, J=5.2 Hz, 1H), 8.63 (s, 1H), 8.58 (s, 1H), 8.32 (s, 1H), 8.14 (d, 2.8 Hz, 1H), 8.05 (m, 2H), 7.92 (dd, J=5.2, 1.6 Hz, 1H), 7.68 (d, J=8.0 Hz, 1H), 7.54 (t, J=8.0 Hz, 1H), 6.50 (d, J=10.0 Hz, 1H), 3.65 (m, 1H), 1.08 (m, 2H), 0.94 (m, 2H).

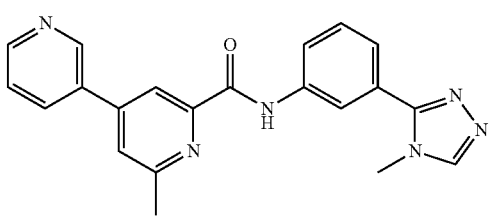 [SMILES: Cc1cc(-c2cccnc2)cc(C(=O)Nc2cccc(-c3nncn3C)c2)n1]

6'-methyl-N-(3-(4-methyl-4H-1,2,4-triazol-3-yl)phenyl)-3,4'-bipyridine-2'-carboxamide $C_{21}H_{18}N_6O$. 371.5 (M+1). $^1$H NMR (DMSO) d 10.73 (s, 1H), 9.09 (d, J=2 Hz, 1H), 8.71 (d, J=3.6 Hz, 1H), 8.59 (s, 1H), 8.26-8.34 (m, 3H), 8.09 (d, J=7.6 Hz, 1H), 7.99 (s, 1H), 7.50-7.61 (m, 3H), 3.80 (s, 3H), 2.73 (s, 3H).

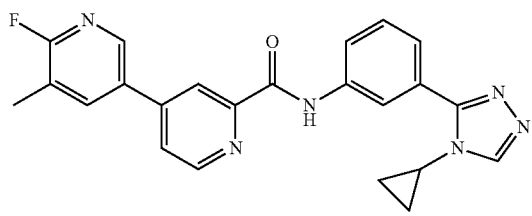 [SMILES: Cc1cc(-c2ccnc(C(=O)Nc3cccc(-c4nncn4C4CC4)c3)c2)cnc1F]

N-(3-(4-cyclopropyl-4H-1,2,4-triazol-3-yl)phenyl)-
6-fluoro-5-methyl-3,4'-bipyridine-2'-carboxamide C$_{23}$H$_{19}$FN$_6$O. 415.3 (M+1). $^1$H NMR (DMSO) d 10.95 (s, 1H), 8.85 (d, J=5.2 Hz, 1H), 8.58-8.64 (m, 3H), 8.43-8.49 (m, 2H), 8.05-8.10 (m, 2H), 7.70 (d, J=8.4 Hz, 1H), 7.55 (t, J=8.4 Hz, 1H), 3.65-3.70 (m, 1H), 2.36 (s, 3H), 1.06-1.12 (m, 2H), 0.92-0.97 (m, 2H).

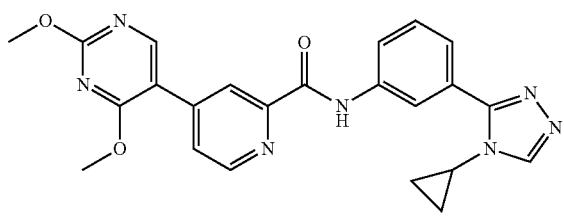 [SMILES: COc1ncc(-c2ccnc(C(=O)Nc3cccc(-c4nncn4C4CC4)c3)c2)c(OC)n1]

N-(3-(4-cyclopropyl-4H-1,2,4-triazol-3-yl)phenyl)-
4-(2,4-dimethoxypyrimidin-5-yl)picolinamide C$_{23}$H$_{21}$N$_7$O$_3$. 444.2 (M+1). $^1$H NMR (DMSO) d 10.92 (s, 1H), 8.80 (d, J=4.8 Hz, 1H), 8.67 (s, 1H), 8.62 (s, 1H), 8.57 (s, 1H), 8.38-8.40 (m, 1H), 8.06 (d, J=8 Hz, 1H), 7.91 (dd, J=1.6, 4.8 Hz, 1H), 7.68 (d, J=8 Hz, 1H), 7.54 (d, J=8 Hz, 1H), 4.02 (s, 3H), 3.99 (s, 3H), 3.62-3.70 (m, 1H), 1.05-1.11 (m, 2H), 0.90-0.96 (m, 2H).

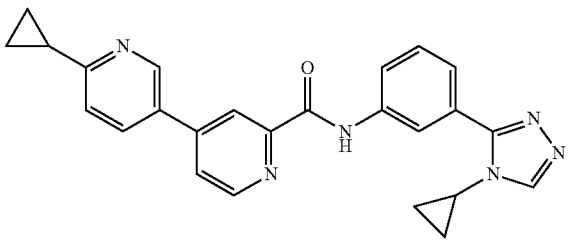 [SMILES: O=C(Nc1cccc(-c2nncn2C2CC2)c1)c1cc(-c2ccc(C3CC3)nc2)ccn1]

6-cyclopropyl-N-(3-(4-cyclopropyl-4H-1,2,4-triazol-
3-yl)phenyl)-3,4'-bipyridine-2'-carboxamide C$_{25}$H$_{22}$N$_6$O. 423.1 (M+1). $^1$H NMR (DMSO) d 10.94 (s, 1H), 8.93 (d, J=2.0 Hz, 1H), 8.82 (d, J=2.8 Hz, 1H), 8.63 (s, 1H), 8.58 (s, 1H), 8.43 (d, J=1.2 Hz, 1H), 8.19 (dd, J=8.0, 2.8 Hz, 1H), 8.06 (m, 2H), 7.68 (d, J=8.0 Hz, 1H), 7.55 (t, J=8.0 Hz, 1H), 7.49 (d, J=8.0 Hz, 1H), 3.66 (m, 1H), 2.21 (m, 1H), 1.02 (m, 8H).

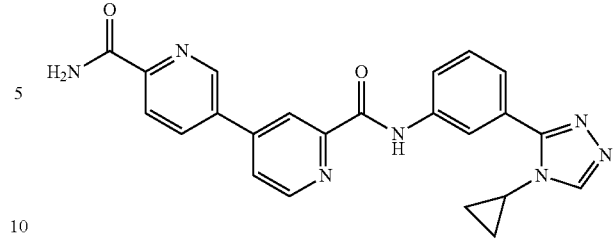

N2'-(3-(4-cyclopropyl-4H-1,2,4-triazol-3-yl)phenyl)-
3,4'-bipyridine-2',6-dicarboxamide C$_{23}$H$_{19}$N$_7$O$_2$. 426.1 (M+1). $^1$H NMR (DMSO) d 10.98 (s, 1H), 9.14 (d, J=1.6 Hz, 1H), 8.90 (d, J=4.8 Hz, 1H), 8.63 (s, 1H), 8.60 (s, 1H), 8.53 (t, J=2.4 Hz, 1H), 8.51 (d, J=2.4 Hz, 1H), 8.17 (m, 3H), 8.08 (d, J=8.0 Hz, 1H), 7.77 (s, 1H), 7.70 (d, J=8.0 Hz, 1H), 7.56 (t, J=8.0 Hz, 1H), 3.67 (m, 1H), 1.08 (m 2H), 0.95 (m, 2H).

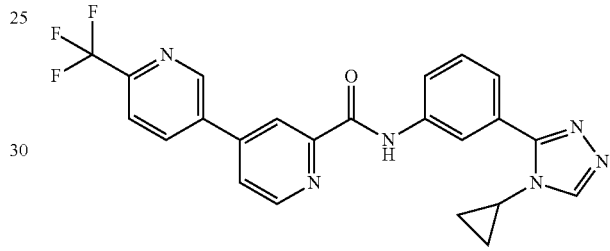

N-(3-(4-cyclopropyl-4H-1,2,4-triazol-3-yl)phenyl)-
6-(trifluormethyl)-3,4'-bipyridine-2'-carboxamide C$_{23}$H$_{17}$F$_3$N$_6$O. 451.1 (M+1). $^1$H NMR (DMSO) d 10.99 (s, 1H), 9.31 (d, J=1.2 Hz, 1H), 8.93 (d, J=4.8 Hz, 1H), 8.64 (s, 1H), 8.63 (s, 1H), 8.60 (s, 1H), 8.56 (d, J=1.2 Hz, 1H), 8.18 (dd, J=5.2, 2.0 Hz, 1H), 8.09 (m, 2H), 7.70 (d, J=8.0 Hz, 1H), 7.56 (t, J=8.0 Hz, 1H), 3.67 (m, 1H), 1.08 (m, 2H), 0.95 (m, 2H). $^{19}$F NMR (DMSO) d −66.4.

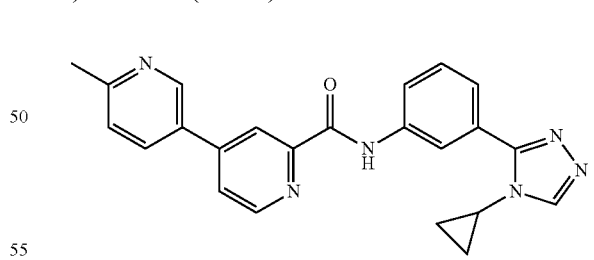

N-(3-(4-cyclopropyl-4H-1,2,4-triazol-3-yl)phenyl)-
6-methyl-3,4'-bipyridine-2'-carboxamide C$_{23}$H$_{20}$N$_6$O. 397.1 (M+1). $^1$H NMR (DMSO) d 10.94 (s, 1H), 8.99 (d, J=2.0 Hz, 1H), 8.84 (d, J=5.2 Hz, 1H), 8.63 (s, 1H), 8.59 (s, 1H), 8.46 (d, J=0.8 Hz, 1H), 8.24 (dd, J=8.0, 2.4 Hz, 1H), 8.08 (m, 2H), 7.69 (d, J=8.0 Hz, 1H), 7.55 (t, J=8.0 Hz, 1H), 7.46 (d, J 8.0 Hz, 1H), 3.67 (m, 1H), 2.56 (s, 3H), 1.08 (m, 2H), 0.95 (m, 2H).

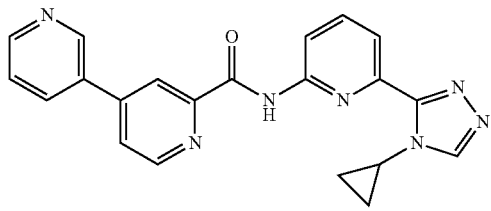 [SMILES: O=C(Nc1cccc(-c2nncn2C2CC2)n1)c1cc(-c2cccnc2)ccn1]

N-(6-(4-cyclopropyl-4H-1,2,4-triazol-3-yl)pyridin-2-yl)-3,4'-bipyridine-2'-carboxamide $C_{21}H_{17}N_7O$. 384.1 (M+1). $^1$H NMR (DMSO) d 10.70 (s, 1H), 9.19 (d, J=2 Hz, 1H), 8.88 (d, J 5 Hz, 1H), 8.74 (dd, J=2.5 Hz, 1H), 8.70 (s, 1H), 8.55 (d, J=1 Hz, 1H), 8.40 (d, J=8 Hz, 1H), 8.35-8.40 (m, 1H), 8.15 (dd, J=2, 5 Hz, 1H), 8.11 (t, J=8 Hz, 1H), 7.87-7.91 (m, 1H), 7.62 (dd, J=5, 8 Hz, 1H), 4.11-4.20 (m, 1H), 0.98-1.10 (m, 4H).

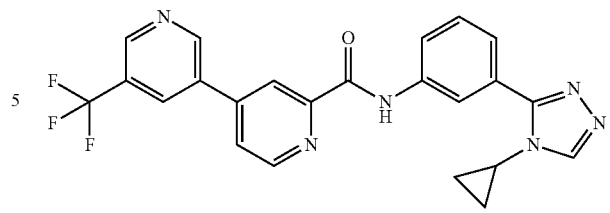

N-(3-(4-cyclopropyl-4H-1,2,4-triazol-3-yl)phenyl)-5-(trifluoromethyl)-3,4'-bipyridine-2'-carboxamide $C_{23}H_{17}F_3N_6O$. 451.1 (M+1). $^1$H NMR (DMSO) d 10.98 (s, 1H), 9.40-9.42 (m, 1H), 9.11-9.13 (m, 1H), 8.90 (d, J=5 Hz, 1H), 8.75-8.78 (m, 1H), 8.63 (s, 1H), 8.58-8.62 (m, 2H), 8.21 (dd, J=2.6 Hz, 1H), 8.05-8.10 (m, 1H), 7.70 (d, J=8 Hz, 1H), 7.56 (t, J=8 Hz, 1H), 3.63-3.68 (m, 1H), 1.05-1.10 (m, 2H), 0.94-0.98 (m, 2H).

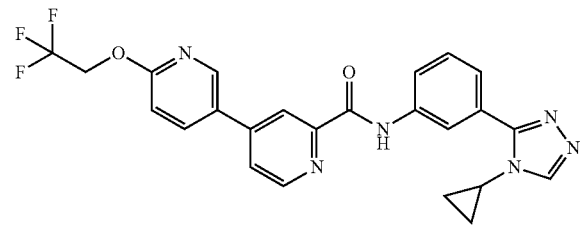 [SMILES: O=C(Nc1cccc(-c2nncn2C2CC2)c1)c1cc(-c2ccc(OCC(F)(F)F)nc2)ccn1]

N-(3-(4-cyclopropyl-4H-1,2,4-triazol-3-yl)phenyl)-6-(2,2,2-trifluoroethoxy)-3,4'-bipyridine-2'-carboxamide $C_{24}H_{19}F_3N_6O_2$. 481.1 (M+1). $^1$H NMR (DMSO) d 10.94 (s, 1H), 8.83 (d, J=4.4 Hz, 1H), 8.79 (d, J=2.4 Hz, 1H), 8.63 (s, 1H), 8.59 (s, 1H), 8.45 (d, J=1.2 Hz, 1H), 8.38 (dd, J=8.8, 2.8 Hz, 1H), 8.07 (m, 2H), 7.69 (d, J=8.0 Hz, 1H), 7.55 (t, J=8.0 Hz, 1H), 7.19 (d, J=8.0 Hz, 1H), 5.10 (q, J=9.0 Hz, 2H), 3.66 (m, 1H), 1.08 (m, 2H), 0.95 (m, 2H). $^{19}$F NMR (DMSO) d −72.28 (t, J=9.0 Hz, 3F).

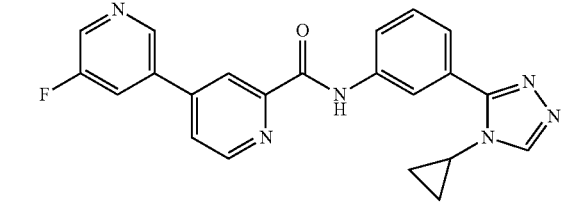

N-(3-(4-cyclopropyl-4H-1,2,4-triazol-3-yl)phenyl)-5-fluoro-3,4'-bipyridine-2'-carboxamide $C_{22}H_{17}FN_6O$. 400.4 (M+1). $^1$H NMR (DMSO) d 10.96 (s, 1H), 9.02 (m, 1H), 8.88 (d, J=5 Hz, 1H), 8.74 (d, J=3 Hz, 1H), 8.63 (s, 1H), 8.59 (s, 1H), 8.51-8.54 (m, 1H), 8.36-8.41 (m, 1H), 8.14 (dd, J=2.6 Hz, 1H), 8.07 (d, J=9 Hz, 1H), 7.69 (d, J=8 Hz, 1H), 7.55 (t, J=8 Hz, 1H), 3.62-3.68 (m, 1H), 1.06-1.12 (m, 2H), 0.94-0.97 (m, 2H).

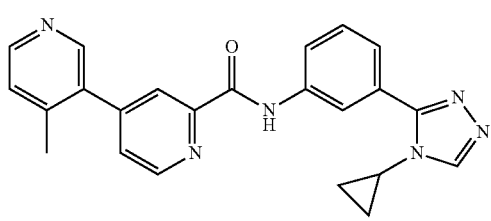 [SMILES: Cc1ccncc1-c1ccnc(C(=O)Nc2cccc(-c3nncn3C3CC3)c2)c1]

N-(3-(4-cyclopropyl-4H-1,2,4-triazol-3-yl)phenyl)-4-methyl-3,4'-bipyridine-2'-carboxamide $C_{23}H_{20}N_6O \times HCO_2H$. 397.1 (M+1). $^1$H NMR (DMSO) d 10.97 (s, 1H), 8.86 (d, J=5.2 Hz, 1H), 8.62 (s, 1H), 8.57 (s, 1H), 8.54 (d, J=5.2 Hz, 1H), 8.50 (s, 1H), 8.16 (d, J=1.2 Hz, 1H), 8.14 (s, 1H), 8.07 (dd, J=8.0, 0.8 Hz, 1H), 7.80 (dd, J=5.2, 2.0 Hz, 1H), 7.69 (d, J=8.0 Hz, 1H), 7.55 (t, J=8.0 Hz, 1H), 7.43 (d, J=5.2 Hz, 1H), 3.66 (m, 1H), 2.33 (s, 3H), 1.08 (m, 2H), 0.94 (m, 2H).

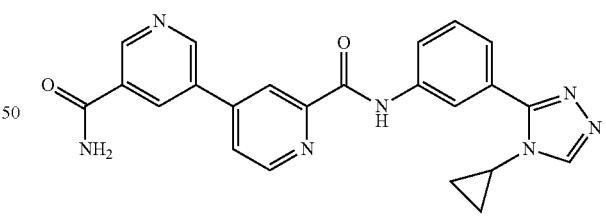

N2'-(3-(4-cyclopropyl-4H-1,2,4-triazol-3-yl)phenyl)-3,4'-bipyridine-2',5-dicarboxamide $C_{23}H_{19}N_7O_2$. 426.1 (M+1). $^1$H NMR (DMSO) d 10.97 (s, 1H), 9.25 (d, J=2 Hz, 1H), 9.14 (d, J=2 Hz, 1H), 8.89 (d, J=5 Hz, 1H), 8.72 (t, J=2 Hz, 1H), 8.63 (s, 1H), 8.58-8.63 (m, 2H), 8.37-8.39 (m, 1H), 8.18 (d, J=2.5 Hz, 1H), 8.06-8.10 (m, 1H), 7.74-7.76 (m, 1H), 7.70 (d, J=8 Hz, 1H), 7.56 (t, J=8 Hz, 1H), 3.65-3.70 (m, 1H), 1.08-1.12 (m, 2H), 0.93-0.97 (m, 2H).

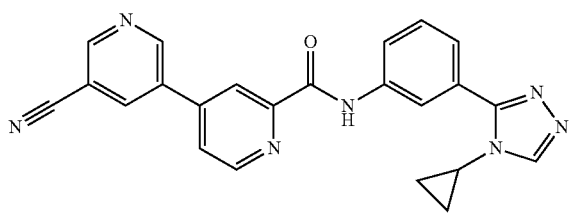 [SMILES: N#Cc1cncc(-c2ccnc(C(=O)Nc3cccc(-c4nncn4C4CC4)c3)c2)c1]

5-cyano-N-(3-(4-cyclopropyl-4H-1,2,4-triazol-3-yl)
phenyl)-3,4'-bipyridine-2'-carboxamide C₂₃H₁₇N₇O. 407.4 (M+1). ¹H NMR (DMSO) d 10.97 (s, 1H), 9.40 (d, J=2 Hz, 1H), 9.16 (d, J=2 Hz, 1H), 8.95 (t, J=2 Hz, 1H), 8.91 (d, J=5 Hz, 1H), 8.63 (s, 1H), 8.57-8.61 (m, 2H), 8.18 (dd, J=2.5 Hz, 1H), 8.05-8.09 (m, 1H), 7.70 (d, J=7 Hz, 1H), 7.56 (t, J=8 Hz, 1H), 3.65-3.69 (m, 1H), 1.05-1.11 (m, 2H), 0.94-0.98 (m, 2H).

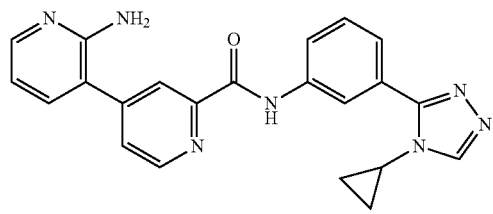 [SMILES: Nc1ncccc1-c1ccnc(C(=O)Nc2cccc(-c3nncn3C3CC3)c2)c1]

2-amino-N-(3-(4-cyclopropyl-4H-1,2,4-triazol-3-yl)
phenyl)-3,4'-bipyridine-2'-carboxamide C₂₂H₁₉N₇O. 398.1 (M+1). ¹H NMR (DMSO) d 10.93 (s, 1H), 8.79 (d, J=5.2 Hz, 1H), 8.62 (s, 1H), 8.58 (s, 1H), 8.24 (s, 1H), 8.05 (m, 2H), 7.76 (dd, J=5.2, 1.2 Hz, 1H), 7.68 (d, J=7.2 Hz, 1H), 7.53 (m, 2H), 6.73 (m, 1H), 6.03 (br, 2H), 3.67 (m, 1H), 1.08 (m, 2H), 0.94 (m, 2H).

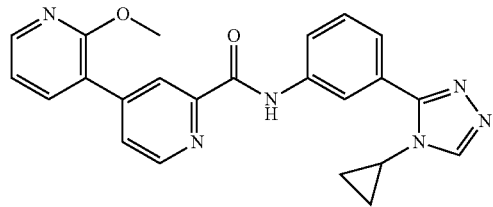 [SMILES: COc1ncccc1-c1ccnc(C(=O)Nc2cccc(-c3nncn3C3CC3)c2)c1]

N-(3-(4-cyclopropyl-4H-1,2,4-triazol-3-yl)phenyl)-
2-methoxy-3,4'-bipyridine-2'-carboxamide C₂₃H₂₀N₆O₂. 413.1 (M+1). ¹H NMR (DMSO) d 10.93 (s, 1H), 8.82 (d, J=5.2 Hz, 1H), 8.62 (s, 1H), 8.56 (s, 1H), 8.38 (s, 1H), 8.32 (dd, J=5.2, 2.0 Hz, 1H), 8.07 (d, J=7.2 Hz, 1H), 8.01 (dd, J=7.2, 1.6 Hz, 1H), 7.91 (dd, J=5.2, 2.0 Hz, 1H), 7.69 (d, J=8.0 Hz, 1H), 7.55 (t, J=8.0 Hz, 1H), 7.20 (dd, J=7.2, 5.2 Hz, 1H), 3.95 (s, 3H), 3.67 (m, 1H), 1.08 (m, 2H), 0.95 (m, 2H).

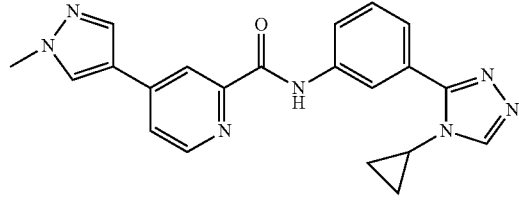 [SMILES: Cn1cc(-c2ccnc(C(=O)Nc3cccc(-c4nncn4C4CC4)c3)c2)cn1]

N-(3-(4-cyclopropyl-4H-1,2,4-triazol-3-yl)phenyl)-
4-(1-methyl-1H-pyrazol-4-yl)picolinamide C₂₁H₁₉N₇O. 386.1 (M+1). ¹H NMR (DMSO) d 10.85 (s, 1H), 8.67 (d, J=5.2 Hz, 1H), 8.62 (s, 1H), 8.58 (s, 1H), 8.56 (s, 1H), 8.29 (d, J=1.2 Hz, 1H), 8.18 (s, 1H), 8.04 (d, J=9.2 Hz, 1H), 7.85 (dd, J=5.2, 1.6 Hz, 1H), 7.68 (d, J=8.0 Hz, 1H), 7.54 (t, J=8.0 Hz, 1H), 3.91 (s, 3H), 3.66 (m, 1H), 1.08 (m, 2H), 0.95 (m, 2H).

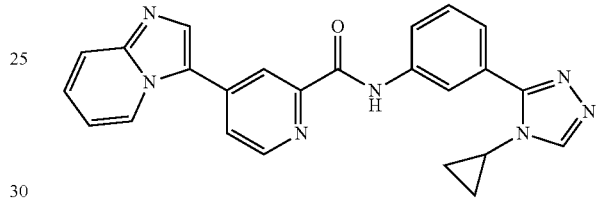

N-(3-(4-cyclopropyl-4H-1,2,4-triazol-3-yl)phenyl)-
4-(imidazo[1,2-a]pyridin-3-yl)picolinamide C₂₄H₁₉N₇O. 422.1 (M+1). ¹H NMR (DMSO) d 10.96 (s, 1H), 8.85 (m, 2H), 8.63 (s, 1H), 8.59 (s, 1H), 8.41 (d, J=1.2 Hz, 1H), 8.20 (s, 1H), 8.09 (d, J=8.0 Hz, 1H), 8.04 (dd, J=5.2, 1.6 Hz, 1H), 7.76 (d, J=9.2 Hz, 1H), 7.70 (d, J=8.0 Hz, 1H), 7.56 (t, J=8.0 Hz, 1H), 7.45 (dt, J=6.8, 1.2 Hz, 1H), 7.12 (dt, J=7.2, 1.2 Hz, 1H), 3.67 (m, 1H), 1.08 (m, 2H), 0.95 (m, 2H).

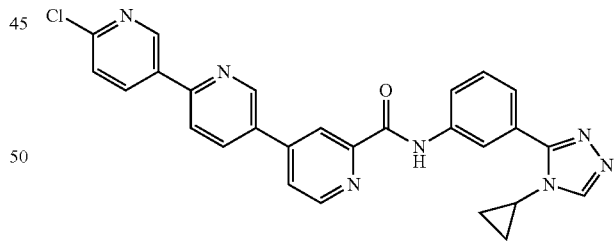

6-Chloro-[3,2';5',4″]terpyridine-2″-carboxylic acid
[3-(4-cyclopropyl-4H-[1,2,4]triazol-3-yl)-phenyl]
amide C₂₇H₂₀ClN₇O. 494.0 (M+1). ¹H NMR (DMSO) d 10.97 (s, 1H), 9.26 (d, J=2 Hz, 1H), 9.22 (d, J=2 Hz, 1H), 8.89 (d, J=5 Hz, 1H), 8.63 (s, 1H), 8.58-8.62 (m, 2H), 8.55-8.56 (m, 1H), 8.52 (d, J=2, 8 Hz, 1H), 8.30 (d, J=8 Hz, 1H), 8.18 (dd, J=2, 8 Hz, 1H), 8.09 (d, J=8 Hz, 1H), 7.70 (d, J=8 Hz, 1H), 7.56 (t, J=8 Hz, 1H), 3.65-3.69 (m, 1H), 1.06-1.11 (m, 2H), 0.94-0.98 (m, 2H).

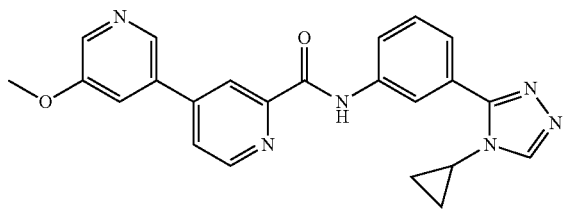 [SMILES: COc1cncc(-c2ccnc(C(=O)Nc3cccc(-c4nncn4C4CC4)c3)c2)c1]

N-(3-(4-cyclopropyl-4H-1,2,4-triazol-3-yl)phenyl)-5-methoxy-3,4'-bipyridine-2'-carboxamide C$_{23}$H$_{20}$N$_6$O$_2$. 413.1 (M+1). $^1$H NMR (DMSO) d 10.96 (s, 1H), 8.86 (d, J=5 Hz, 1H), 8.68 (d, J=2 Hz, 1H), 8.63 (s, 1H), 8.58-8.60 (m, 1H), 8.49-8.51 (m, 1H), 8.44 (d, J=2 Hz, 1H), 8.11 (dd, J=2.5 Hz, 1H), 8.08 (d, J=5 Hz, 1H), 7.88 (t, J=8 Hz, 1H), 7.69 (t, J=8 Hz, 1H), 7.55 (t, J=8 Hz, 1H), 3.96 (s, 3H), 3.65-3.68 (m, 1H), 1.06-1.12 (m, 2H), 0.92-0.95 (m, 2H).

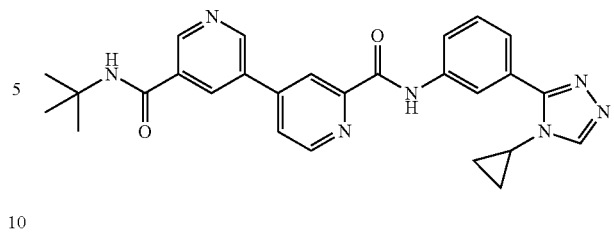

N5-tert-butyl-N2'-(3-(4-cyclopropyl-4H-1,2,4-triazol-3-yl)phenyl)-3,4'-bipyridine-2',5-dicarboxamide C$_{27}$H$_{27}$N$_7$O$_2$×HCO$_2$H. 482.1 (M+1). $^1$H NMR (DMSO) d 10.98 (s, 1H), 9.20 (d, J=2 Hz, 1H), 9.05 (d, J=2 Hz, 1H), 8.89 (d, J=5 Hz, 1H), 8.63 (s, 1H), 8.58-8.62 (m, 3H), 8.22 (s, 1H), 8.17 (dd, J=2.5 Hz, 1H), 8.08 (d, J=8 Hz, 1H), 7.70 (d, J=8 Hz, 1H), 7.70 (d, J=8 Hz, 1H), 7.56 (t, J=8 Hz, 1H), 3.64-3.70 (m, 1H), 1.43 (s, 9H), 1.06-1.11 (m, 2H), 0.92-0.97 (m, 2H).

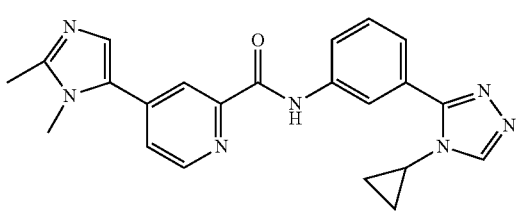 [SMILES: Cc1ncc(-c2ccnc(C(=O)Nc3cccc(-c4nncn4C4CC4)c3)c2)n1C]

N-(3-(4-cyclopropyl-4H-1,2,4-triazol-3-yl)phenyl)-4-(1,2-dimethyl-1H-imidazol-5-yl)picolinamide C$_{22}$H$_{21}$N$_7$O. 400.1 (M+1). $^1$H NMR (DMSO) d 10.91 (s, 1H), 8.76 (d, J=5.2, 1H), 8.62 (s, 1H), 8.56 (s, 1H), 8.18 (d, J=0.8 Hz, 1H), 8.07 (d, J=8.0 Hz, 1H), 7.77 (dd, J=5.2, 1.6 Hz, 1H), 7.68 (d, J=8.0 Hz, 1H), 7.54 (t, J=8.0 Hz, 1H), 7.33 (s, 1H), 3.69 (s, 3H), 3.66 (m, 1H), 2.40 (s, 3H), 1.08 (m, 2H), 0.95 (m, 2H).

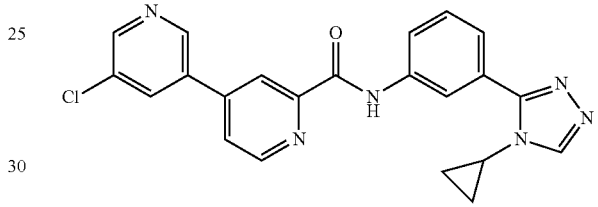

5-chloro-N-(3-(4-cyclopropyl-4H-1,2,4-triazol-3-yl)phenyl)-3,4'-bipyridine-2'-carboxamide C$_{22}$H$_{17}$ClN$_6$O. 417.1 (M+1). $^1$H NMR (DMSO) d 10.96 (s, 1H), 9.06 (s, 1H), 8.85 (d, J=5 Hz, 1H), 8.76 (s, 1H), 8.60 (s, 1H), 8.58 (s, 1H), 8.56 (s, 1H), 8.50 (d, J=2 Hz, 1H), 8.10 (d, J=5 Hz, 1H), 8.04 (d, J=9 Hz, 1H), 7.66 (d, J=8 Hz, 1H), 7.52 (d, J=8 Hz, 1H), 3.65-3.68 (m, 1H), 1.06-1.12 (m, 2H), 0.93-0.98 (m, 2H).

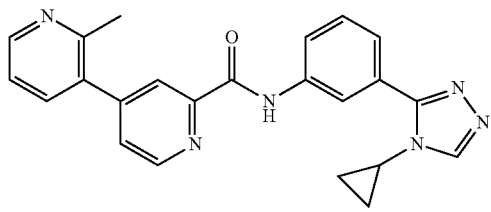 [SMILES: Cc1ncccc1-c1ccnc(C(=O)Nc2cccc(-c3nncn3C3CC3)c2)c1]

N-(3-(4-cyclopropyl-4H-1,2,4-triazol-3-yl)phenyl)-2-methyl-3,4'-bipyridine-2'-carboxamide C$_{23}$H$_{20}$N$_6$O. 397.1 (M+1). $^1$H NMR (DMSO) d 10.97 (s, 1H), 8.85 (d, J=4.8 Hz, 1H), 8.62 (s, 1H), 8.58 (s, 1H), 8.57 (s, 1H), 8.16 (s, 1H), 8.07 (d, J=8.0 Hz, 1H), 7.80 (m, 2H), 7.69 (d, J=8.0 Hz, 1H), 7.54 (t, J=8.0 Hz, 1H), 7.40 (dd, J=7.8, 1.2 Hz, 1H), 3.66 (m, 1H), 2.48 (s, 3H), 1.07 (m, 2H), 0.95 (m, 2H).

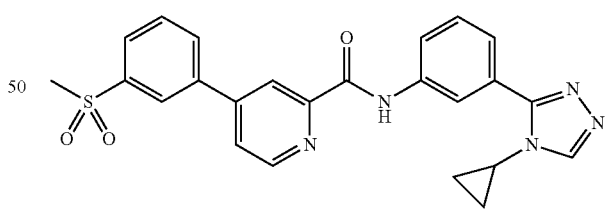

N-(3-(4-cyclopropyl-4H-1,2,4-triazol-3-yl)phenyl)-4-(3-(methylsulfonyl)phenyl)picolinamide C$_{24}$H$_{21}$N$_5$O$_3$S. 460.0 (M+1). $^1$H NMR (DMSO) d 10.97 (s, 1H), 8.89 (d, J=6 Hz, 1H), 8.63 (s, 1H), 8.60 (s, 1H), 8.54 (s, 1H), 8.40 (s, 1H), 8.28 (d, J=8 Hz, 1H), 8.11-8.16 (m, 1H), 8.08 (d, J=8 Hz, 2H), 7.86 (t, J=8 Hz, 1H), 7.70 (d, J=8 Hz, 1H), 7.56 (t, J=8 Hz, 1H), 3.64-3.70 (m, 1H), 3.35 (s, 3H), 1.06-1.12 (m, 2H), 0.92-0.97 (m, 2H).

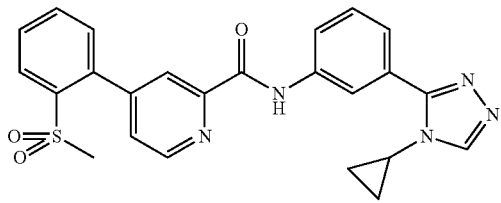 [SMILES: CS(=O)(=O)c1ccccc1-c1ccnc(C(=O)Nc2cccc(-c3nncn3C3CC3)c2)c1]

N-(3-(4-cyclopropyl-4H-1,2,4-triazol-3-yl)phenyl)-
4-(2-(methylsulfonyl)-phenyl)picolinamide $C_{24}H_{21}N_5O_3S$. 460.1 (M+1). $^1$H NMR (DMSO) d 10.97 (s, 1H), 8.82 (d, J=4 Hz, 1H), 8.62 (s, 1H), 8.55-8.57 (m, 1H), 8.13-8.17 (m, 2H), 8.04-8.08 (m, 1H), 7.74-7.88 (m, 3H), 7.69 (d, J=8 Hz, 1H), 7.55 (t, J=8 Hz, 1H), 7.50 (dd, J=2, 8 Hz, 1H), 3.63-3.67 (m, 1H), 3.07 (s, 3H), 1.06-1.09 (m, 2H), 0.92-0.96 (m, 2H).

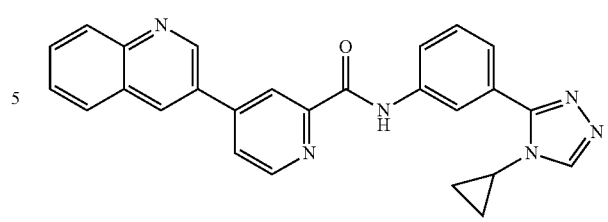

N-(3-(4-cyclopropyl-4H-1,2,4-triazol-3-yl)phenyl)-
4-(quinolin-3-yl)picolinamide $C_{26}H_{20}N_6O$. 423.1 (M+1). $^1$H NMR (DMSO) d 10.99 (s, 1H), 9.44 (d, J=2.0 Hz, 1H), 9.02 (s, 1H), 8.92 (d, J=5.2 Hz, 1H), 8.66 (s, 1H), 8.63 (s, 1H), 8.62 (s, 1H), 8.28 (d, J=4.0 Hz, 1H), 8.18 (d, J=8.0 Hz, 1H), 8.11 (m, 2H), 7.87 (t, J=7.2 Hz, 1H), 7.72 (m, 2H), 7.56 (t, J=8.0 Hz, 1H), 3.68 (m, 1H), 1.08 (m, 2H), 0.95 (m, 2H).

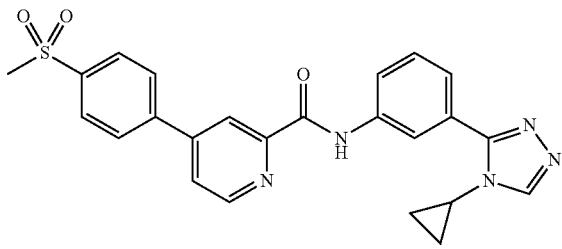 [SMILES: CS(=O)(=O)c1ccc(-c2ccnc(C(=O)Nc3cccc(-c4nncn4C4CC4)c3)c2)cc1]

N-(3-(4-cyclopropyl-4H-1,2,4-triazol-3-yl)phenyl)-
4-(4-(methylsulfonyl)phenyl)picolinamide $C_{24}H_{21}N_5O_3S$. 460.1 (M+1). $^1$H NMR (DMSO) d 10.97 (s, 1H), 8.89 (d, J=5 Hz, 1H), 8.61 (d, J=5 Hz, 1H), 8.61 (d, J=13 Hz, 1H), 8.49 (d, J=1 Hz, 1H), 8.19 (d, J=8 Hz, 2H), 8.05-8.14 (m, 4H), 7.70 (d, J=8 Hz, 1H), 7.56 (t, J=8 Hz, 1H), 3.64-3.69 (m, 1H), 3.30 (s, 3H), 1.06-1.12 (m, 2H), 0.92-0.97 (m, 2H).

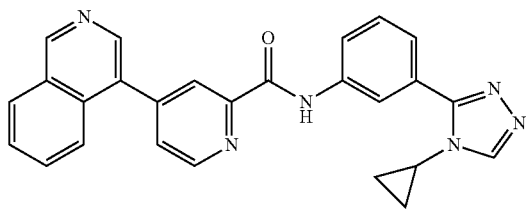

N-(3-(4-cyclopropyl-4H-1,2,4-triazol-3-yl)phenyl)-
4-(isoquinolin-4-yl)picolinamide $C_{26}H_{20}N_6O$. 433.1 (M+1). $^1$H NMR (DMSO) d 11.03 (s, 1H), 9.47 (s, 1H), 8.95 (d, 5.2 Hz, 1H), 8.62 (s, 1H), 8.59 (m, 2H), 8.30 (m, 2H), 8.09 (d, J=12.0 Hz, 1H), 7.94 (d, J=5.2 Hz, 1H), 7.91 (m, 2H), 7.81 (m, 1H), 7.70 (d, J=8.0 Hz, 1H), 7.56 (t, J=8.0 Hz, 1H), 3.67 (m, 1H), 1.08 (m, 2H), 0.95 (m, 2H).

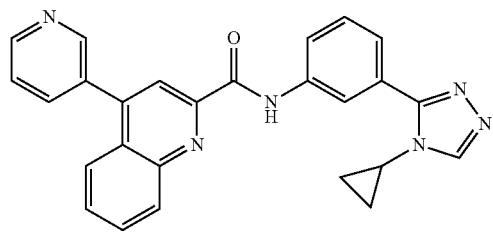 [SMILES: O=C(Nc1cccc(-c2nncn2C2CC2)c1)c1cc(-c2cccnc2)c2ccccc2n1]

N-(3-(4-cyclopropyl-4H-1,2,4-triazol-3-yl)phenyl)-
4-(pyridin-3-yl)quinoline-2-carboxamide $C_{26}H_{20}N_6O$. 433.1 (M+1). $^1$H NMR (DMSO) d 11.04 (s, 1H), 8.84 (d, J=2 Hz, 1H), 8.80 (dd, J=1, 5 Hz, 1H), 8.64 (s, 1H), 8.62 (s, 1H), 8.40 (d, J=8 Hz, 1H), 8.18 (s, 1H), 8.11 (d, J=8 Hz, 2H), 8.00 (t, J=7 Hz, 1H), 7.93 (d, J=8 Hz, 1H), 7.79 (t, J=8 Hz, 1H), 7.73 (d, J=8 Hz, 1H), 7.67 (dd, J=6, 8 Hz, 1H), 7.59 (t, J=8 Hz, 1H), 3.65-3.70 (m, 1H), 1.06-1.12 (m, 2H), 0.93-0.98 (m, 2H).

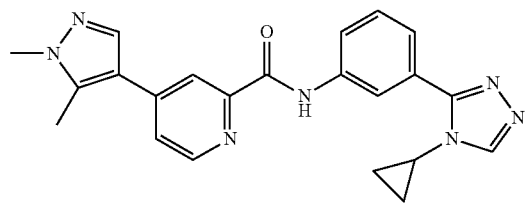 [SMILES: Cc1c(-c2ccnc(C(=O)Nc3cccc(-c4nncn4C4CC4)c3)c2)cnn1C]

N-(3-(4-cyclopropyl-4H-1,2,4-triazol-3-yl)phenyl)-
4-(1,5-dimethyl-1H-pyrazol-4-yl)picolinamide $C_{22}H_{21}N_7O$. 400.1 (M+1). $^1$H NMR (DMSO) d 10.87 (s, 1H), 8.70 (d, J=5.2 Hz, 1H), 8.62 (s, 1H), 8.56 (s, 1H), 8.18 (d, J=1.2 Hz, 1H), 8.05 (d, J=9.2 Hz, 1H), 7.92 (s, 1H), 7.73 (dd, J=5.2, 2.0 Hz, 1H), 7.67 (d, J=8.0 Hz, 1H), 7.54 (t, J=8.0 Hz, 1H), 3.83 (s, 3H), 3.66 (m, 1H), 2.50 (s, 3H), 1.07 (m, 2H), 0.94 (m, 2H).

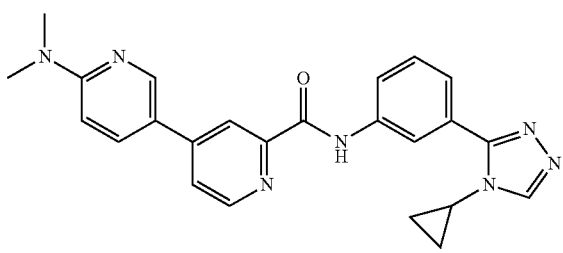

N-(3-(4-cyclopropyl-4H-1,2,4-triazol-3-yl)phenyl)-
6-(dimethylamino)-3,4'-bipyridine-2'-carboxamide C₂₄H₂₃N₇O. 426.1 (M+1). ¹H NMR (DMSO) d 10.89 (s, 1H), 8.70 (m, 2H), 8.62 (s, 1H), 8.58 (s, 1H), 8.36 (d, J=1.2 Hz, 1H), 8.07 (m, 2H), 8.96 (dd, J=5.6, 2.0 Hz, 1H), 7.68 (d, J=8.0 Hz, 1H), 7.54 (t, J=8.0 Hz, 1H), 6.79 (d, J=8.8 Hz, 1H), 3.66 (m, 1H), 3.12 (s, 6H), 1.08 (m, 2H), 0.95 (m, 2H).

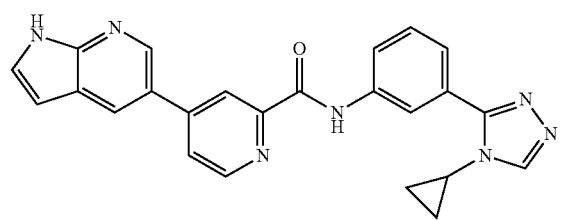 [SMILES: O=C(Nc1cccc(-c2nncn2C2CC2)c1)c1cc(-c2cnc3[nH]ccc3c2)ccn1]

N-(3-(4-cyclopropyl-4H-1,2,4-triazol-3-yl)phenyl)-
4-(1H-pyrrolo[2,3-b]pyridin-5-yl)picolinamide C₂₄H₁₉N₇O. 422.1 (M+1). ¹H NMR (DMSO) d 11.91 (s, 1H), 10.94 (s, 1H), 8.81 (d, J=5.2 Hz, 1H), 7.50 (d, J=2.0, 1H), 8.63 (s, 1H), 8.60 (s, 1H), 8.52 (m, 2H), 8.10 (m, 2H), 7.69 (d, J=8.0 Hz, 1H), 7.58 (m, 2H), 6.59 (dd, J=8.0, 4.0 Hz, 1H). 3.67 (m, 1H), 1.09 (m, 2H), 0.95 (m, 2H).

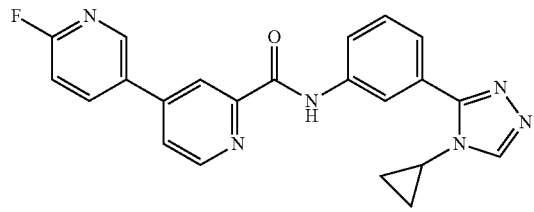 [SMILES: O=C(Nc1cccc(-c2nncn2C2CC2)c1)c1cc(-c2ccc(F)nc2)ccn1]

N-(3-(4-cyclopropyl-4H-1,2,4-triazol-3-yl)phenyl)-
6-fluoro-3,4'-bipyridine-2'-carboxamide C₂₂H₁₇FN₆O. 422.1 (M+1). ¹H NMR (DMSO) d 10.96 (s, 1H), 8.86 (d, J=4.8 Hz, 1H), 8.82 (d, J=2.4 Hz, 1H), 8.63 (s, 1H), 8.57 (m, 2H), 8.48 (d, J=1.2 Hz, 1H), 8.09 (m, 2H), 7.69 (d, J=8.0 Hz, 1H), 7.55 (t, J=8.0 Hz, 1H), 7.40 (dd, J=8.4, 2.8 Hz, 1H), 3.66 (m, 1H), 1.08 (m, 2H), 0.96 (m, 2H). ¹⁹F NMR (DMSO) d −68.2 (d, J=8.0 Hz, 1F).

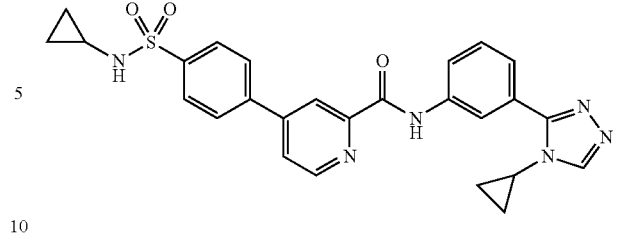

N-(3-(4-cyclopropyl-4H-1,2,4-triazol-3-yl)phenyl)-
4-(4-(N-cyclopropylsulfamoyl)-phenyl)picolinamide C₂₆H₂₄N₆O₃S. 500.6 (M+1). ¹H NMR (DMSO) d 10.97 (s, 1H), 8.88 (d, J=5 Hz, 1H), 8.63 (s, 1H), 8.60 (s, 1H), 8.40 (s, 1H), 8.16 (d, J=8 Hz, 1H), 8.05-8.12 (m, 3H), 7.98 (d, J=8 Hz, 2H), 7.69 (d, J=8 Hz, 2H), 7.55 (t, J=8 Hz, 1H), 3.63-3.68 (m, 1H), 2.12-2.20 (m, 1H), 1.06-1.10 (m, 2H), 0.93-0.97 (m, 2H), 0.50-0.54 (m, 2H), 0.40-0.44 (m, 2H).

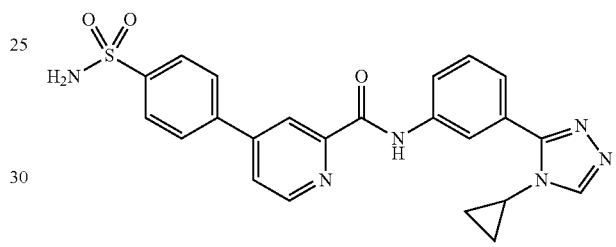

N-(3-(4-cyclopropyl-4H-1,2,4-triazol-3-yl)phenyl)-
4-(4-sulfamoylphenyl)picolinamide C₂₃H₂₀N₆O₃S. 461.0 (M+1). ¹H NMR (DMSO) d 10.96 (s, 1H), 8.87 (d, J=5 Hz, 1H), 8.63 (s, 1H), 8.60 (s, 1H), 8.48 (d, J=1 Hz, 1H), 8.12 (d, J=8 Hz, 2H), 8.09 (dd, J=2.5 Hz, 1H), 8.07 (s, 1H), 7.99 (d, J=8 Hz, 2H), 7.70 (d, J=8 Hz, 1H), 7.55 (t, J=8 Hz, 1H), 7.51 (s, 2H), 3.63-3.68 (m, 1H), 1.06-1.12 (m, 2H), 0.92-0.97 (m, 2H).

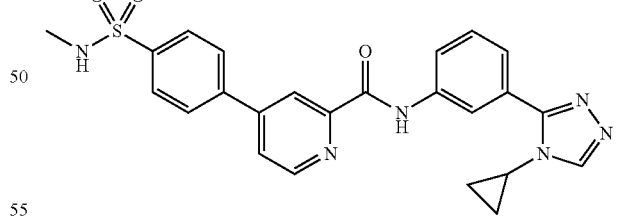

N-(3-(4-cyclopropyl-4H-1,2,4-triazol-3-yl)phenyl)-
4-(4-(N-methylsulfamoyl)-phenyl)picolinamide C₂₄H₂₂N₆O₃S. 475.0 (M+1). ¹H NMR (DMSO) d 10.97 (s, 1H), 8.88 (d, J=5 Hz, 1H), 8.63 (s, 1H), 8.60 (s, 1H), 8.49 (s, 1H), 8.15 (d, J=8 Hz, 2H), 8.09 (dt, J=2.5 Hz, 1H), 7.95 (d, J=8 Hz, 2H), 7.69 (d, J=8 Hz, 1H), 7.61 (q, J=8 Hz, 1H), 7.56 (t, 18 Hz, 1H), 3.64-3.69 (m, 1H), 2.46 (s, 3H), 1.06-1.12 (m, 2H), 0.92-0.97 (m, 2H).

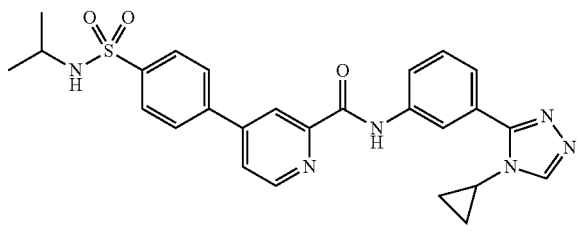

N-(3-(4-cyclopropyl-4H-1,2,4-triazol-3-yl)phenyl)-
4-(4-(N-isopropylsulfamoyl)-phenyl)picolinamide C$_{24}$H$_{22}$N$_6$O$_3$S. 503.1 (M+1). $^1$H NMR (DMSO) d 10.96 (s, 1H), 8.87 (d, J=5 Hz, 1H), 8.63 (s, 1H), 8.60 (s, 1H), 8.48 (s, 1H), 8.13 (d, J=8 Hz, 2H), 8.06-8.10 (m, 2H), 7.97 (d, J=8 Hz, 2H), 7.74 (d, J=7 Hz, 1H), 7.69 (d, J=8 Hz, 1H), 7.55 (t, J=8 Hz, 1H), 3.65-3.68 (m, 1H), 3.28 (m, 1H), 0.94-1.10 (m, 10H).

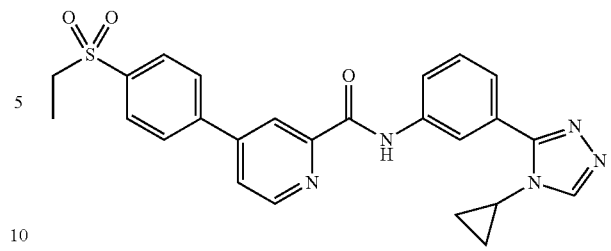 [SMILES: CNS(=O)(=O)c1ccc(-c2ccnc(C(=O)Nc3cccc(-c4nncn4C4CC4)c3)c2)cc1]

N-(3-(4-cyclopropyl-4H-1,2,4-triazol-3-yl)phenyl)-
4-(4-(ethylsulfonyl)phenyl)picolinamide C$_{25}$H$_{23}$N$_5$O$_3$S. 474.1 (M−1). $^1$H NMR (DMSO) d 10.97 (s, 1H), 8.89 (d, J=5 Hz, 1H), 8.61 (d, J=13 Hz, 2H), 8.50 (s, 1H), 8.20 (d, J=8 Hz, 2H), 8.11 (d, J=4 Hz, 1H), 8.04-8.10 (m, 3H), 7.70 (d, J=8 Hz, 1H), 7.56 (t, J=8 Hz, 1H), 3.64-3.68 (m, 1H), 3.38 (q, J=7 Hz, 2H), 1.15 (t, J=7 Hz, 3H), 1.06-1.10 (m, 2H), 0.93-0.98 (m, 2H).

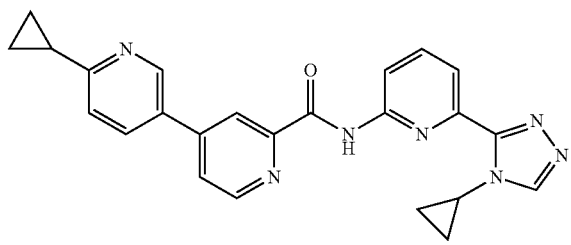 [SMILES: O=C(Nc1cccc(-c2nncn2C2CC2)n1)c1cc(-c2ccc(C3CC3)nc2)ccn1]

6-cyclopropyl-N-(6-(4-cyclopropyl-4H-1,2,4-triazol-
3-yl)pyridin-2-yl)-3,4'-bipyridine-2'-carboxamide C$_{24}$H$_{21}$N$_7$O. 424.1 (M+1). $^1$H NMR (DMSO) d 10.67 (s, 1H), 8.94 (d, J=2 Hz, 1H), 8.83 (d, J=8 Hz, 1H), 8.69 (s, 1H), 8.49 (d, J=1 Hz, 1H), 8.39 (d, J=8 Hz, 2H), 8.20 (dd, J=2, 8 Hz, 1H), 8.07-8.11 (m, 2H), 7.88 (d, J=7 Hz, 1H), 7.49 (d, J=8 Hz, 1H), 4.08-4.12 (m, 1H), 2.18-2.24 (m, 1H), 0.98-1.10 (m, 8H).

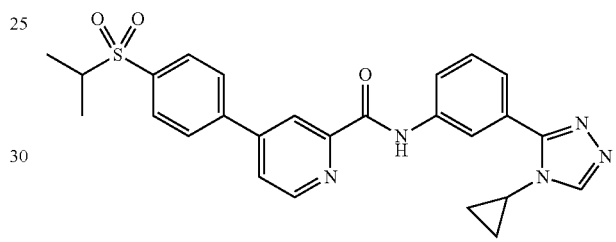

N-(3-(4-cyclopropyl-4H-1,2,4-triazol-3-yl)phenyl)-
4-(4-(isopropylsulfonyl)phenyl)picolinamide C$_{26}$H$_{25}$N$_5$O$_3$S. 488.0 (M+1). $^1$H NMR (DMSO) d 10.97 (s, 1H), 8.89 (d, J=5 Hz, 1H), 8.61 (d, J=12 Hz, 2H), 8.50 (s, 1H), 8.20 (d, J=8 Hz, 2H), 8.12 (d, J=5 Hz, 1H), 8.08 (d, J=8 Hz, 1H), 8.03 (d, J=8 Hz, 2H), 7.70 (d, J=8 Hz, 1H), 7.55 (t, J=8 Hz, 1H), 3.65-3.69 (m, 1H), 3.52 (sept, J=7 Hz, 1H), 1.19 (d, J=7 Hz, 6H), 1.04-1.10 (m, 2H), 0.93-0.98 (m, 2H).

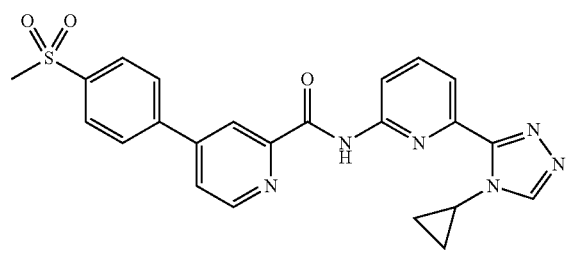 [SMILES: CS(=O)(=O)c1ccc(-c2ccnc(C(=O)Nc3cccc(-c4nncn4C4CC4)n3)c2)cc1]

N-(6-(4-cyclopropyl-4H-1,2,4-triazol-3-yl)pyridin-2-
yl)-4-(4-(methylsulfonyl)-phenyl)picolinamide C$_{23}$H$_{20}$N$_6$O$_3$S. 461.1 (M+1). $^1$H NMR (DMSO) d 10.70 (s, 1H), 8.90 (d, J=5 Hz, 1H), 8.69 (s, 1H), 8.54 (d, J=1 Hz, 1H), 8.41 (d, J=8 Hz, 1H), 8.21 (d, J=8 Hz, 2H), 8.09-8.17 (m, 4H), 7.89 (d, J=8 Hz, 1H), 4.09-4.13 (m, 1H), 3.30 (s, 3H), 0.98-1.08 (m, 2H).

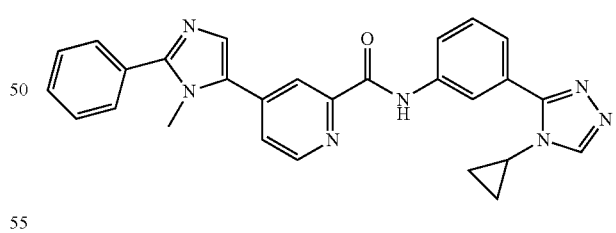

N-(3-(4-cyclopropyl-4H-1,2,4-triazol-3-yl)phenyl)-
4-(1-methyl-2-phenyl-1H-imidazol-5-yl)picolina-
mide C$_{27}$H$_{23}$N$_7$O. 462.1 (M+1). $^1$H NMR (DMSO) d 10.94 (s, 1H), 8.82 (d, J=4.8 Hz, 1H), 8.63 (s, 1H), 8.58 (s, 1H), 8.32 (d, J=1.2 Hz, 1H), 8.08 (d, J=8.0 Hz, 1H), 7.89 (dd, J=5.2, 2.0 Hz, 1H), 7.78 (m, 2H), 7.69 (d, J=8.0 Hz, 1H), 7.61 (s, 1H), 7.54 (m, 4H), 3.82 (s, 3H), 3.67 (m, 1H), 1.08 (m, 2H), 0.95 (m, 2H).

77

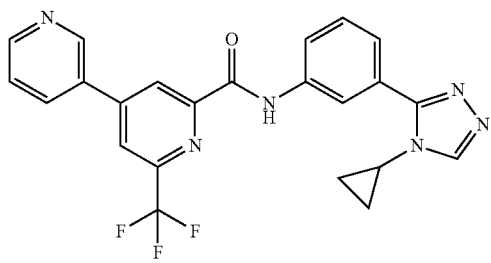 [SMILES: O=C(Nc1cccc(-c2nncn2C2CC2)c1)c1cc(-c2cccnc2)cc(C(F)(F)F)n1]

N-(3-(4-cyclopropyl-4H-1,2,4-triazol-3-yl)phenyl)-6'-(trifluoromethyl)-3,4'-bipyridine-2'-carboxamide $C_{23}H_{17}F_3N_6O$. 451.1 (M+1). $^1$H NMR (DMSO) d 10.72 (s, 1H), 9.22 (s, 1H), 8.76 (d, J=4 Hz, 1H), 8.70 (d, J=1 Hz, 1H), 8.63 (s, 1H), 8.58 (d, J=1 Hz, 1H), 8.52 (s, 1H), 8.46 (dt, J=2, 8 Hz, 1H), 7.99-8.15 (m, 1H), 7.74 (d, J=8 Hz, 1H), 7.56-7.76 (m, 2H), 3.64-3.68 (m, 1H), 1.05-1.09 (m, 2H) 0.94-0.98 (m, 2H).

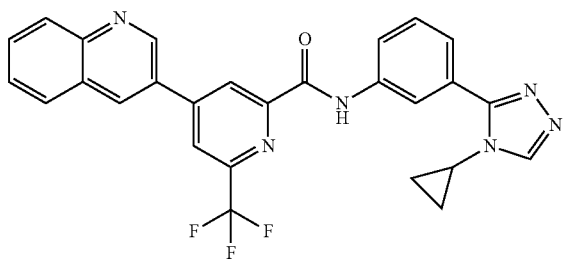 [SMILES: O=C(Nc1cccc(-c2nncn2C2CC2)c1)c1cc(-c2cnc3ccccc3c2)cc(C(F)(F)F)n1]

N-(3-(4-cyclopropyl-4H-1,2,4-triazol-3-yl)phenyl)-4-(quinolin-3-yl)-6-(trifluoromethyl)picolinamide $C_{27}H_{19}F_3N_6O$. 501.0 (M+1). $^1$H NMR (DMSO) d 10.75 (s, 1H), 9.53 (d, J=2 Hz, 1H), 9.15 (d, J=2 Hz, 1H), 8.88 (s, 1H), 8.74 (d, J=1 Hz, 1H), 8.64 (s, 1H), 8.55 (s, 1H), 8.15 (dd, J=8.15 Hz, 2H), 8.03 (d, J=10 Hz, 1H), 7.86-7.92 (m, 1H), 7.70-7.76 (m, 2H), 7.59 (t, J=8 Hz, 1H), 3.63-3.68 (m, 1H), 1.07-1.12 (m, 2H) 0.94-0.98 (m, 2H).

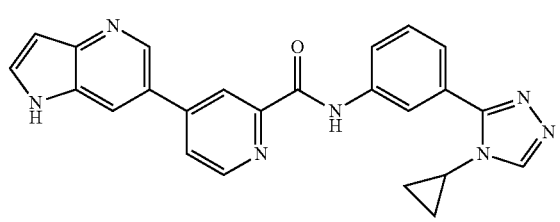 [SMILES: O=C(Nc1cccc(-c2nncn2C2CC2)c1)c1cc(-c2cnc3cc[nH]c3c2)ccn1]

N-(3-(4-cyclopropyl-4H-1,2,4-triazol-3-yl)phenyl)-4-(1H-pyrrolo[3,2-b]pyridin-6-yl)picolinamide $C_{24}H_{19}N_7O$. 422.1 (M+1). $^1$H NMR (DMSO) d 11.70 (s, 1H), 10.95 (s, 1H), 8.89 (d, J=2.0 Hz, 1H), 8.82 (d, J=4.4 Hz, 1H), 8.64 (s, 1H), 8.61 (s, 1H), 8.51 (d, J=1.2 Hz, 1H), 8.33 (s, 1H), 8.13 (dd, J=4.4, 1.6 Hz, 1H), 8.08 (d, J=8.0 Hz, 1H), 7.85 (t, J=2.8 Hz, 1H), 7.69 (d, J=8.0 Hz, 1H), 7.56 (t, J=8.0 Hz, 1H), 6.68 (s, 1H), 3.67 (m, 1H), 1.08 (m, 2H), 0.95 (m, 2H).

78

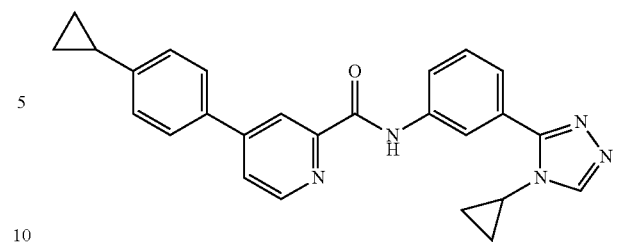

N-(3-(4-cyclopropyl-4H-1,2,4-triazol-3-yl)phenyl)-4-(4-cyclopropylphenyl)picolinamide $C_{26}H_{23}N_5O$. 422.1 (M+1). $^1$H NMR (DMSO) d 10.92 (s, 1H), 8.78 (d, J=5.2 Hz, 1H), 8.63 (s, 1H), 8.59 (s, 1H), 8.39 (d, J=1.2 Hz, 1H), 8.07 (d, J=8.0 Hz, 1H), 7.99 (dd, J=5.2, 1.2 Hz, 1H), 7.79 (d, J=8.0 Hz, 2H), 7.69 (d, J=8.0 Hz, 1H), 7.55 (t, J=8.0 Hz, 1H), 7.27 (d, J=8.0 Hz, 2H), 3.66 (m, 1H), 2.01 (m, 1H), 1.08 (m, 2H), 1.05 (m, 2H), 0.95 (m, 2H), 0.76 (m, 2H).

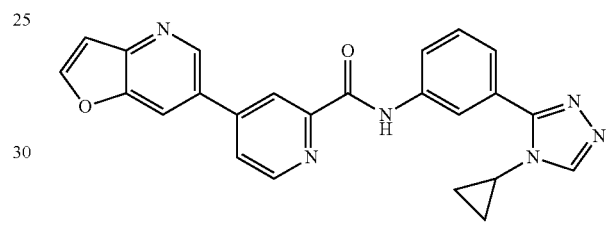

N-(3-(4-cyclopropyl-4H-1,2,4-triazol-3-yl)phenyl)-4-(furo[3,2-b]pyridin-6-yl)picolinamide $C_{24}H_{18}N_6O_2$. 423.1 (M+1). $^1$H NMR (DMSO) d 11.01 (s, 1H), 9.09 (s, 1H), 8.87 (m, 2H), 8.68 (s, 1H), 8.64 (s, 1H), 8.57 (s, 1H), 8.47 (s, 1H), 8.18 (m, 1H), 8.11 (m, 1H), 7.70 (d, J=8.0 Hz, 1H), 7.59 (t, J=8.0 Hz, 1H), 7.26 (s, 1H), 3.71 (m, 1H), 1.11 (m, 2H), 0.99 (m, 2H).

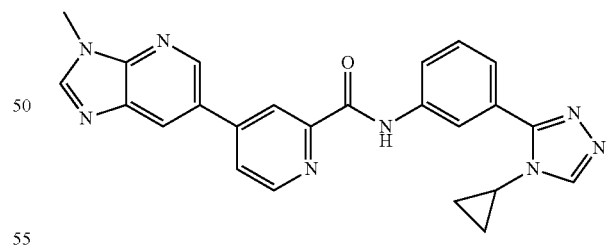

N-(3-(4-cyclopropyl-4H-1,2,4-triazol-3-yl)phenyl)-4-(3-methyl-3H-imidazo[4,5-b]pyridin-6-yl)picolinamide $C_{24}H_{20}N_8O$. 437.1 (M+1). $^1$H NMR (DMSO) d 10.96 (s, 1H), 8.92 (s, 1H), 8.84 (d, J=5.2 Hz, 1H), 8.60 (m, 5H), 8.15 (d, J=5.2 Hz, 1H), 8.09 (d, J=8.0 Hz, 1H), 7.70 (d, J=8.0 Hz, 1H), 7.56 (t, J=8.0 Hz, 1H), 3.91 (s, 3H), 3.68 (m, 1H), 1.09 (m, 2H), 0.95 (m, 2H).

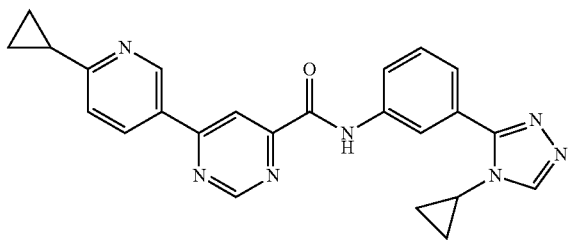 [SMILES: O=C(Nc1cccc(-c2nncn2C2CC2)c1)c1cc(-c2ccc(C3CC3)nc2)ncn1]

N-(3-(4-cyclopropyl-4H-1,2,4-triazol-3-yl)phenyl)-6-(6-cyclopropylpyridin-3-yl)pyrimidine-4-carboxamide $C_{24}H_{21}N_7O$. 424.1 (M+1). $^1$H NMR (DMSO) d 11.10 (s, 1H), 9.47 (d, J=1.6 Hz, 1H), 9.31 (d, J=1.6 Hz, 1H), 8.65 (d, J=1.6 Hz, 1H), 8.63 (s, 1H), 8.57 (s, 1H), 8.54 (dd, J=8.0, 2.0 Hz, 1H), 8.07 (d, J=8.0 Hz, 1H), 7.72 (d, J=8.0 Hz, 1H), 7.58 (d, J=8.0 Hz, 1H), 7.53 (t, J=8.0 Hz, 1H), 3.66 (m, 1H), 2.24 (m, 1H), 1.05 (m, 6H), 0.96 (m, 2H).

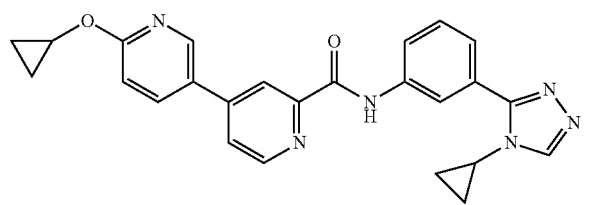 [SMILES: O=C(Nc1cccc(-c2nncn2C2CC2)c1)c1cc(-c2ccc(OC3CC3)nc2)ccn1]

6-cyclopropoxy-N-(3-(4-cyclopropyl-4H-1,2,4-triazol-3-yl)phenyl)-3,4'-bipyridine-2'-carboxamide $C_{25}H_{22}N_6O_2$. 439.1 (M+1). $^1$H NMR (DMSO) d 10.93 (s, 1H), 8.81 (d, 5.2 Hz, 1H), 8.78 (d, J=2.4 Hz, 1H), 8.63 (s, 1H), 8.58 (s, 1H), 8.43 (d, J=0.8 Hz, 1H), 8.30 (dd, J=8.4, 2.4 Hz, 1H), 8.04 (m, 2H), 7.69 (d, J=8.0 Hz, 1H), 7.55 (t, J=8.0 Hz, 1H), 7.05 (d, J=8.0 Hz, 1H), 4.30 (m, 1H), 3.67 (m, 1H), 1.08 (m, 2H), 0.95 (m, 2H), 0.81 (m, 2H), 0.74 (m, 2H).

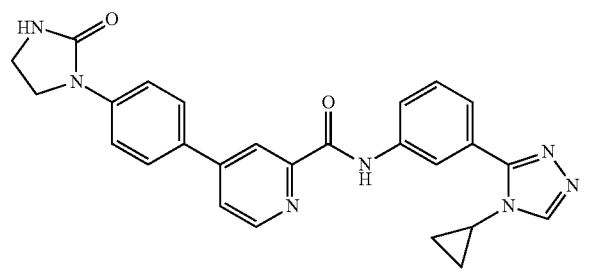 [SMILES: O=C(Nc1cccc(-c2nncn2C2CC2)c1)c1cc(-c2ccc(N3CCNC3=O)cc2)ccn1]

N-(3-(4-cyclopropyl-4H-1,2,4-triazol-3-yl)phenyl)-4-(4-(2-oxoimidazolidin-1-yl)phenyl)picolinamide $C_{26}H_{23}N_7O_2 \times HCl$. 466.1 (M+1). $^1$H NMR (DMSO) d 11.03 (s, 1H), 9.28 (s, 1H), 8.77 (d, S=5.2 Hz, 1H), 8.68 (s, 1H), 8.43 (d, J=1.2 Hz, 1H), 8.14 (d, J=8.0 Hz, 1H), 8.02 (dd, J=5.2, 2.0 Hz, 1H), 7.90 (d, J=8.8 Hz, 2H), 7.76 (d, J=8.8 Hz, 2H), 7.72 (d, J=8.0 Hz, 1H), 7.62 (t, J=8.0 Hz, 1H), 7.12 (b, 1H), 3.93 (t, J=8.0 Hz, 2H), 3.79 (m, 1H), 3.45 (t, J=8.0 Hz, 2H), 1.06 (m, 2H), 0.95 (m, 2H).

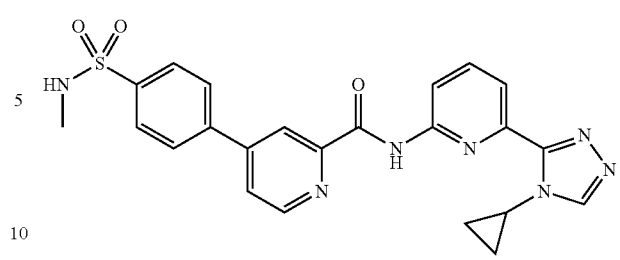

N-(6-(4-cyclopropyl-4H-1,2,4-triazol-3-yl)pyridin-2-yl)-4-(4-(N-methylsulfamoyl)phenyl)picolinamide $C_{23}H_{21}N_7O_3S$. 476.2 (M+1). $^1$H NMR (DMSO) d 10.74 (s, 1H), 9.00 (s, 1H), 8.89 (d, J=5 Hz, 1H), 8.54 (d, J=1 Hz, 1H), 8.44 (d, J=8 Hz, 1H), 8.12-8.19 (m, 4H), 7.90-7.97 (m, 3H), 7.64 (d, J=8 Hz, 2H), 4.14-4.18 (m, 1H), 2.46 (s, 3H), 1.04-1.12 (m, 4H).

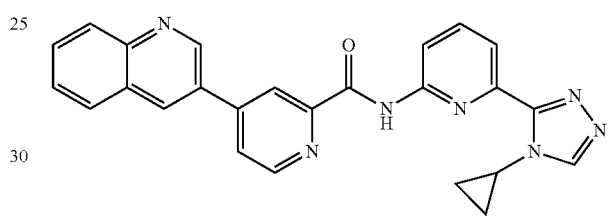

N-(6-(4-cyclopropyl-4H-1,2,4-triazol-3-yl)pyridin-2-yl)-4-(quinolin-3-yl)picolinamide $C_{25}H_{19}N_7O$. 434.1 (M+1). $^1$H NMR (DMSO) d 10.73 (s, 1H), 9.44 (s, 1H), 9.03 (s, 1H), 8.92 (d, J=5 Hz, 1H), 8.70 (d, J=7 Hz, 2H), 8.42 (d, J=8 Hz, 1H), 8.31 (d, J=4 Hz, 1H), 8.17 (d, J=8 Hz, 1H), 8.12 (t, J=8 Hz, 2H), 7.85-7.91 (m, 2H), 7.72 (t, J=8 Hz, 1H), 4.09-4.13 (m, 1H), 0.97-1.11 (m, 4H).

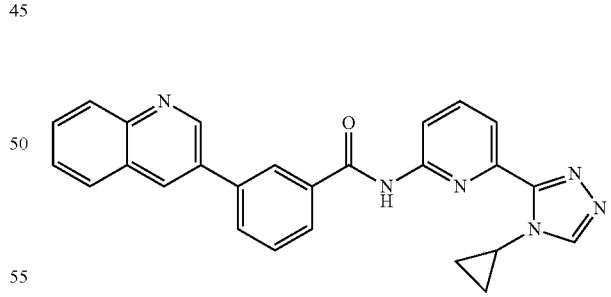

N-(6-(4-cyclopropyl-4H-1,2,4-triazol-3-yl)pyridin-2-yl)-3-(quinolin-3-yl)benzamide $C_{26}H_{20}N_6O$. 433.1 (M+1). $^1$H NMR (DMSO) d 10.94 (s, 1H), 9.38 (d, J=2 Hz, 1H), 8.79 (d, J=2 Hz, 1H), 8.65 (s, 1H), 8.47 (s, 1H), 8.31 (d, J=8 Hz, 1H), 8.16 (d, J=8 Hz, 1H), 8.02-8.10 (m, 4H), 7.77-7.83 (m, 2H), 7.74 (t, J=8 Hz, 1H), 7.68 (t, J=8 Hz, 1H), 4.24-4.28 (m, 1H), 0.92-1.02 (m, 4H).

81

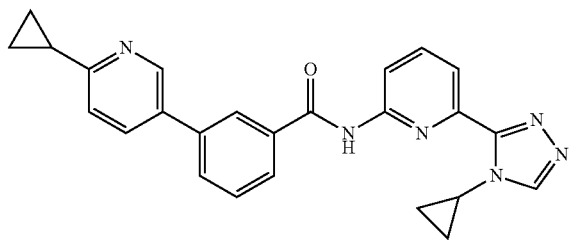

N-(6-(4-cyclopropyl-4H-1,2,4-triazol-3-yl)pyridin-2-yl)-3-(6-cyclopropylpyridin-3-yl)benzamide $C_{25}H_{22}N_6O$. 423.1 (M+1). $^1$H NMR (DMSO) d 10.87 (s, 1H), 8.82 (d, J=2 Hz, 1H), 8.65 (s, 1H), 8.28 (d, J=8 Hz, 1H), 8.25 (s, 1H), 8.05 (d, J=8 Hz, 1H), 8.04 (t, J=8 Hz, 1H), 7.95 (t, J=7 Hz, 2H), 7.81 (d, J=8 Hz, 1H), 7.65 (t, J=8 Hz, 1H), 7.42 (d, J=8 Hz, 1H), 4.22-4.27 (m, 1H), 2.14-2.19 (m, 1H), 0.91-1.02 (m, 8H).

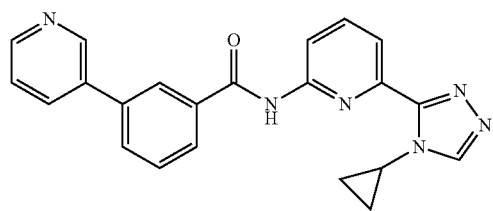 [SMILES: O=C(Nc1cccc(-c2nncn2C2CC2)n1)c1cccc(-c2cccnc2)c1]

N-(6-(4-cyclopropyl-4H-1,2,4-triazol-3-yl)pyridin-2-yl)-3-(pyridin-3-yl)benzamide $C_{22}H_{18}N_6O$. 383.1 (M+1). $^1$H NMR (DMSO) d 10.90 (s, 1H), 9.02 (d, J=2 Hz, 1H), 8.65 (s, 1H), 8.62 (dd, J=1, 4 Hz, 1H), 8.30 (d, J=2 Hz, 1H), 8.28 (s, 1H), 8.21 (dt, J=2, 8 Hz, 1H), 8.05 (t, J=8 Hz, 1H), 8.00 (d, J=8 Hz, 2H), 7.81 (d, J=7 Hz, 1H), 7.69 (t, J=8 Hz, 1H), 7.54 (dd, J=5, 8 Hz, 1H), 4.25 (dddd, J=4, 8, 12, 16 Hz, 1H), 0.90-1.02 (m, 4H).

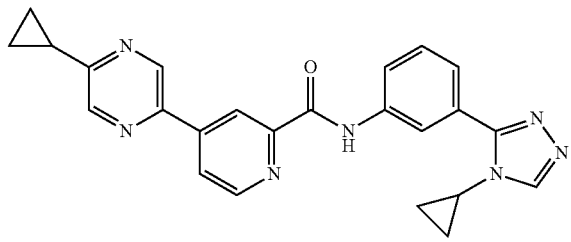 [SMILES: O=C(Nc1cccc(-c2nncn2C2CC2)c1)c1cc(-c2cnc(C3CC3)cn2)ccn1]

N-(3-(4-cyclopropyl-4H-1,2,4-triazol-3-yl)phenyl)-4-(5-cyclopropylpyrazin-2-yl)picolinamide $C_{24}H_{21}N_7O$. 422.1 (M+1). $^1$H NMR (DMSO) d 10.95 (s, 9.31 (d, J=0.8 Hz, 1H), 8.89 (d, J=4.4 Hz, 1H), 8.83 (d, J=1.2 Hz, 2H), 8.63 (s, 1H), 8.60 (s, 1H), 8.386 (dd, J=5.2, 1.6 Hz, 1H), 8.07 (d, J=8.0 Hz, 1H), 7.67 (d, J=8.0 Hz, 1H), 7.55 (t, J=8.0 Hz, 1H), 3.66 (m, 1H), 2.35 (m, 1H), 1.10 (m, 6H), 0.95 (m, 2H).

82

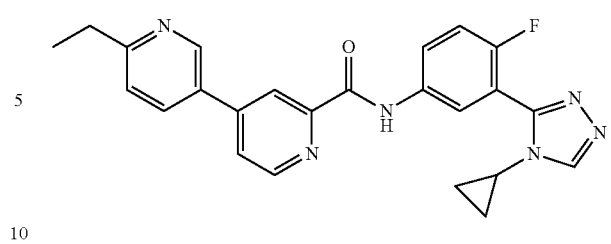

N-(3-(4-cyclopropyl-4H-1,2,4-triazol-3-yl)-4-fluorophenyl)-6-ethyl-3,4'-bipyridine-2'-carboxamide $C_{24}H_{21}FN_6O$. 429.2 (M+1). $^1$H NMR (DMSO) d 11.02 (s, 1H), 9.00 (d, J=2 Hz, 1H), 8.83 (d, J=5 Hz, 1H), 8.70 (s, 1H), 8.44 (s, 1H), 8.22-8.28 (m, 2H), 8.14-8.19 (m, 1H), 8.08 (dd, J=2.5 Hz, 1H), 7.47 (t, J=9 Hz, 2H), 3.40-3.45 (m, 1H), 2.84 (q, J=8 Hz, 2H), 1.28 (t, J=8 Hz, 3H), 0.81-0.93 (m, 4H).

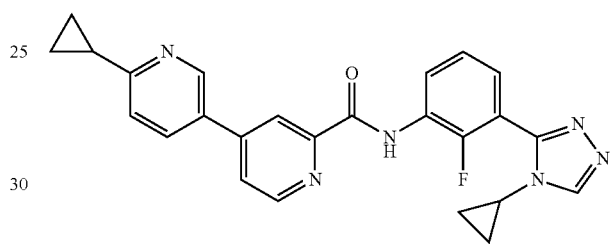

6-cyclopropyl-N-(3-(4-cyclopropyl-4H-1,2,4-triazol-3-yl)-2-fluorophenyl)-3,4'-bipyridine-2'-carboxamide $C_{25}H_{21}FN_6O$. 441.1 (M+1). $^1$H NMR (DMSO) d 10.63 (s, 1H), 8.94 (d, J=2 Hz, 1H), 8.82 (d, J=9 Hz, 1H), 8.72 (s, 1H), 8.45 (s, 1H), 8.25-8.30 (m, 1H), 8.20 (dd, J=2, 8 Hz, 1H), 8.08 (dd, J=2.5 Hz, 1H), 7.24-7.50 (m, 3H), 3.43-3.47 (m, 1H), 2.18-2.24 (m, 1H), 1.00-1.07 (m, 4H), 0.82-0.93 (m, 4H).

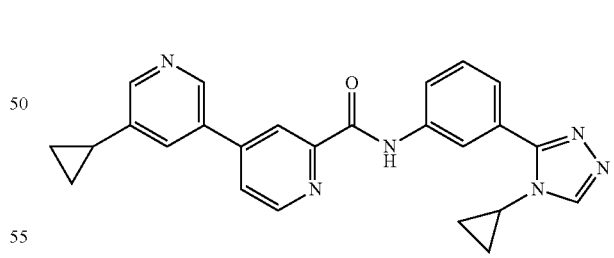

5-cyclopropyl-N-(3-(4-cyclopropyl-4H-1,2,4-triazol-3-yl)phenyl)-3,4'-bipyridine-2'-carboxamide $C_{25}H_{22}N_6O$. 423.1 (M+1). $^1$H NMR (DMSO) d 10.94 (s, 1H), 8.84 (m, 2H), 8.63 (s, 1H), 8.59 (s, 1H), 8.54 (d, J=2.0 Hz, 1H), 8.47 (d, J=0.8 Hz, 1H), 8.08 (m, 2H), 7.90 (t, J=2.0 Hz, 1H), 7.69 (d, J=8.0 Hz, 1H), 7.55 (t, J=8.0 Hz, 1H), 3.66 (m, 1H), 2.07 (m, 1H), 1.06 (m, 4H), 0.96 (m, 4H).

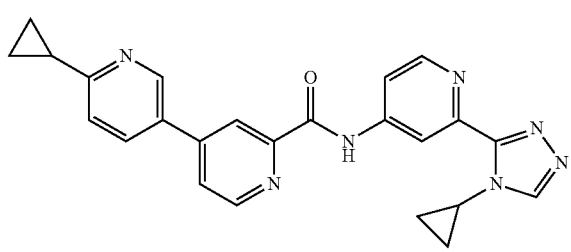

6-cyclopropyl-N-(2-(4-cyclopropyl-4H-1,2,4-triazol-3-yl)pyridin-4-yl)-3,4'-bipyridine-2'-carboxamide C₂₄H₂₁N₇O. 424.2 (M+1). ¹H NMR (DMSO) d 11.31 (s, 1H), 8.94 (d, J=2 Hz, 1H), 8.84 (d, J=5 Hz, 1H), 8.77 (d, J=5 Hz, 1H), 8.66 (t, J=2 Hz, 2H), 8.45 (d, J=2 Hz, 1H), 8.20 (dd, J=2, 8 Hz, 1H), 8.09 (dd, J=2.5 Hz, 1H), 8.06 (dd, J=2, 6 Hz, 1H), 7.50 (d, J=8 Hz, 1H), 3.98-4.02 (m, 1H), 2.07-2.21 (m, 1H), 0.93-1.05 (m, 8H).

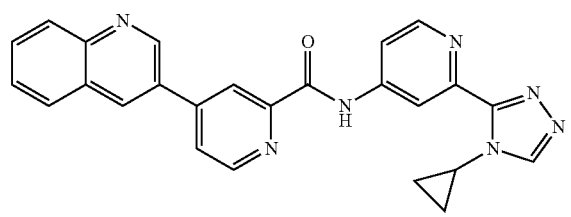 [SMILES: O=C(Nc1ccnc(-c2nncn2C2CC2)c1)c1cc(-c2cnc3ccccc3c2)ccn1]

N-(2-(4-cyclopropyl-4H-1,2,4-triazol-3-yl)pyridin-4-yl)-4-(quinolin-3-yl)picolinamide C₂₅H₁₉N₇O. 434.1 (M+1). ¹H NMR (DMSO) d 11.36 (s, 1H), 9.44 (d, J=2 Hz, 1H), 9.02 (d, J=2 Hz, 1H), 8.94 (d, J=13 Hz, 1H), 8.78 (d, J=2 Hz, 1H), 8.68 (s, 1H), 8.67 (s, 2H), 8.31 (dd, J=2.5 Hz, 1H), 8.18 (d, J=8 Hz, 1H), 8.12 (d, J=8 Hz, 1H), 8.09 (dd, J=2, 6 Hz, 1H), 7.84-7.89 (m, 1H), 7.72 (t, J=8 Hz, 1H), 3.97-4.04 (m, 1H), 0.93-1.04 (m, 4H).

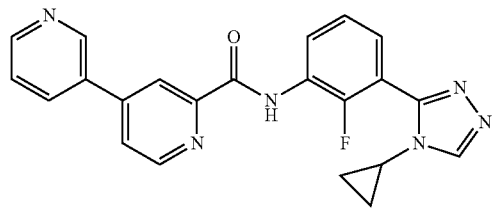 [SMILES: O=C(Nc1cccc(-c2nncn2C2CC2)c1F)c1cc(-c2cccnc2)ccn1]

N-(3-(4-cyclopropyl-4H-1,2,4-triazol-3-yl)-2-fluorophenyl)-3,4'-bipyridine-2'-carboxamide C₂₂H₁₇FN₆O. 401.1 (M+1). ¹H NMR (DMSO) d 10.63 (s, 1H), 9.12 (d, J=2 Hz, 1H), 8.87 (d, J=5 Hz, 1H), 8.71-8.74 (m, 2H), 8.50 (d, J=1 Hz, 1H), 8.32-8.36 (m, 1H), 8.25-8.29 (m, 1H), 8.14 (dd, J=2.5 Hz, 1H), 7.58-7.62 (m, 1H), 7.42-7.49 (m, 2H), 3.43-3.47 (m, 1H), 0.82-0.93 (m, 4H).

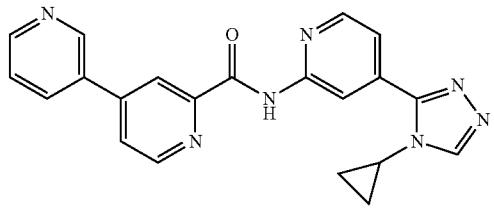 [SMILES: O=C(Nc1cc(-c2nncn2C2CC2)ccn1)c1cc(-c2cccnc2)ccn1]

N-(4-(4-cyclopropyl-4H-1,2,4-triazol-3-yl pyridin-2-yl)-3,4'-bipyridine-2'-carboxamide C₂₁H₁₇N₇O. 384.2 (M+1). ¹H NMR (DMSO) d 10.64 (s, 1H), 9.13 (d, J=2 Hz, 1H), 9.02 (s, 1H), 8.89 (d, J=5 Hz, 1H), 8.76 (s, 1H), 8.71-8.74 (m, 1H), 8.59 (d, J=6 Hz, 1H), 8.54 (s, 1H), 8.33-8.37 (m, 1H), 8.17 (dd, J=2.5 Hz, 1H), 7.83 (dd, J=1, 5 Hz, 1H), 7.60 (dd, J=5, 8 Hz, 1H), 3.73-3.77 (m, 1H), 1.04-1.21 (m, 4H).

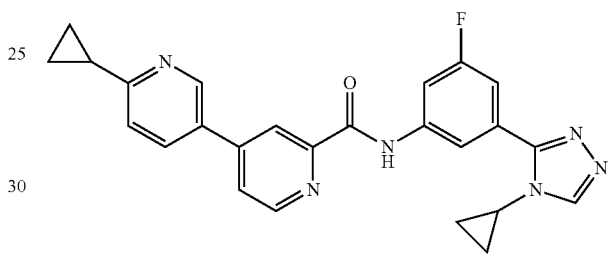

6-cyclopropyl-N-(3-(4-cyclopropyl-4H-1,2,4-triazol-3-yl)-5-fluorophenyl)-3,4'-bipyridine-2'-carboxamide C₂₅H₂₁FN₆O. 441.2 (M+1). ¹H NMR (DMSO) d 11.17 (s, 1H), 8.93 (d, J=2 Hz, 1H), 8.83 (d, J=5 Hz, 1H), 8.66 (s, 1H), 8.42-8.47 (m, 2H), 8.19 (dd, J=2, 8 Hz, 1H), 7.47-7.53 (m, 2H), 3.67-3.73 (m, 1H), 2.17-2.23 (m, 1H), 0.95-1.06 (m, 8H).

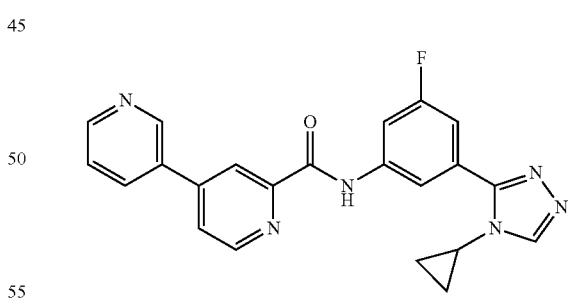

N-(3-(4-cyclopropyl-4H-1,2,4-triazol-3-yl)-5-fluorophenyl)-3,4'-bipyridine-2'-carboxamide C₇₇H₁₇FN₆O. 401.1 (M+1). ¹H NMR (DMSO) d 10.20 (s, 1H), 9.12 (d, J=2 Hz, 1H), 8.87 (d, J=5 Hz, 1H), 8.73 (dd, J=2.5 Hz, 1H), 8.67 (s, 1H), 8.48 (d, J=5 Hz, 2H), 8.34 (d, J=8 Hz, 1H), 8.11-8.15 (m, 1H), 8.06 (d, J=8 Hz, 1H), 7.60 (dd, J=2, 8 Hz, 1H), 7.52 (d, J=9 Hz, 1H), 3.69-3.72 (m, 1H), 1.08-1.13 (m, 2H), 0.93-0.98 (m, 2H).

85

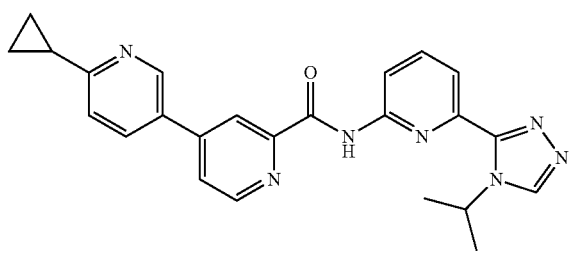 [SMILES: CC(C)n1cnnc1-c1cccc(NC(=O)c2cc(-c3ccc(C4CC4)nc3)ccn2)n1]

6-cyclopropyl-N-(6-(4-isopropyl-4H-1,2,4-triazol-3-yl)pyridin-2-yl)-3,4'-bipyridine-2'-carboxamide C$_{24}$H$_{23}$N$_7$O. 426.3 (M+1). $^1$H NMR (DMSO) d 10.70 (s, 1H), 8.95 (d, J=2 Hz, 1H), 8.91 (s, 1H), 8.85 (d, J=5 Hz, 1H), 8.49 (d, J=1 Hz, 1H), 8.36 (d, J=8 Hz, 1H), 8.21 (dd, J=2, 8 Hz, 1H), 8.07-8.15 (m, 2H), 7.91 (d, J=7 Hz, 1H), 7.50 (d, J=8.0 Hz, 1H), 5.53 (sept, J=6 Hz, 1H), 2.18-2.24 (m, 1H), 1.51 (d, J=6 Hz, 6H) 0.98-1.06 (m, 4H).

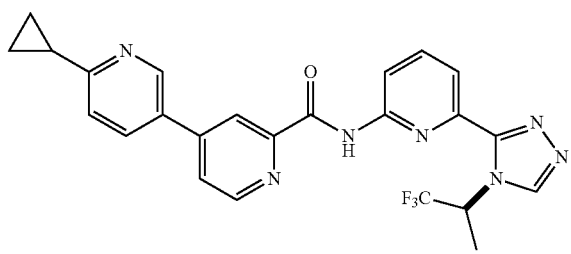

(S)-6-cyclopropyl-N-(6-(4-(1,1,1-trifluoropropan-2-yl)-4H-1,2,4-triazol-3-yl)pyridin-2-yl)-3,4'-bipyridine-2'-carboxamide C$_{24}$H$_{20}$F$_3$N$_7$O×HCl. 480.1 (M+1). $^1$H NMR (DMSO) d 11.10 (s, 1H), 9.17 (s, 1H), 9.04 (s, 1H), 8.89 (d, J=9 Hz, 1H), 8.52 (s, 1H), 8.40 (br s, 1H), 8.30 (d, J=8 Hz, 1H), 8.08-8.14 (m, 2H), 7.99 (d, J=8 Hz, 1H), 7.59 (d, J=8 Hz, 1H), 7.06 (app p, J=7 Hz, 1H), 6.00 (br s, 1H), 2.30-2.34 (m, 1H), 1.85 (d, J=7 Hz, 3H), 1.08-1.15 (m, 4H).

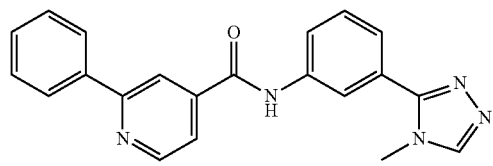 [SMILES: Cn1cnnc1-c1cccc(NC(=O)c2ccnc(-c3ccccc3)c2)c1]

86

5-(2,5-difluorophenyl)-N-(3-(4-methyl-4H-1,2,4-triazol-3-yl)phenyl)nicotinamide

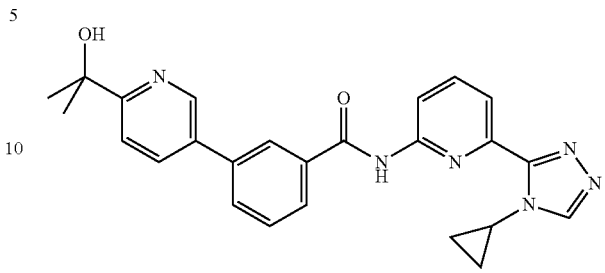

N-(6-(4-cyclopropyl-4H-1,2,4-triazol-3-yl)pyridin-2-yl)-3-(6-(2-hydroxypropan-2-yl)pyridin-3-yl)benzamide C$_{25}$H$_{4}$N$_6$O$_2$×HCl. 441.1 (M+1). $^1$H NMR (DMSO) d 11.18 (s, 1H), 9.32 (s, 1H), 9.10 (d, J=1.6 Hz, 1H), 8.94 (d, J=8.0 Hz, 1H), 8.48 (s, 1H), 8.35 (d, J=8.0 Hz, 1H), 8.22 (d, J=8.0 Hz, 1H), 8.10 (m, 3H), 7.88 (d, J=8.0 Hz, 1H), 7.75 (t, J=8.0 Hz, 1H), 4.43 (m, 1H), 1.65 (s, 6H), 1.05 (m, 4H).

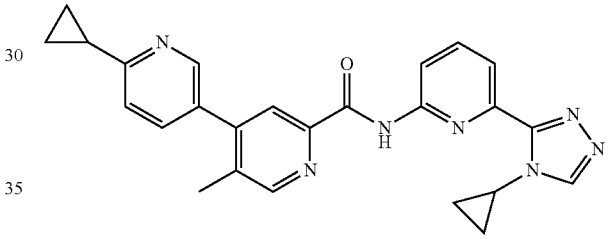

6-cyclopropyl-N-(6-(4-cyclopropyl-4H-1,2,4-triazol-3-yl)pyridin-2-yl)-5'-methyl-3,4'-bipyridine-2'-carboxamide C$_{25}$H$_{23}$N$_7$O. 438.6 (M+1). $^1$H NMR (DMSO) d 10.62 (s, 1H), 8.72 (s, 1H), 8.69 (s, 1H), 8.55 (s, 1H), 8.37 (d, J=8 Hz, 1H). 8.09 (t, J=8 Hz, 1H), 8.04 (s, 1H), 7.87 (d, J=8 Hz, 1H), 7.84 (dd, J=2, 8 Hz, 1H), 7.47 (d, J=8 Hz, 1H), 4.07-4.11 (m, 1H), 2.39 (s, 3H) 2.18-2.22 (m, 1H), 0.98-1.07 (m, 8H).

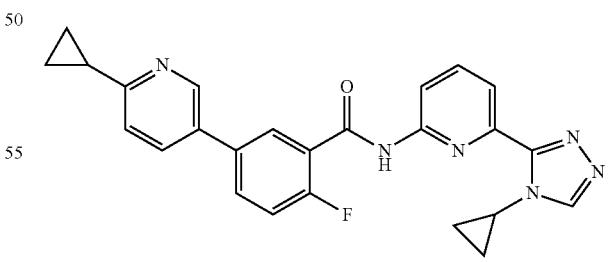

N-(6-(4-cyclopropyl-4H-1,2,4-triazol-3-yl)pyridin-2-yl)-5-(6-cyclopropylpyridin-3-yl)-2-fluorobenzamide C$_{25}$H$_{21}$FN$_6$O. 441.2 (M+1). $^1$H NMR (DMSO) d 10.98 (s, 1H), 8.76 (d, 2 Hz, 1H), 8.64 (s, 1H), 8.29 (d, J=9 Hz, 1H), 8.05 (t, J=8 Hz, 1H), 8.01 (d, J=2 Hz, 1H), 7.98-8.00 (m, 1H), 7.88-7.94 (m, 1H), 7.86 (d, J=8 Hz, 1H), 7.48 (t, J=8 Hz, 1H), 7.40 (d, J=8 Hz, 1H), 4.18-4.22 (m, 1H), 2.17-2.20 (m, 1H), 0.91-1.07 (m, 8H).

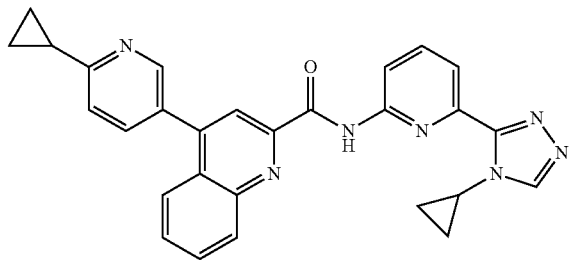 [SMILES: O=C(Nc1cccc(-c2nncn2C2CC2)n1)c1cc(-c2ccc(C3CC3)nc2)c2ccccc2n1]

N-(6-(4-cyclopropyl-4H-1,2,4-triazol-3-yl)pyridin-2-yl)-4-(6-cyclopropylpyridin-3-yl)quinoline-2-carboxamide $C_{28}H_{23}N_7O$. 474.4 (M+1). $^1$H NMR (DMSO) d 10.83 (s, 1H), 8.68 (s, 1H), 8.62 (d, J=1 Hz, 1H), 8.39 (d, J=9 Hz, 1H), 8.32 (d, J=8 Hz, 1H), 8.17 (s, 1H), 8.10 (t, J=8 Hz, 1H), 7.91-797 (m, 3H), 7.88 (d, J=8 Hz, 1H), 7.77 (t, J=8 Hz, 1H), 7.54 (d, J=8 Hz, 1H), 4.07-4.10 (m, 1H), 2.21-2.24 (m, 1H), 1.01-1.10 (m, 8H).

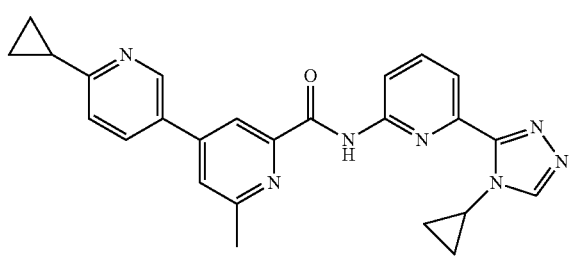 [SMILES: Cc1cc(-c2ccc(C3CC3)nc2)cc(C(=O)Nc2cccc(-c3nncn3C3CC3)n2)n1]

6-cyclopropyl-N-(6-(4-cyclopropyl-4H-1,2,4-triazol-3-yl)pyridin-2-yl)-6'-methyl-3,4'-bipyridine-2'-carboxamide $C_{25}H_{23}N_7O$. 438.2 (M+1). $^1$H NMR (DMSO) d 10.65 (s, 1H), 9.91 (s, 1H), 8.69 (s, 1H), 8.38 (d, J=8 Hz, 1H), 8.29 (s, 1H), 8.17 (d, J=8 Hz, 1H), 8.10 (t, J=8 Hz, 1H), 7.98 (s, 1H), 7.88 (d, J=8 Hz, 1H), 7.47 (d, J=8 Hz, 1H), 3.96-4.00 (m, 1H), 2.68 (s, 3H), 2.18-2.22 (m, 1H), 1.00-1.11 (m, 8H).

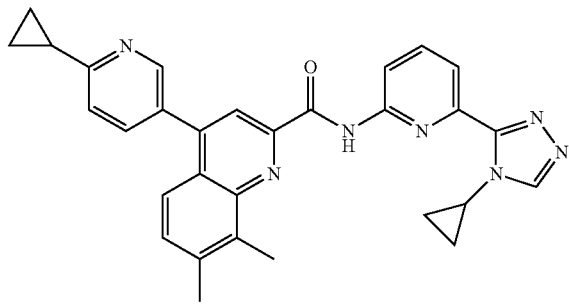 [SMILES: Cc1ccc2c(-c3ccc(C4CC4)nc3)cc(C(=O)Nc3cccc(-c4nncn4C4CC4)n3)nc2c1C]

N-(6-(4-cyclopropyl-4H-1,2,4-triazol-3-yl)pyridin-2-yl)-4-(6-cyclopropylpyridin-3-yl)-7,8-dimethylquinoline-2-carboxamide $C_{30}H_{27}N_7O$. 502.3 (M+1). $^1$H NMR (DMSO) d 10.83 (s, 1H), 8.71 (s, 1H), 8.61 (s, 1H), 8.40 (d, J=9 Hz, 1H), 8.08-8.14 (m, 2H), 7.90-7.95 (m, 2H), 7.69 (d, J=8 Hz, 1H), 7.61 (d, J=9 Hz, 1H), 7.55 (d, J=8 Hz, 1H), 4.09-4.14 (m, 1H), 2.84 (s, 3H), 2.55 (s, 3H), 2.11-2.15 (m, 1H), 1.03-1.15 (m, 8H).

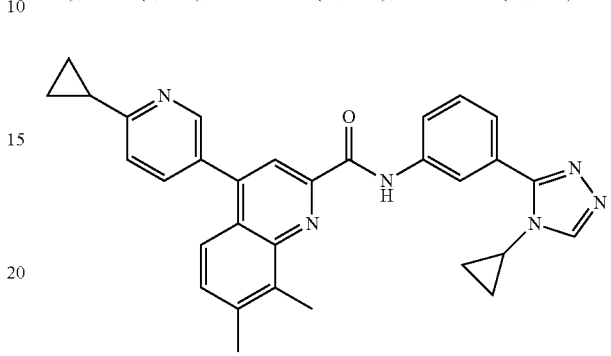

N-(3-(4-cyclopropyl-4H-1,2,4-triazol-3-yl)phenyl)-4-(6-cyclopropylpyridin-3-yl)-7,8-dimethylquinoline-2-carboxamide $C_{30}H_{27}N_7O$. 502.3 (M+1). $^1$H NMR (DMSO) d 10.83 (s, 1H), 8.71 (s, 1H), 8.61 (s, 1H), 8.40 (d, J=9 Hz, 1H), 8.08-8.14 (m, 2H), 7.90-7.95 (m, 2H), 7.69 (d, J=8 Hz, 1H), 7.61 (d, J=9 Hz, 1H), 7.55 (d, J=8 Hz, 1H), 4.09-4.14 (m, 1H), 2.84 (s, 3H), 2.55 (s, 3H), 2.11-2.15 (m, 1H), 1.03-1.15 (m, 8H).

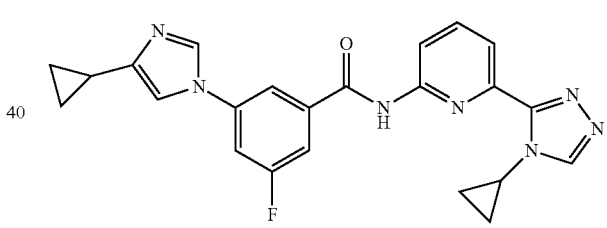

3-(4-cyclopropyl-1H-imidazol-1-yl)-N-(6-(4-cyclopropyl-4H-1,2,4-triazol-3-yl)pyridin-2-yl)-5-fluorobenzamide $C_{23}H_{20}FN_7O$. 430.2 (M+1). $^1$H NMR (MeOH) d 9.62 (s, 1H), 9.52 (d, J=1 Hz, 1H), 8.50 (d, J=8 Hz, 1H), 8.23 (s, 1H), 8.15 (t, J=8 Hz, 1H), 7.90-8.01 (m, 3H), 7.88 (d, J=9 Hz, 1H), 4.42-4.45 (m, 1H), 2.04-2.09 (m, 1H), 1.23-1.27 (m, 2H), 1.14-1.19 (m, 4H) 0.91-0.95 (m, 2H).

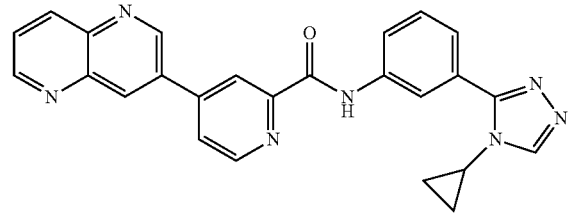 [SMILES: O=C(Nc1cccc(-c2nncn2C2CC2)c1)c1cc(-c2cnc3cccnc3c2)ccn1]

N-(3-(4-cyclopropyl-4H-1,2,4-triazol-3-yl)phenyl)-4-(1,5-naphthyridin-3-yl)picolinamide C₂₅H₁₉N₇O. 434.1 (M+1). ¹H NMR (DMSO) d 11.14 (s, 1H), 9.56 (d, J=2.4 Hz, 1H), 9.16 (d, J=1.6 Hz, 1H), 9.14 (d, J=1.6 Hz, 1H), 8.99 (d, J=1.2 Hz, 1H), 8.95 (d, J=5.2 Hz, 1H), 8.73 (s, 1H), 8.69 (d, J=1.2 Hz, 1H), 8.59 (d, J=8.0 Hz, 1H), 8.35 (dd, J=5.2, 2.0 Hz, 1H), 8.19 (d, J=8.0 Hz, 1H), 7.92 (dd, J=8.4, 4.4 Hz, 1H), 2.75 (d, J=8.0 Hz, 1H), 2.66 (t, J=8.0 Hz, 1H), 3.84 (m, 1H), 1.15 (m, 4H).

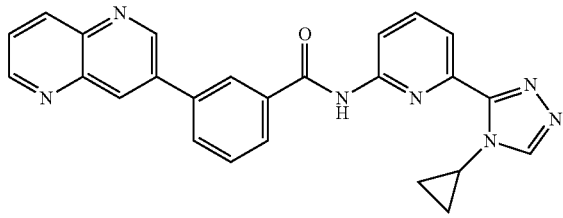 [SMILES: O=C(Nc1cccc(-c2nncn2C2CC2)n1)c1cccc(-c2cnc3cccnc3c2)c1]

N-(6-(4-cyclopropyl-4H-1,2,4-triazol-3-yl)pyridin-2-yl)-3-(1,5-naphthyridin-3-yl)benzamide C₂₅H₁₉N₇O. 434.1 (M+1). ¹H NMR (DMSO) d 11.01 (s, 1H), 9.51 (d, J=2.4 Hz, 1H), 9.09 (dd, J=4.4, 1.6 Hz, 1H), 8.86 (s, 1H), 8.86 (s, 1H), 8.54 (m, 2H), 8.32 (d, J=8.0 Hz, 1H), 8.24 (d, J=8.0 Hz, 1H), 8.07 (m, 2H), 7.83 (m, 2H), 7.77 (t, J=8.0 Hz, 1H), 4.27 (m, 1H), 1.00 (m, 4H).

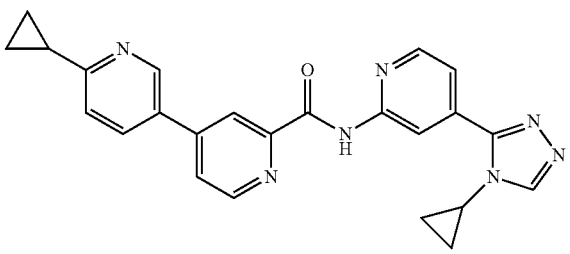 [SMILES: O=C(Nc1cc(-c2nncn2C2CC2)ccn1)c1cc(-c2ccc(C3CC3)nc2)ccn1]

6-cyclopropyl-N-(4-(4-cyclopropyl-4H-1,2,4-triazol-3-yl)pyridin-2-yl)-3,4'-bipyridine-2'-carboxamide C₂₄H₂₁N₇O. 424.2 (M+1). ¹H NMR (DMSO) d 10.65 (s, 1H), 8.97-9.02 (m, 1H), 8.91-8.95 (m, 1H), 8.83 (d, J=5 Hz, 1H), 8.75 (s, 1H), 8.57 (d, J=8 Hz, 1H), 8.49 (s, 1H), 8.18-8.22 (m, 1H), 8.09 (s, 1H), 7.77-7.81 (m, 1H), 7.49 (d, J=8 Hz, 1H), 3.73-3.76 (m, 1H), 2.17-2.21 (m, 1H), 1.00-1.19 (m, 8H).

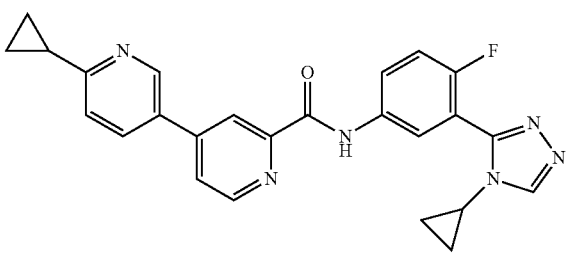 [SMILES: O=C(Nc1ccc(F)c(-c2nncn2C2CC2)c1)c1cc(-c2ccc(C3CC3)nc2)ccn1]

6-cyclopropyl-N-(3-(4-cyclopropyl-4H-1,2,4-triazol-3-yl)-4-fluorophenyl)-3,4'-bipyridine-2'-carboxamide C₂₅H₂₁FN₆O. 441.3 (M+1). ¹H NMR (DMSO) d 11.01 (s, 1H), 8.92 (d, J=1 Hz, 1H), 8.81 (d, J=5 Hz, 1H), 8.70 (s, 1H), 8.42 (d, J=1 Hz, 1H), 8.27 (dd, J=2, 6 Hz, 1H), 8.13-8.19 (m, 2H), 8.05 (dd, J=2.5 Hz, 1H), 7.44-7.50 (m, 2H), 3.40-3.44 (m, 1H), 2.17-2.23 (m, 1H), 0.81-1.06 (m, 8H).

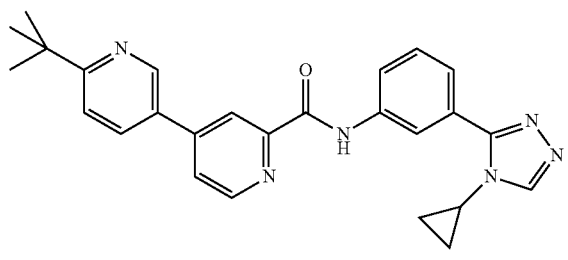 [SMILES: CC(C)(C)c1ccc(-c2ccnc(C(=O)Nc3cccc(-c4nncn4C4CC4)c3)c2)cn1]

6-tert-butyl-N-(3-(4-cyclopropyl-4H-1,2,4-triazol-3-yl)phenyl)-3-carboxamide C₂₆H₂₆N₆O. 439.1 (M+1). ¹H NMR (DMSO) d 10.94 (s, 1H), 9.04 (d, J=1.6 Hz, 1H), 8.85 (d, J=5.2 Hz, 1H), 8.63 (s, 1H), 8.58 (s, 1H), 8.46 (d, J=1.2 Hz, 1H), 8.28 (dd, J=8.4, 2.4 Hz, 1H), 8.08 (m, 2H), 7.69 (d, J=8.0 Hz, 1H), 7.62 (d, J=8.0 Hz, 1H), 7.55 (d, J=8.0 Hz, 1H), 3.67 (m, 1H), 1.37 (s, 9H), 1.08 (m, 2H), 0.95 (m, 2H).

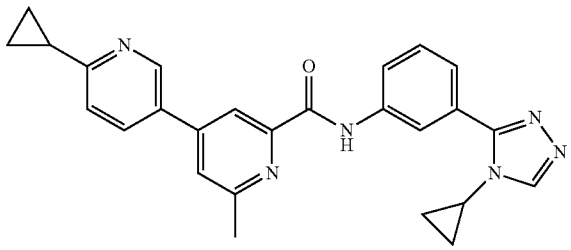 [SMILES: Cc1cc(-c2ccc(C3CC3)nc2)cc(C(=O)Nc2cccc(-c3nncn3C3CC3)c2)n1]

6-cyclopropyl-N-(3-(4-cyclopropyl-4H-1,2,4-triazol-3-yl)phenyl)-6'-methyl-3,4'-bipyridine-2'-carboxamide C₂₆H₂₄N₆O. 437.2 (M+1). ¹H NMR (DMSO) d 10.69 (s, 1H), 8.90 (s, 1H), 8.63 (s, 1H), 8.55 (s, 1H), 8.23 (s, 1H), 8.15 (dd, J=2, 8 Hz, 1H), 8.03 (d, J=8 Hz, 1H), 7.93 (s, 1H), 7.70 (d, J=8 Hz, 1H), 7.56 (t, J=8.0 Hz, 1H), 7.47 (d, J=8 Hz, 1H), 3.65-3.69 (m, 1H), 2.71 (s, 3H), 2.19-2.22 (m, 1H), 0.94-1.10 (m, 8H).

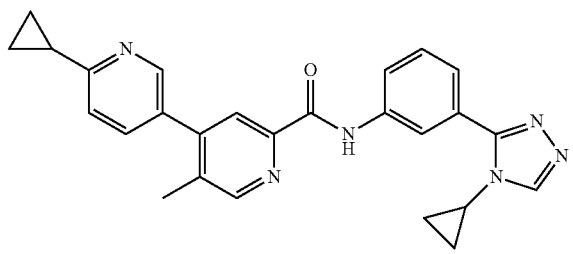 [SMILES: Cc1cnc(C(=O)Nc2cccc(-c3nncn3C3CC3)c2)cc1-c1ccc(C2CC2)nc1]

6-cyclopropyl-N-(3-(4-cyclopropyl-4H-1,2,4-triazol-3-yl)phenyl)-5'-methyl-3,4'-bipyridine-2'-carboxamide C₂₆H₂₄N₆O. 437.2 (M+1). ¹H NMR (DMSO) d 10.89 (s, 1H), 8.71 (s, 1H), 8.62 (s, 1H), 8.57 (s, 1H), 8.54 (d, J=2 Hz, 1H), 8.06 (d, J=8 Hz, 1H), 7.99 (s, 1H), 7.83 (dd, J=2, 8 Hz, 1H), 7.67 (d, J=8 Hz, 1H), 7.53 (t, J=8.0 Hz, 1H), 7.46 (d, J=8 Hz, 1H), 3.63-3.67 (m, 1H), 2.39 (s, 3H), 2.18-2.22 (m, 1H), 0.91-1.08 (m, 8H).

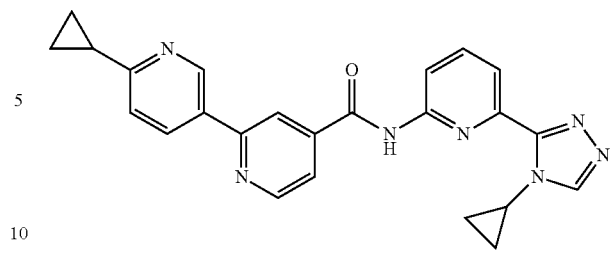

6'-cyclopropyl-N-(6-(4-cyclopropyl-4H-1,2,4-triazol-3-yl)pyridin-2-yl)-2,3'-bipyridine-4-carboxamide C₂₄H₂₁N₇O. 424.2 (M+1). ¹H NMR (DMSO) d 11.10 (s, 1H), 9.18 (d, J=2 Hz, 1H), 8.87 (d, J=5 Hz, 1H), 8.66 (s, 1H), 8.44 (s, 1H), 8.38 (dd, J=2, 8 Hz, 1H), 8.29 (d, J=8 Hz, 1H), 8.08 (t, J=8 Hz, 1H), 7.85 (d, J=7 Hz, 1H), 7.81 (dd, J=1, 5 Hz, 1H), 7.45 (d, J=8 Hz, 1H), 4.19-4.24 (m, 1H), 2.15-2.21 (m, 1H), 0.90-1.04 (m, 8H).

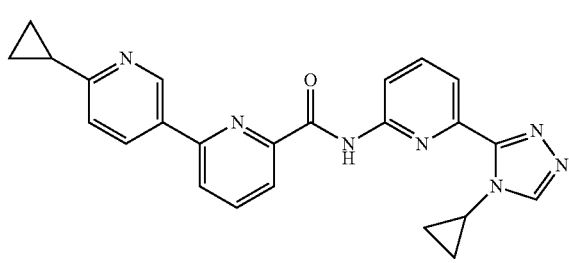 [SMILES: O=C(Nc1cccc(-c2nncn2C2CC2)n1)c1cccc(-c2ccc(C3CC3)nc2)n1]

6'-cyclopropyl-N-(6-(4-cyclopropyl-4H-1,2,4-triazol-3-yl)pyridin-2-yl)-2,3'-bipyridine-6-carboxamide C₂₄H₂₁N₇O. 424.3 (M+1). ¹H NMR (DMSO) d 10.83 (s, 1H), 9.23 (d, J=2 Hz, 1H), 8.70 (s, 1H), 8.44 (dd, J=2, 8 Hz, 1H), 8.33 (t, J=5 Hz, 2H), 8.18-8.24 (m, 2H), 8.13 (t, J=8 Hz, 1H), 7.92 (d, J=8 Hz, 1H), 7.47 (d, J=8 Hz, 1H), 4.10-4.14 (m, 1H), 2.19-2.23 (m, 1H), 0.99-1.11 (m, 8H).

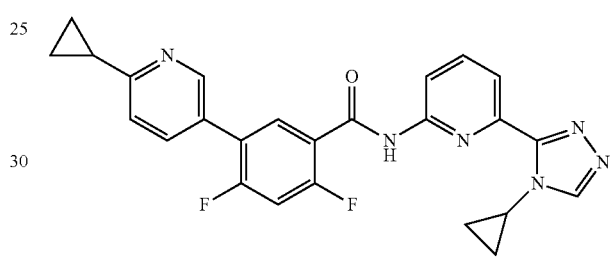

N-(6-(4-cyclopropyl-4H-1,2,4-triazol-3-yl)pyridin-2-yl)-5-(6-cyclopropylpyridin-3-yl)-2,4-difluorobenzamide C₂₅H₂₀F₂N₆O. 459.3 (M+1). ¹H NMR (DMSO) d 10.98 (s, 1H), 8.65 (s, 1H), 8.62 (s, 1H), 8.26 (d, J=8 Hz, 1H), 8.05 (t, J=8 Hz, 1H), 7.95 (t, J=8 Hz, 1H), 7.84-7.90 (m, 2H), 7.63 (t, J=10 Hz, 1H), 7.44 (t, J=8 Hz, 1H), 4.16-4.20 (m, 1H), 2.15-2.19 (m, 1H), 0.93-1.01 (m, 8H).

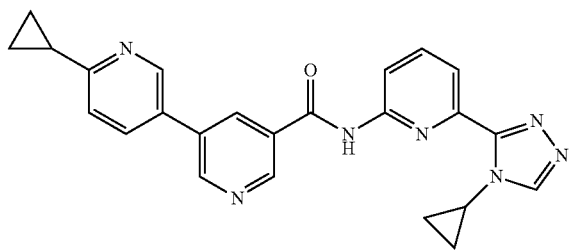 [SMILES: O=C(Nc1cccc(-c2nncn2C2CC2)n1)c1cncc(-c2ccc(C3CC3)nc2)c1]

6'-cyclopropyl-N-(6-(4-cyclopropyl-4H-1,2,4-triazol-3-yl)pyridin-2-yl)-2,3'-bipyridine-5-carboxamide C₂₄H₂₁N₇O×HCOOH. 424.2 (M+1). ¹H NMR (DMSO) d 11.05 (s, 1H), 9.12 (d, J=2 Hz, 1H), 9.08 (d, J=2 Hz, 1H), 8.66 (s, 1H), 8.60 (t, J=2 Hz, 1H), 8.29 (d, J=8 Hz, 1H), 8.19 (br s, 1H), 8.12 (dd, J=2, 8 Hz, 1H), 8.07 (t, J=8 Hz, 1H), 7.83 (d, J=7 Hz, 1H), 7.46 (d, J=8 Hz, 1H), 4.20-4.24 (m, 1H), 2.17-2.21 (m, 1H), 0.90-1.03 (m, 8H).

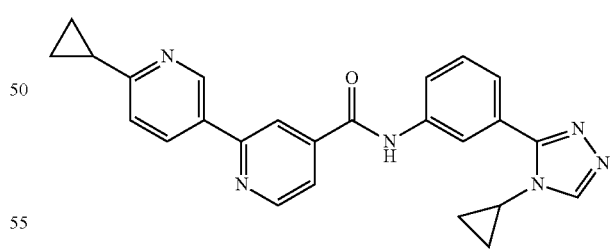

6'-cyclopropyl-N-(3-(4-cyclopropyl-4H-1,2,4-triazol-3-yl)phenyl)-2,3'-bipyridine-4-carboxamide C₂₅H₂₂N₆O. 423.3 (M+1). ¹H NMR (DMSO) d 10.72 (s, 1H), 9.18 (d, J=2 Hz, 1H), 8.88 (d, J=5 Hz, 1H), 8.63 (s, 1H), 8.43 (d, J=9 Hz, 2H), 8.38 (dd, J=2, 8 Hz, 1H), 7.94 (d, J=8 Hz, 1H), 7.83 (dd, J=1, 9 Hz, 1H), 7.74 (d, J=8 Hz, 1H), 7.56 (t, J=8 Hz, 1H), 7.46 (d, J=8 Hz, 1H), 3.62-3.66 (m, 1H), 2.16-2.21 (m, 1H), 0.93-1.01 (m, 8H).

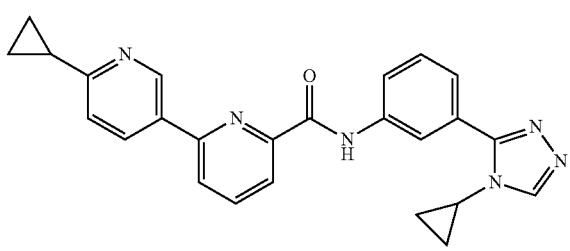 [SMILES: O=C(Nc1cccc(-c2nncn2C2CC2)c1)c1cccc(-c2ccc(C3CC3)nc2)n1]

6'-cyclopropyl-N-(3-(4-cyclopropyl-4H-1,2,4-triazol-3-yl)phenyl)-2,3'-bipyridine-6-carboxamide $C_{25}H_{22}N_6O$. 423.3 (M+1). $^1$H NMR (DMSO) d 10.72 (s, 1H), 9.42 (d, J=2 Hz, 1H), 8.64 (s, 1H), 8.62 (dd, J=2, 8 Hz, 1H), 8.52 (s, 1H), 8.28 (dd, J=1, 7 Hz, 1H), 8.11-8.18 (m, 2H), 8.04 (d, J=8 Hz, 1H), 7.72 (d, J=8 Hz, 1H), 7.58 (d, J=8 Hz, 1H), 7.48 (d, J=8 Hz, 1H), 3.64-3.68 (m, 1H), 2.18-2.22 (m, 1H), 0.93-1.08 (m, 8H):

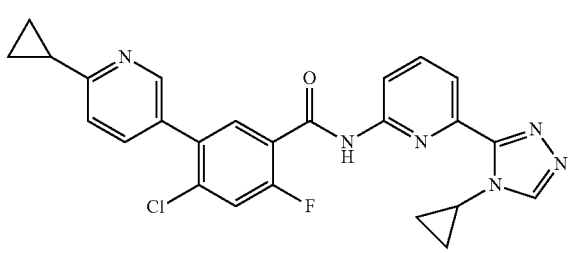 [SMILES: O=C(Nc1cccc(-c2nncn2C2CC2)n1)c1cc(-c2ccc(C3CC3)nc2)c(Cl)cc1F]

4-chloro-N-(6-(4-cyclopropyl-4H-1,2,4-triazol-3-yl)pyridin-2-yl)-5-(6-cyclopropylpyridin-3-yl)-2-fluorobenzamide $C_{25}H_{20}ClFN_6O$. 475.2 (M+1). $^1$H NMR (DMSO) d 11.01 (s, 1H), 8.65 (s, 1H), 8.50 (d, J=2 Hz, 1H), 8.25 (d, J=8 Hz, 1H), 8.04 (t, J=8 Hz, 1H), 7.76-7.85 (m, 4H), 7.42 (d, J=8 Hz, 1H), 4.14-4.18 (m, 1H), 2.15-2.19 (m, 1H), 0.92-1.02 (m, 8H).

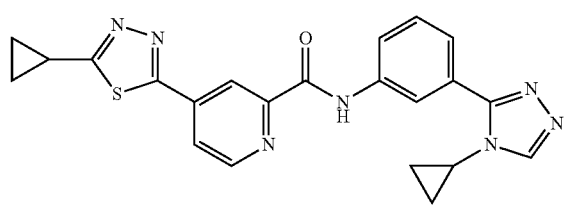 [SMILES: O=C(Nc1cccc(-c2nncn2C2CC2)c1)c1cc(-c2nnc(C3CC3)s2)ccn1]

4-(5-cyclopropyl-1,3,4-thiadiazol-2-yl)-N-(3-(4-cyclopropyl-4H-1,2,4-triazol-3-yl)phenyl)picolinamide $C_{22}H_{19}N_7OS$. 430.1 (M+1). $^1$H NMR (DMSO) d 11.02 (s, 1H), 8.92 (d, J=4.8, 1H), 8.65 (s, 1H), 8.59 (s, 1H), 8.54 (d, J=1.2 Hz, 1H), 8.17 (dd, J=5.2, 2.0 Hz, 1H), 8.07 (d, J=8.0 Hz, 1H), 7.70 (d, J=8.0 Hz, 1H), 7.55 (t, J=8.0 Hz, 1H), 3.67 (m, 1H), 2.67 (m, 1H), 1.33 (m, 2H), 1.15 (m, 2H), 1.08 (m, 2H), 0.95 (m, 2H).

C. Similarly, following the procedures as described in Examples 1-13 where appropriate, other compounds of formula (I) are prepared.

EXAMPLE 14

Preparation of Compounds of Formula I via N-arylation of Haloarenes

A. Preparation of a Compound of Formula (I) in which $X^2$, $X^3$, $X^4$, $X^6$, $X^7$ and $X^8$ are (CR4), $X^1$ and $X^5$ are N, $R^1$ is Cyclopropyl. $R^2$ is Hydrogen, and $R^3$ is 4-Imidazol-1-yl A. Preparation of N-(3-(4-cyclopropyl-4H-1,2,4-triazol-3-yl)phenyl)-4-(1H-imidazol-1-1)picolinamide

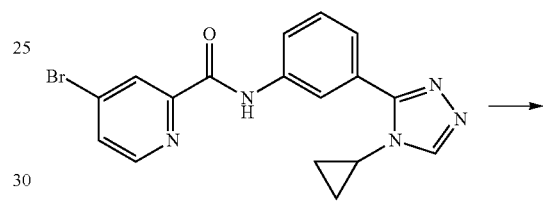

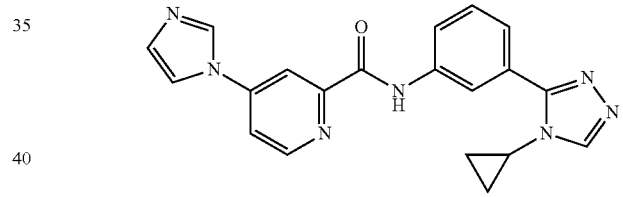

A suspension of 4-bromo-N-(3-(4-cyclopropyl-4H-1,2,4-triazol-3-yl)phenyl)picolinamide (35 mg, 0.091 mmol), imidazole (8 mg, 0.117 mmol), cupric oxide (1 mg, 0.007 mmol), 4,7-dimethoxy-1,10-phenanthroline (3 mg, 0.012 mmol (or 8-hydroxyquinoline may be used as the ligand with comparable results), cesium carbonate (41 mg, 0.126 mmol), and PEG-3350 (20 mg) in butyronitrile (1 mL) was heated at 120° C. for 16 hours. The solvent was removed under reduced pressure and the residue purified by reverse-phase HPLC to give N-(3-(4-cyclopropyl-4H-1,2,4-triazol-3-yl)phenyl)-4-(1H-imidazol-1-yl)picolinamide as a white powder (14 mg, 0.377 mmol, 41% yield).

$C_{20}H_{17}N_7O$. 372.3 (M+1). $^1$H NMR (DMSO) d 10.98 (s, 1H), 8.83 (d, J=5.6 Hz, 1H), 8.72 (s, 1H), 8.64 (s, 1H), 8.58 (s, 1H), 8.44 (d, J=2.4 Hz, 1H), 8.15 (s, 1H), 8.07 (m, 2H), 7.70 (d, J=8.0 Hz, 1H), 7.55 (t, J=8.0 Hz, 1H), 7.21 (s, 1H), 3.66 (m, 1H), 1.08 (m, 2H), 0.95 (m, 2H).

B. Similarly, following the procedure of Example 14, optionally replacing 4-bromo-N-(3-(4-cyclopropyl-4H-1,2,4-triazol-3-yl)phenyl)picolinamide with other compounds of formula (5), and optionally replacing imidazole with other amines, the following compounds of Formula I were prepared:

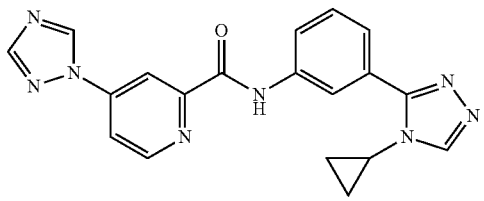 [SMILES: O=C(Nc1cccc(-c2nncn2C2CC2)c1)c1cc(-n2cncn2)ccn1]

N-(3-(4-cyclopropyl-4H-1,2,4-triazol-3-yl)phenyl)-
4-(1H-1,2,4-triazol-1-yl)picolinamide $C_{19}H_{16}N_8O$. 373.6 (M+1). $^1$H NMR (DMSO) d 11.02 (s, 1H), 9.74 (s, 1H), 8.91 (d, J=9.2 Hz, 1H), 8.65 (m, 2H), 8.59 (s, 1H), 8.41 (s, 1H), 8.21 (dd, J=5.6, 2.0 Hz, 1H), 8.07 (d, J=8.8 Hz, 1H), 7.70 (d, J=8.0 Hz, 1H), 7.56 (t, J=8.0 Hz, 1H), 3.67 (m, 1H), 1.08 (m, 2H), 0.95 (m, 2H).

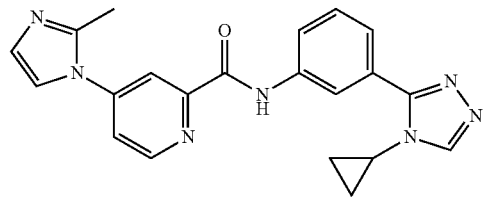

N-(3-(4-cyclopropyl-4H-1,2,4-triazol-3-yl)phenyl)-
4-(2-methyl-1H-imidazol-1-yl)picolinamide $C_{21}H_{19}N_7O$. 386.1 (M+1). $^1$H NMR (DMSO) d 10.99 (s, 1H), 8.88 (d, J=5.2 Hz, 1H), 8.62 (s, 1H), 8.56 (s, 1H), 8.18 (d, J=2.0 Hz, 1H), 8.07 (d, J=8.0 Hz, 1H), 7.87 (dd, J=5.2, 2.0 Hz, 1H), 7.70 (d, J=8.0 Hz, 1H), 7.62 (s, 1H), 7.55 (t, 8.0 Hz, 1H), 7.02 (s, 1H), 3.65 (m, 1H), 2.47 (s, 3H), 1.07 (m, 2H), 0.94 (m, 2H).

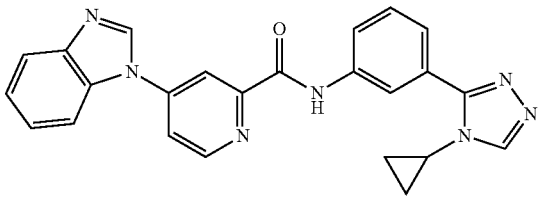 [SMILES: O=C(Nc1cccc(-c2nncn2C2CC2)c1)c1cc(-n2cnc3ccccc32)ccn1]

4-(1H-benzo[d]imidazol-1-yl)-N-(3-(4-cyclopropyl-
4H-1,2,4-triazol-3-yl)phenyl)picolinamide $C_{24}H_{19}N_7O$. 422.0 (M+1). $^1$H NMR (DMSO) d 11.03 (s, 1H), 8.95 (d, J=5.6 Hz, 1H), 8.91 (s, 1H), 8.63 (s, 1H), 8.60 (s, 1H), 8.48 (d, J=1.6 Hz, 1H), 8.12 (m, 2H), 7.89 (d, J=7.6 Hz, 1H), 7.84 (d, J=7.6 Hz, 1H), 7.71 (d, 8.0 Hz, 1H), 7.56 (t, 8.0 Hz, 1H), 7.42 (m, 2H), 3.67 (m, 1H), 1.08 (m, 2H), 0.95 (m, 2H).

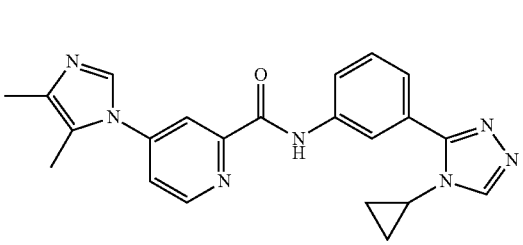

N-(3-(4-cyclopropyl-4H-1,2,4-triazol-3-yl)phenyl)-
4-(4-methyl-1H-imidazol-1-yl)picolinamide $C_{21}H_{19}N_7O$. 386.1 (M+1). $^1$H NMR (DMSO) d 10.94 (s, 1H), 8.80 (d, J=5.2 Hz, 1H), 8.63 (s, 1H), 8.58 (s, 1H), 8.57 (s, 1H), 8.36 (d, J=2.4 Hz, 1H), 8.06 (d, J=8.0 Hz, 1H), 7.99 (d, J=5.6, 2.4 Hz, 1H), 7.81 (s, 1H), 7.69 (d, J=8.0 Hz, 1H), 7.55 (t, J=8.0 Hz, 1H). 3.66 (m, 1H), 2.19 (s, 3H), 1.08 (m, 2H), 0.94 (m, 2H).

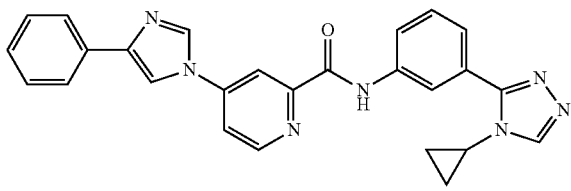 [SMILES: O=C(Nc1cccc(-c2nncn2C2CC2)c1)c1cc(-n2cnc(-c3ccccc3)c2)ccn1]

N-(3-(4-cyclopropyl-4H-1,2,4-triazol-3-yl)phenyl)-
4-(4-phenyl-1H-imidazol-1-yl)picolinamide $C_{26}H_{21}N_7O$. 448.6 (M+1). $^1$H NMR (DMSO) d 10.97 (s, 1H), 8.86 (d, J=5.6 Hz, 1H), 8.80 (d, J=1.6 Hz, 1H), 8.71 (d, J=1.6 Hz, 1H), 8.63 (s, 1H), 8.60 (s, 1H), 8.53 (d, J=2.0 Hz, 1H), 8.12 (dd, J=5.6, 2.4 Hz, 1H), 8.08 (d, J=8.0 Hz, 1H), 7.93 (d, J=7.6 Hz, 2H), 7.71 (d, J=7.6 Hz, 1H), 7.56 (t, J=8.0 Hz, 1H), 7.43 (t, J=7.6 Hz, 2H), 7.29 (t, J=7.6 Hz, 1H), 3.67 (m, 1H), 1.09 (m, 2H), 0.95 (m, 2H).

N-(3-(4-cyclopropyl-4H-1,2,4-triazol-3-yl)phenyl)-
4-(4,5-dimethyl-1H-imidazol-1-yl)picolinamide $C_{22}H_{21}N_7O$. 400.1 (M+1). $^1$H NMR (DMSO) d 10.98 (s, 1H), 8.87 (d, J=5.2 Hz, 1H), 8.62 (s, 1H), 8.56 (s, 1H), 8.16 (s, 1H), 8.07 (d, J=8.8 Hz, 1H), 8.00 (s, 1H), 7.82 (dd, J=5.2, 1.6 Hz, 1H), 7.70 (d, J=8.0 Hz, 1H), 7.55 (t, J=8.0 Hz, 1H), 3.66 (m, 1H), 2.24 (s, 3H), 2.14 (s, 3H), 1.07 (m, 2H), 0.94 (m, 2H).

97

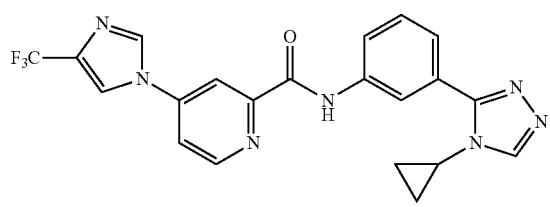 [SMILES: O=C(Nc1cccc(-c2nncn2C2CC2)c1)c1cc(-n2cnc(C(F)(F)F)c2)ccn1]

N-(3-(4-cyclopropyl-4H-1,2,4-triazol-3-yl)phenyl)-4-(4-(trifluoromethyl)-1H-imidazol-1-yl)picolinamide $C_{21}H_{16}F_3N_7O$. 440.4 (M+1). $^1$H NMR (DMSO) d 10.98 (s, 1H), 8.89 (m, 3H), 8.63 (s, 1H), 8.57 (m, 2H), 8.15 (dd, J=6.0, 2.4 Hz, 1H), 8.07 (d, J=8.0 Hz, 1H), 7.71 (d, J=8.0 Hz, 1H), 7.56 (t, J=8.0 Hz, 1H), 3.66 (m, 1H), 1.08 (m, 2H), 0.95 (m, 2H). $^{19}$F NMR (DMSO) d −61.55.

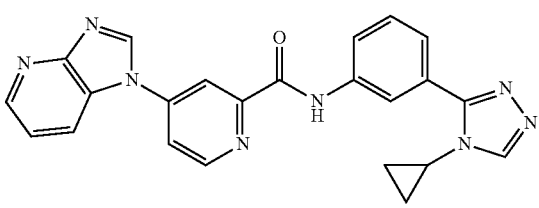 [SMILES: O=C(Nc1cccc(-c2nncn2C2CC2)c1)c1cc(-n2cnc3ncccc32)ccn1]

N-(3-(4-cyclopropyl-4H-1,2,4-triazol-3-yl)phenyl)-4-(1H-imidazo[4,5-b]pyridin-1-yl)picolinamide $C_{23}H_{18}N_8O$. 423.1 (M+1). $^1$H NMR (DMSO) d 11.03 (s, 1H), 9.21 (s, 1H), 8.97 (d, J=5.2 Hz, 1H), 8.63 (s, 1H), 8.58 (m, 2H), 8.50 (d, J=2.0 Hz, 1H), 8.35 (dd, J=8.0, 1.2 Hz, 1H), 8.15 (dd, J=5.2, 2.0 Hz, 1H), 8.09 (d, J=8.0 Hz, 1H), 7.71 (d, J=8.0 Hz, 1H), 7.57 (t, J=8.0 Hz, 1H), 7.48 (dd, J=8.0, 4.8 Hz, 1H), 3.67 (m, 1H), 1.09 (m, 2H), 0.95 (m, 2H).

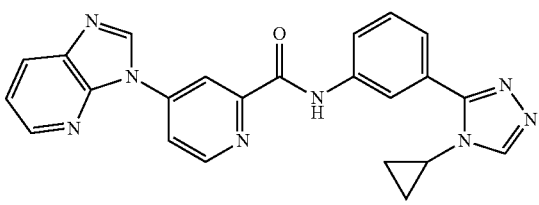 [SMILES: O=C(Nc1cccc(-c2nncn2C2CC2)c1)c1cc(-n2cnc3cccnc32)ccn1]

N-(3-(4-cyclopropyl-4H-1,2,4-triazol-3-yl)phenyl)-4-(3H-imidazo[4,5-b]pyridin-3-yl)picolinamide $C_{23}H_{18}N_8O$. 423.1 (M+1). $^1$H NMR (DMSO) d 11.00 (s, 1H), 9.33 (s, 1H), 9.13 (d, J=1.6 Hz, 1H), 8.95 (d, J=5.6 Hz, 1H), 8.63 (s, 1H), 8.60 (s, 1H), 8.57 (dd, J=4.8, 1.6 Hz, 1H), 8.52 (dd, J=5.6, 2.0 Hz, 1H), 8.29 (dd, J=8.0, 1.2 Hz, 1H), 8.09 (d, J=8.0 Hz, 1H), 7.71 (d, J=8.0 Hz, 1H), 7.56 (t, J=8.0 Hz, 1H), 7.50 (dd, J=8.0, 4.8 Hz, 1H), 3.67 (m, 1H), 1.09 (m, 2H), 0.95 (m, 2H).

98

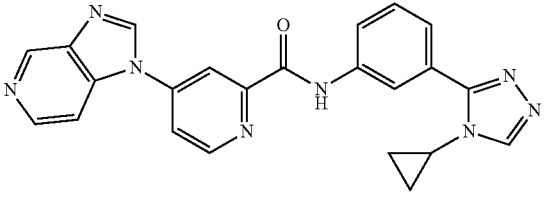 [SMILES: O=C(Nc1cccc(-c2nncn2C2CC2)c1)c1cc(-n2cnc3cnccc32)ccn1]

N-(3-(4-cyclopropyl-4H-1,2,4-triazol-3-yl)phenyl)-4-(1H-imidazo[4,5-c]pyridin-1-yl)picolinamide $C_{23}H_{18}N_8O$. 423.1 (M+1). $^1$H NMR (DMSO) d 11.04 (s, 1H), 9.14 (s, 1H), 9.07 (s, 1H), 8.99 (d, J=4.8 Hz, 1H), 8.63 (s, 1H), 8.60 (s, 1H), 8.55 (d, J=5.6 Hz, 1H), 8.50 (d, J=1.6 Hz, 1H), 8.15 (dd, J=5.2, 2.0 Hz, 1H), 8.09 (dd, J=8.0, 1.2 Hz, 1H), 7.93 (dd, J=5.6, 0.8 Hz, 1H), 7.71 (d, J=8.0 Hz, 1H), 7.57 (t, J=8.0 Hz, 1H), 3.67 (m, 1H), 1.08 (m, 2H), 0.95 (m, 2H).

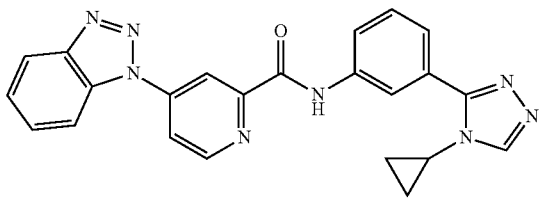 [SMILES: O=C(Nc1cccc(-c2nncn2C2CC2)c1)c1cc(-n2nnc3ccccc32)ccn1]

4-(1H-benzo[d][1,2,3]triazol-1-yl)-N-(3-(4-cyclopropyl-4H-1,2,4-triazol-3-yl)phenyl)picolinamide $C_{23}H_{18}N_8O$. 423.1 (M+1). $^1$H NMR (DMSO) d 11.07 (s, 1H), 9.03 (d, J=5.6 Hz, 1H), 9.69 (d, J=1.6 Hz, 1H), 8.63 (s, 1H), 8.61 (s, 1H), 8.35 (dd, J=5.2, 2.0 Hz, 1H), 8.30 (d, J=8.0 Hz, 1H), 8.23 (d, J=8.0 Hz, 1H), 8.10 (d, J=9.2 Hz, 1H), 7.81 (t, J=8.0 Hz, 1H), 7.71 (d, J=8.0 Hz, 1H), 7.62 (t, J=8.0 Hz, 1H), 7.57 (t, J=8.0 Hz, 1H), 3.67 (m, 1H), 1.08 (m, 2H), 0.95 (m, 2H).

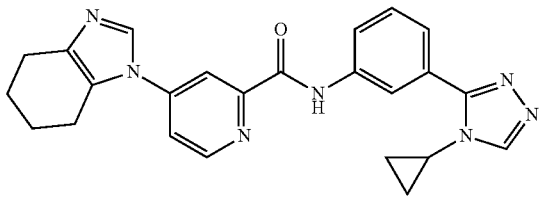 [SMILES: O=C(Nc1cccc(-c2nncn2C2CC2)c1)c1cc(-n2cnc3c2CCCC3)ccn1]

N-(3-(4-cyclopropyl-4H-1,2,4-triazol-3-yl)phenyl)-4-(4,5,6,7-tetrahydro-1H-benzo[d]imidazol-1-yl)picolinamide $C_{24}H_{23}N_7O$. 426.1 (M+1). $^1$H NMR (DMSO) d 10.93 (s, 1H), 8.81 (d, J=5.2 Hz, 1H), 8.59 (s, 1H), 8.53 (s, 1H), 8.16 (d, J=1.6 Hz, 1H), 8.13 (s, 1H), 8.03 (d, J=8.0 Hz, 1H), 7.81 (dd, J=5.6, 2.0 Hz, 1H), 7.66 (d, J=8.0 Hz, 1H), 7.52 (t, J=8.0 Hz, 1H), 3.65 (m, 1H), 2.70 (br, 2H), 2.51 (br, 2H), 1.76 (br, 4H), 1.05 (m, 2H), 0.90 (m, 2H).

99

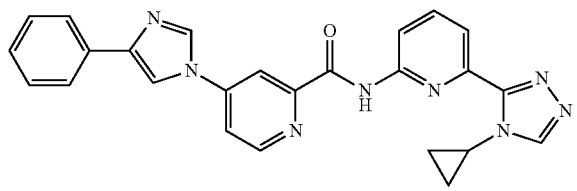 [SMILES: O=C(Nc1cccc(-c2nncn2C2CC2)n1)c1cc(-n2cnc(-c3ccccc3)c2)ccn1]

N-(6-(4-cyclopropyl-4H-1,2,4-triazol-3-yl)pyridin-2-yl)-4-(4-phenyl-1H-imidazol-1-yl)picolinamide $C_{25}H_{20}N_8O\times HCl$. 449.1 (M+1). $^1$H NMR (DMSO) d 10.73 (s, 1H), 9.10 (s, 1H), 8.92 (d, J=3 Hz, 1H), 8.90 (br s, 1H), 8.82 (s, 1H), 8.63 (s, 1H), 8.42 (br s, 1H), 8.20 (d, J=4 Hz, 1H), 8.15 (t, J=8 Hz, 1H), 7.94 (d, J=8 Hz, 3H), 7.47 (t, J=8 Hz, 2H), 7.34 (t, J=7 Hz, 1H), 4.91 (br s, 1H), 4.11-4.14 (m, 1H), 1.01-1.14 (m, 4H).

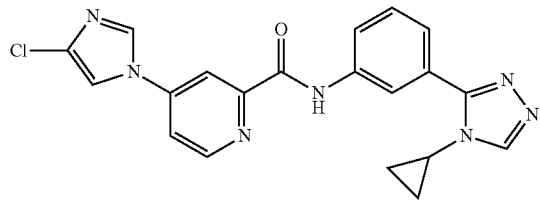 [SMILES: O=C(Nc1cccc(-c2nncn2C2CC2)c1)c1cc(-n2cnc(Cl)c2)ccn1]

4-(4-chloro-1H-imidazol-1-yl)-N-(3-(4-cyclopropyl-4H-1,2,4-triazol-3-yl)phenyl)picolinamide $C_{20}H_{16}ClN_7O$. 406.0 (M+1). $^1$H NMR (DMSO) d 10.96 (s, 1H), 8.86 (d, J=5.2 Hz, 1H), 8.72 (d, J=1.6 Hz, 1H), 8.63 (s, 1H), 8.58 (s, 1H), 8.46 (d, J=2.4 Hz, 1H), 8.32 (d, J=1.6 Hz, 1H), 8.05 (m, 2H), 7.70 (d, J=8.0 Hz, 1H), 7.55 (t, J=8.0 Hz, 1H), 3.66 (m, 1H), 1.08 (m, 2H), 0.95 (m, 2H).

4-(4-cyclopropyl-1H-imidazol-1-yl)-N-(3-(4-cyclopropyl-4H-1,2,4-triazol-3-yl)phenyl)picolinamide $C_{23}H_{21}N_7O$. 412.1 (M+1). $^1$H NMR (DMSO) d 10.93 (s, 1H), 8.79 (d, J=5.6 Hz, 1H), 8.63 (s, 1H), 8.58 (s, 1H), 8.55 (s, 1H), 8.36 (s, 1H), 8.06 (d, J=8.0 Hz, 1H), 7.98 (m, 1H), 7.85 (m, 1H), 7.69 (d, J=8.0 Hz, 1H), 7.56 (t, J=8.0 Hz, 1H), 3.66 (m, 1H), 1.88 (m, 1H), 1.08 (m, 2H), 0.94 (m, 2H), 0.85 (m, 2H), 0.73 (m, 2H).

100

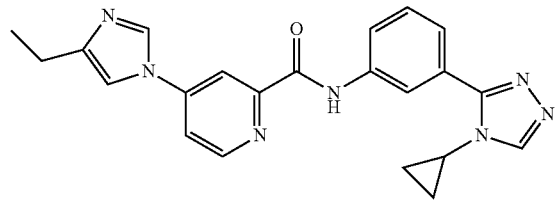 [SMILES: CCc1cn(-c2ccnc(C(=O)Nc3cccc(-c4nncn4C4CC4)c3)c2)cn1]

N-(3-(4-cyclopropyl-4H-1,2,4-triazol-3-yl)phenyl)-4-(4-ethyl-1H-imidazol-1-yl)picolinamide $C_{22}H_{21}N_7O$. 400.1 (M+1). $^1$H NMR (DMSO) d 10.93 (s, 1H), 8.80 (d, J=5.6 Hz, 1H), 8.63 (s, 1H), 8.59 (m, 2H), 8.38 (d, J=2.4 Hz, 1H), 8.06 (d, J=9.2 Hz, 1H), 8.01 (dd, J=5.6, 2.4 Hz, 1H), 7.82 (s, 1H), 7.70 (d, J=8.0 Hz, 1H), 7.55 (t, J=8 Hz, 1H), 3.66 (m, 1H), 2.56 (q, J=7.6 Hz, 2H), 1.22 (t, J=7.6 Hz, 3H), 1.07 (m, 2H), 0.95 (m, 2H).

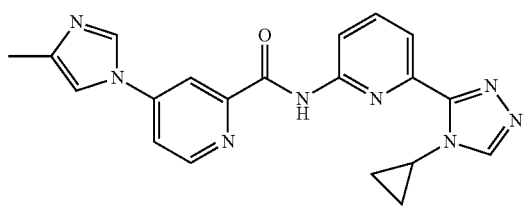 [SMILES: Cc1cn(-c2ccnc(C(=O)Nc3cccc(-c4nncn4C4CC4)n3)c2)cn1]

N-(6-(4-cyclopropyl-4H-1,2,4-triazol-3-yl)pyridin-2-yl)-4-(4-methyl-1H-imidazol-1-yl)picolinamide $C_{20}H_{18}N_8O$. 387.1 (M+1). $^1$H NMR (DMSO) d 10.66 (s, 1H), 8.81 (d, J=6 Hz, 1H), 8.67 (s, 1H), 8.61 (s, 1H), 8.43 (d, J=2 Hz, 1H), 8.38 (d, J=8 Hz, 1H), 8.11 (t, J=8 Hz, 1H), 8.02 (dd, J=2, 6 Hz, 1H), 7.89 (d, J=7 Hz, 1H), 7.83 (s, 1H), 4.07-4.11 (m, 1H), 2.19 (s, 3H), 0.91-1.06 (m, 4H).

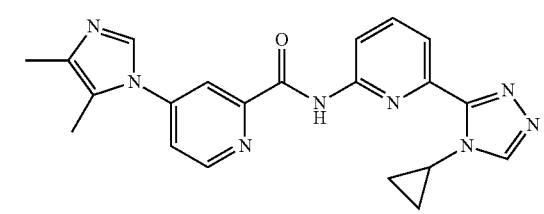 [SMILES: Cc1ncn(-c2ccnc(C(=O)Nc3cccc(-c4nncn4C4CC4)n3)c2)c1C]

N-(6-(4-cyclopropyl-4H-1,2,4-triazol-3-yl)pyridin-2-yl)-4-(4,5-dimethyl-1H-imidazol-1-yl)picolinamide $C_{21}H_{20}N_8O$. 401.1 (M+1). $^1$H NMR (DMSO) d 10.68 (s, 1H), 8.88 (d, J=5 Hz, 1H), 8.69 (s, 1H), 8.37 (d, J=8 Hz, 1H), 8.22 (d, J=2 Hz, 1H), 8.11 (t, J=8 Hz, 1H), 7.89 (d, J=8 Hz, 1H), 7.86 (dd, J=2.5 Hz, 1H), 4.08-4.13 (m, 1H), 2.25 (s, 3H) 2.14 (s, 3H), 0.96-1.08 (m, 4H).

101

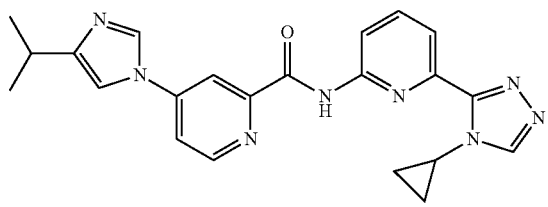 [SMILES: CC(C)c1cn(-c2ccnc(C(=O)Nc3cccc(-c4nncn4C4CC4)n3)c2)cn1]

N-(6-(4-cyclopropyl-4H-1,2,4-triazol-3-yl)pyridin-2-yl)-4-(4-isopropyl-1H-imidazol-1-yl)picolinamide $C_{22}H_{22}N_8O$. 415.1 (M+1). $^1$H NMR (DMSO) d 10.69 (s, 1H), 9.00 (br s, 1H), 8.87 (d, J=5 Hz, 1H), 8.70 (s, 1H), 8.53 (d, J=2 Hz, 1H), 8.38 (d, J=8 Hz, 1H), 8.09-8.15 (m, 2H), 8.00 (s, 1H), 7.89 (d, J=7 Hz, 1H), 4.08-4.13 (m, 1H), 2.90 (sept, J=7 Hz, 1H), 1.27 (d, J=6 Hz, 6H), 0.98-1.06 (m, 4H).

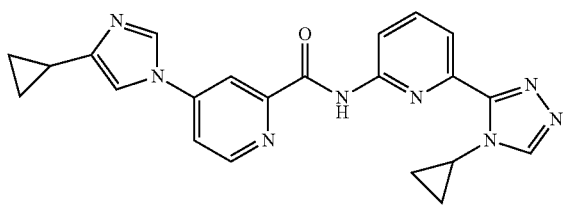 [SMILES: O=C(Nc1cccc(-c2nncn2C2CC2)n1)c1cc(-n2cnc(C3CC3)c2)ccn1]

4-(4-cyclopropyl-1H-imidazol-1-yl)-N-(6-(4-cyclopropyl-4H-1,2,4-triazol-3-yl)pyridin-2-yl)picolinamide $C_{22}H_{20}FN_8O$. 413.1 (M+1). $^1$H NMR (DMSO) d 10.67 (s, 1H), 8.80 (d, J=5 Hz, 1H), 8.69 (s, 1H), 8.57 (s, 1H), 8.43 (d, J=2 Hz, 1H), 8.38 (d, J=8 Hz, 1H), 8.11 (t, J=8 Hz, 1H), 8.01-8.04 (m, 1H), 7.87-7.91 (m, 2H), 4.08-4.11 (m, 1H), 1.83-1.89 (m, 1H), 0.94-1.06 (m, 4H), 0.73-0.85 (m, 4H).

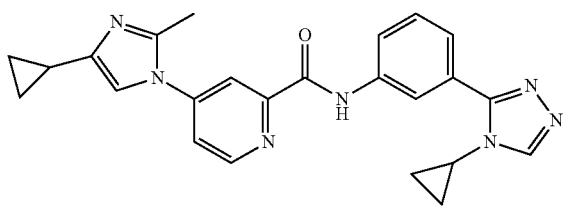 [SMILES: Cc1nc(C2CC2)cn1-c1ccnc(C(=O)Nc2cccc(-c3nncn3C3CC3)c2)c1]

4-(4-cyclopropyl-2-methyl-1H-imidazol-1-yl)-N-(3-(4-cyclopropyl-4H-1,2,4-triazol-3-yl)phenyl)picolinamide $C_{24}H_{23}N_7O×HCl$. 426.1 (M+1). $^1$H NMR (DMSO) d 11.12 (s, 1H), 9.11 (s, 1H), 9.03 (d, J=5.2 Hz, 1H), 8.62 (s, 1H), 8.37 (d, J=1.6 Hz, 1H), 8.12 (d, J=8.0 Hz, 1H), 7.99 (dd, J=51, 2.0 Hz, 1H), 7.84 (s, 1H), 7.73 (d, J=8.0 Hz, 1H), 7.61 (t, J=8.0 Hz, 1H), 3.74 (m, 1H), 2.62 (s, 3H), 2.01 (m, 1H), 1.10 (m, 6H), 0.86 (m, 2H).

102

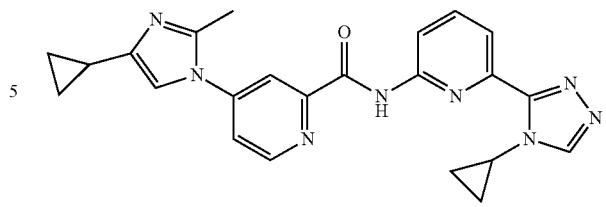

4-(4-cyclopropyl-2-methyl-1H-imidazol-1-yl)-N-(6-(4-cyclopropyl-4H-1,2,4-triazol-3-yl)pyridin-2-yl)picolinamide $C_{23}H_{22}N_8O×HCl$. 427.1 (M+1). $^1$H NMR (DMSO) d 10.76 (s, 1H), 9.04 (d, J=5.2 Hz, 1H), 8.98 (s, 1H), 8.43 (d, J=1.6 Hz, 1H), 8.38 (d, J=8.0 Hz, 1H), 8.15 (t, J=8.0 Hz, 1H), 8.03 (dd, J=5.2, 2.0 Hz, 1H), 7.93 (d, J=8.0 Hz, 1H), 7.85 (s, 1H), 4.18 (m, 1H), 2.63 (s, 3H), 2.01 (m, 1H), 1.05 (m, 6H), 0.89 (m, 2H).

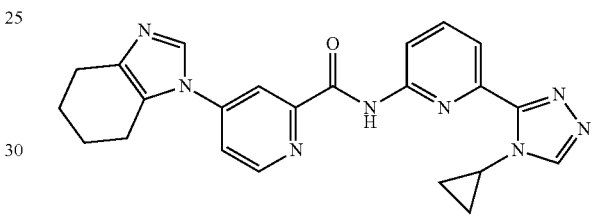

N-(6-(4-cyclopropyl-4H-1,2,4-triazol-3-yl)pyridin-2-yl)-4-(4,5,6,7-tetrahydro-1H-benzo[d]imidazol-1-yl)picolinamide $C_{23}H_{22}N_8O×HCl$. 427.1 (M+1). $^1$H NMR (DMSO) d 10.76 (br, 1H), 9.38 (s, 1H), 9.06 (d, J=4.8 Hz, 1H), 8.92 (br, 1H), 8.50 (s, 1H), 8.40 (br, 1H), 8.15 (t, J=8.0 Hz, 1H), 8.08 (d, J=8.0 Hz, 1H), 7.96 (br, 1H), 4.15 (m, 1H), 2.67 (m, 4H), 1.83 (m, 4H), 1.10 (m, 4H).

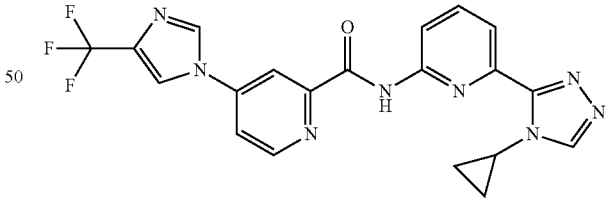

N-(6-(4-cyclopropyl-4H-1,2,4-triazol-3-yl)pyridin-2-yl)-4-(4-(trifluoromethyl)-1H-imidazol-1-yl)picolinamide $C_{20}H_{15}F_3N_8O×HCl$. 441.1 (M+1). $^1$H NMR (DMSO) d 10.73 (s, 1H), 8.92 (m, 4H), 8.64 (d, J=2.0 Hz, 1H), 8.42 (d, J=8.0 Hz, 1H), 8.19 (dd, J=5.6, 2.4 Hz, 1H), 8.15 (t, J=8.0 Hz, 1H), 7.92 (d, J=7.2 Hz, 1H), 4.16 (m, 1H), 1.05 (m, 4H). $^{19}$F NMR (DMSO) d −61.59 (s, 3F).

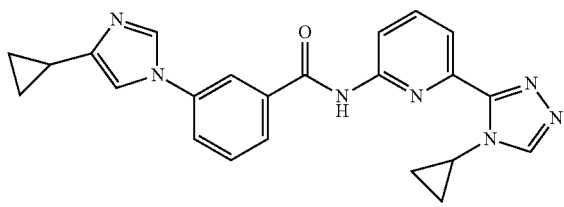 [SMILES: O=C(Nc1cccc(-c2nncn2C2CC2)n1)c1cccc(-n2cnc(C3CC3)c2)c1]

3-(4-cyclopropyl-1H-imidazol-1-yl)-N-(6-(4-cyclopropyl-4H-1,2,4-triazol-3-yl)pyridin-2-yl)benzamide $C_{23}H_{21}N_7O$. 412.1 (M+1). $^1$H NMR (DMSO) d 10.86 (s, 1H), 8.65 (s, 1H), 8.27 (d, J=8.0 Hz, 1H), 8.21 (s, 1H), 8.15 (s, 1H), 8.05 (t, J=8.0 Hz, 1H), 7.83 (m, 3H), 7.66 (t, J=8.0 Hz, 1H), 7.60 (s, 1H), 4.24 (m, 1H), 1.86 (m, 1H), 1.00 (m, 4H), 0.82 (m, 2H), 0.79 (m, 2H).

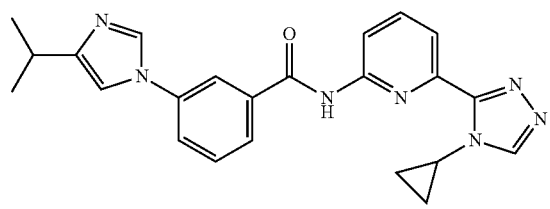 [SMILES: CC(C)c1cn(-c2cccc(C(=O)Nc3cccc(-c4nncn4C4CC4)n3)c2)cn1]

N-(6-(4-cyclopropyl-4H-1,2,4-triazol-3-yl)pyridin-2-yl)-3-(4-isopropyl-1H-imidazol-1-yl)benzamide $C_{23}H_{23}N_7O$. 414.1 (M+1). $^1$H NMR (DMSO) d 10.91 (s, 1H), 8.90 (br, 1H), 8.66 (s, 1H), 8.27 (m, 2H), 8.06 (t, J=8.0 Hz, 1H), 7.97 (m, 2H), 7.82 (m, 2H), 7.74 (t, J=8.0 Hz, 1H), 4.25 (m, 1H), 2.94 (sept, 6.8 Hz, 1H), 1.27 (d, J=6.8 Hz, 6H), 0.95 (m, 4H).

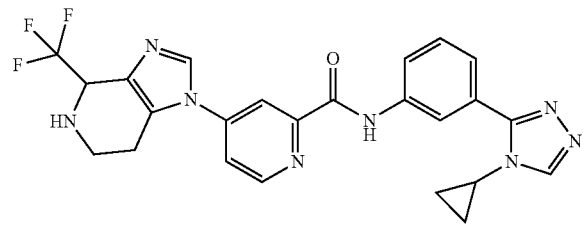 [SMILES: O=C(Nc1cccc(-c2nncn2C2CC2)c1)c1cc(-n2cnc3c2CCNC3C(F)(F)F)ccn1]

N-(3-(4-cyclopropyl-4H-1,2,4-triazol-3-yl)phenyl)-4-(4-(trifluoromethyl)-4,5,6,7-tetrahydro-1H-imidazo[4,5-c]pyridin-1-yl)picolinamide $C_{24}H_{21}F_3N_8O$. 495.1 (M+1). $^1$H NMR (DMSO) d 10.99 (s, 1H), 8.88 (d, J=5.2 Hz, 1H), 8.64 (s, 1H), 8.57 (s, 1H), 8.33 (s, 1H), 8.24 (d, J=2.0 Hz, 1H), 8.07 (d, J=8.0 Hz, 1H), 8.07 (d, J=8.0 Hz, 1H), 7.90 (dd, J=5.2, 2.0 Hz, 1H), 7.70 (d, J=8.0 Hz, 1H), 7.55 (t, J=8.0 Hz, 1H), 4.58 (br, 1H), 3.66 (m, 1H), 3.07 (br, 2H), 2.80 (br, 2H), 1.08 (m, 2H), 0.94 (m, 2H). $^{19}$F NMR (DMSO) d −71.5 (br, 3F).

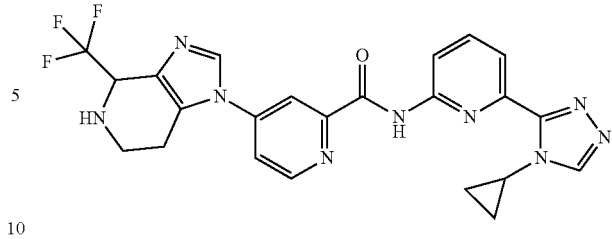

N-(6-(4-cyclopropyl-4H-1,2,4-triazol-3-yl)pyridin-2-yl)-4-(4-(trifluoromethyl)-4,5,6,7-tetrahydro-1H-imidazo[4,5-c]pyridin-1-yl)picolinamide $C_{23}H_{21}F_3N_9O \times HCl$. 495.1 (M+1). $^1$H NMR (DMSO) d 10.78 (s, 1H), 9.13 (s, 1H), 8.95 (d, J=5.6 Hz, 1H), 8.55 (s, 1H), 8.42 (d, J=8 Hz, 1H), 8.32 (d, J=2.0 Hz, 1H), 8.16 (t, J=8.0 Hz, 1H), 7.97 (m, 2H), 5.65 (m, 1H), 4.19 (m, 1H), 3.51 (m, 1H), 3.43 (m, 1H), 3.21 (m, 1H), 3.12 (m, 1H), 1.08 (m, 4H). $^{19}$F NMR (DMSO) d −69.2 (br, 3F).

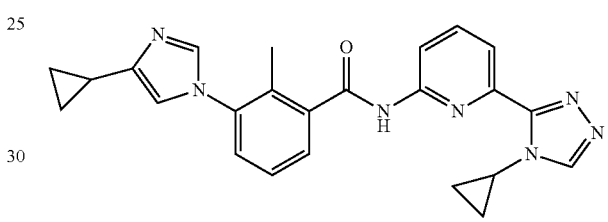

3-(4-cyclopropyl-1H-imidazol-1-yl)-N-(6-(4-cyclopropyl-4H-1,2,4-triazol-3-yl)pyridin-2-yl)-2-methylbenzamide $C_{24}H_{23}N_7O$. 426.3 (M+1). $^1$H NMR (DMSO) d 11.12 (s, 1H), 9.11 (br s, 1H), 8.64 (s, 1H), 8.29 (d, J=8 Hz, 1H), 8.04 (t, J=8 Hz, 1H), 7.87 (d, J=8.0 Hz, 1H), 7.75 (d, J=7 Hz, 1H), 7.60-7.66 (m, 2H), 7.54-7.58 (m, 1H), 4.23-4.27 (m, 1H), 2.22 (s, 3H), 2.00-2.07 (m, 1H), 0.85-1.04 (m, 8H).

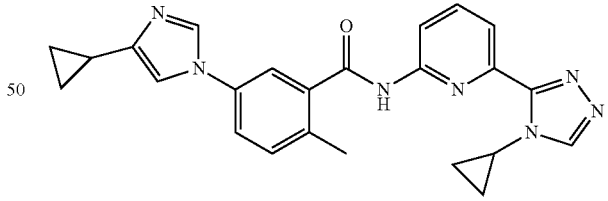

5-(4-cyclopropyl-1H-imidazol-1-yl)-N-(6-(4-cyclopropyl-4H-1,2,4-triazol-3-yl)pyridin-2-yl)-2-methylbenzamide $C_{24}H_{23}N_7O$. 426.1 (M+1). $^1$H NMR (DMSO) d 10.99 (s, 1H), 8.63 (s, 1H), 8.43 (s, 1H), 8.31 (d, J=8 Hz, 1H), 8.04 (t, J=8 Hz, 1H), 7.86 (d, J=7 Hz, 1H), 7.81 (d, J=2 Hz, 1H), 7.67 (dd, J=2, 9 Hz, 1H), 7.65 (s, 1H), 7.47 (d, J=8 Hz, 1H), 4.25-4.29 (m, 1H), 2.43 (s, 3H), 1.84-1.88 (m, 1H), 0.82-1.00 (m, 6H), 0.70-0.73 (m, 2H).

105

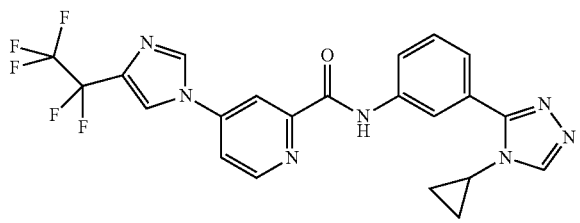 [SMILES: O=C(Nc1cccc(-c2nncn2C2CC2)c1)c1cc(-n2cnc(C(F)(F)C(F)(F)F)c2)ccn1]

N-(3-(4-cyclopropyl-4H-1,2,4-triazol-3-yl)phenyl)-
4-(4-(perfluoroethyl)-1H-imidazol-1-yl)picolinamide $C_{22}H_{16}F_5N_7O \times HCl$. 490.1 (M+1). $^1$H NMR (DMSO) d 11.03 (s, 1H), 8.98 (s, 1H), 8.92 (m, 3H), 8.63 (s, 1H), 8.59 (s, 1H), 8.18 (dd, J=5.2, 2.0 Hz, 1H), 8.12 (d, J=8.8 Hz, 1H), 7.72 (d, J=8.0 Hz, 1H), 7.60 (t, J=8.0 Hz, 1H), 3.72 (m, 1H), 1.13 (m, 2H), 1.01 (m, 2H). $^{19}$F NMR (DMSO) d −83.3 (s, 3H), −111.7 (s, 2H).

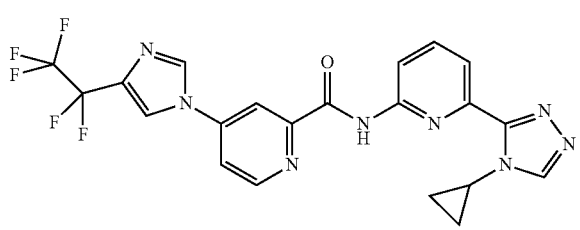 [SMILES: O=C(Nc1cccc(-c2nncn2C2CC2)n1)c1cc(-n2cnc(C(F)(F)C(F)(F)F)c2)ccn1]

N-(6-(4-cyclopropyl-4H-1,2,4-triazol-3-yl)pyridin-2-yl)-4-(4-(perfluoroethyl)-1H-imidazol-1-yl)picolinamide $C_{21}H_{15}F_5N_8O \times HCl$. 491.1 (M+1). $^1$H NMR (DMSO) d 10.71 (s, 1H), 8.94 (m, 3H), 8.77 (s, 1H), 8.65 (d, J=2.4 Hz, 1H), 8.39 (d, 8.0 Hz, 1H), 8.21 (dd, J=5.6, 2.4 Hz, 1H), 8.13 (t, J=8.0 Hz, 1H), 7.90 (d, J=6.8 Hz, 1H), 4.13 (m, 1H), 1.02 (m, 4H). $^{19}$F NMR (DMSO) d −83.3 (s, 3H), −111.7 (s, 2H).

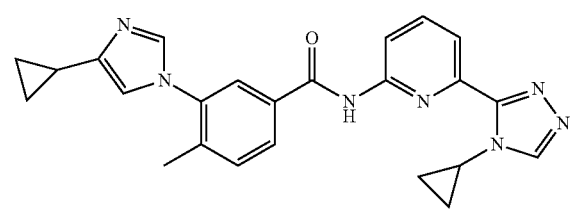 [SMILES: Cc1ccc(C(=O)Nc2cccc(-c3nncn3C3CC3)n2)cc1-n1cnc(C2CC2)c1]

3-(4-cyclopropyl-1H-imidazol-1-yl)-N-(6-(4-cyclopropyl-4H-1,2,4-triazol-3-yl)pyridin-2-yl)-4-methylbenzamide $C_{24}H_{23}N_7O \times HCO_2H$. 426.2 (M+1). $^1$H NMR (DMSO) d 10.79 (s, 1H), 8.65 (s, 1H), 8.24 (d, J=8 Hz, 1H), 7.98-8.06 (m, 3H), 7.96 (s, 1H), 7.79 (d, J=7 Hz, 1H), 7.60 (d, J=8 Hz, 1H), 7.34 (hr s, 1H), 6.52 (s, 1H), 4.20-4.24 (m, 1H), 2.28 (s, 3H), 1.83-1.89 (m, 1H), 0.84-0.99 (m, 6H), 0.73-0.76 (m, 2H).

106

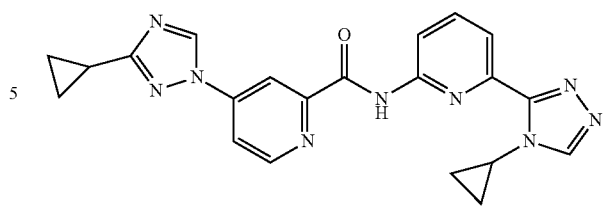

4-(3-cyclopropyl-1H-1,2,4-triazol-1-yl)-N-(6-(4-cyclopropyl-4H-1,2,4-triazol-3-yl)pyridin-2-yl)picolinamide $C_{21}H_{19}N_9O \times HCl$. 414.1 (M+1). $^1$H NMR (DMSO) d 10.70 (s, 1H), 9.55 (s, 1H), 8.88 (m, 2H), 8.62 (d, J=1.6 Hz, 1H), 8.40 (d, J=8.8 Hz, 1H), 8.15 (m, 2H), 7.91 (d, J=8.0 Hz, 1H), 4.14 (m, 1H), 2.15 (m, 1H), 1.05 (m, 6H), 0.94 (m, 2H).

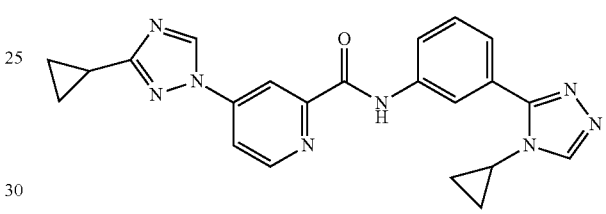

4-(3-cyclopropyl-1H-1,2,4-triazol-1-yl)-N-(3-(4-cyclopropyl-4H-1,2,4-triazol-3-yl)phenyl)picolinamide $C_{22}H_{20}N_8O \times HCl$. 413.1 (M+1). $^1$H NMR (DMSO) d 11.01 (s, 1H), 9.53 (s, 1H), 8.90 (s, 1H), 8.87 (d, J=5.2 Hz, 1H), 8.62 (s, 1H), 8.57 (s, 1H), 8.10 (m, 2H), 7.71 (d, J=8.0 Hz, 1H), 7.59 (t, J=8.0 Hz, 1H), 3.72 (m, 1H), 2.15 (m, 1H), 1.02 (m, 8H).

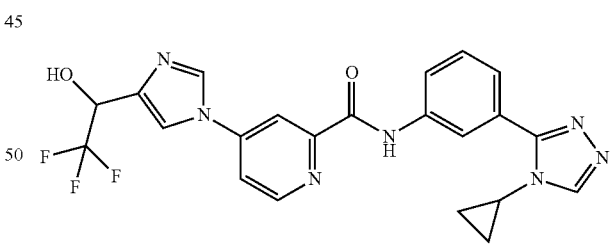

N-(3-(4-cyclopropyl-4H-1,2,4-triazol-3-yl)phenyl)-
4-(4-(2,2,2-trifluoro-1-hydroxyethyl)-1H-imidazol-1-yl)picolinamide $C_{21}H_{18}F_3N_7O_2 \times HCl$. 470.1 (M+1). $^1$H NMR (DMSO) d 11.09 (m, 1H), 9.42 (m, 1H), 9.01 (s, 1H), 8.88 (d, J=5.2 Hz, 1H), 8.68 (s, 1H), 8.50 (d, J=2.0 Hz, 1H), 8.17 (m, 3H), 7.73 (t, J=8.0 Hz, 1H), 7.64 (t, J=8.0 Hz, 1H), 5.18 (q, J=7.2 Hz, 1H), 3.80 (m, 1H), 1.01 (m, 4H). $^{19}$F NMR (DMSO) d 76.48 (d, J=7.2 Hz, 3F).

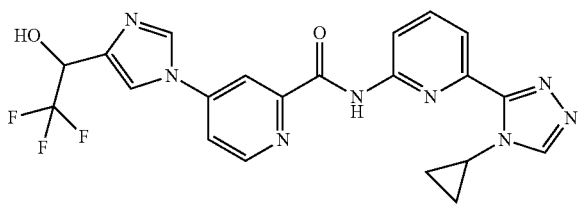 [SMILES: O=C(Nc1cccc(-c2nncn2C2CC2)n1)c1cc(-n2cnc(C(O)C(F)(F)F)c2)ccn1]

N-(6-(4-cyclopropyl-4H-1,2,4-triazol-3-yl)pyridin-2-yl)-4-(4-(2,2,2-trifluoro-1-hydroxyethyl)-1H-imidazol-1-yl)picolinamide $C_{21}H_{17}F_3N_8O_2 \times HCl$. 471.1 (M+1). $^1$H NMR (DMSO) d 10.72 (s, 1H), 8.89 (m, 3H), 8.55 (s, 1H), 8.41 (d, J=8.0 Hz, 1H), 8.26 (s, 1H), 8.15 (m, 2H), 7.92 (d, J=8.0 Hz, 1H), 5.15 (d, J=7.2 Hz, 1H), 4.16 (m, 1H), 1.06 (m, 4H). $^{19}$F NMR (DMSO) d 76.41 (d, J=7.2 Hz, 3F).

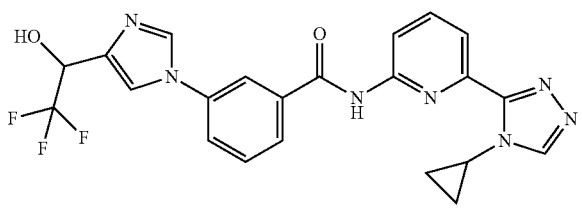 [SMILES: O=C(Nc1cccc(-c2nncn2C2CC2)n1)c1cccc(-n2cnc(C(O)C(F)(F)F)c2)c1]

N-(6-(4-cyclopropyl-4H-1,2,4-triazol-3-yl)pyridin-2-yl)-3-(4-(2,2,2-trifluoro-1-hydroxyethyl)-1H-imidazol-1-yl)benzamide $C_{22}H_{18}F_3N_7O_2$. 470.1 (M+1). $^1$H NMR (DMSO) d 10.91 (s, 1H), 8.66 (s, 1H), 8.34 (s, 1H), 8.27 (d, J=8.0 Hz, 1H), 8.23 (s, 1H), 8.06 (t, J=8.0 Hz, 1H), 7.93 (m, 3H), 7.81 (d, J=8.0 Hz, 1H), 7.70 (t, J=8.0 Hz, 1H), 6.71 (d, J=5.2 Hz, 1H), 5.06 (m, 1H), 4.23 (m, 1H), 0.98 (m, 2H), 0.94 (m, 2H). $^{19}$F NMR (DMSO) d 76.44 (d, J=7.2 Hz, 3F).

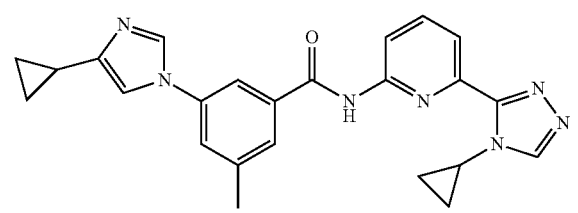 [SMILES: Cc1cc(C(=O)Nc2cccc(-c3nncn3C3CC3)n2)cc(-n2cnc(C3CC3)c2)c1]

3-(4-cyclopropyl-1H-imidazol-1-yl)-N-(6-(4-cyclopropyl-4H-1,2,4-triazol-3-yl)pyridin-2-yl)-5-methyl-benzamide $C_{24}H_{23}N_7O$. 426.3 (M+1). $^1$H NMR (DMSO) d 10.81 (s, 1H), 8.65 (s, 1H), 8.26 (d, J=8 Hz, 1H), 8.20 (br s, 1H), 8.05 (t, J=8 Hz, 1H), 7.95 (s, 1H), 7.81 (d, J=8 Hz, 1H), 7.68-7.72 (m, 2H), 7.60 (br s, 1H), 4.21-4.27 (m, 1H), 2.46 (s, 3H) 1.83-1.86 (m, 1H), 0.89-0.98 (m, 8H).

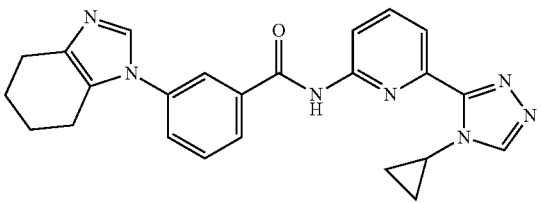 [SMILES: O=C(Nc1cccc(-c2nncn2C2CC2)n1)c1cccc(-n2cnc3c2CCCC3)c1]

N-(6-(4-cyclopropyl-4H-1,2,4-triazol-3-yl)pyridin-2-yl)-3-(4,5-dimethyl-1H-imidazol-1-yl)benzamide $C_{22}H_{21}N_7O \times HCl$. 400.1 (M+1). $^1$H NMR (DMSO) d 11.11 (s, 1H), 9.42 (s, 1H), 9.10 (s, 1H), 8.30 (d, J=8.0 Hz, 1H), 8.24 (m, 2H), 8.10 (t, J=8.0 Hz, 1H), 7.86 (m, 3H), 4.37 (m, 1H), 2.34 (s, 3H), 2.18 (s, 3H), 1.01 (m, 4H).

N-(6-(4-cyclopropyl-4H-1,2,4-triazol-3-yl)pyridin-2-yl)-3-(4,5,6,7-tetrahydro-1H-benzo[d]imidazol-1-yl)benzamide $C_{24}H_{23}N_7O \times HCl$. 426.1 (M+1). $^1$H NMR (DMSO) d 11.11 (s, 1H), 9.50 (s, 1H), 9.11 (s, 1H), 8.30 (m, 2H), 8.20 (d, J=8.0 Hz, 1H), 8.10 (t, J=8.0 Hz, 1H), 7.87 (m, 3H), 4.39 (m, 1H), 2.71 (m, 2H), 2.61 (m, 2H), 1.83 (4H), 1.01 (m, 4H).

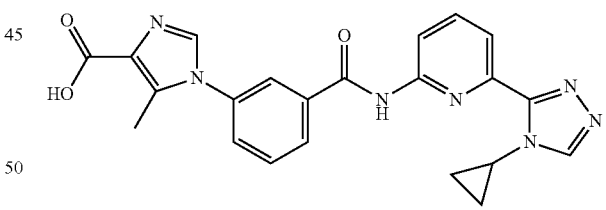

1-(3-(6-(4-cyclopropyl-4H-1,2,4-triazol-3-yl)pyridin-2-ylcarbamoyl)phenyl)-5-methyl-1H-imidazole-4-carboxylic acid $C_{22}H_{19}N_7O_3 \times HCl$. 430.1 (M+1). $^1$H NMR (DMSO) d 11.05 (s, 1H), 9.35 (s, 1H), 9.13 (s, 1H), 8.29 (d, J=8.0 Hz, 1H), 8.19 (m, 2H), 8.09 (t, J=8.0 Hz, 1H), 7.87 (m, 3H), 7.82 (d, J=8.0 Hz, 1H), 7.73 (t, J=8.0 Hz, 1H), 4.38 (m, 1H), 2.59 (s, 3H), 1.03 (m, 4H).

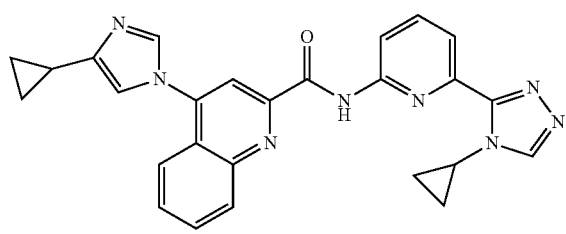 [SMILES: O=C(Nc1cccc(-c2nncn2C2CC2)n1)c1cc(-n2cnc(C3CC3)c2)c2ccccc2n1]

4-(4-cyclopropyl-1H-imidazol-1-yl)-N-(6-(4-cyclo-
propyl-4H-1,2,4-triazol-3-yl)pyridin-2-yl)quinoline-
2-carboxamide $C_{26}H_{22}N_8O$. 463.3 (M+1). $^1$H NMR (DMSO) d 10.85 (s, 1H), 8.71 (s, 1H), 8.40 (t, J=8 Hz, 2H), 8.22 (s, 1H), 8.14 (t, J=8 Hz, 1H), 8.12 (s, 1H), 8.02-8.08 (m, 2H), 7.85-7.92 (m, 2H), 7.60 (s, 1H), 4.10-4.14 (m, 1H), 1.93-1.97 (m, 1H), 1.05-1.12 (m, 4H), 0.80-0.90 (m, 4H).

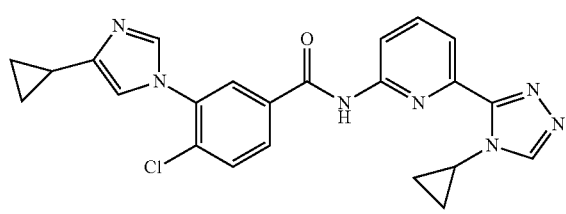 [SMILES: O=C(Nc1cccc(-c2nncn2C2CC2)n1)c1ccc(Cl)c(-n2cnc(C3CC3)c2)c1]

4-chloro-3-(4-cyclopropyl-1H-imidazol-1-yl)-N-(6-
(4-cyclopropyl-4H-1,2,4-triazol-3-yl)pyridin-2-yl)
benzamide $C_{23}H_{20}ClN_7O$. 446.2 (M+1). $^1$H NMR (DMSO) d 10.92 (s, 1H), 8.66 (s, 1H), 8.24 (d, J=8 Hz, 1H), 8.13 (s, 1H), 8.03-8.07 (m, 3H), 7.92 (br s, 1H), 7.87 (d, J=8 Hz, 1H), 7.81 (d, J=7 Hz, 1H), 7.34 (br s, 1H), 4.18-4.21 (m, 1H), 1.87-1.90 (m, 1H), 0.72-1.00 (m, 8H).

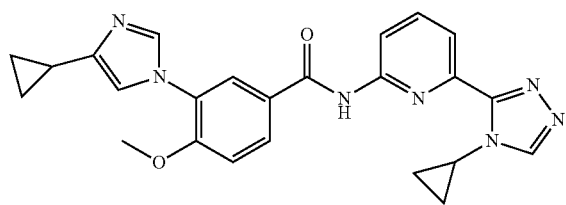 [SMILES: COc1ccc(C(=O)Nc2cccc(-c3nncn3C3CC3)n2)cc1-n1cnc(C2CC2)c1]

3-(4-cyclopropyl-1H-imidazol-1-yl)-N-(6-(4-cyclo-
propyl-4H-1,2,4-triazol-3-yl)pyridin-2-yl)-4-meth-
oxybenzamide $C_{24}H_{23}N_7O_2$. 442.3 (M+1). $^1$H NMR (DMSO) d 10.71 (s, 1H), 8.66 (s, 1H), 8.25 (d, J=8 Hz, 1H), 8.00-8.11 (m, 4H), 7.78 (d, J=6 Hz, 1H), 7.40 (d, J=9 Hz, 1H), 7.40 (br s, 1H), 4.20-4.23 (m, 1H), 3.93 (s, 3H), 1.86-1.89 (m, 1H), 0.70-1.00 (m, 8H).

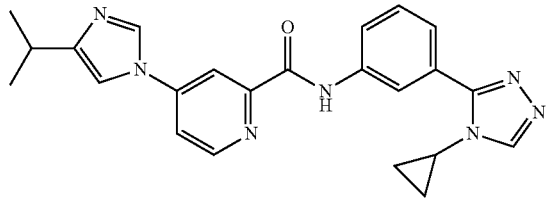 [SMILES: CC(C)c1cn(-c2ccnc(C(=O)Nc3cccc(-c4nncn4C4CC4)c3)c2)cn1]

N-(3-(4-cyclopropyl-4H-1,2,4-triazol-3-yl)phenyl)-
4-(4-isopropyl-1H-imidazol-1-yl)picolinamide $C_{23}H_{23}N_7O$. 414.1 (M+1). $^1$H NMR (DMSO) d 10.93 (s, 1H), 8.79 (d, J=5.6 Hz, 1H), 8.63 (s, 1H), 8.60 (s, 1H), 8.58 (s, 1H), 8.40 (d, J=2.4 Hz, 1H), 8.06 (d, J=8.8 Hz, 1H), 8.02 (dd, J=5.6, 2.4 Hz, 1H), 7.81 (s, 1H), 7.70 (d, J=8.0 Hz, 1H), 7.55 (t, J=8.0 Hz, 1H), 3.66 (m, 1H), 2.84 (sept, J=7.2 Hz, 1H), 1.24 (d, J=7.2 Hz, 6H), 1.08 (m, 2H), 0.95 (m, 2H).

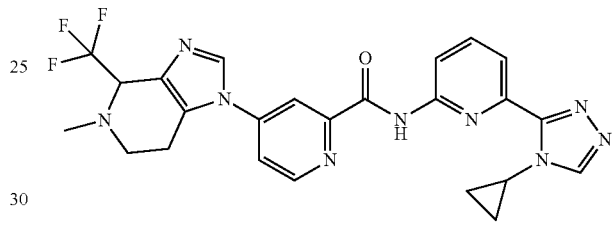

N-(6-(4-cyclopropyl-4H-1,2,4-triazol-3-yl)pyridin-2-
yl)-4-(5-methyl-4-(trifluoromethyl)-4,5,6,7-tetrahy-
dro-1H-imidazo[4,5-c]pyridin-1-yl)picolinamide $C_{24}H_{22}F_3N_9O\times HCl$. 510.1 (M+1). $^1$H NMR (DMSO) d 10.69 (s, 1H), 8.90 (d, J=5.6 Hz, 1H), 8.69 (s, 1H), 8.36 (m, 3H), 8.12 (t, J=8.0 Hz, 1H), 7.98 (dd, J=5.2, 2.4 Hz, 1H), 7.89 (d, J=8.0 Hz, 1H), 4.30 (q, J=8.4 Hz, 1H), 4.11 (m, 1H), 3.10 (m, 4H), 2.56 (s, 3H), 1.04 (m, 2H), 0.99 (m, 2H). $^{19}$F NMR (DMSO) d −70.54 (d, J=8.8 Hz, 3F).

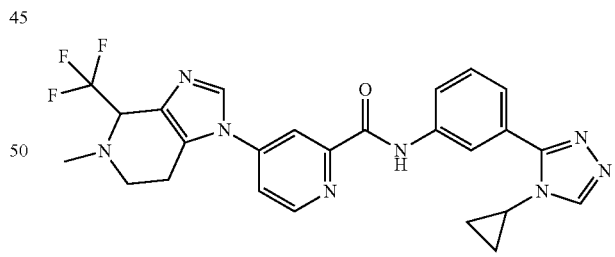

N-(3-(4-cyclopropyl-4H-1,2,4-triazol-3-yl)phenyl)-
4-(5-methyl-4-(trifluoromethyl)-4,5,6,7-tetrahydro-
1H-imidazo[4,5-c]pyridin-1-yl)picolinamide $C_{25}H_{23}F_3N_8O\times HCl$. 509.1 (M+1). $^1$H NMR (DMSO) d 10.99 (s, 1H), 8.89 (d, J=5.2 Hz, 1H), 8.63 (s, 1H), 8.57 (s, 1H), 8.34 (s, 1H), 8.29 (m, 1H), 8.06 (d, J=8.8 Hz, 1H), 7.94 (dd, J=5.6 Hz, 1H), 7.70 (d, J=8.0 Hz, 1H), 7.55 (t, 18.0 Hz, 1H), 4.29 (q, 8.8 Hz, 1H), 3.66 (m, 1H), 3.10 (m, 4H), 2.55 (s, 3H), 1.08 (m, 2H), 0.98 (m, 2H). $^{19}$F NMR (DMSO) d −70.55 (d, J=8.8 Hz, 3F).

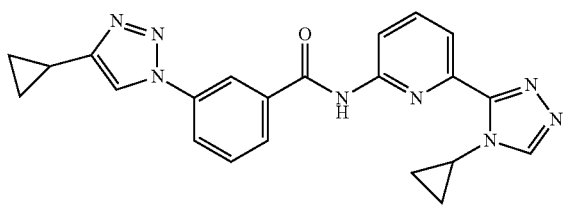 [SMILES: O=C(Nc1cccc(-c2nncn2C2CC2)n1)c1cccc(-n2cc(C3CC3)nn2)c1]

3-(4-cyclopropyl-1H-1,2,3-triazol-1-yl)-N-(6-(4-cyclopropyl-4H-1,2,4-triazol-3-yl)pyridin-2-yl)benzamide $C_{22}H_{20}N_8O$. 413.1 (M+1). $^1$H NMR (DMSO) d 10.96 (s, 1H), 8.67 (s, 1H), 8.66 (s, 1H), 8.41 (s, 1H), 8.27 (d, J=8.0 Hz, 1H), 8.10 (m, 3H), 7.83 (d, J=8.0 Hz, 1H), 7.76 (t, J=8.0 Hz, 1H), 4.27 (m, 1H), 2.03 (m, 1H), 1.00 (m, 6H), 0.82 (m, 2H).

C. Similarly, following the procedure of Example 14, optionally replacing 4-bromo-N-(3-(4-cyclopropyl-4H-1,2,4-triazol-3-yl)phenyl)picolinamide with other compounds of formula (5), and optionally replacing imidazole with other amines, other compounds of Formula I are prepared.

EXAMPLE 15

Preparation of Compounds of Formula (I) via Triazole Formation from an Acyl Hydrazide A. Preparation of a Compound of Formula (I) in which $X^2$, $X^3$, $X^4$, $X^6$, $X^7$ and $X^8$ are C($R^4$), $X^1$ and $X^5$ are N, $R^1$ is 2-Methoxy-1-methylethyl, $R^2$ is Hydrogen, and $R^3$ is 2-Cyclopropylpyridin3-yl A. Preparation of (S)-6-cyclopropyl-N-(6-(4-(1-methoxypropan-2-yl)-4H-1,2,4-triazol-3-yl)pyridin-2-yl)-3,4'-bipyridine-2'-carboxamide

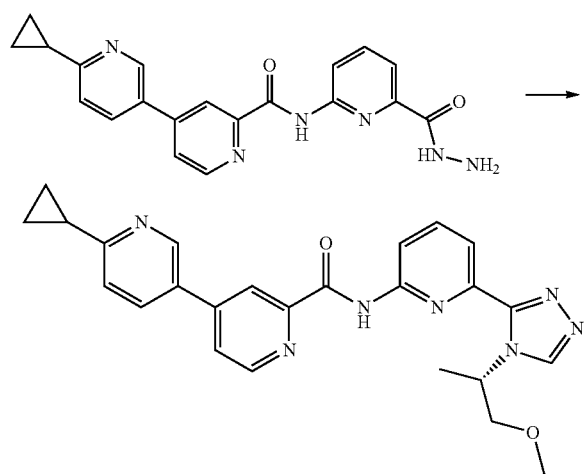

To a suspension of 6-cyclopropyl-N-(6-(hydrazinecarbonyl)pyridin-2-yl)-3,4'-bipyridine-2'-carboxamide, a compound of formula (3) (75 mg, 0.20 mmol) in toluene (0.20 M) was added N,N-dimethylformamide/N,N-dimethylacetamide (67 µL, 0.50 mmol), (S)-2-methoxy-1-methyl-ethylamine (72 mg µL, 0.80 mmol), and acetic acid (11 µL, 0.20 mmol). The reaction was heated to 150° C. for 30 minutes in a microwave reactor. The reaction mixture was concentrated under reduced pressure, and the residue suspended in acetonitrile/diethyl ether (15 mL, 1:1 ratio), filtered and washed with acetonitrile/diethyl ether (2×10 mL). The solid thus obtained was dried under reduced pressure to afford 57 mg (63% yield) of (S)-6-cyclopropyl-N-(6-(4-(1-methoxypropan-2-yl)-4H-1,2,4-triazol-3-yl)pyridin-2-yl)-3,4'-bipyridine-2'-carboxamide as a white solid.

$C_{25}H_{25}N_7O_2$. 456.2 (M+1). $^1$H NMR (DMSO) d 10.71 (s, 1H), 8.95 (d, J=2 Hz, 1H), 8.85 (s, 1H), 8.84 (d, J=5 Hz, 1H), 8.49 (s, 1H), 8.35 (d, J=8 Hz, 1H), 8.21 (dd, J=2, 8 Hz, 1H), 8.08-8.12 (m, 2H), 7.92 (d, J=8 Hz, 1H), 7.50 (d, J=8 Hz, 1H), 5.65-5.71 (m, 1H), 3.73 (dd, J=7, 10 Hz, 1H), 3.60 (dd, J=5, 10 Hz, 1H), 3.24 (s, 3H), 2.18-2.25 (m, 1H), 1.51 (d, J=7 Hz, 3H), 0.98-1.06 (m, 4H).

B. Preparation of other Compounds of Formula (I) Via Triazole formation from an Acyl Hydrazide Similarly, optionally replacing 6-cyclopropyl-N-(6-(hydrazinecarbonyl)pyridin-2-yl)-3,4'-bipyridine-2'-carboxamide with other compounds of formula (3) and optionally replacing (S)-2-methoxy-1-methyl-ethylamine with other alkyl amines, and following the procedures of Example 15, the following compounds of Formula (I) were prepared.

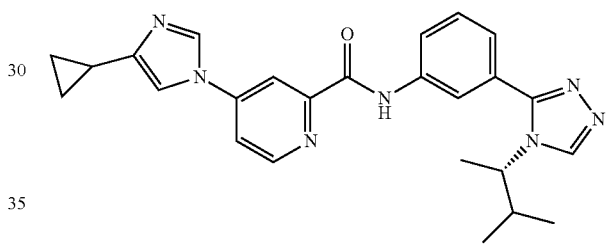

(S)-4-(4-cyclopropyl-1H-imidazol-1-yl)-N-(3-(4-(3-methylbutan-2-yl)-4H-1,2,4-triazol-3-yl)phenyl)picolinamide $C_{25}H_{27}N_7O\times HCl$. 442.1 (M-(1). $^1$H NMR (DMSO) d 10.98 (s, 1H), 8.85 (s, 1H), 8.79 (d, J=5.6 Hz, 1H), 8.55 (s, 1H), 8.36 (d, J=2.0 Hz, 1H), 8.16 (s, 1H), 8.10 (d, J=8.8 Hz, 1H), 7.99 (dd, J=5.6 Hz, 1H), 7.86 (s, 1H), 7.57 (t, J=8.0 Hz, 1H), 7.32 (d, J=8.0 Hz, 1H), 4.00 (m, 1H), 1.95 (m, 1H), 1.87 (m, 1H), 1.51 (d, J=6.8 Hz, 3H), 0.82 (d, J=6.8 Hz, 6H), 0.74 (m, 2H), 0.55 (m, 2H).

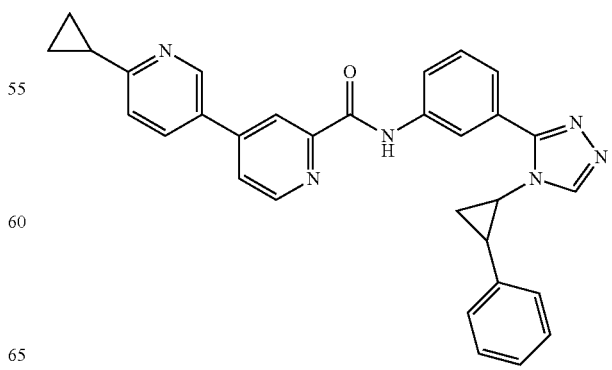

6-cyclopropyl-N-(3-(4-(2-phenylcyclopropyl)-4H-1,2,4-triazol-3-yl)phenyl)-3,4'-bipyridine-2'-carboxamide $C_{31}H_{26}N_6O$. 499.1 (M+1). $^1$H NMR (DMSO) d 10.70 (s, 1H), 8.94 (d, J=2.4 Hz, 1H), 8.81 (d, J=5.2 Hz, 1H), 8.78 (s, 1H), 8.41 (d, J=1.2 Hz, 1H), 8.38 (s, 1H), 8.19 (m, 1H), 8.06 (m, 2H), 7.57 (d, J=8.0 Hz, 1H), 7.50 (d, J=8.0 Hz, 1H), 7.41 (t, J=8.0 Hz, 1H), 7.21 (m, 2H), 7.08 (m, 3H), 3.86 (m, 1H), 2.48 (m, 1H), 2.20 (m, 1H), 1.61 (m, 2H), 1.01 (m, 4H).

C. Preparation of other Compounds of Formula (I) via Triazole Formation from an Acyl Hydrazide Similarly, optionally replacing 6-cyclopropyl-N-(6-(hydrazinecarbonyl)pyridin-2-yl)-3,4'-bipyridine-2'-carboxamide with other compounds of formula (3) and optionally replacing (S)-2-methoxy-1-methyl-ethylamine with other alkyl amines, and following the procedures of Example 15, other compounds of Formula (I) are prepared.

EXAMPLE 16

Preparation of Compounds of Formula (I) via Triazole Formation from Oxadiazoles

A. Preparation of a Compound of Formula (I) in which $X^2$, $X^3$, $X^4$, $X^6$, $X^7$ and $X^8$ are $C(R^4)$, $X^1$ and $X^5$ are N, $R^1$ is 2-Hydroxy-1-methylethyl. $R^2$ is Hydrogen, and $R^3$ is Pyridin3-yl A. Preparation of (R)—N-(3-(4-(1-hydroxypropan-2-yl)-4H-1,2,4-triazol-3-yl)phenyl)-3,4'-bipyridine-2'-carboxamide

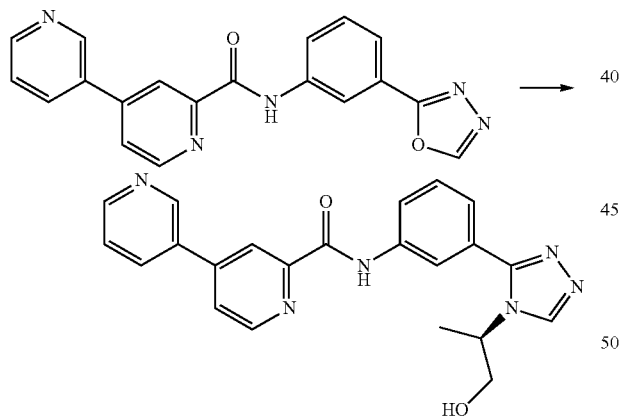

A suspension of N-(3-(1,3,4-oxadiazol-2-yl)phenyl)-3,4'-bipyridine-2'-carboxamide (210 mg, 0.61 mmol), (R)-2-amino-1-propanol (0.3 mL), and trifluoroacetic acid (0.05 mL) in n-butanol was heated in a microwave to 150° C. for 1 hour. The solvent was removed under reduced pressure and the residue was purified by reverse-phase HPLC to give (R)—N-(3-(4-(1-hydroxypropan-2-yl)-4H-1,2,4-triazol-3-yl)phenyl)-3,4'-bipyridine-2'-carboxamide as a white powder (55 mg, 0.138 mmol, 23% yield).

$C_{22}H_{20}N_6O_2$. 401.5 (M+1). $^1$H NMR (DMSO) d 10.97 (s, 1H), 9.11 (d, J=2.0 Hz, 1H), 8.87 (d, J=4.4 Hz, 1H), 8.80 (s, 1H), 8.73 (dd, J=4.8, 1.6 Hz, 1H), 8.48 (d, J=1.2 Hz, 1H), 8.34 (dt, J=4.0, 1.6 Hz, 1H), 8.21 (s, 1H), 8.11 (m, 2H), 7.59 (m, 2H), 7.41 J=8.0 Hz, 1H), 5.14 (t, J=5.2 Hz, 1H), 4.38 (m, 1H), 3.64 (m, 2H), 1.42 (d, J=6.8 Hz, 3H).

B. Similarly, optionally replacing N-(3-(1,3,4-oxadiazol-2-yl)phenyl)-3,4'-bipyridine-2'-carboxamide with other compounds of formula (4), and optionally replacing (R)-2-amino-1-propanol with other amines of formula $R^1NH_2$, and following the procedure of Example 16A, the following compounds of Formula (I) were prepared:

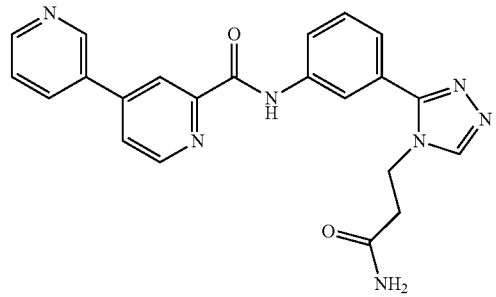 [SMILES: NC(=O)CCn1cnnc1-c1cccc(NC(=O)c2cc(-c3cccnc3)ccn2)c1]

N-(3-(4-(3-amino-3-oxopropyl)-4H-1,2,4-triazol-3-yl)phenyl)-3,4'-bipyridine-2'-carboxamide $C_{22}H_{19}N_7O_2$. 414.2 (M+1). $^1$H NMR (DMSO) d 10.99 (s, 1H), 9.11 (d, J=1.6 Hz, 1H), 8.87 (m, 1H), 8.73 (dd, J=4.8, 1.6 Hz, 1H), 8.56 (s, 1H), 8.48 (d, J=0.8 Hz, 1H), 8.34 (m, 1H), 8.28 (s, 1H), 8.12 (m, 2H), 7.60 (m, 2H), 7.47 (d, J=7.2 Hz, 1H), 7.39 (s, 1H), 6.96 (s, 1H), 4.34 (t, J=6.8 Hz, 2H), 2.56 (t, J=6.8 Hz, 2H).

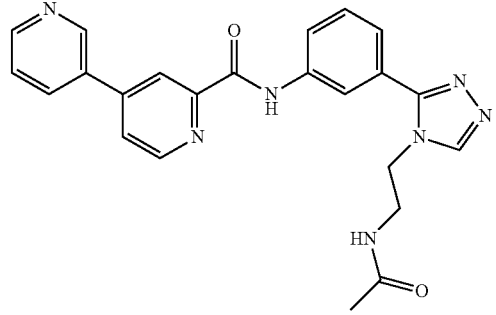 [SMILES: CC(=O)NCCn1cnnc1-c1cccc(NC(=O)c2cc(-c3cccnc3)ccn2)c1]

N-(3-(4-(2-acetamidoethyl)-4H-1,2,4-triazol-3-yl)phenyl)-3,4'-bipyridine-2'-carboxamide $C_{23}H_{21}N_7O_2$. 428.1 (M+1). $^1$H NMR (DMSO) d 10.97 (s, 1H), 9.11 (d, J=1.6 Hz, 1H), 8.87 (d, J=4.8 Hz, 1H), 8.72 (dd, J=4.8, 1.2 Hz, 1H), 8.61 (s, 1H), 8.48 (d, J=1.2 Hz, 1H), 8.34 (m, 1H), 8.26 (s, 1H), 8.12 (m, 2H), 7.98 (m, 1H), 7.59 (m, 2H), 7.42 (d, J=8.0 Hz, 1H), 4.18 (t, J=6.0 Hz, 2H), 3.34 (t, J=6.0 Hz, 2H), 1.67 (s, 3H).

115

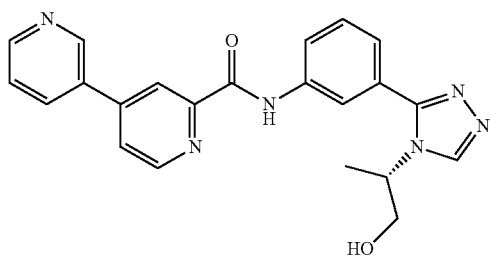 [SMILES: C[C@@H](CO)n1cnnc1-c1cccc(NC(=O)c2cc(-c3cccnc3)ccn2)c1]

(S)—N-(3-(4-(1-hydroxypropan-2-yl)-4H-1,2,4-triazol-3-yl)phenyl)-3,4'-bipyridine-2'-carboxamide $C_{22}H_{20}N_6O_7O_2$. 401.5 (M+1). $^1$H NMR (DMSO) d 10.97 (s, 1H), 9.11 (d, J=2.0 Hz, 1H), 8.87 (d, J=4.4 Hz, 1H), 8.80 (s, 1H), 8.73 (dd, J=4.8, 1.6 Hz, 1H), 8.48 (d, J=1.2 Hz, 1H), 8.34 (dt, J=4.0, 1.6 Hz, 1H), 8.21 (s, 1H), 8.11 (m, 2H), 7.59 (m, 2H), 7.41 (d, J=8.0 Hz, 1H), 5.14 (t, J=5.2 Hz, 1H), 4.38 (m, 1H), 3.64 (m, 2H), 1.42 (d, J=6.8 Hz, 3H).

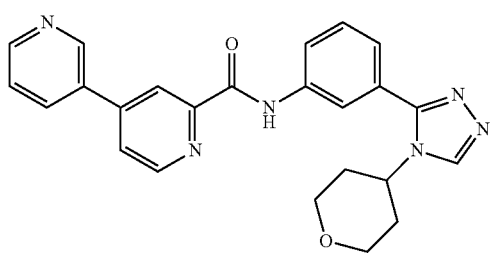 [SMILES: O=C(Nc1cccc(-c2nncn2C2CCOCC2)c1)c1cc(-c2cccnc2)ccn1]

N-(3-(4-(tetrahydro-2H-pyran-4-yl)-4H-1,2,4-triazol-3-yl)phenyl)-3,4'-bipyridine-2'-carboxamide $C_{24}H_{22}N_6O_2$, 427.1 (M+1). $^1$H NMR (DMSO) d 11.02 (s, 1H), 9.11 (d, J=1.6 Hz, 1H), 8.95 (s, 1H), 8.87 (d, J=4.8 Hz, 1H), 8.73 (dd, J=4.8, 1.6 Hz, 1H), 8.47 (d, J=1.2 Hz, 1H), 8.35 (m, 1H), 8.26 (s, 1H), 8.11 (m, 2H), 7.60 (m, 2H), 7.40 (d, J=7.6 Hz, 1H), 4.37 (m, 1H), 3.95 (m, 2H), 3.40 (m, 2H), 2.00 (m, 4H).

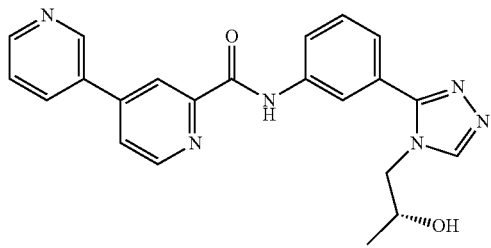 [SMILES: C[C@@H](O)Cn1cnnc1-c1cccc(NC(=O)c2cc(-c3cccnc3)ccn2)c1]

(R)—N-(3-(4-(2-hydroxypropyl)-4H-1,2,4-triazol-3-yl)phenyl)-3,4'-bipyridine-2'-carboxamide $C_{22}H_{20}N_6O_2$. 401.2 (M+1). $^1$H NMR (DMSO) d 10.97 (s, 1H), 9.11 (d, J=1.6 Hz, 1H), 8.87 (d, J=4.8 Hz, 1H), 8.73 (dd, J=4.8, 1.2 Hz, 1H), 8.59 (s, 1H), 8.48 (d, J=1.2 Hz, 1H), 8.34 (m, 1H), 8.27 (s, 1H), 8.11 (m, 2H), 7.60 (m, 2H), 7.47 (d, J=8.0 Hz, 1H), 5.09 (br, 1H), 4.10 (dd, J=13.6, 4.0 Hz, 1H), 3.96 (m, 1H), 3.86 (br, 1H), 1.01 (d, J=6.0 Hz, 3H).

116

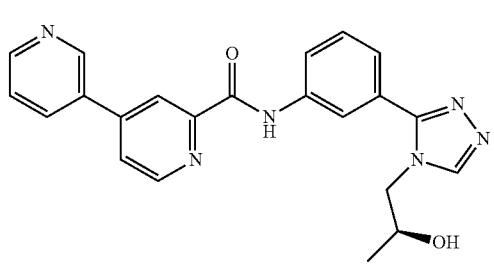 [SMILES: C[C@H](O)Cn1cnnc1-c1cccc(NC(=O)c2cc(-c3cccnc3)ccn2)c1]

(S)—N-(3-(4-(2-hydroxypropyl)-4H-1,2,4-triazol-3-yl)phenyl)-3,4'-bipyridine-2'-carboxamide $C_{22}H_{20}N_6O_2$. 401.2 (M+1). $^1$H NMR (DMSO) d 10.97 (s, 1H), 9.11 (d, J=1.6 Hz, 1H), 8.87 (d, J=4.8 Hz, 1H), 8.73 (dd, J=4.8, 1.2 Hz, 1H), 8.59 (s, 1H), 8.48 (d, J=1.2 Hz, 1H), 8.34 (m, 1H), 8.27 (s, 1H), 8.11 (m, 2H), 7.60 (m, 2H), 7.47 (d, J=8.0 Hz, 1H), 5.09 (br, 1H), 4.10 (dd, J=13.6, 4.0 Hz, 1H), 3.96 (m, 1H), 3.86 (br, 1H), 1.01 (d, J=6.0 Hz, 3H).

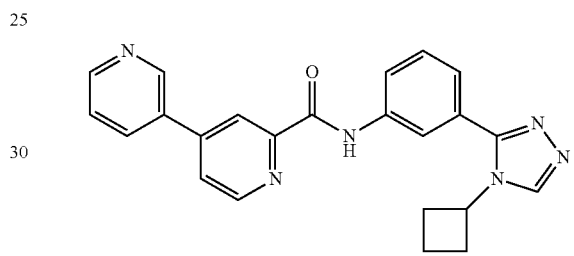

N-(3-(4-cyclobutyl-4H-1,2,4-triazol-3-yl)phenyl)-3,4'-bipyridine-2'-carboxamide;

$C_{23}H_{20}N_6O$. 397.2 (M+1). $^1$H NMR (DMSO) d 10.99 (s, 1H), 9.11 (d, J=1.6 Hz, 1H), 8.95 (s, 1H), 8.87 (d, J=5.2 Hz, 1H), 8.72 (m, 1H), 8.48 (s, 1H), 8.33 (m, 1H), 8.25 (s, 1H), 8.10 (m, 2H), 7.58 (m, 2H), 7.38 (d, J=7.2 Hz, 1H), 4.78 (quintet, J=8.4 Hz, 1H), 2.45 (m, 4H), 1.80 (m, 2H).

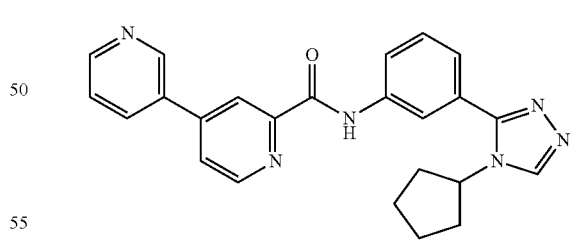

N-(3-(4-cyclopentyl-4H-1,2,4-triazol-3-yl)phenyl)-3,4'-bipyridine-2'-carboxamide $C_{24}H_{22}N_6O$. 411.2 (M+1). $^1$H NMR (DMSO) d 10.99 (s, 1H), 9.11 (m, 1H), 8.87 (d, J=4.8 Hz, 1H), 8.80 (s, 1H), 8.72 (d, J=4.4 Hz, 1H), 8.48 (s, 1H), 8.34 (d, 8.0 Hz, 1H), 8.26 (s, 1H), 8.10 (m, 2H), 7.59 (m, 2H), 7.39 (d, J=8.0 Hz, 1H), 4.61 (m, 1H), 2.18 (m, 2H), 1.84 (m, 4H), 1.63 (m, 2H).

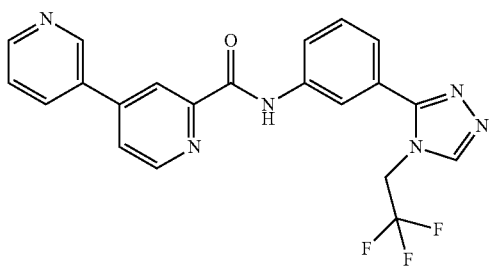 [SMILES: O=C(Nc1cccc(-c2nncn2CC(F)(F)F)c1)c1cc(-c2cccnc2)ccn1]

N-(3-(4-(2,2,2-trifluoroethyl)-4H-1,2,4-triazol-3-yl)phenyl)-3,4'-bipyridine-2'-carboxamide $C_{21}H_{15}F_3N_6O$. 425.8 (M+1). $^1$H NMR (DMSO) d 10.99 (s, 1H), 9.11 (d, J=1.6 Hz, 1H), 8.87 (d, J=5.2 Hz, 1H), 8.77 (s, 1H), 8.73 (dd, J=5.2, 1.6 Hz, 1H), 8.48 (d, J=1.2 Hz, 1H), 8.34 (m, 1H), 8.19 (m, 2H), 8.12 (dd, J=5.2, 2.0 Hz, 1H), 7.61 (d, J=8.0 Hz, 1H), 7.59 (t, J=8.0 Hz, 1H), 7.44 (d, J=8.0 Hz, 1H), 5.25 (q, J=9.0 Hz, 2H). $^{19}$F NMR (DMSO) d –70.31 (t, J=9.0 Hz, 3F).

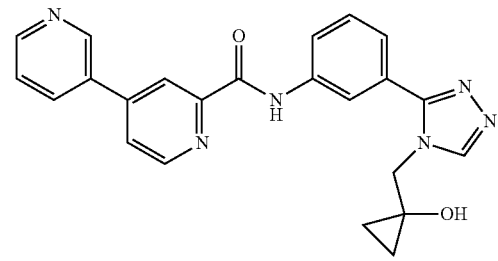 [SMILES: O=C(Nc1cccc(-c2nncn2CC2(O)CC2)c1)c1cc(-c2cccnc2)ccn1]

N-(3-(4-((1-hydroxycyclopropyl)methyl)-4H-1,2,4-triazol-3-yl)phenyl)-3,4'-bipyridine-2'-carboxamide $C_{23}H_{20}N_6O_2$. 413.1 (M+1). $^1$H NMR (DMSO) d 10.95 (s, 1H), 9.12 (d, J=2.0 Hz, 1H), 8.87 (d, J=5.6 Hz, 1H), 8.74 (s, 1H), 8.73 (s, 1H), 8.48 (d, J=0.8 Hz, 1H), 8.36 (d, J=8.0 Hz, 1H), 8.25 (s, 1H), 8.11 (m, 2H), 7.62 (dd, J=8.0, 5.2 Hz, 1H), 7.56 (t, J=8.0 Hz, 1H), 7.50 (d, J=8.0 Hz, 1H), 4.19 (s, 2H), 0.64 (m, 2H), 0.59 (m, 2H).

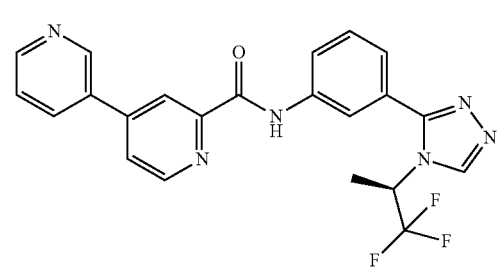 [SMILES: C[C@@H](n1cnnc1-c1cccc(NC(=O)c2cc(-c3cccnc3)ccn2)c1)C(F)(F)F]

(R)—N-(3-(4-(1,1,1-trifluoropropan-2-yl)-4H-1,2,4-triazol-3-yl)phenyl)-3,4'-bipyridine-2'-carboxamide $C_{22}H_{17}F_3N_6O$. 439.2 (M+1). $^1$H NMR (DMSO) d 10.97 (s, 1H), 9.11 (d, J=1.6 Hz, 1H), 9.09 (s, 1H), 8.86 (dd, J=4.8, 1.2 Hz, 1H), 8.73 (dd, J=5.2, 1.6 Hz, 1H), 8.48 (d, J=1.2 Hz, 1H), 8.34 (m, 1H), 8.19 (d, J=8.0 Hz, 1H), 8.12 (m, 2H), 7.61 (d, J=8.0 Hz, 1H), 7.59 (t, J=8.0 Hz, 1H), 7.38 (d, J=8.0 Hz, 1H), 5.29 (app sept, J=7.2 Hz, 1H), 1.82 (d, J=7.2 Hz, 3H).

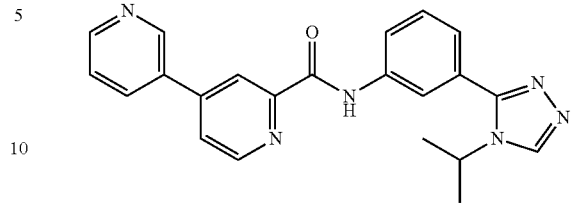

N-(3-(4-isopropyl-4H-1,2,4-triazol-3-yl)phenyl)-3,4'-bipyridine-2'-carboxamide $C_{22}H_{20}N_6O\times HCl$. 385.1 (M+1). $^1$H NMR (DMSO) d 11.12 (s, 1H), 9.56 (s, 1H), 9.28 (d, J=2.0 Hz, 1H), 8.92 (d, J=5.2 Hz, 1H), 8.86 (dd, J=5.2, 1.2 Hz, 1H), 8.66 (d, J=8.0 Hz, 1H), 8.55 (s, 1H), 8.40 (s, 1H), 8.18 (m, 2H), 7.86 (dd, J=8.0, 1.2 Hz, 1H), 7.66 (t, J=8.0 Hz, 1H), 7.47 (d, J=8.0 Hz, 1H), 4.64 (sept, J=6.8 Hz, 1H), 1.51 (d, J=6.8 Hz, 6H).

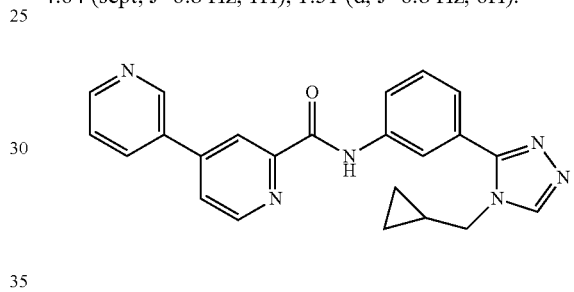

N-(3-(4-(cyclopropylmethyl)-4H-1,2,4-triazol-3-yl)phenyl)-3,4'-bipyridine-2'-carboxamide $C_{23}H_{20}N_6O\times HCl$. 397.1 (M+1). $^1$H NMR (DMSO) d 11.11 (s, 1H), 9.48 (s, 1H), 9.32 (s, 1H), 8.92 (d, J=5.2 Hz, 1H), 8.89 (d, J=5.2 Hz, 1H), 8.73 (d, J=8.0 Hz, 1H), 8.57 (s, 1H), 8.40 (s, 1H), 8.19 (m, 2H), 7.93 (dd, J=8.0, 5.6 Hz, 1H), 7.65 (t, J=8.0 Hz, 1H), 7.55 (d, J=8.0 Hz, 1H), 4.12 (d, J=7.6 Hz, 2H), 1.26 (m, 1H), 0.58 (, 2H), 0.40 (m, 2H).

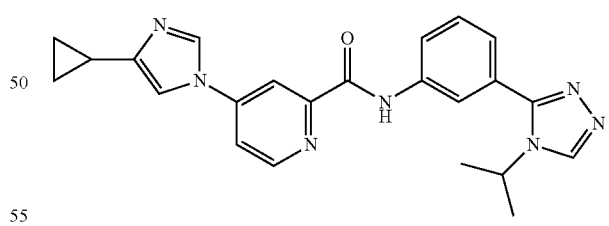

4-(4-cyclopropyl-1H-imidazol-1-yl)-N-(3-(4-isopropyl-4H-1,2,4-triazol-3-yl)phenyl)picolinamide $C_{23}H_{23}N_7O\times HCl$. 414.1 (M+1). $^1$H NMR (DMSO) d 11.17 (s, 1H), 9.94 (s, 1H), 9.66 (s, 1H), 8.99 (d, J=5.6 Hz, 1H), 8.59 (d, J=2.0 Hz, 1H), 8.37 (s, 1H), 8.34 (s, 1H), 8.18 (m, 2H), 7.67 (t, J=8.0 Hz, 1H), 7.50 (d, J=8.0 Hz, 1H), 4.64 (sept, J=6.8 Hz, 1H), 2.03 (m, 1H), 1.52 (d, J=6.8 Hz, 6H), 1.06 (m, 2H), 0.91 (m, 2H).

119

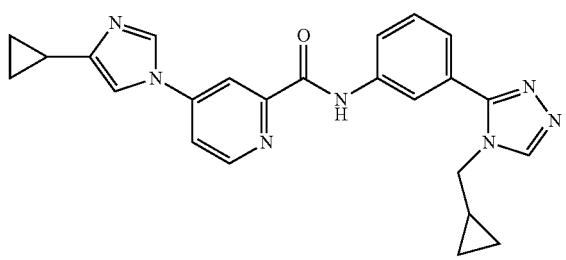 [SMILES: O=C(Nc1cccc(-c2nncn2CC2CC2)c1)c1cc(-n2cnc(C3CC3)c2)ccn1]

4-(4-cyclopropyl-1H-imidazol-1-yl)-N-(3-(4-(cyclo-propylmethyl)-4H-1,2,4-triazol-3-yl)phenyl)picoli-namide $C_{24}H_{23}N_7O \times HCl$. 426.1 (M+1). $^1H$ NMR (DMSO) d 11.14 (s, 1H), 9.93 (s, 1H), 9.46 (s, 1H), 9.00 (d, J=5.6 Hz, 1H), 8.59 (d, J=2.0 Hz, 1H), 8.37 (s, 2H), 8.20 (m, 2H), 7.64 (t, J=8.0 Hz, 1H), 7.56 (d, J=8.0 Hz, 1H), 4.11 (d, J=7.6 Hz, 2H), 2.04 (m, 1H), 1.24 (m, 1H), 1.06 (m, 2H), 0.91 (m, 2H), 0.57 (m, 2H), 0.38 (m, 2H).

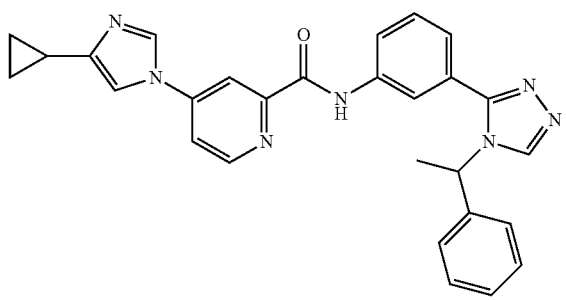 [SMILES: CC(c1ccccc1)n1cnnc1-c1cccc(NC(=O)c2cc(-n3cnc(C4CC4)c3)ccn2)c1]

4-(4-cyclopropyl-1H-imidazol-1-yl)-N-(3-(4-(cyclo-propylmethyl)-4H-1,2,4-triazol-3-yl)phenyl)picoli-namide $C_{28}H_{25}N_7O \times HCl$. 476.1 (M+1). $^1H$ NMR (DMSO) d 11.02 (s, 1H), 9.75 (br, 1H), 9.16 (s, 1H), 8.97 (d, J=5.2 Hz, 1H), 8.55 (d, J=2.0 Hz, 1H), 8.29 (s, He, 8.18 (s, 1H), 8.13 (m, 2H), 7.51 (t, J=8.0 Hz, 1H), 7.27 (m, 4H), 7.11 (d, J=6.8 Hz, 2H), 5.70 (q, J=6.8 Hz, 1H), 2.01 (m, 1H), 1.90 (d, J=6.8 Hz, 3H), 1.05 (m, 2H), 0.95 (m, 2H).

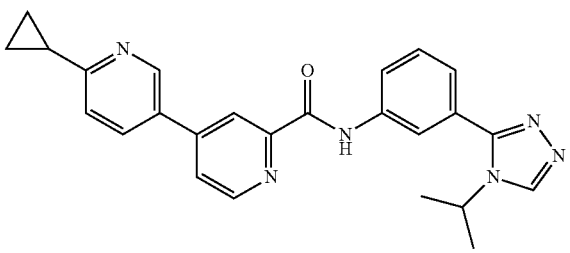 [SMILES: CC(C)n1cnnc1-c1cccc(NC(=O)c2cc(-c3ccc(C4CC4)nc3)ccn2)c1]

6-cyclopropyl-N-(3-(4-isopropyl-4H-1,2,4-triazol-3-yl)phenyl)-3,4'-bipyridine-2'-carboxamide $C_{25}H_{24}N_6O$. 425.1 (M+1). $^1H$ NMR (DMSO) d 10.98 (s, 1H), 8.93 (d, J=2.0 Hz, 1H), 8.87 (s, 1H), 8.82 (d, J=5.2 Hz, 1H), 8.43 (d, J=1.2 Hz, 1H), 8.17 (m, 3H), 8.05 (dd, J=5.2, 2.0 Hz, 1H), 7.57 (t, J=8.0 Hz, 1H), 7.49 (d, J=8.0 Hz, 1H), 7.37 (d, J=8.0 Hz, 1H), 4.52 (sept, J=6.8 Hz, 1H), 2.21 (m, 1H), 1.45 (d, J=6.8 Hz, 6H), 1.01 (m, 4H).

120

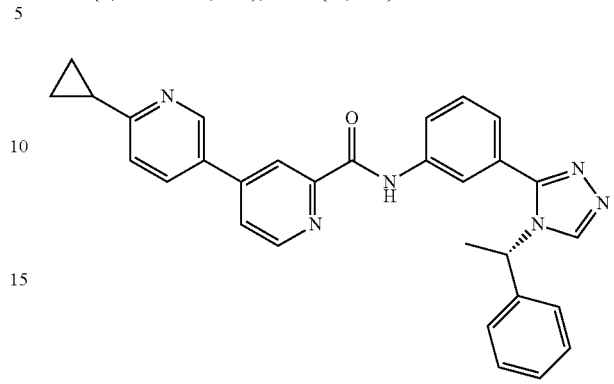

(S)-6-cyclopropyl-N-(3-(4-(1-phenylethyl)-4H-1,2,4-triazol-3-yl)phenyl)-3,4'-bipyridine-2'-carboxamide $C_{30}H_{26}N_6O$. 489.1 (M+1). $^1H$ NMR (DMSO) d 10.92 (s, 1H), 8.97 (s, 1H), 8.93 (d, J=2.4 Hz, 1H), 8.82 (d, J=5.6 Hz, 1H), 8.43 (s, 1H), 8.19 (m, 2H), 8.06 (m, 2H), 7.48 (m, 2H), 7.31 (m, 3H), 7.20 (d, J=8.0 Hz, 1H), 7.10 (d, J=6.8 Hz, 2H), 5.66 (q, J=7.2 Hz, 1H), 2.21 (m, 1H), 1.88 (d, J=7.2 Hz, 3H), 1.02 (m, 4H).

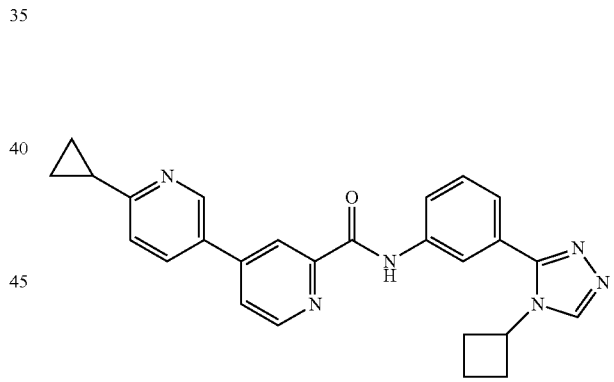

N-(3-(4-cyclobutyl-4H-1,2,4-triazol-3-yl)phenyl)-6-cyclopropyl-3,4'-bipyridine-2'-carboxamide $C_{26}H_{24}N_6O$. 437.1 (M+1). $^1H$ NMR (DMSO) d 10.96 (s, 1H), 8.93 (m, 2H), 8.83 (d, J=4.8 Hz, 1H), 8.43 (d, J=1.2 Hz, 1H), 8.24 (s, 1H), 8.19 (dd, J=8.0, 2.8 Hz, 1H), 8.05 (m, 2H), 7.56 (t, J=8.0 Hz, 1H), 7.48 (d, J=8.0 Hz, 1H), 7.38 (d, J=8.0 Hz, 1H), 4.77 (p, J=7.2 Hz, 1H), 2.44 (m, 4H), 2.20 (m, 1H), 1.78 (m, 2H), 1.78 (m, 4H).

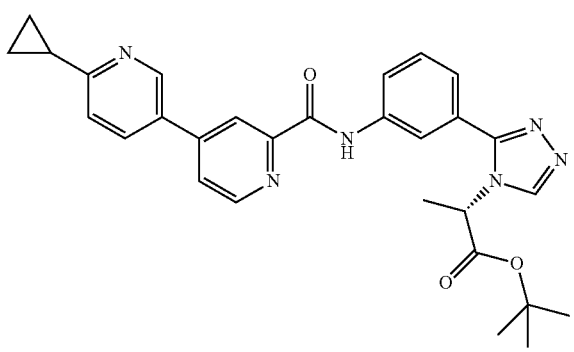 [SMILES: C[C@@H](C(=O)OC(C)(C)C)n1cnnc1-c1cccc(NC(=O)c2cc(-c3ccc(C4CC4)nc3)ccn2)c1]

(S)-tert-butyl 2-(3-(3-(6-cyclopropyl-3,4'-bipyridine-2'-carboxamido)phenyl)-4H-1,2,4-triazol-4-yl)propanoate C<sub>29</sub>H<sub>30</sub>N<sub>6</sub>O<sub>3</sub>. 511.1 (M+1). ¹H NMR (DMSO) d 10.94 (s, 1H), 8.93 (d, J=2.0 Hz, 1H), 8.85 (m, 2H), 8.42 (s, 1H), 8.17 (m, 2H), 8.06 (m, 2H), 7.56 (t, J=8.0 Hz, 1H), 7.49 (d, J=8.0 Hz, 1H), 7.32 (d, J=8.0 Hz, 1H), 5.07 (q, J=7.2 Hz, 1H), 2.21 (m, 1H), 1.75 (d, J=7.2 Hz, 3H), 1.30 (s, 9H), 1.01 (m, 4H).

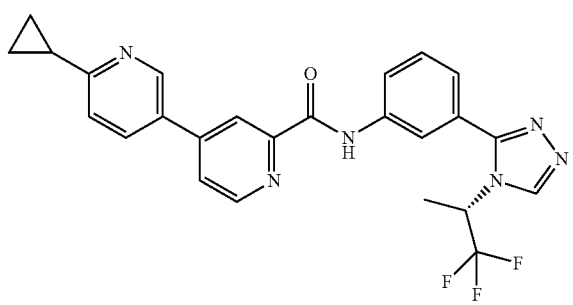 [SMILES: C[C@H](n1cnnc1-c1cccc(NC(=O)c2cc(-c3ccc(C4CC4)nc3)ccn2)c1)C(F)(F)F]

(S)-6-cyclopropyl-N-(3-(4-(1,1,1-trifluoropropan-2-yl)-4H-1,2,4-triazol-3-yl)phenyl)-3,4'-bipyridine-2'-carboxamide C<sub>25</sub>H<sub>21</sub>F<sub>3</sub>N<sub>6</sub>O×HCl. 479.1 (M+1). ¹H NMR (DMSO) d 11.01 (s, 1H), 9.16 (s, 1H), 9.13 (d, J=2.0 Hz, 1H), 8.89 (d, J=5.2 Hz, 1H), 8.65 (d, J=8.0 Hz, 1H), 8.55 (s, 1H), 8.17 (m, 3H), 7.69 (d, J=8.0 Hz, 1H), 7.61 (t, J=8.0 Hz, 1H), 7.39 (d, J=8.0 Hz, 1H), 5.30 (sept, J=7.2 Hz, 1H), 2.48 (m, 1H), 1.82 (d, J=7.2 Hz, 3H), 1.10 (m, 4H). ¹⁹F NMR (DMSO) d −75.10 (d, J=7.2 Hz, 3F).

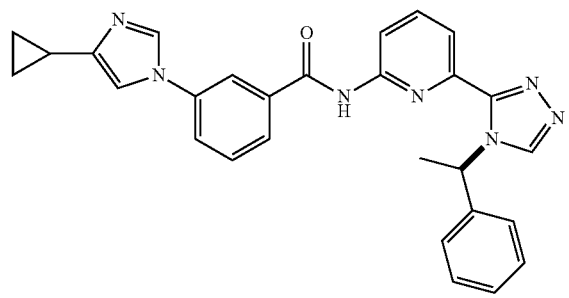

(R)-3-(4-cyclopropyl-1H-imidazol-1-yl)-N-(6-(4-(1-phenylethyl)-4H-1,2,4-triazol-3-yl)pyridin-2-yl)benzamide C<sub>28</sub>H<sub>25</sub>N<sub>7</sub>O×HCl. 476.2 (M+1). ¹H NMR (DMSO) d 11.16 (s, 1H), 9.79 (s, 1H), 9.13 (s, 1H), 8.43 (s, 1H), 8.21 (s, 1H), 8.16 (dd, J=8, 14 Hz, 2H), 8.05 (dd, J=2, 8 Hz, 1H), 7.98 (t, J=8 Hz, 1H), 7.86 (t, J=8 Hz, 1H), 7.79 (d, J=7 Hz, 1H), 7.17-7.25 (m, 5H), 7.11 (q, J=7 Hz, 3H), 4.15 (br s, 1H), 2.02-2.07 (m, 1H), 1.89 (d, J=7 Hz, 3H), 1.05-1.09 (m, 2H), 0.87-0.91 (m, 2H).

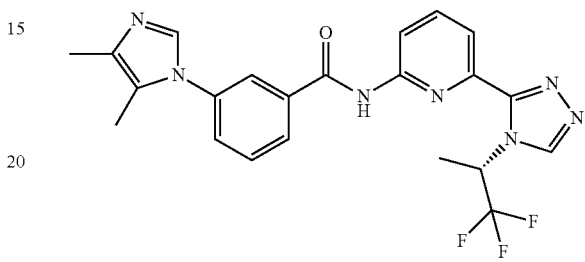

(S)-3-(4,5-dimethyl-1H-imidazol-1-yl)-N-(6-(4-(1,1,1-trifluoropropan-2-yl)-4H-1,2,4-triazol-3-yl)pyridin-2-yl)benzamide C<sub>22</sub>H<sub>20</sub>F<sub>3</sub>N<sub>7</sub>O. 456.2 (M+1). ¹H NMR (DMSO) d 10.99 (s, 1H), 9.13 (s, 1H), 8.12 (d, J=7 Hz, 1H), 8.07 (t, J=8 Hz, 1H), 7.92-8.02 (m, 3H), 7.89 (br s, 1H), 7.75 (t, J=8 Hz, 1H), 7.68-7.72 (m, 1H), 7.16 (m, 1H), 2.14 (s, 6H), 1.83 (d, J=7 Hz, 3H).

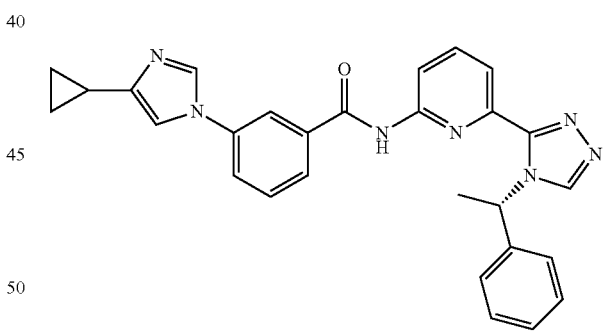

(S)-3-(4,5-dimethyl-1H-imidazol-1-yl)-N-(6-(4-(1,1,1-trifluoropropan-2-yl)-4H-1,2,4-triazol-3-yl)pyridin-2-yl)benzamide C<sub>28</sub>H<sub>25</sub>N<sub>7</sub>O. 476.3 (M+1). ¹H NMR (DMSO) d 10.95 (s, 1H), 9.02 (s, 1H), 8.24 (s, 1H), 8.18 (d, J=8 Hz, 1H), 8.15 (s, 1H), 7.96 (s, 1H), 7.86-7.91 (m, 1H), 7.78 (d, J=7 Hz, 1H), 7.70 (t, J=8 Hz, 1H), 7.64 (br s, 1H), 7.16-7.27 (m, 5H), 7.07 (q, J=7 Hz, 1H), 1.88 (d, J=7 Hz, 3H), 1.86-1.89 (m, 1H), 0.80-0.83 (m, 2H), 0.69-0.71 (m, 2H).

123

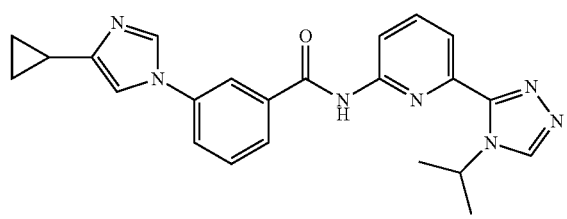 [SMILES: CC(C)n1cnnc1-c1cccc(NC(=O)c2cccc(-n3cnc(C4CC4)c3)c2)n1]

3-(4-cyclopropyl-1H-imidazol-1-yl)-N-(6-(4-isopropyl-4H-1,2,4-triazol-3-yl)pyridin-2-yl)benzamide $C_{23}H_{23}N_7O$. 414.3 (M+1). $^1$H NMR (DMSO) d 10.88 (s, 1H), 8.88 (s, 1H), 8.34 (s, 1H), 8.18-8.21 (m, 1H), 8.16 (s, 1H), 8.05 (t, J=8 Hz, 1H), 7.86-7.91 (m, 3H), 7.68 (t, J=8 Hz, 2H), 5.65 (sept, J=6 Hz, 1H), 1.86-1.89 (m, 1H), 1.43 (d, J=6 Hz, 6H), 0.81-0.84 (m, 2H), 0.71-0.74 (m, 2H).

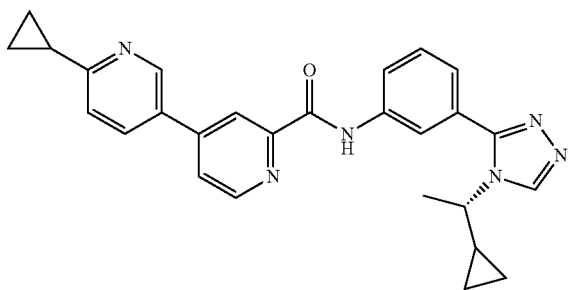 [SMILES: C[C@@H](C1CC1)n1cnnc1-c1cccc(NC(=O)c2cc(-c3ccc(C4CC4)nc3)ccn2)c1]

(S)-6-cyclopropyl-N-(3-(4-(1-cyclopropylethyl)-4H-1,2,4-triazol-3-yl)phenyl)-3,4'-bipyridine-2'-carboxamide $C_{27}H_{26}N_6O$. 451.1 (M+1). $^1$H NMR (DMSO) d 10.95 (s, 1H), 8.93 (m, 2H), 8.82 (d, J=4.8 Hz, 1H), 8.42 (d, J=1.2 Hz, 1H), 8.19 (dd, J=8.0, 2.4 Hz, 1H), 8.14 (s, 1H), 8.10 (d, J=8.0 Hz, 1H), 8.05 (dd, J=5.2, 2.0 Hz, 1H), 7.55 (t, J=8.0 Hz, 1H), 7.49 (d, J=8.0 Hz, 1H), 7.32 (d, J=8.0 Hz, 1H), 3.70 (p, J=6.8 Hz, 1H), 2.21 (m, 1H), 1.51 (d, J=6.4 Hz, 3H), 1.35 (m, 1H), 1.01 (m, 4H), 0.57 (m, 1H), 0.41 (m, 1H), 0.33 (m, 1H), 0.01 (m, 1H).

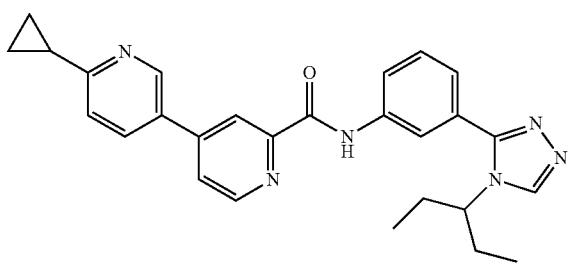 [SMILES: CCC(CC)n1cnnc1-c1cccc(NC(=O)c2cc(-c3ccc(C4CC4)nc3)ccn2)c1]

6-cyclopropyl-N-(3-(4-(pentan-3-yl)-4H-1,2,4-triazol-3-yl)phenyl)-3,4'-bipyridine-2'-carboxamide $C_{27}H_{28}N_6O$. 453.1 (M+1). $^1$H NMR (DMSO) d 10.98 (s, 1H), 8.93 (d, J=2.0 Hz, 1H), 8.82 (m, 2H), 8.42 (s, 1H), 8.22 (s, 1H), 8.19 (dd, J=8.0, 6.4 Hz, 1H), 8.05 (m, 2H), 7.56 (t, 8.0 Hz, 1H), 7.49 (d, J=8.0 Hz, 1H), 7.29 (d, J=8.0 Hz, 1h), 4.02 (p, J=7.6 Hz, 1H), 2.21 (m, 1H), 1.82 (p, J=7.6, 4H), 1.01 (m, 4H), 0.71 (t, J=7.6 Hz, 6H).

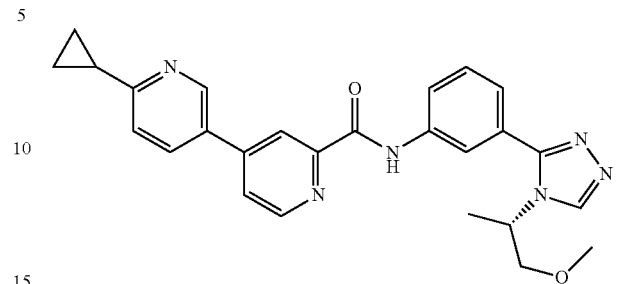

(S)-6-cyclopropyl-N-(3-(4-(1-methoxypropan-2-yl)-4H-1,2,4-triazol-3-yl)phenyl)-3,4'-bipyridine-2'-carboxamide $C_{26}H_{26}N_6O_2$. 455.1 (M+1). $^1$H NMR (DMSO) d 10.95 (s, 1H), 8.93 (d, J=2.0 Hz, 1H), 8.82 (m, 2H), 8.43 (s, 1H), 8.18 (m, 2H), 8.10 (d, J=8.0 Hz, 1H), 8.05 (dd, J=5.2, 2.0 Hz, 1H), 7.56 (t, J=8.0 Hz, 1H), 7.48 (d, J=8.0 Hz, 1H), 7.37 (d, J=8.0 Hz, 1H), 4.55 (m, 1H), 3.63 (m, 1H), 3.54 (m, 1H), 3.15 (s, 3H), 2.21 (m, 1H), 1.44 (d, J=6.8 Hz, 3H), 1.01 (m, 4H).

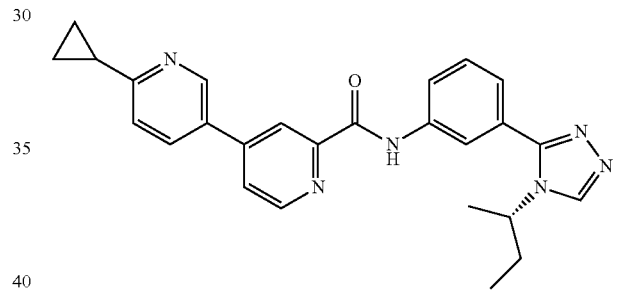

(S)—N-(3-(4-sec-butyl-4H-1,2,4-triazol-3-yl)phenyl)-6-cyclopropyl-3,4'-bipyridine-2'-carboxamide $C_{26}H_{26}N_6O$. 439.1 (M+1). $^1$H NMR (DMSO) d 10.98 (s, 1H), 8.93 (d, J=2.0 Hz, 1H), 8.85 (s, 1H), 8.82 (d, J=5.2 Hz, 1H), 8.43 (d, J=1.2 Hz, 1H), 8.19 (m, 2H), 8.10 (d, J=8.0 Hz, 1H), 8.05 (dd, J=5.2 Hz, 1H), 7.57 (t, J=8.0 Hz, 1H), 7.49 (d, J=8.0 Hz, 1H), 7.34 (d, J=8.0 Hz, 1H), 4.24 (sex, J=8.0 Hz, 1H), 2.21 (m, 1H), 1.79 (m, 2H), 1.48 (d, J=6.8 Hz, 3H), 1.01 (m, 4H), 0.67 (t, J=7.2 Hz, 3H).

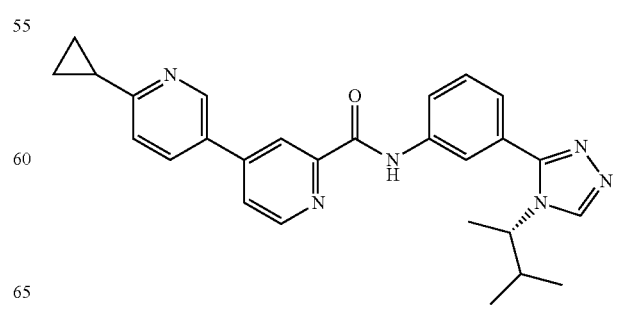

(S)-6-cyclopropyl-N-(3-(4-(3-methylbutan-2-yl)-4H-1,2,4-triazol-3-yl)phenyl)-3,4'-bipyridine-2'-carboxamide $C_{27}H_{28}N_6O$. 453.1 (M+1). $^1$H NMR (DMSO) d 10.97 (s, 1H), 8.93 (d, J=2.4 Hz, 1H), 8.84 (s, 1H), 8.82 (d, J=5.2 Hz, 1H), 8.43 (d, J=1.2 Hz, 1H), 8.18 (m, 2H), 8.10 (d, J=8.0 Hz, 1H), 8.05 (dd, J=5.2, 2.0 Hz, 1H), 7.56 (t, J=8.0 Hz, 1H), 7.49 (d, J=8.0 Hz, 1H), 7.32 (d, J=8.0 Hz, 1H), 4.01 (m, 1H), 2.21 (m, 1H), 1.97 (m, 1H), 1.51 (d, J=6.8 Hz, 3H), 1.01 (m, 4H), 0.83 (d, J=6.8 Hz, 3H), 0.57 (d, J=6.8 Hz, 3H).

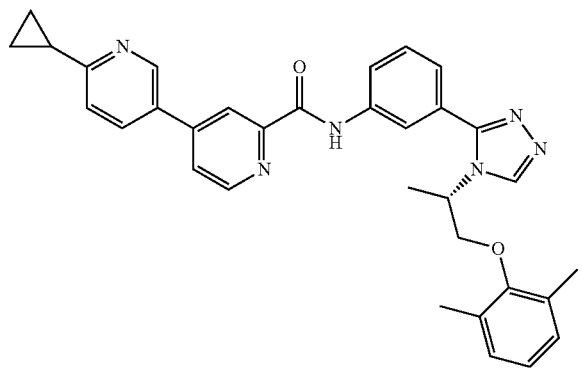 [SMILES: Cc1cccc(C)c1OC[C@H](C)n1cnnc1-c1cccc(NC(=O)c2cc(-c3ccc(C4CC4)nc3)ccn2)c1]

(S)-6-cyclopropyl-N-(3-(4-(1-(2,6-dimethylphenoxy)propan-2-yl)-4H-1,2,4-triazol-3-yl)phenyl)-3,4'-bipyridine-2'-carboxamide $C_{33}H_{32}N_6O_2$. 545.1 (M+1). $^1$H NMR (DMSO) d 10.95 (s, 1H), 9.01 (s, 1H), 8.92 (s, J=2.4 Hz, 1H), 8.81 (d, J=5.2 Hz, 1H), 8.42 (d, J=1.2 Hz, 1H), 8.26 (d, J=5.2 Hz, 1H), 8.18 (dd, J=8.0, 2.4 Hz, 1H), 8.14 (d, J=8.0 Hz, 1H), 8.05 (dd, J=5.2, 2.0 Hz, 1H), 7.57 (t, J=8.0 Hz, 1H), 7.49 (d, J=8.0 Hz, 1H), 7.45 (d, J=8.0 Hz, 1H), 6.96 (d, J=7.2 Hz, 2H), 6.88 (t, J=7.2 Hz, 1H), 4.81 (m, 1H), 3.97 (m, 2H), 2.20 (m, 1H), 1.98 (s, 6H), 1.62 (d, J=6.8 Hz, 3H), 1.01 (m, 4H).

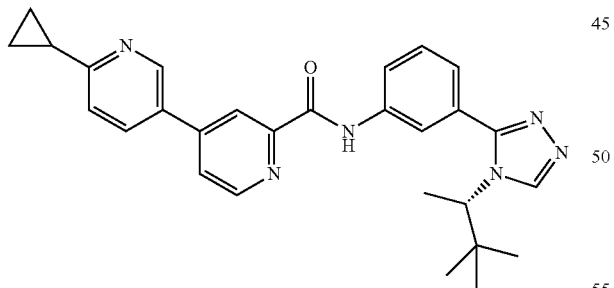

(S)-6-cyclopropyl-N-(3-(4-(3,3-dimethylbutan-2-yl)-4H-1,2,4-triazol-3-yl)phenyl)-3,4'-bipyridine-2'-carboxamide $C_{28}H_{30}N_6O$. 467.1 (M+1). $^1$H NMR (DMSO) d 10.96 (s, 1H), 8.93 (d, J=2.0 Hz, 1H), 8.82 (m, 2H), 8.43 (d, J=1.2 Hz, 1H), 8.19 (dd, J=8.0, 2.4 Hz, 1H), 8.14 (m, 2H), 8.05 (dd, J=5.2, 2.0 Hz, 1H), 7.56 (t, J=8.0 Hz, 1H), 7.49 (d, J=8.0 Hz, 1H), 7.31 (d, J=8.0 Hz, 1H), 4.25 (q, J=6.8 Hz, 1H), 2.20 (m, 1H), 1.56 (d, J=6.8 Hz, 3H), 1.01 (m, 4H), 0.80 (s, 9H).

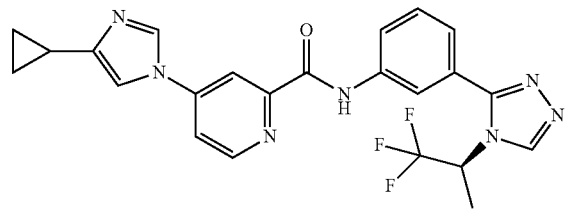 [SMILES: C[C@H](n1cnnc1-c1cccc(NC(=O)c2cc(-n3cnc(C4CC4)c3)ccn2)c1)C(F)(F)F]

(S)-4-(4-cyclopropyl-1H-imidazol-1-yl)-N-(3-(4-(1,1,1-trifluoropropan-2-yl)-4H-1,2,4-triazol-3-yl)phenyl)picolinamide $C_{23}H_{20}F_3N_7O$. 468.1 (M+1). $^1$H NMR (DMSO) d 10.94 (s, 1H), 9.09 (s, 1H), 8.80 (d, J=5.6 Hz, 1H), 8.54 (d, J=1.2 Hz, 1H), 8.36 (d, J=2.0 Hz, 1H), 8.17 (d, J=8.0 Hz, 1H), 8.10 (s, 1H), 7.99 (dd, J=5.6, 2.4 Hz, 1H), 7.85 (s, 1H), 7.60 (t, J=8.0 Hz, 1H), 7.38 (d, J=7.2 Hz, 1H), 5.28 (m, 1H), 1.86 (m, 1H), 1.82 (d, J=6.8 Hz, 3H), 0.84 (m, 2H), 0.74 (m, 2H). $^{19}$F NMR (DMSO) d −75.13 (d, J=7.2 Hz, 3F).

C. Similarly, optionally replacing N-(3-(1,3,4-oxadiazol-2-yl)phenyl)-3,4'-bipyridine-2'-carboxamide with other compounds of formula (4), and optionally replacing (R)-2-amino-1-propanol with other amines of formula $R^1NH_2$, and following the procedure of Example 16A, other compounds of Formula (I) are prepared:

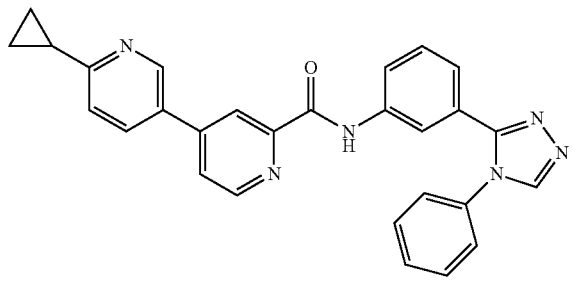 [SMILES: O=C(Nc1cccc(-c2nncn2-c2ccccc2)c1)c1cc(-c2ccc(C3CC3)nc2)ccn1]

6-cyclopropyl-N-(3-(4-phenyl-4H-1,2,4-triazol-3-yl)phenyl)-3,4'-bipyridine-2'-carboxamide

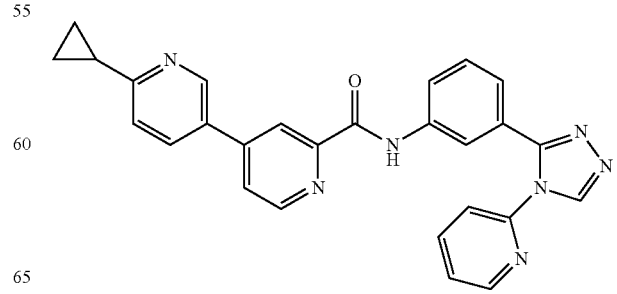

| 127 | 128 |
|---|---|
| 6-cyclopropyl-N-(3-(4-(pyridin-2-yl)-4H-1,2,4-triazol-3-yl)phenyl)-3,4'-bipyridine-2'-carboxamide | 6-cyclopropyl-N-(3-(4-(pyrimidin-5-yl)-4H-1,2,4-triazol-3-yl)phenyl)-3,4'-bipyridine-2'-carboxamide |

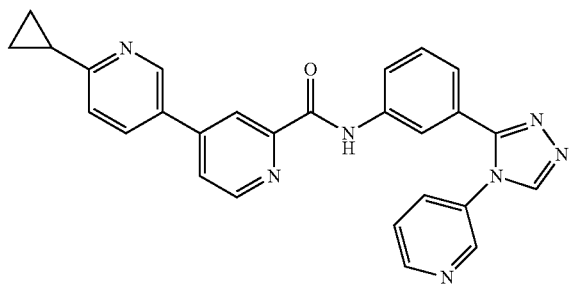 [SMILES: O=C(Nc1cccc(-c2nncn2-c2cccnc2)c1)c1cc(-c2ccc(C3CC3)nc2)ccn1]

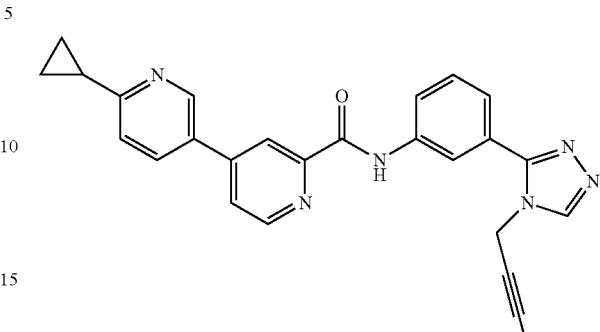

6-cyclopropyl-N-(3-(4-(pyridin-3-yl)-4H-1,2,4-triazol-3-yl)phenyl)-3,4'-bipyridine-2'-carboxamide N-(3-(4-(but-2-ynyl)-4H-1,2,4-triazol-3-yl)phenyl)-6-cyclopropyl-3,4'-bipyridine-2'-carboxamide

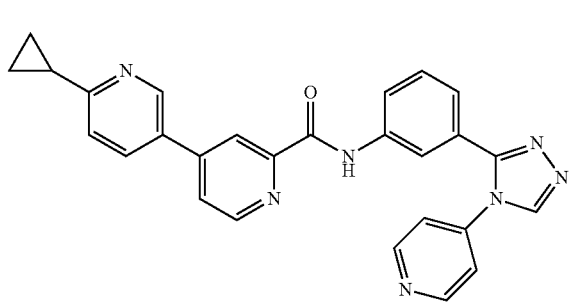 [SMILES: O=C(Nc1cccc(-c2nncn2-c2ccncc2)c1)c1cc(-c2ccc(C3CC3)nc2)ccn1]

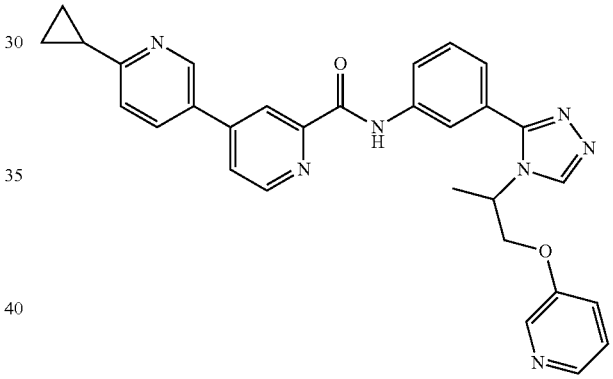

6-cyclopropyl-N-(3-(4-(1-(pyridin-3-yloxy)propan-2-yl)-4H-1,2,4-triazol-3-yl)phenyl)-3,4'-bipyridine-2'-carboxamide 6-cyclopropyl-N-(3-(4-(pyridin-4-yl)-4H-1,2,4-triazol-3-yl)phenyl)-3,4'-bipyridine-2'-carboxamide

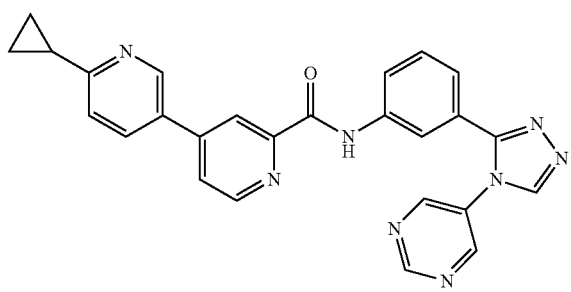 [SMILES: O=C(Nc1cccc(-c2nncn2-c2cncnc2)c1)c1cc(-c2ccc(C3CC3)nc2)ccn1]

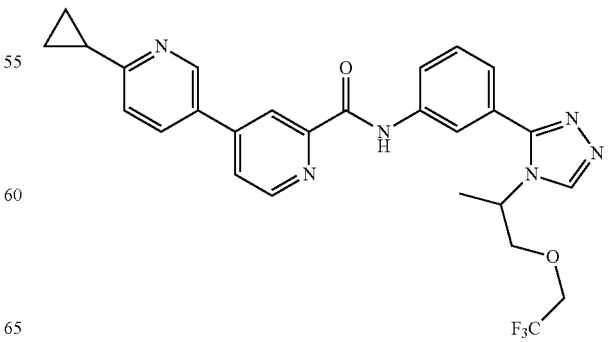

129

6-cyclopropyl-N-(3-(4-(1-(2,2,2-trifluoroethoxy)
propan-2-yl)-4H-1,2,4-triazol-3-yl)phenyl)-3,4'-bi-
pyridine-2'-carboxamide

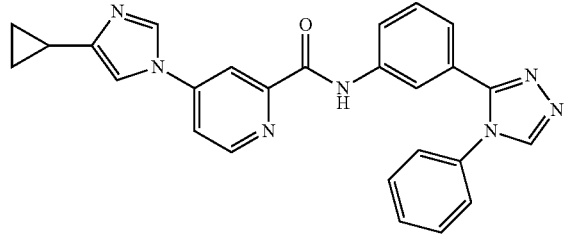 [SMILES: O=C(Nc1cccc(-c2nncn2-c2ccccc2)c1)c1cc(-n2cnc(C3CC3)c2)ccn1]

4-(4-cyclopropyl-1H-imidazol-1-yl)-N-(3-(4-phenyl-
4H-1,2,4-triazol-3-yl)phenyl)picolinamide

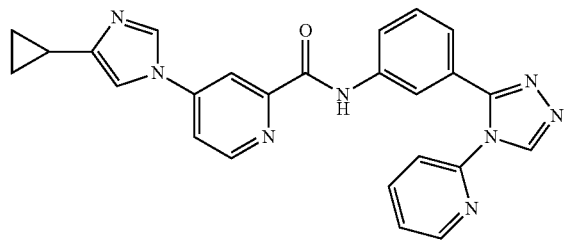 [SMILES: O=C(Nc1cccc(-c2nncn2-c2ccccn2)c1)c1cc(-n2cnc(C3CC3)c2)ccn1]

4-(4-cyclopropyl-1H-imidazol-1-yl)-N-(3-(4-(pyri-
din-2-yl)-4H-1,2,4-triazol-3-yl)phenyl)picolinamide

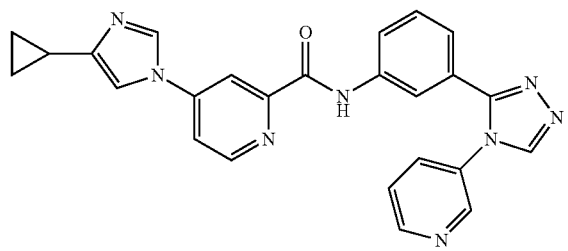 [SMILES: O=C(Nc1cccc(-c2nncn2-c2cccnc2)c1)c1cc(-n2cnc(C3CC3)c2)ccn1]

4-(4-cyclopropyl-1H-imidazol-1-yl)-N-(3-(4-(pyri-
din-3-yl)-4H-1,2,4-triazol-3-yl)phenyl)picolinamide

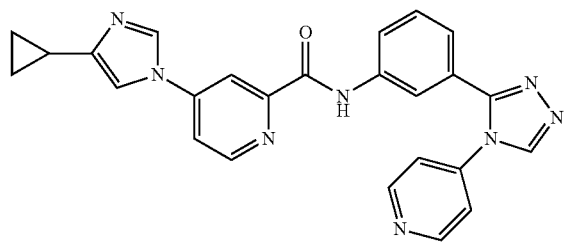 [SMILES: O=C(Nc1cccc(-c2nncn2-c2ccncc2)c1)c1cc(-n2cnc(C3CC3)c2)ccn1]

130

4-(4-cyclopropyl-1H-imidazol-1-yl)-N-(3-(4-(pyri-
din-4-yl)-4H-1,2,4-triazol-3-yl)phenyl)picolinamide

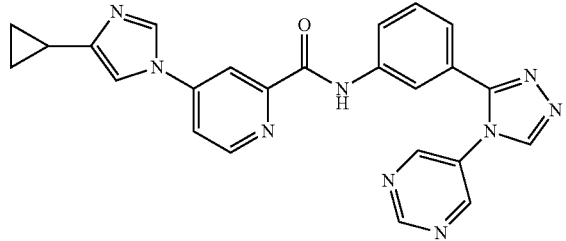 [SMILES: O=C(Nc1cccc(-c2nncn2-c2cncnc2)c1)c1cc(-n2cnc(C3CC3)c2)ccn1]

4-(4-cyclopropyl-1H-imidazol-1-yl)-N-(3-(4-(pyri-
midin-5-yl)-4H-1,2,4-triazol-3-yl)phenyl)picolina-
mide N-(3-(4-(but-2-ynyl)-4H-1,2,4-triazol-3-yl)phenyl)-
4-(4-cyclopropyl-1H-imidazol-1-yl)picolinamide

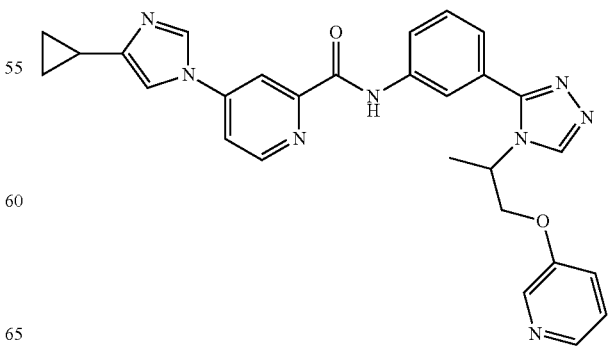

4-(4-cyclopropyl-1H-imidazol-1-yl)-N-(3-(4-(1-(py-ridin-3-yloxy)propan-2-yl)-4H-1,2,4-triazol-3-yl)phenyl)picolinamide and

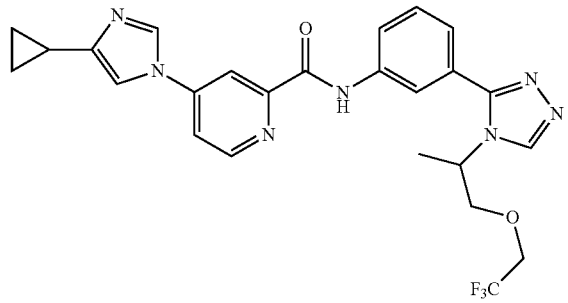 [SMILES: CC(COCC(F)(F)F)n1cnnc1-c1cccc(NC(=O)c2cc(-n3cnc(C4CC4)c3)ccn2)c1]

4-(4-cyclopropyl-1H-imidazol-1-yl)-N-(3-(4-(1-(2,2,2-trifluoroethoxy)propan-2-yl)-4H-1,2,4-triazol-3-yl)phenyl)picolinamide

EXAMPLE 17

Preparation of Compounds of Formula (I)

A. Preparation of a Compound of Formula (I) in which $X^2$, $X^3$, $X^4$, $X^6$, $X^7$ and $X^8$ are $C(R^4)$, $X^1$ and $X^5$ are N, $R^1$ is Cyclopropyl, $R^2$ is Hydrogen, and $R^3$ is 2-Cyclobutoxypyridin3-yl A. Preparation of 6-cyclobutoxy-N-(3-(4-cyclopropyl-4H-1,2,4-triazol-3-yl)phenyl)-3,4'-bipyridine-2'-carboxamide

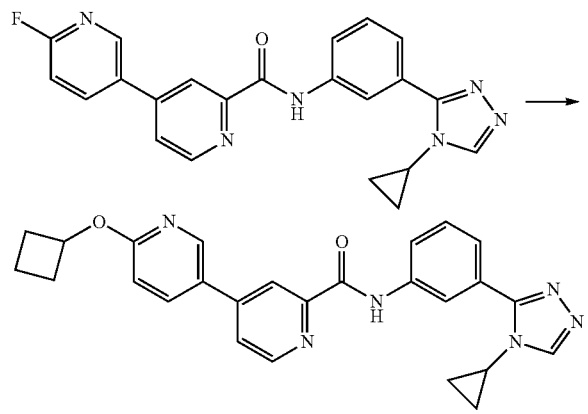

Sodium hydride (60% in mineral oil, 15 mg, 0.38 mmol) was added to 0.5 mL of cyclobutanol and the reaction mixture was stirred for 10 minutes at room temperature. (N-(3-(4-cyclopropyl-4H-1,2,4-triazol-3-yl)phenyl)-6-fluoro-3,4'-bipyridine-2'-carboxamide) (24 mg, 0.06 mmol) in cyclobutanol (0.2 mL) was added and the reaction mixture was heated to 90° C. for 30 minutes. The reaction mixture was concentrated under reduced pressure, neutralized with 1 M HCl and purified by reverse-phase HPLC to give the product as a white powder (15 mg, 55% yield).

$C_{26}H_{24}N_6O_2$. 453.1 (M+1). $^1$H NMR (DMSO) d 10.92 (s, 1H), 8.79 (d, J=5.2 Hz, 1H), 8.72 (d, J=2.4 Hz, 1H), 8.62 (s, 1H), 8.58 (s, 1H), 8.41 (d, J=1.2 Hz, 1H), 8.26 (dd, J=4.8, 2.4 Hz, 1H), 8.07 (d, J=8.0 Hz, 1H), 8.03 (dd, J=5.2, 2.0 Hz, 1H), 7.68 (d, J=8.0 Hz, 1H), 7.55 (t, J=8.0 Hz, 1H), 6.95 (d, J=8.8 Hz, 1H), 5.22 (p, J=7.6 Hz, 1H), 3.66 (m, 1H), 2.45 (m, 2H), 2.10 (m, 2H), 1.85 (m, 1H), 1.70 (m, 1H), 1.08 (m, 2H), 0.95 (m, 2H).

EXAMPLE 18

Preparation of Compounds of Formula (I)

A. Preparation of a Compound of Formula (I) in which $X^2$, $X^3$, $X^4$, $X^6$, $X^7$ and $X^8$ are $C(R^4)$, $X^1$ and $X^5$ are N, $R^1$ is Cyclopropyl, $R^2$ is Hydrogen, and $R^3$ is N-cyclopropylpyridin-2-ylamine A. Preparation of N-(3-(4-cyclopropyl-4H-1,2,4-triazol-3-yl)phenyl)-6-(cyclopropylamino)-3,4'-bipyridine-2'-carboxamide

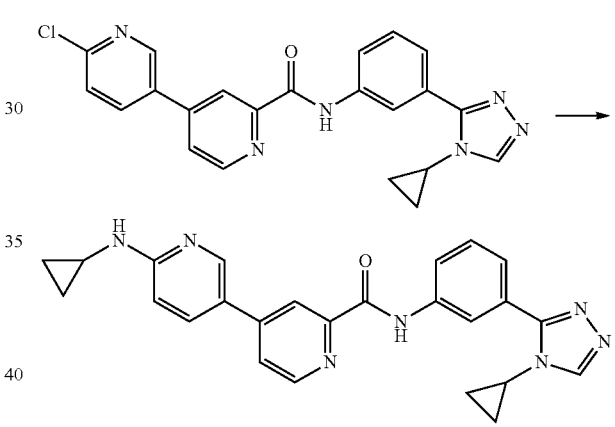

6-Chloro-N-(3-(4-cyclopropyl-4H-1,2,4-triazol-3-yl)phenyl)-3,4'-bipyridine-2'-carboxamide (60.0 mg, 0.144 mmol) was dissolved in cyclopropylamine (250 µL), and the mixture was heated to 110° C. for 2 days. The amine was removed under reduced pressure, and the residue was purified by reverse phase HPLC. The product (N-(3-(4-cyclopropyl-4H-1,2,4-triazol-3-yl)phenyl)-6-(cyclopropylamino)-3,4'-bipyridine-2'-carboxamide, 31.2 mg, 50% yield) was isolated as a white solid.

$C_{25}H_{23}N_7O$. 438.1 (M+1). $^1$H NMR (DMSO) d 10.88 (s, 1H), 8.70 (d, J=5 Hz, 1H), 8.60-8.64 (m, 2H), 8.58 (s, 1H), 8.35 (d, J=1 Hz, 1H), 8.02-8.08 (m, 2H), 7.95 (dd, J=2.5 Hz, 1H), 7.68 (d, J=8 Hz, 1H), 7.54 (t, J=8 Hz, 1H), 7.30 (d, J=2 Hz, 1H), 6.73 (d, J=9 Hz, 1H), 3.64-3.68 (m, 1H), 2.58-2.62 (m, 1H), 1.09 (q, J=6 Hz, 2H), 0.91-0.96 (m, 2H), 0.72-0.77 (m, 2H) 0.46-0.49 (m, 2H).

B. Similarly, following the procedure of Example 18A, optionally replacing 6-chloro-N-(3-(4-cyclopropyl-4H-1,2,4-triazol-3-yl)phenyl)-3,4'-bipyridine-2'-carboxamide with other compounds of formula (5), and optionally replacing cyclopropylamine with other amines of formula $R^1NH_2$, the following compounds of Formula (I) were prepared:

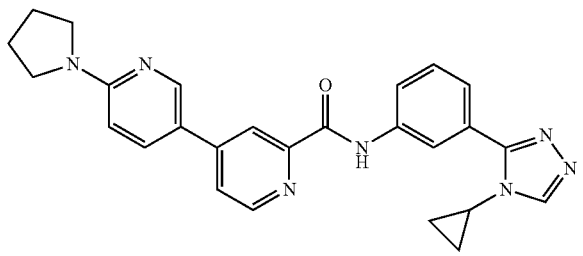 [SMILES: O=C(Nc1cccc(-c2nncn2C2CC2)c1)c1cc(-c2ccc(N3CCCC3)nc2)ccn1]

N-(3-(4-cyclopropyl-4H-1,2,4-triazol-3-yl)phenyl)-
6-(pyrrolidin-1-yl)-3,4'-bipyridine-2'-carboxamide $C_{26}H_{25}N_7O$. 452.2 (M+1). $^1$H NMR (DMSO) d 10.88 (s, 1H), 8.68-8.71 (m, 2H), 8.63 (s, 1H), 8.58 (s, 1H), 8.35 (s, 1H), 8.06 (d, J=8 Hz, 2H), 7.94-7.96 (m, 1H), 7.66-7.69 (m, 1H), 7.54 (t, J=8 Hz, 1H), 6.60 (d, J=7.2 Hz, 1H), 3.64-3.70 (m, 1H), 3.42-3.54 (m, 4H), 1.92-2.04 (m, 4H), 1.06-1.12 (m, 2H), 0.91-0.97 (m, 2H).

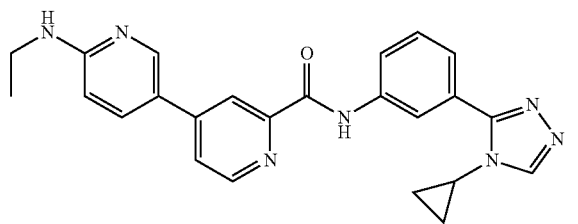 [SMILES: CCNc1ccc(-c2ccnc(C(=O)Nc3cccc(-c4nncn4C4CC4)c3)c2)cn1]

N-(3-(4-cyclopropyl-4H-1,2,4-triazol-3-yl)phenyl)-
6-(ethylamino)-3,4'-bipyridine-2'-carboxamide $C_{24}H_{23}N_7O$. 426.1 (M+1). $^1$H NMR (DMSO) d 10.88 (s, 1H), 8.69 (d, J=5 Hz, 1H), 8.62 (s, 1H), 8.59 (d, J=2 Hz, 1H), 8.58 (s, 1H), 8.33 (d, J=1 Hz, 1H), 8.06 (d, J=8 Hz, 1H), 7.91-7.96 (m, 2H), 7.68 (d, J=8 Hz, 1H), 7.54 (t, J=8 Hz, 1H), 7.04 (t, J=6 Hz, 1H), 6.60 (d, J=9 Hz, 1H), 3.66 (dddd, J=4, 8, 12, 16 Hz, 1H), 3.35 (q, J=7 Hz, 2H), 1.16 (t, J=7 Hz, 3H), 1.08 (app q, J=8 Hz, 2H), 0.93-0.97 (m, 2H).

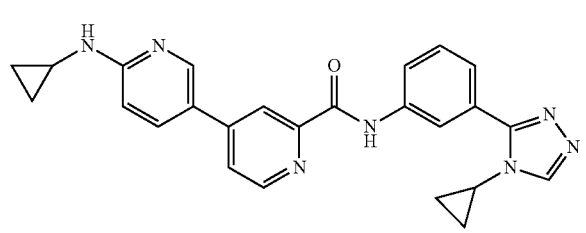 [SMILES: O=C(Nc1cccc(-c2nncn2C2CC2)c1)c1cc(-c2ccc(NC3CC3)nc2)ccn1]

N-(3-(4-cyclopropyl-4H-1,2,4-triazol-3-yl)phenyl)-
6-(cyclopropylamino)-3,4'-bipyridine-2'-carboxamide $C_{25}H_{23}N_7O$. 438.1 (M+1). $^1$H NMR (DMSO) d 10.88 (s, 1H), 8.70 (d, J=5 Hz, 1H), 8.60-8.64 (m, 2H), 8.58 (s, 1H), 8.35 (d, J=1 Hz, 1H), 8.02-8.08 (m, 2H), 7.95 (dd, J=2, 5 Hz, 1H), 7.68 (d, J=8 Hz, 1H), 7.54 (t, J=8 Hz, 1H), 7.30 (d, J=2 Hz, 1H), 6.73 (d, J=9 Hz, 1H), 3.64-3.68 (m, 1H), 2.58-2.62 (m, 1H), 1.09 (q, J=6 Hz, 2H), 0.91-0.96 (m, 2H), 0.72-0.77 (m, 2H) 0.46-0.49 (m, 2H).

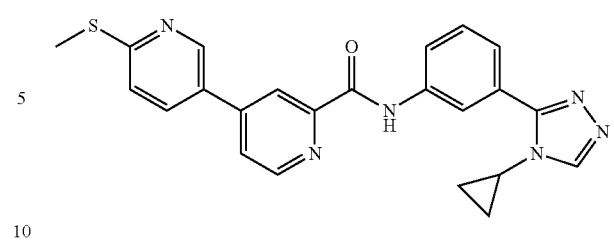

N-(3-(4-cyclopropyl-4H-1,2,4-triazol-3-yl)phenyl)-
6-(methylthio)-3,4'-bipyridine-2'-carboxamide $C_{23}H_{20}N_6OS$. 429.3 (M+1). $^1$H NMR (DMSO) d 10.93 (s, 1H), 8.99 (s, 1H), 8.82 (d, J=5 Hz, 1H), 8.63 (s, 1H), 8.59 (s, 1H), 8.46 (s, 1H), 8.19-8.22 (m, 1H), 8.05-8.09 (m, 2H), 7.69 (d, J=8 Hz, 1H), 7.55 (t, J=8 Hz, 1H), 7.49 (d, J=8 Hz, 1H), 3.65-3.68 (m, 1H), 2.56 (s, 3H), 1.08-1.12 (m, 2H) 0.93-0.96 (m, 2H).

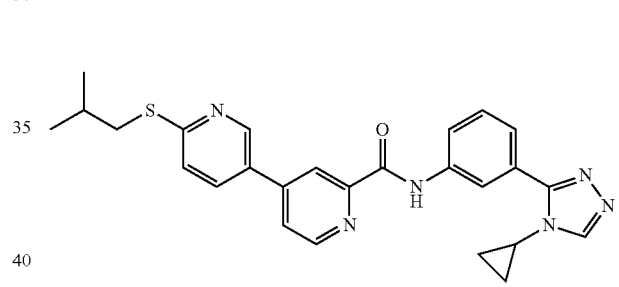

N-(3-(4-cyclopropyl-4H-1,2,4-triazol-3-yl)phenyl)-
6-(isobutylthio)-3,4'-bipyridine-2'-carboxamide $C_{26}H_{26}N_6OS$. 472.1 (M+1). $^1$H NMR (DMSO) d 10.94 (s, 1H), 8.98 (s, 1H), 8.82 (d, J=5 Hz, 1H), 8.63 (s, 1H), 8.59 (s, 1H), 8.45 (s, 1H), 8.17 (dd, J=2, 8 Hz, 1H), 8.05-8.10 (m, 2H), 7.69 (d, J=8 Hz, 1H), 7.55 (t, J=8 Hz, 1H), 7.48 (d, J=9 Hz, 1H), 3.65-3.70 (m, 1H), 3.14 (d, J=6 Hz, 2H), 1.94 (sept, J=6 Hz, 1H), 1.07-1.10 (m, 2H), 1.02 (d, J=6 Hz, 6H), 0.92-0.97 (m, 2H).

C. Similarly, following the procedure of Example 18A, optionally replacing 6-chloro-N-(3-(4-cyclopropyl-4H-1,2,4-triazol-3-yl)phenyl)-3,4'-bipyridine-2'-carboxamide with other compounds of formula (5), and optionally replacing cyclopropylamine with other amines of formula R¹NH₂, other compound s of Formula (I) are prepared.

EXAMPLE 19

Preparation of Compounds of Formula (I) Utilizing Iron Catalyzed Alkyl-Grignard Cross-Coupling Preparation of a Compound of Formula (I) in which $X^2, X^3, X^4, X^6, X^7$ and $X^8$ are $C(R^4)$, $X^1$ and $X^5$ are N, $R^1$ is Cyclopropyl $R^2$ is Hydrogen, and $R^3$ is N-cyclopropylpyrimidine A. Preparation of N-(3-(4-cyclopropyl-4H-1,2,4-thiazol-3-yl)phenyl)-4-(2-cyclopropylpyrimidin-5-yl) picolinamide

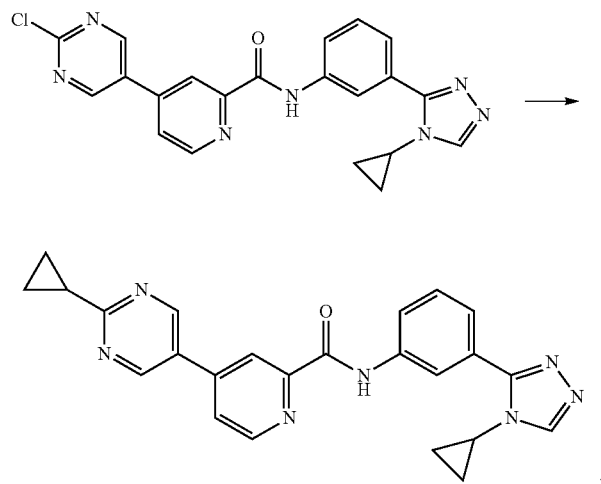

Cyclopropyl magnesium bromide (0.5 M solution in tetrahydrofuran, 6.3 mL, 3 equiv) was added to a solution of 4-(2-chloropyrimidin-5-yl)-N-(3-(4-cyclopropyl-4H-1,2,4-triazol-3-yl)phenyl)picolinamide (440 mg, 1.06 mmol) and Fe(acac)₃ (37 mg, 10 mmol %) in N-methylpyridine (20 mL) and tetrahydrofuran (5 mL). After stirring for 5 minutes, the brown solution was quenched with 1 M hydrochloric acid (6 mL) and concentrated under reduced pressure at 70° C. The residue was purified by reverse-phase HPLC to give N-(3-(4-cyclopropyl-4H-1,2,4-triazol-3-yl)phenyl)-4-(2-cyclopropylpyrimidin-5-yl)picolinamide as a pale-yellow powder (200 mg, 45% yield).

$C_{24}H_{21}N_7O$. 424.1 (M+1). ¹H NMR (DMSO) d 10.95 (s, 1H), 9.18 (s, 2H), 8.86 (d, J=5.2 Hz, 1H), 8.63 (s, 1H), 8.58 (s, 1H), 8.51 (d, J=1.2 Hz, 1H), 8.11 (dd, J=5.2, 2.0 Hz, 1H), 8.07 (d, J=8.0 Hz, 1H), 7.69 (d, J=8.0 Hz, 1H), 7.55 (t, J=8.0 Hz, 1H), 3.66 (m, 1H), 2.32 (m, 1H), 1.10 (m, 6H), 0.95 (m, 2H).

B. Similarly, following the procedure of Example 19A, optionally replacing 4-(2-chloropyrimidin-5-yl)-N-(3-(4-cyclopropyl-4H-1,2,4-triazol-3-yl)phenyl)picolinamide with other compounds of formula (5), and optionally replacing cyclopropyl magnesium bromide with other Grignard reagents, the following compound s of Formula (I) were prepared:

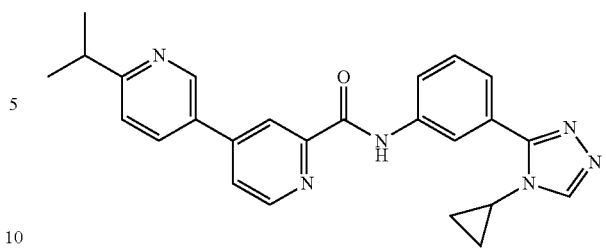

N-(3-(4-cyclopropyl-4H-1,2,4-triazol-3-yl)phenyl)-6-isopropyl-3,4'-bipyridine-2'-carboxamide $C_{25}H_{24}N_6O$. 425.1 (M+1). ¹H NMR (DMSO) d 10.94 (s, 1H), 9.02 (d, J=2.0 Hz, 1H), 8.84 (d, J=5.2 Hz, 1H), 8.63 (s, 1H), 8.58 (s, 1H), 8.46 (d, J=1.2 Hz, 1H), 8.25 (dd, J=8.0, 2.4 Hz, 1H), 8.08 (m, 2H), 7.69 (d, J=8.0 Hz, 1H), 7.55 (t, J=8.0 Hz, 1H), 7.48 (d, J=8.0 Hz, 1H), 3.67 (m, 1H), 3.12 (sept, J=7.2 Hz, 1H), 1.29 (d, J=7.2 Hz, 6H), 1.08 (m, 2H), 0.95 (m, 2H).

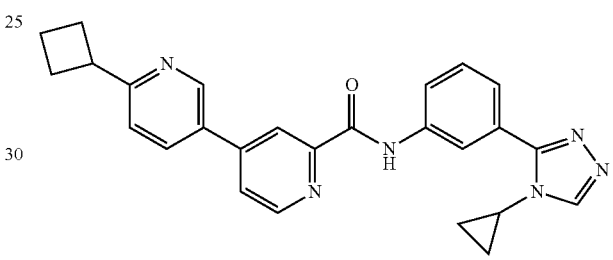

6-cyclobutyl-N-(3-(4-cyclopropyl-4H-1,2,4-triazol-3-yl)phenyl)-3,4'-bipyridine-2'-carboxamide $C_{26}H_{24}N_6O$. 437.1 (M+1). ¹H NMR (DMSO) d 10.94 (s, 1H), 9.05 (d, J=2.0 Hz, 1H), 8.84 (d, J=51 Hz, 1H), 8.63 (s, 1H), 8.59 (s, 1H), 8.46 (d, J=1.2 Hz, 1H), 8.24 (dd, J=8.0, 2.0 Hz, 1H), 8.08 (m, 2H), 7.69 (d, J=8.0 Hz, 1H), 7.55 (1, J=8.0 Hz, 1H), 7.44 (d, J=8.0 Hz, 1H), 3.72 (p, J=8.8 Hz, 1H), 3.66 (m, 1H), 2.33 (m, 4H), 2.04 (m, 1H), 1.89 (m, 1H), 1.08 (m, 2H), 0.95 (m, 2H).

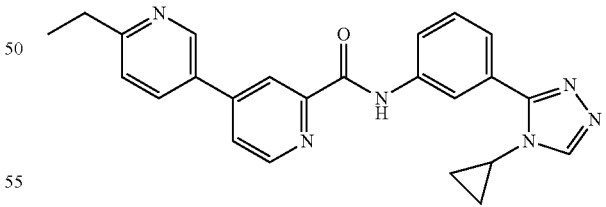

N-(3-(4-cyclopropyl-4H-1,2,4-triazol-3-yl)phenyl)-6-ethyl-3,4'-bipyridine-2'-carboxamide $C_{24}H_{22}N_6O$. 411.1 (M+1). ¹H NMR (DMSO) d 10.94 (s, 1H), 9.01 (d, J=2.0 Hz, 1H), 8.84 (d, J=5.2 Hz, 1H), 8.63 (s, 1H), 8.59 (s, 1H), 8.46 (d, J=1.2 Hz, 1H), 8.25 (dd, J=8.4, 2.4 Hz, 1H), 8.08 (m, 2H), 7.69 (d, 8.0 Hz, 1H), 7.55 (t, J=8.0 Hz, 1H), 7.47 (d, J=8.0 Hz, 1H), 3.66 (m, 1H), 2.85 (q, 7.2 Hz, 2H), 1.28 (t, J=7.2 Hz, 3H), 1.08 (m, 2H), 0.95 (m, 2H).

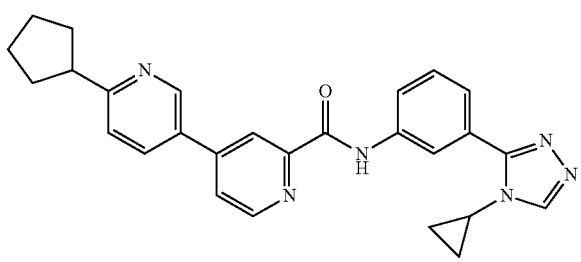 [SMILES: O=C(Nc1cccc(-c2nncn2C2CC2)c1)c1cc(-c2ccc(C3CCCC3)nc2)ccn1]

6-cyclopentyl-N-(3-(4-cyclopropyl-4H-1,2,4-triazol-3-yl)phenyl)-3,4'-bipyridine-2'-carboxamide $C_{27}H_{26}N_6O$. 451.1 (M+1). $^1$H NMR (DMSO) d 10.94 (s, 1H), 9.02 (d, J=2.0 Hz, 1H), 8.84 (d, J=5.2 Hz, 1H), 8.63 (s, 1H), 8.58 (s, 1H), 8.45 (d, J=1.2 Hz, 1H), 8.23 (dd, J=8.0, 2.4 Hz, 1H), 8.07 (m, 2H), 7.69 (d, J=8.0 Hz, 1H), 7.55 (t, J=8.0 Hz, 1H), 7.47 (d, J=8.0 Hz, 1H), 3.66 (m, 1H), 3.25 (m, 1H), 2.05 (m, 2H), 1.78 (m, 4H), 1.70 (m, 2H), 1.08 (m, 2H), 0.95 (m, 2H).

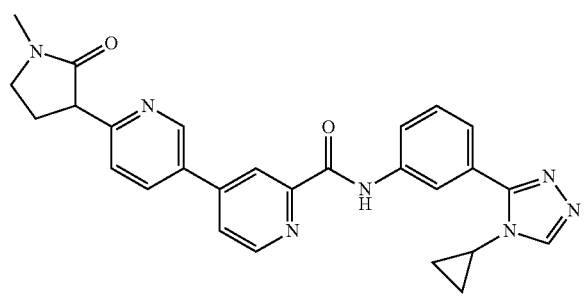 [SMILES: CN1CCC(c2ccc(-c3ccnc(C(=O)Nc4cccc(-c5nncn5C5CC5)c4)c3)cn2)C1=O]

N-(3-(4-cyclopropyl-4H-1,2,4-triazol-3-yl)phenyl)-6-(1-methyl-2-oxopyrrolidin-3-yl)-3,4'-bipyridine-2'-carboxamide $C_{27}H_{25}N_7O_2$. 480.1 (M+1). $^1$H NMR (DMSO) d 10.95 (s, 1H), 9.04 (d, J=2.4 Hz, 1H), 8.86 (d, J=4.8 Hz, 1H), 8.63 (s, 1H), 8.59 (s, 1H), 8.47 (d, J=1.2 Hz, 1H), 8.29 (dd, J=8.0, 2.4 Hz, 1H), 8.08 (m, 2H), 7.69 (d, J=8.0 Hz, 1H), 7.55 (m, 2H), 3.92 (t, J=8.8 Hz, 1H), 3.67 (m, 1H), 3.50 (m, 2H), 2.80 (s, 3H), 2.42 (q, 8.8 Hz, 2H), 1.08 (m, 2H), 0.95 (m, 2H).

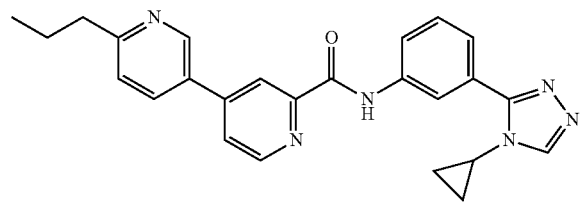 [SMILES: CCCc1ccc(-c2ccnc(C(=O)Nc3cccc(-c4nncn4C4CC4)c3)c2)cn1]

N-(3-(4-cyclopropyl-4H-1,2,4-triazol-3-yl)phenyl)-6-propyl-3,4'-bipyridine-2'-carboxamide $C_{25}H_{24}N_6O$. 425.1 (M+1). $^1$H NMR (DMSO) d 10.94 (s, 1H), 9.01 (d, J=2.0 Hz, 1H), 8.84 (d, J=5.2 Hz, 1H), 8.63 (s, 1H), 8.59 (s, 1H), 8.46 (d, J=0.8 Hz, 1H), 8.24 (dd, J=8.0, 2.4 Hz, 1H), 8.08 (m, 2H), 7.69 (d, J=8.0 Hz, 1H), 7.55 (t, J=8.0 Hz, 1H), 7.45 (d, J=8.0 Hz, 1H), 3.66 (m, 1H), 2.80 (t, J=8.0 Hz, 2H), 1.75 (q, J=8.0 Hz, 2H), 1.08 (m, 2H), 0.96 (m, 5H).

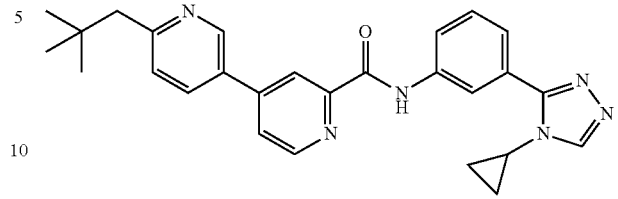

N-(3-(4-cyclopropyl-4H-1,2,4-triazol-3-yl)phenyl)-6-neopentyl-3,4'-bipyridine-2'-carboxamide $C_{27}H_{28}N_6O$. 453.1 (M+1). $^1$H NMR (DMSO) d 10.95 (s, 1H), 9.03 (d, J=2.0 Hz, 1H), 8.84 (d, J=4.8 Hz, 1H), 8.63 (s, 1H), 8.59 (s, 1H), 8.47 (s, 1H), 8.25 (dd, J=8.0, 2.8 Hz, 1H), 8.10 (m, 2H), 7.69 (d, J=8.0 Hz, 1H), 7.55 (t, J=8.0 Hz, 1H), 7.41 (d, J=8.0 Hz, 1H), 3.66 (m, 1H), 2.73 (s, 2H), 1.08 (m, 2H), 1.00 (m, 11H).

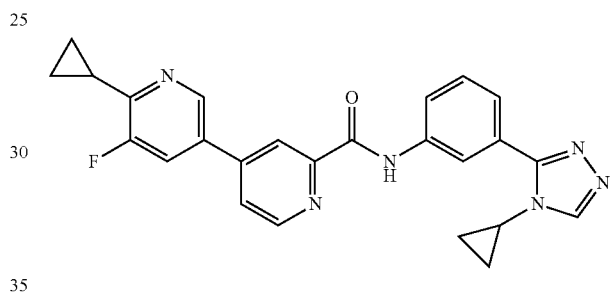

6-cyclopropyl-N-(3-(4-cyclopropyl-4H-1,2,4-triazol-3-yl)phenyl)-5-fluoro-3,4'-bipyridine-2'-carboxamide $C_{25}H_{21}FN_6O$. 441.1 (M+1). $^1$H NMR (DMSO) d 10.94 (s, 1H), 8.84 (m, 2H), 8.63 (s, 1H), 8.58 (s, 1H), 8.48 (d, J=1.2 Hz, 1H), 8.25 (dd, J=11.2, 2.0 Hz, 1H), 8.09 (m, 2H), 7.69 (d, J=8.0 Hz, 1H), 7.55 (t, J=8.0 Hz, 1H), 3.66 (m, 1H), 2.32 (m, 1H), 1.08 (m, 6H), 0.95 (m, 2H).

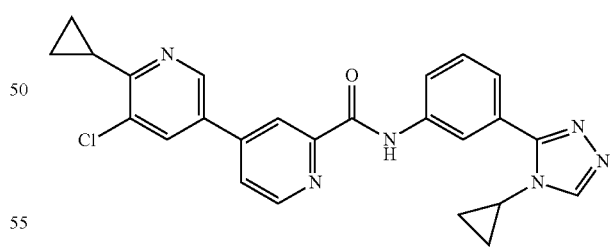

5-chloro-6-cyclopropyl-N-(3-(4-cyclopropyl-4H-1,2,4-triazol-3-yl)phenyl)-3,4'-bipyridine-2'-carboxamide $C_{25}H_{21}ClN_6O$. 457.0 (M+1). $^1$H NMR (DMSO) d 10.94 (s, 1H), 8.92 (d, J=2.0 Hz, 1H), 8.84 (d, J=5.2 Hz, 1H), 8.63 (s, 1H), 8.59 (s, 1H), 8.45 (s, 1H), 8.44 (d, J=2.0 Hz, 1H), 8.09 (m, 2H), 7.69 (d, J=8.0 Hz, 1H), 7.55 (t, J=8.0 Hz, 1H), 3.66 (m, 1H), 2.55 (m, 1H), 1.08 (m, 6H), 0.95 (m, 2H).

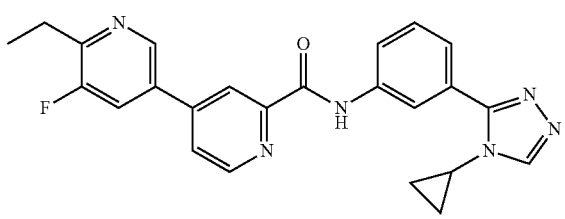 [SMILES: CCc1ncc(-c2ccnc(C(=O)Nc3cccc(-c4nncn4C4CC4)c3)c2)cc1F]

N-(3-(4-cyclopropyl-4H-1,2,4-triazol-3-yl)phenyl)-
6-ethyl-5-fluoro-3,4'-bipyridine-2'-carboxamide $C_{24}H_{21}FN_6O$. 429.1 (M+1). $^1$H NMR (DMSO) d 10.95 (s, 1H), 8.92 (s, 1H), 8.87 (d, J=4.8 Hz, 1H), 8.63 (s, 1H), 8.59 (s, 1H), 8.51 (s, 1H), 8.28 (d, 10.8 Hz, 1H), 8.12 (d, J=5.2 Hz, 1H), 8.07 (d, J=8.0 Hz, 1H), 7.70 (d, J=8.0 Hz, 1H), 7.56 (t, J=8.0 Hz, 1H), 3.66 (m, 1H), 2.89 (q, J=7.2 Hz, 2H), 1.28 (t, J=7.2 Hz, 3H), 1.08 (m, 2H), 0.95 (m, 2H). $^{19}$F NMR (DMSO) d −126.5 (d, J=10.8 Hz, 1F).

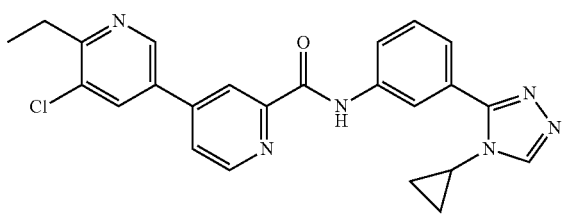 [SMILES: CCc1ncc(-c2ccnc(C(=O)Nc3cccc(-c4nncn4C4CC4)c3)c2)cc1Cl]

5-chloro-N-(3-(4-cyclopropyl-4H-1,2,4-triazol-3-yl)
phenyl)-6-ethyl-3,4'-bipyridine-2'-carboxamide $C_{24}H_{21}ClN_6O$. 445.1 (M+1). $^1$H NMR (DMSO) d 10.96 (s, 1H), 9.01 (s, 1H), 8.86 (m, 1H), 8.63 (s, 1H), 8.59 (s, 1H), 8.51 (s, 1H), 8.47 (s, 1H), 8.09 (m, 2H), 7.69 (d, J=8.0 Hz, 1H), 7.55 (t, J=8.0 Hz, 1H), 3.66 (m, 1H), 2.97 (q, J=7.6 Hz, 2H), 1.31 (t, J=7.6 Hz, 3H), 1.08 (m, 2H), 0.95 (m, 2H).

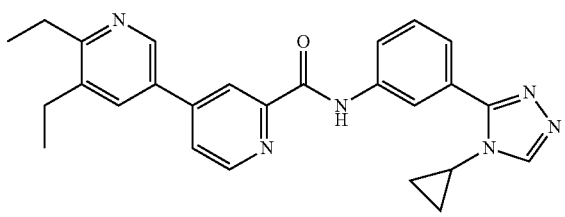 [SMILES: CCc1cc(-c2ccnc(C(=O)Nc3cccc(-c4nncn4C4CC4)c3)c2)cnc1CC]

N-(3-(4-cyclopropyl-4H-1,2,4-triazol-3-yl)phenyl)-5,
6-diethyl-3,4'-bipyridine-2'-carboxamide $C_{26}H_{26}N_6O$. 439.1 (M+1). $^1$H NMR (DMSO) d 10.94 (s, 1H), 8.86 (s, 1H), 8.84 (d, J=5.2 Hz, 1H), 8.63 (s, 1H), 8.59 (s, 1H), 8.47 (s, 1H), 8.07 (m, 3H), 7.69 (d, J=8.0 Hz, 1H), 7.56 (t, J=8.0 Hz, 1H), 3.67 (m, 1H), 2.85 (q, J=7.6 Hz, 2H), 2.75 (q, J=7.6 Hz, 2H), 1.26 (m, 6H), 1.09 (m, 2H), 0.94 (m, 2H).

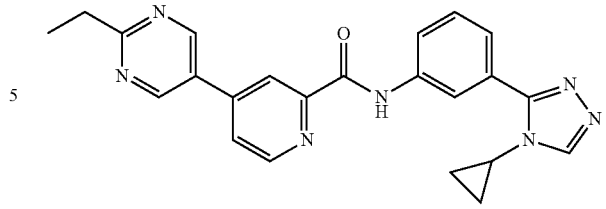

N-(3-(4-cyclopropyl-4H-1,2,4-triazol-3-yl)phenyl)-
4-(2-ethylpyrimidin-5-yl)picolinamide $C_{23}H_{21}N_7O$. 412.1 (M+1). $^1$H NMR (DMSO) d 10.96 (s, 1H), 9.27 (s, 2H), 8.89 (d, J=5.2 Hz, 1H), 8.63 (s, 1H), 8.59 (s, 1H), 8.54 (d, J=0.8 Hz, 1H), 8.14 (dd, J=5.2, 2.0 Hz, 1H), 8.08 (d, J=9.2 Hz, 1H), 7.70 (d, J=8.0 Hz, 1H), 7.55 (1, J=8.0 Hz, 1H), 3.66 (m, 1H), 3.00 (q, J=7.2 Hz, 2H), 1.39 (t, J=7.2 Hz, 3H), 1.08 (m, 2H), 0.95 (m, 2H).

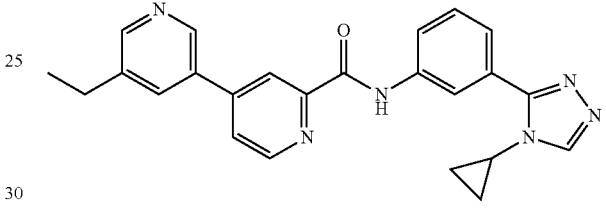

N-(3-(4-cyclopropyl-4H-1,2,4-triazol-3-yl)phenyl)-
5-ethyl-3,4'-bipyridine-2'-carboxamide $C_{24}H_{22}N_6O$. 411.1 (M+1). $^1$H NMR (DMSO) d 10.96 (s, 1H), 8.93 (d, J=2.4 Hz, 1H), 8.86 (d, J=5.6 Hz, 1H), 8.63 (s, 1H), 8.60 (s, 1H), 8.59 (s, 1H), 8.49 (d, J=1.2 Hz, 1H), 8.19 (s, 1H), 8.10 (m, 2H), 7.69 (d, J=8.0 Hz, 1H), 7.55 (t, J=8.0 Hz, 1H), 3.67 (m, 1H), 2.75 (q, J=7.6 Hz, 2H), 1.28 (t, J=7.6 Hz, 3H), 1.08 (m, 2H), 0.95 (m, 2H).

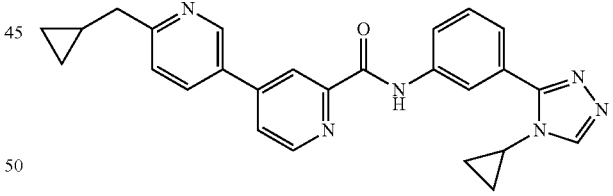

N-(3-(4-cyclopropyl-4H-1,2,4-triazol-3-yl)phenyl)-
6-(cyclopropylmethyl)-3,4'-bipyridine-2'-carboxamide $C_{26}H_{24}N_6O$. 437.1 (M+1). $^1$H NMR (DMSO) d 10.97 (s, 1H), 9.01 (d, J=2.4 Hz, 1H), 8.85 (d, 5.6 Hz, 1H), 8.64 (s, 1H), 8.59 (s, 1H), 8.46 (s, 1H), 8.28 (dd, J=8.0 Hz, 1H), 8.09 (m, 2H), 7.69 (d, J=8.0 Hz, 1H), 7.55 (m, 2H), 3.67 (m, 1H), 2.73 (d, J=6.8 Hz, 2H), 1.09 (m, 3H), 0.94 (m, 2H), 0.50 (m, 2H), 0.26 (m, 2H).

C. Similarly, following the procedure of Example 19A, optionally replacing 4-(2-chloropyrimidin-5-yl)-N-(3-(4-cyclopropyl-4H-1,2,4-triazol-3-yl)phenyl)picolinamide with other compounds of formula (5), and optionally replacing cyclopropyl magnesium bromide with other Grignard reagents, other compounds of Formula (I) are prepared.

EXAMPLE 20

Preparation of Compounds of Formula (I)

Preparation of a Compound of Formula (I) in which $X^2$, $X^3$, $X^4$, $X^6$, $X^7$ and $X^8$ are $C(R^4)$, $X^1$ and $X^5$ are N, $R^1$ is Cyclopropyl, $R^2$ is Hydrogen, and $R^3$ is Morpholin-yl A. Preparation of N-(3-(4-methyl-4H-1,2,4-triazol-3-yl)phenyl)-4-morpholinopicolinamide

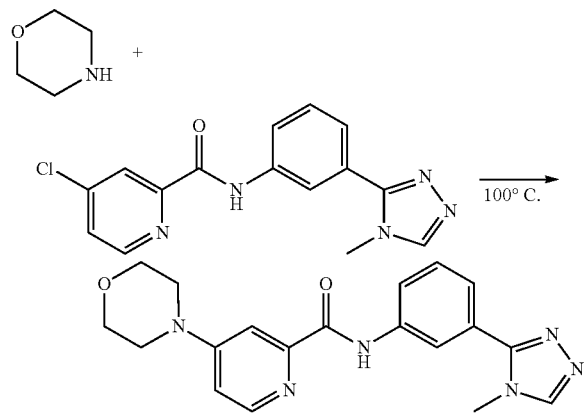

4-Chloro-N-(3-(4-methyl-4H-1,2,4-triazol-3-yl)phenyl) picolinamide (0.112 mmol, 35.0 mg) was treated with an excess (400 μL) of morpholine and heated to 100° C. for 2 hours. The reaction mixture was diluted with water (400 μL) and purified by RP-HPLC to afford 37.0 (91% yield) of N-(3-(4-methyl-4H-1,2,4-triazol-3-yl)phenyl)-4-morpholinopicolinamide.

$C_{19}H_{20}N_6O_2$. 365.2 (M+1). $^1$H NMR (DMSO) d 10.81 (s, 1H), 8.58 (s, 1H), 8.34 (d, J=5.6 Hz, 1H), 8.29-8.31 (m, 1H), 8.05-8.09 (m, 1H), 7.59 (d, J=2.4 Hz, 1H), 7.53 (t, J=8 Hz, 1H), 7.48-7.51 (m, 1H), 7.09 (dd, J=2.4, 6 Hz, 1H), 3.79 (s, 3H), 3.74 (t, J=8.8 Hz, 4H), 3.40 (t, J=8.8 Hz, 4H).

B. Similarly, following the procedure of Example 20A, but optionally replacing 4-chloro-N-(3-(4-methyl-4H-1,2,4-triazol-3-yl)phenyl)picolinamide with other compounds of formula (5), and optionally replacing morpholine with other amines, the following compounds of Formula (I) were prepared:

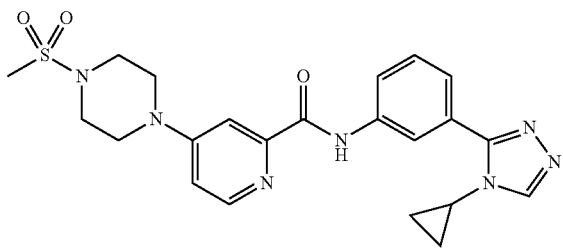 [SMILES: CS(=O)(=O)N1CCN(c2ccnc(C(=O)Nc3cccc(-c4nncn4C4CC4)c3)c2)CC1]

N-(3-(4-cyclopropyl-4H-1,2,4-triazol-3-yl)phenyl)-4-(4-(methylsulfonyl)piperazin-1-yl)picolinamide $C_{22}H_{25}N_7O_3S$. 468.1 (M+1). $^1$H NMR (DMSO) d 10.77 (s, 1H), 8.62 (s, 1H), 8.56 (s, 1H), 8.35 (d, J=6 Hz, 1H), 8.01 (d, J=8 Hz, 1H), 7.66 (d, J=8 Hz, 1H), 7.62 (d, J=2 Hz, 1H), 7.52 (t, J=8 Hz, 1H), 7.13 (dd, J=3, 6 Hz, 1H), 3.63-3.67 (m, 1H), 3.59 (t, J=4 Hz, 4H), 3.25 (t, J=5 Hz, 4H), 2.93 (s, 3H), 1.06 (dd, J=6, 9 Hz, 2H), 0.91-0.95 (m, 2H).

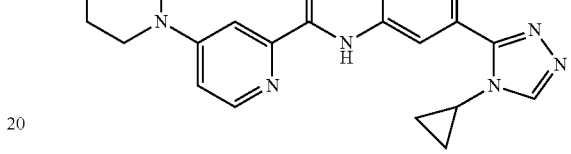

N-(3-(4-cyclopropyl-4H-1,2,4-triazol-3-yl)phenyl)-4-(3-hydroxypiperidin-1-yl)picolinamide $C_{22}H_{24}N_6O_2$. 405.1 (M+1). $^1$H NMR (DMSO) d 10.74 (s, 1H), 8.62 (s, 1H), 8.55 (s, 1H), 8.26 (d, J=6 Hz, 1H), 8.01 (d, J=8 Hz, 1H), 7.65 (d, J=8 Hz, 1H), 7.54 (s, 1H), 7.52 (t, J=8 Hz, 1H), 7.02 (dd, J=3, 6 Hz, 1H), 4.95 (d, J=4 Hz, 1H), 3.32-3.81 (m, 4H), 3.02-3.11 (m, 1H), 2.96 (dd, J=8, 12 Hz, 1H), 1.83-1.92 (m, 1H), 1.70-1.80 (m, 1H), 1.42-1.48 (m, 2H), 1.07 (dd, J=7, 13 Hz, 2H), 0.90-0.95 (m, 2H).

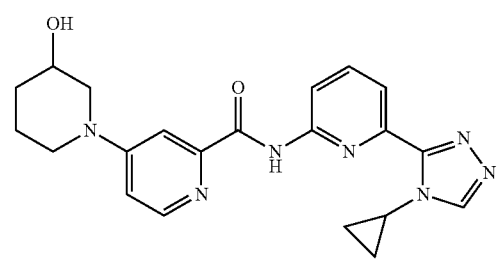 [SMILES: O=C(Nc1cccc(-c2nncn2C2CC2)n1)c1cc(N2CCCC(O)C2)ccn1]

N-(6-(4-cyclopropyl-4H-1,2,4-triazol-3-yl)pyridin-2-yl)-4-(3-hydroxypiperidin-1-yl)picolinamide $C_{21}H_{23}N_7O_2 \times HCO_2H$. 406.1 (M+1). $^1$H NMR (DMSO) d 10.64 (s, 1H), 8.68 (s, 1H), 8.36 (d, J=8 Hz, 1H), 8.25 (d, J=6 Hz, 1H), 8.14 (s, 1H), 8.08 (t, J=8 Hz, 1H), 7.85 (d, J=7 Hz, 1H), 7.58 (d, J=2 Hz, 1H), 7.04 (dd, J=3, 6 Hz, 1H), 4.95 (s, 1H), 3.98-4.04 (m, 1H), 3.79 (dd, J=3, 13 Hz, 1H), 3.72 (d, J=14 Hz, 1H), 3.56-3.59 (m, 1H), 3.07-3.14 (m, 1H), 3.00 (dd, J=8, 13 Hz, 1H), 1.86-1.90 (m, 1H), 1.74-1.78 (m, 1H), 1.42-1.48 (m, 2H), 0.95-1.07 (m, 4H).

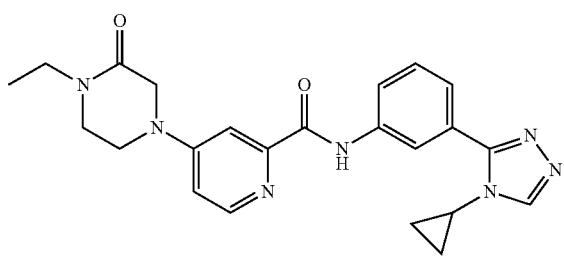 [SMILES: CCN1CCN(c2ccnc(C(=O)Nc3cccc(-c4nncn4C4CC4)c3)c2)CC1=O]

N-(3-(4-cyclopropyl-4H-1,2,4-triazol-3-yl)phenyl)-4-(4-ethyl-3-oxopiperazin-1-yl)picolinamide $C_{23}H_{25}N_7O_2 \times HCO_2H$. 432.1 (M+1), $^1H$ NMR (DMSO) d 10.79 (s, 1H), 8.62 (s, 1H), 8.56 (s, 1H), 8.34 (d, J=6 Hz, 1H), 8.13 (s, 1H), 8.01 (d, J=9 Hz, 1H), 7.66 (d, J=8 Hz, 1H), 7.50-7.55 (m, 2H), 7.05 (dd, J=2, 6 Hz, 1H), 4.02 (s, 2H), 3.72 (t, J=5 Hz, 2H), 3.63-3.67 (m, 1H), 3.50 (t, J=6 Hz, 2H), 3.41 (q, J=8 Hz, 2H), 1.03-1.10 (m, 5H), 0.90-0.95 (m, 2H).

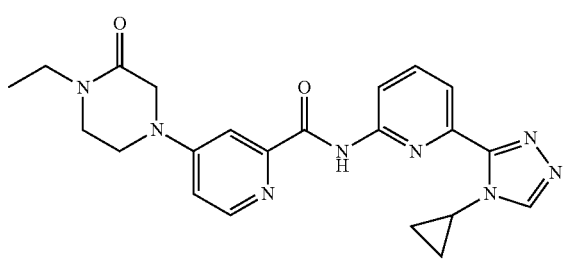 [SMILES: CCN1CCN(c2ccnc(C(=O)Nc3cccc(-c4nncn4C4CC4)n3)c2)CC1=O]

N-(6-(4-cyclopropyl-4H-1,2,4-triazol-3-yl)pyridin-2-yl)-4-(4-ethyl-3-oxopiperazin-1-yl)picolinamide $C_{22}H_{24}N_8O_2$. 433.1 (M+1). $^1H$ NMR (DMSO) d 10.78 (s, 1H), 8.69 (s, 1H), 8.34 (t, J=7 Hz, 2H), 8.09 (t, J=8 Hz, 1H), 7.86 (d, J=7 Hz, 1H), 7.64 (br s, 1H), 7.10 (br s, 1H), 4.01-4.12 (m, 3H), 3.76 (s, 2H), 3.51 (t, J=5 Hz, 2H), 3.41 (q, J=7 Hz, 2H), 1.08 (t, J=7 Hz, 3H), 0.95-1.06 (m, 4H).

C. Similarly, following the procedure of Example 20A, but optionally replacing 4-chloro-N-(3-(4-methyl-4H-1,2,4-triazol-3-yl)phenyl)picolinamide with other compounds of formula (5), and optionally replacing morpholine with other amines, other compounds of Formula (I) are prepared.

EXAMPLE 21

Preparation of Compounds of Formula (I) in which $X^1$ is $C(R^4)$

Preparation of a Compound of Formula (I) in which X, $X^3$, $X^4$, $X^6$, $X^7$ and $X^8$ are $C(R^4)$, $X^2$ and $X^5$ are N, $R^1$ is Cyclopropyl, $R^2$ is Hydrogen, and $R^3$ is Quinolin-3-yl A. Preparation of N-6-(1-cyclopropyl-1H-imidazol-5-yl)pyridin-2-yl)-4-(quinolin-3-yl)picolinamide

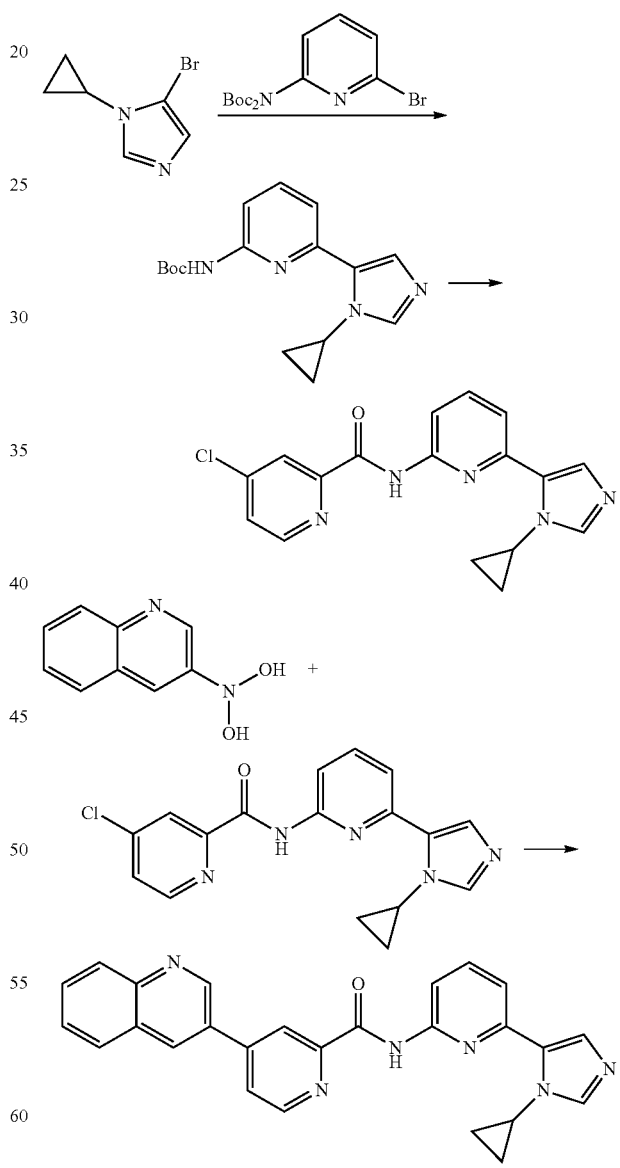

Steps 1 and 2: To a stirred solution of 5-bromo-1-cyclopropyl-1H-imidazole (780 mg, 1.90 mmol), in tetrahydrofuran (3 mL) at −78° C. was added n-butyllithium (911 µL 2.5 M solution, 2.28 mmol) and the reaction mixture was stirred for 30 minutes at −78° C. A solution of zinc bromide (ZnBr$_2$, (641 mg, 2.85 mmol, dried under vacuum at 100° C. for 3 hours) in tetrahydrofuran (3 mL) was added, the mixture warmed to room temperature and stirred an additional 2.5 hours. A solution of 6-(di-Boc-amino)-2-bromopyridine and Pd(PPh$_3$)$_4$ in 3 mL tetrahydrofuran was added to the reaction via cannula and the mixture was stirred overnight. The reaction was concentrated under reduced pressure and the residue was purified by flash chromatography (5% methanol in methylene chloride, gradient flash: 4%→10% methanol in methylene chloride,). The product was isolated as mixture of the mono- and bis-Boc protected 6-(1-cyclopropyl-1H-imidazol-5-yl)pyridin-2-amine. This mixture was used directly in the next step Step 3: The material from the above sequence was dissolved in dichloroethane (2 mL), trifluoroacetic acid was added, and the mixture was heated to 50° C. and stirred for 1 hour. The material was purified by reverse phase HPLC to afford 150 mg (40% yield) of 6-(3-cyclopropyl-3H-imidazol-4-yl)-pyridin-2-ylamine as a white solid. M+1=201.2

Step 4: A solution of 4-chloro-pyridine-2-carboxylic acid (141 mg, 0.895 mmol), 6-(3-cyclopropyl-3H-imidazol-4-yl)-pyridin-2-ylamine (150 mg, 0.750 mmol), (2-(7-Aza-1H-benzotriazole-1-yl)-1,1,3,3-tetramethyluronium hexafluorophosphate (HATU) (342 g, 0.899 mmol), and N-methylmorpholine (250 μL, 2.70 mmol) in N,N-dimethylformamide was stirred at room temperature for 12 hours. The solvent was removed under reduced pressure, the residue suspended in acetonitrile, and the solid isolated by filtration, washed with water (80 mL), acetonitrile (80 mL) and diethyl ether (80 mL), and dried under reduced pressure to afford 4-chloro-N-(6-(1-cyclopropyl-1H-imidazol-5-yl)pyridin-2-yl)picolinamide as a white powder (120 mg, 47% yield). M+1=340.1

Step 5: A suspension of 4-chloro-N-(6-(1-cyclopropyl-1H-imidazol-5-yl)pyridin-2-yl)picolinamide (38.9 mg, 0.115 mmol), boronic acid (29 mg, 0.138 mmol), dppf(Pd)Cl$_2$ (4.2 mg, 0.00575), potassium carbonate (47.7 mg, 0.345 mmol) in degassed toluene (1 mL), degassed water (0.5 mL) and degassed isopropanol (0.5 mL) was heated at 95° C. for 2 hours. The aqueous phase was discarded and the solvent removed from the organic portion under reduced pressure. Purification by reverse phase HPLC provided N-(6-(1-cyclopropyl-1H-imidazol-5-yl)pyridin-2-yl)-4-(quinolin-3-yl)picolinamide (10.1 mg, 20%) as a white solid. C$_{26}$H$_{20}$N$_6$O× HCO$_2$H. 433.1 (M+1). $^1$H NMR (DMSO) d 10.64 (s, 1H), 9.45 (d, J=2 Hz, 1H), 9.05 (d, J=2 Hz, 1H), 8.93 (d, J=5 Hz, 1H), 8.72 (d, J=1 Hz, 1H), 8.30-8.33 (m, 2H), 8.18 (d, J=8 Hz, 1H), 8.12 (d, J=8 Hz, 1H), 8.04 (t, J=8 Hz, 1H), 7.82-7.89 (m, 2H), 7.73 (t, J=8 Hz, 1H), 7.37 (s, 1H), 7.04 (s, 1H), 4.23-4.27 (m, 1H), 1.04-1.09 (m, 2H) 0.91-0.95 (m, 2H).

B. Similarly, following the procedure of Example 21A, the following compound of Formula (I) was prepared:

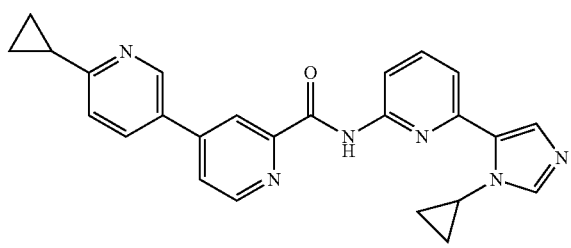 [SMILES: O=C(Nc1cccc(-c2cncn2C2CC2)c1)c1cc(-c2ccc(C3CC3)nc2)ccn1]

6-cyclopropyl-N-(6-(1-cyclopropyl-1H-imidazol-5-yl)pyridin-2-yl)-3,4'-bipyridine-2'-carboxamide C$_{25}$H$_{22}$N$_6$O. 423.1 (M+1). $^1$H NMR (DMSO) d 10.61 (s, 1H), 8.95 (d, J=2 Hz, 1H), 8.83 (d, J=5 Hz, 1H), 8.49 (s, 1H), 8.32 (d, J=8 Hz, 1H), 8.21 (dd, J=2, 8 Hz, 1H), 8.10 (dd, J=2.5 Hz, 1H), 8.05 (t, J=8.0 Hz, 1H), 7.85 (d, J=8 Hz, 1H), 7.50 (d, J=8 Hz, 1H), 4.20-4.25 (m, 1H), 2.19-2.23 (m, 1H), 0.95-1.10 (m, 8H).

C. Similarly, following the procedure of Example 21A, other compounds of Formula (I) are prepared.

EXAMPLE 22

Preparation of Compounds of Formula (I) in which X$^1$ is C(R$^4$)

Preparation of a Compound of Formula (I) in which X$^1$, X$^2$, X$^3$, X$^4$, X$^6$, X$^7$ and X$^8$ are C(R$^4$), X$^5$ is N, R$^1$ is Cyclopropyl, R$^2$ is Hydrogen, and R$^3$ is Pyridin-3-yl A. Preparation of N-(3-(1-cyclopropyl-1H-imidazol-5-yl)phenyl)-3,4'-bipyridine-2'-carboxamide

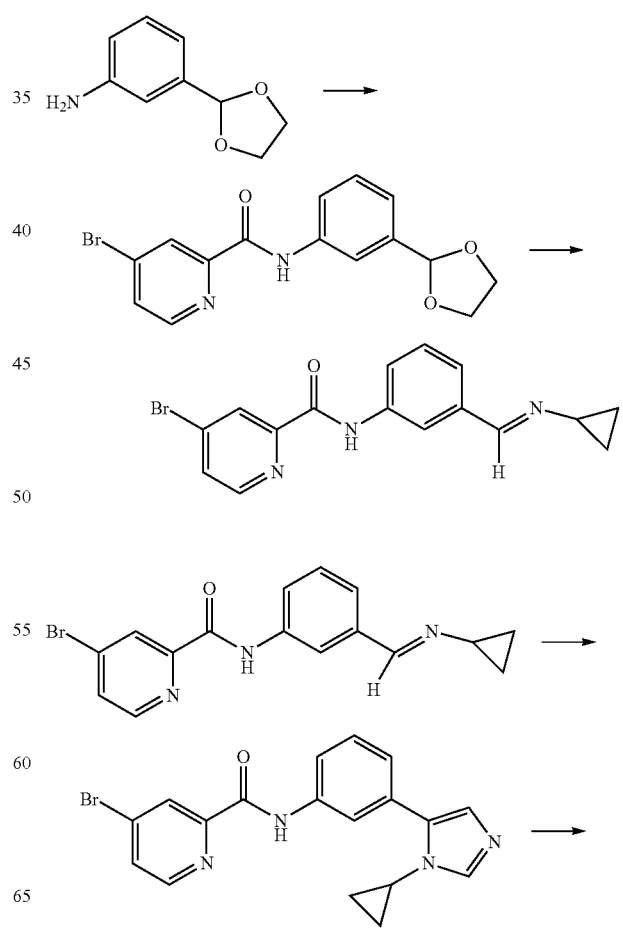

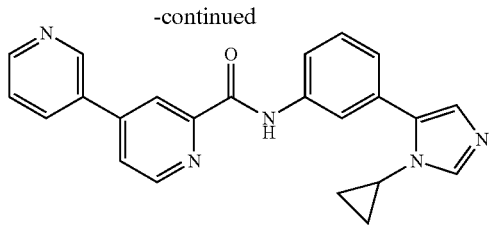

Step 1: A solution of 3-(1,3-dioxolan-2-yl)aniline (3.26 g, 19.7 mmol), 4-bromopicolinic acid (4.38 g, 21.7 mmol), (2-(7-Aza-1H-benzotriazole-1-yl)-1,1,3,3-tetramethyluronium hexafluorophosphate (HATU) (8.99 g, 23.6 mmol), and N-methylmorpholine (2.6 mL, 23.6 mmol) in N,N-dimethylformamide was stirred at room temperature for 30 minutes. The solvent was removed under reduced pressure, and the residue was purified by flash chromatography (1:1 Hexanes/ethyl acetate) to afford a mixture of N-(3-(1,3-dioxolan-2-yl)phenyl)-4-bromopicolinamide acetal and the corresponding aldehyde (5.56 g, ~81% yield, contains ~15% aldehyde). M+1=349.1

Step 2/3: To a solution of the product of Step (1.12 g, 3.23 mmol) in acetone/water (4:1, 0.2 M), was added 4-methylbenzenesulfonic acid (61 mg, 0.323 mmol), and the mixture was stirred overnight. The reaction was diluted with methylene chloride and washed with brine (2×). The organics were dried over magnesium sulfate, filtered and the solvent removed from the filtrate under reduced pressure, to provide a white solid. This material was dissolved in methylene chloride, (0.1 M), 4 Å powdered molecular sieves (3.2 g, 1 g/mmol) and cyclopropyl amine (1.12 mL, 12.9 mmol) were added and the reaction mixture was stirred for 6 hours. The molecular sieves were filtered off, washed with methylene chloride and solvent removed from the filtrate under reduced pressure, to afford 1.1 g (quantitative yield) of 4-promo-N-(3-((cyclopropylimino)methyl)phenyl)-picolinamide as a white solid. M+1=343.1.

Step 4: To a solution of 4-bromo-N-(3-((cyclopropylimino)methyl)phenyl)-picolinamide (970 mg, 2.83 mmol) in dimethoxyethane/methanol (2:1, 0.1M) were added toluenesulfonylmethyl isocyanide (1.10 g, 5.65 mmol) and cyclopropylamine (392 µL, 5.65 mmol). The reaction mixture was stirred for 14 hours at 52° C., and additional toluenesulfonylmethyl isocyanide (550 mg, 2.83 mmol) was added. The reaction mixture was stirred an additional 6 hours, the solvent removed under reduced pressure, concentrated, and the residue purified by flash chromatography (2-8% methanol in methylene chloride) to afford 110 mg of 4-bromo-N-(3-(1-cyclopropyl-1H-imidazol-5-yl)phenyl)picolinamide. M+1=383.1

Step 5: A suspension of 4-bromo-N-(3-(1-cyclopropyl-1H-imidazol-5-yl)phenyl)picolinamide (75.0 mg, 0.196 mmol), boronic acid (33.8 mg, 0.274 mmol), dppf(Pd)Cl$_2$ (14.3 mg, 0.0196), potassium carbonate (81.3 mg, 0.588 mmol) in degassed toluene (1 mL), degassed water (0.5 mL) and degassed isopropanol (0.5 mL) was heated at 95° C. for 2 hours. The aqueous phase was discarded and the solvent removed under reduced pressure from the organic portion. Purification by reverse phase HPLC provided N-(3-(1-cyclopropyl-1H-imidazol-5-yl)phenyl)-3,4'-bipyridine-2'-carboxamide (17.3 mg, 23%) as a white solid.

$C_{23}H_{19}N_5O \times HCO_2H$. 382.0 (M+1). $^1$H NMR (DMSO) d 10.83 (s, 1H), 9.11 (d, J=2 Hz, 1H), 8.86 (d, J=5 Hz, 1H), 8.72 (dd, J=2.5 Hz, 1H), 8.48 (d, J=1 Hz, 1H), 8.48 (d, J=1 Hz, 1H), 8.32-8.36 (m, 1H), 8.27 (s, 1H), 8.20 (s, 1H), 8.10 (dd, J=2, 5 Hz, 1H), 7.96 (d, J=8 Hz, 1H), 7.76 (s, 1H), 7.60 (dd, J=5, 8 Hz, 1H), 7.46 (t, J=8 Hz, 1H), 7.41 (d, J=8 Hz), 3.57-3.61 (m, 1H), 0.99-1.04 (m, 2H), 0.86-0.91 (m, 2H).

B. Similarly, following the procedure of Example 22A, but optionally replacing 3-(1,3-dioxolan-2-yl)aniline with other aromatic amines, optionally replacing 4-bromopicolinic acid with other acids, and optionally replacing cyclopropylamine with other amines, the following compounds of Formula (I) were prepared:

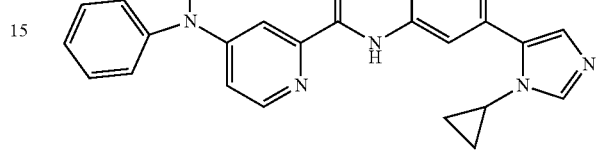

4-(1H-benzo[d]imidazol-1-yl)-N-(3-(1-cyclopropyl-1H-imidazol-5-yl)phenyl)picolinamide $C_{25}H_{20}N_6O$. 421.0 (M+1). $^1$H NMR (DMSO) d 10.90 (s, 1H), 8.95 (d, J=5 Hz, 1H), 8.91 (s, 1H), 8.48 (d, J=2 Hz, 1H), 8.28 (s, 1H), 8.13 (dd, J=2.5 Hz, 1H), 7.97 (d, J=5 Hz, 1H), 7.89 (d, J=8 Hz, 1H), 7.84 (d, J=8 Hz, 1H), 7.76 (s, 1H), 7.38-7.49 (m, 4H), 7.11 (s, 1H), 3.57-3.61 (m, 1H), 0.98-1.04 (m, 2H), 0.86-0.91 (m, 2H).

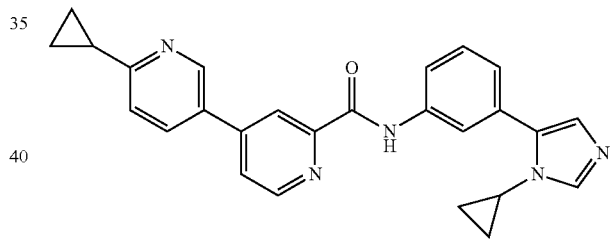

6-cyclopropyl-N-(3-(1-cyclopropyl-1H-imidazol-5-yl)phenyl)-3,4'-bipyridine-2'-carboxamide $C_{26}H_{23}N_5O$. 422.1 (M+1). $^1$H NMR (CDCl$_3$) d 10.19 (s, 1H), 8.80 (d, J=2 Hz, 1H), 8.68 (d, J=5 Hz, 1H), 8.49 (d, J=1 Hz, 1H), 8.31-8.33 (m, 1H), 8.22 (br s, 1H), 7.89 (dd, J=2, 8 Hz, 1H), 7.70 (dd, J=2, 7 Hz, 1H), 7.66 (d, J=8 Hz, 1H), 7.49 (t, J=8 Hz, 1H), 7.66 (d, J=8 Hz, 1H), 7.27-7.31 (m, 3H), 3.48-3.58 (m, 1H), 2.09-2.16 (m, 1H), 1.03-1.27 (m, 8H).

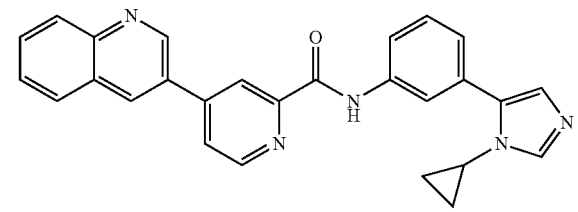 [SMILES: O=C(Nc1cccc(-c2cncn2C2CC2)c1)c1cc(-c2cnc3ccccc3c2)ccn1]

N-(3-(1-cyclopropyl-1H-imidazol-5-yl)phenyl)-4-(quinolin-3-yl)picolinamide $C_{27}H_{21}N_5O$. 432.1 (M+1). $^1$H NMR (CDCl$_3$) d 10.19 (s, 1H), 9.25 (d, J=2 Hz, 1H), 8.76 (d, J=5 Hz, 1H), 8.66 (d, J=1 Hz, 1H), 8.53 (d, J=2 Hz, 1H), 8.25-8.28 (m, 1H), 8.16 (d, J=8 Hz, 1H), 7.94 (d, J=8 Hz, 1H), 7.85-7.88 (m, 2H), 7.80 (dt, J=3, 7, 8 Hz, 1H), 7.61-7.68 (m, 2H), 7.46 (t, J=8 Hz, 1H), 7.32 (d, J=8 Hz, 1H), 7.20 (s, 1H), 3.48-3.53 (m, 1H), 1.07-1.11 (m, 2H), 0.95-1.01 (m, 2H).

C. Similarly, following the procedure of Example 22A, but optionally replacing 3-(1,3-dioxolan-2-yl)aniline with other aromatic amines, optionally replacing 4-bromopicolinic acid with other acids, and optionally replacing cyclopropylamine with other amines, other compounds of Formula (I) are prepared.

EXAMPLE 23

Preparation of Compounds of Formula I

A. Preparation of N-(3-(4-cyclopropyl-4H-1,2,4-triazol-3-yl)phenyl)-4-(1-isopropyl-1H-pyrrolo[3,2-b]pyridin-6-yl)picolinamide

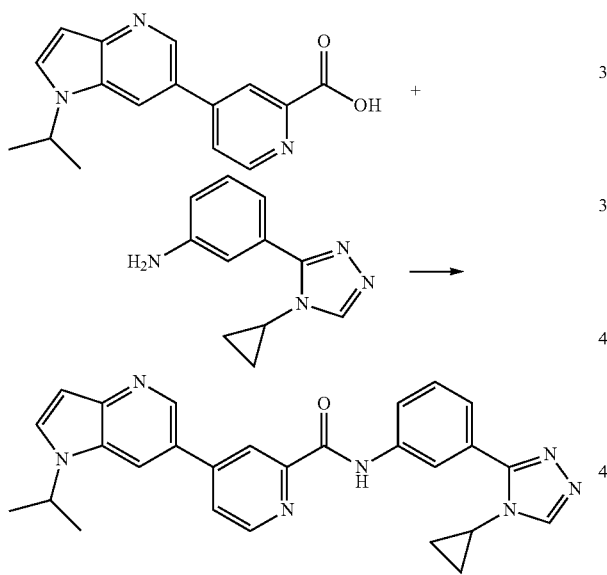

A suspension of 4-(1-isopropyl-1H-pyrrolo[3,2-b]pyridin-6-yl)picolinic acid (50 mg, 0.178 mmol), 3-(4-cyclopropyl-4H-1,2,4-triazol-3-yl)aniline (40 mg, 0.20 mmol), HATU (75 mg, 0.20 mmol) and diisopropylethylamine (0.06 mL, 0.35 mmol) in N,N-dimethylformamide (2 mL) was stirred at room temperature for 1 hour. The solvent was removed under reduced pressure and the residue was suspended and sonicated in 2:1 water:acetonitrile. The solid was isolated by filtration to give N-(3-(4-cyclopropyl-4H-1,2,4-triazol-3-yl)phenyl)-4-(1-isopropyl-1H-pyrrolo[3,2-b]pyridin-6-yl)picolinamide as a white powder (HPF$_6$ salt, 75 mg, 90% yield). $C_{27}H_{25}N_7O\times HPF_6$. 464.1 (M+1). $^1$H NMR (DMSO) d 11.01 (s, 1H), 9.22 (m, 2H), 8.92 (d, J=5.2 Hz, 1H), 8.76 (s, 1H), 8.63 (s, 1H), 8.42 (d, J=3.2 Hz, 1H), 8.26 (m, 2H), 8.10 (d, J=8.0 Hz, 1H), 7.71 (d, J=8.0 Hz, 1H), 7.58 (t, J=8.0 Hz, 1H), 6.91 (d, J=3.2 Hz, 1H), 5.23 (sept, J=6.4 Hz, 1H), 3.69 (m, 1H), 1.56 (d, J=6.4 Hz, 6H), 1.12 (m, 2H), 0.98 (m, 2H).

B. Similarly, following the procedure of Example 23A, but optionally replacing 4-(1-isopropyl-1H-pyrrolo[3,2-b]pyridin-6-yl)picolinic acid with other compounds of formula (1), and optionally replacing 3-(4-cyclopropyl-4H-1,2,4-triazol-3-yl)aniline with other compounds of formula (2), the following compounds of Formula (I) were prepared:

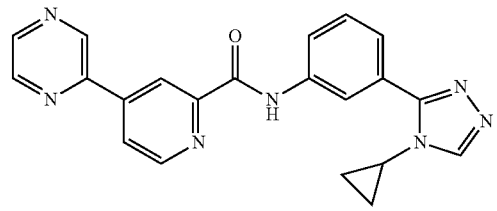

N-(3-(4-cyclopropyl-4H-1,2,4-triazol-3-yl)phenyl)-4-(pyrazin-2-yl)picolinamide $C_{21}H_{17}N_7O$. 384.1 (M+1). $^1$H NMR (DMSO) d 10.98 (s, 1H), 9.53 (d, J=1.2 Hz, 1H), 8.94 (d, J=5.2 Hz, 1H), 8.88 (m, 2H), 8.81 (d, J=2.4 Hz, 1H), 8.63 (s, 1H), 8.60 (s, 1H), 8.43 (dd, J=5.2, 2.0 Hz, 1H), 8.08 (d, J=9.2 Hz, 1H), 7.70 (d, J=8.0 Hz, 1H), 7.56 (t, J=8.0 Hz, 1H), 3.66 (m, 1H), 1.08 (m, 2H), 0.95 (m, 2H).

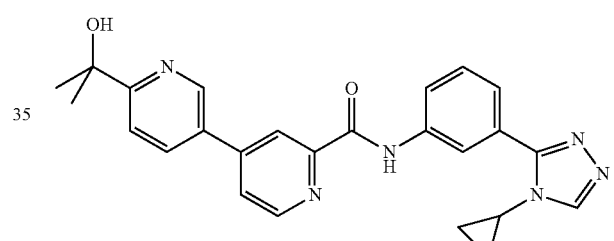

N-(3-(4-cyclopropyl-4H-1,2,4-triazol-3-yl)phenyl)-6-(2-hydroxypropan-2-yl)-3,4'-bipyridine-2'-carboxamide $C_{25}H_{24}N_6O_2$. 441.1 (M+1). $^1$H NMR (DMSO) d 10.95 (s, 1H), 9.01 (d, J=1.6 Hz, 1H), 8.85 (d, J=5.2 Hz, 1H), 8.63 (s, 1H), 8.59 (s, 1H), 8.47 (d, J=1.2 Hz, 1H), 8.32 (dd, J=8.4, 2.4 Hz, 1H), 8.01 (m, 2H), 7.84 (d, J=8.4 Hz, 1H), 7.69 (d, J=8.0 Hz, 1H), 7.55 (t, J=8.0 Hz, 1H), 5.38 (br, 1H), 3.67 (m, 1H), 1.50 (s, 6H), 1.08 (m, 2H), 0.95 (m, 2H).

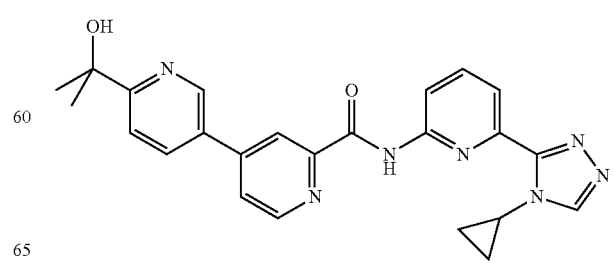

151

N-(6-(4-cyclopropyl-4H-1,2,4-triazol-3-yl)pyridin-2-yl)-6-(2-hydroxypropan-2-yl)-3,4'-bipyridine-2'-carboxamide $C_{24}H_{23}N_7O_2$. 442.1 (M+1). $^1$H NMR (DMSO) d 10.70 (s, 1H), 9.03 (d, J=1.6 Hz, 1H), 8.86 (d, J=5.6 Hz, 1H), 8.70 (s, 1H), 8.53 (d, J=1.2 hz, 1H), 8.41 (d, J=7.6 Hz, 1H), 8.34 (dd, J=8.0, 2.4 Hz, 1H), 8.14 (m, 2H), 7.89 (d, J=6.8 Hz, 1H), 7.84 (d, J=8.4 Hz, 1H), 5.38 (s, 1H), 4.11 (m, 1H), 1.49 (s, 6H), 1.04 (m, 4H).

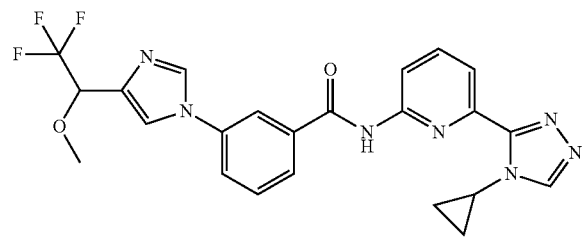 [SMILES: COC(c1cn(-c2cccc(C(=O)Nc3cccc(-c4nncn4C4CC4)n3)c2)cn1)C(F)(F)F]

N-(6-(4-cyclopropyl-4H-1,2,4-triazol-3-yl)pyridin-2-yl)-3-(4-(2,2,2-trifluoro-1-methoxyethyl)-1H-imidazol-1-yl)benzamide $C_{23}H_{20}F_3N_7O_2 \times HPF_6$. 484.1 (M+1). $^1$H NMR (DMSO) d 10.93 (s, 1H), 8.78 (s, 1H), 8.59 (s, 1H), 8.28 (m, 2H), 8.07 (m, 2H), 7.97 (m, 2H), 7.82 (d, J=8.0 Hz, 1H), 7.72 (t, 8.0 Hz, 1H), 5.02 (q, J=7.2 Hz, 1H), 4.25 (m, 1H), 3.41 (s, 3H), 0.99 (m, 4H). $^{19}$F NMR (DMSO) d −70.20 (d, J=710 Hz, HPF$_6$), −74.79 (d, J=7.2 Hz, 3F).

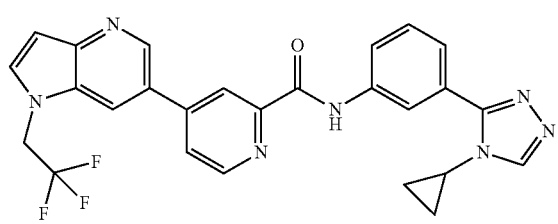 [SMILES: O=C(Nc1cccc(-c2nncn2C2CC2)c1)c1cc(-c2cnc3ccn(CC(F)(F)F)c3c2)ccn1]

N-(3-(4-cyclopropyl-4H-1,2,4-triazol-3-yl)phenyl)-4-(1-(2,2,2-trifluoroethyl)-1H-pyrrolo[3,2-b]pyridin-6-yl)picolinamide $C_{26}H_{20}F_3N_7O \times HPF_6$. 504.1 (M+1). $^1$H NMR (DMSO) d 11.02 (s, 1H), 9.11 (s, 1H), 9.02 (s, 1H), 8.90 (d, J=5.2 Hz, 1H), 8.86 (s, 2H), 8.63 (s, 1H), 8.18 (dd, J=8.8, 2.0 Hz, 1H), 8.12 (d, J=8.8 Hz, 1H), 8.04 (d, J=3.2 Hz, 1H), 7.71 (d, J=8.0 Hz, 1H), 7.59 (t, J=8.0 Hz, 1H), 6.89 (d, J=3.2 Hz, 1H), 5.49 (q, J=8.8 Hz, 1H), 3.71 (m, 1H), 1.10 (m, 2H), 0.99 (m, 2H). $^{19}$F NMR (DMSO) d −70.20 (d, J=710 Hz, HPF$_6$), −70.38 (t, J=8.8 Hz, 3F).

152

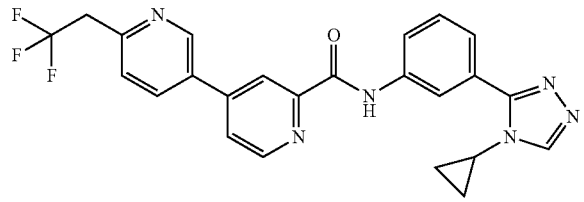 [SMILES: O=C(Nc1cccc(-c2nncn2C2CC2)c1)c1cc(-c2ccc(CC(F)(F)F)nc2)ccn1]

N-(3-(4-cyclopropyl-4H-1,2,4-triazol-3-yl)phenyl)-6-(2,2,2-trifluoroethyl)-3,4'-bipyridine-2'-carboxamide $C_{24}H_{19}F_3N_6O$. 465.1 (M+1). $^1$H NMR (DMSO) d 10.98 (s, 1H), 9.12 (d, J=2.4 Hz, 1H), 8.88 (d, J=5.6 Hz, 1H), 8.64 (s, 1H), 8.59 (s, 1H), 8.50 (s, 1H), 8.40 (dd, J=4.4, 2.4 Hz, 1H), 8.11 (m, 2H), 7.69 (m, 2H), 7.57 (t, J=8.0 Hz, 1H), 3.95 (q, J=11.6 Hz, 2H), 3.67 (m, 1H), 1.08 (m, 2H), 0.94 (m, 2H). $^{19}$F NMR (DMSO) d −62.91 (t, J=11.6 Hz, 3F).

N-(3-(4-cyclopropyl-4H-1,2,4-triazol-3-yl)phenyl)-4-(5,6,7,8-tetrahydro-1,6-naphthyridin-3-yl)picolinamide $C_{25}H_{23}N_7O \times HCl$. 438.1 (M+1). $^1$H NMR (DMSO) d 11.11 (s, 1H), 9.97 (br, 2H), 9.56 (s, 1H), 9.10 (s, 1H), 8.90 (d, J=5.2 Hz, 1H), 8.70 (s, 1H), 8.54 (s, 1H), 8.45 (s, 1H), 8.17 (m, 2H), 7.75 (d, J=8.0 Hz, 1H), 7.65 (t, J=8.0 Hz, 1H), 4.44 (m, 2H), 3.83 (m, 1H), 3.52 (m, 2H), 3.26 (m, 2H), 1.12 (m, 4H).

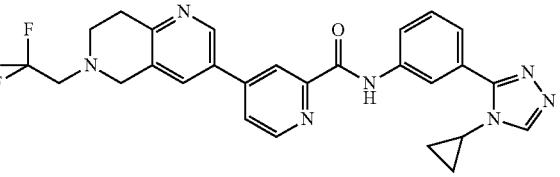

N-(3-(4-cyclopropyl-4H-1,2,4-triazol-3-yl)phenyl)-4-(6-(2,2,2-trifluoroethyl)-5,6,7,8-tetrahydro-1,6-naphthyridin-3-yl)picolinamide $C_{27}H_{24}F_3N_7O$. 520.1 (M+1). $^1$H NMR (DMSO) d 10.94 (s, 1H), 8.90 (d, J=2.0 Hz, 1H), 8.84 (d, J=5.2 Hz, 1H), 8.63 (s, 1H), 8.59 (s, 1H), 8.48 (d, J=1.2 Hz, 1H), 8.08 (m, 3H), 7.79 (d, J=8.0 Hz, 1H), 7.55 (t, J=8.0 Hz, 1H), 3.98 (s, 2H), 3.66 (m, 1H), 3.44 (q, J=10.4 Hz, 2H), 3.09 (m, 2H), 2.99 (m, 2H), 1.08 (m, 2H), 0.95 (m, 2H). $^{19}$F NMR (DMSO) d −68.2 (t, J=10.4 Hz, 3F).

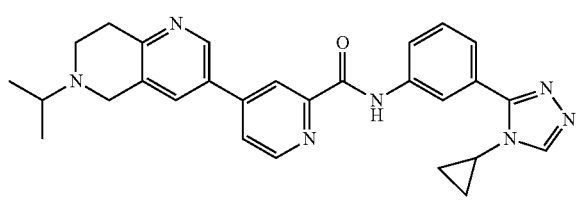 [SMILES: CC(C)N1CCc2ncc(-c3ccnc(C(=O)Nc4cccc(-c5nncn5C5CC5)c4)c3)cc2C1]

N-(3-(4-cyclopropyl-4H-1,2,4-triazol-3-yl)phenyl)-
4-(6-isopropyl-5,6,7,8-tetrahydro-1,6-naphthyridin-
3-yl)picolinamide $C_{28}H_{29}N_7O$. 480.1 (M+1). $^1$H NMR (DMSO) d 10.96 (s, 1H), 8.87 (s, 1H), 8.84 (d, J=4.8 Hz, 1H), 8.63 (s, 1H), 8.60 (s, 1H), 8.47 (s, 1H), 8.07 (m, 3H), 7.69 (d, J=8.0 Hz, 1H), 7.55 (t, J=8.0 Hz, 1H), 3.81 (m, 1H), 3.67 (m, 1H), 2.96 (m, 4H), 2.87 (m, 2H), 1.09 (m, 8H), 0.95 (m, 2H).

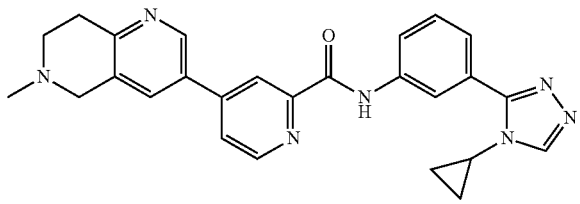 [SMILES: CN1CCc2ncc(-c3ccnc(C(=O)Nc4cccc(-c5nncn5C5CC5)c4)c3)cc2C1]

N-(3-(4-cyclopropyl-4H-1,2,4-triazol-3-yl)phenyl)-
4-(6-methyl-5,6,7,8-tetrahydro-1,6-naphthyridin-3-
yl)picolinamide $C_{26}H_{25}N_7O$. 452.1 (M+1). $^1$H NMR (DMSO) d 10.96 (s, 1H), 8.88 (d, J=2.0 Hz, 1H), 8.84 (d, J=5.6 Hz. 1H), 8.63 (s, 1H), 8.59 (s, 1H), 8.47 (d, J=0.8 Hz, 1H), 8.08 (m, 3H), 7.69 (d, J=8.0 Hz, 1H), 7.55 (t, J=8.0 Hz, 1H), 3.67 (m, 3H), 2.98 (m, 2H), 2.77 (m, 2H), 2.41 (s, 3H), 1.08 (m, 2H), 0.95 (m, 2H).

C. Similarly, following the procedure of Example 23A, but optionally replacing 4-(1-isopropyl-1H-pyrrolo[3,2-b]pyridin-6-yl)picolinic acid with other compounds of formula (1), and optionally replacing 3-(4-cyclopropyl-4H-1,2,4-triazol-3-yl)aniline with other compounds of formula (2), other compounds of Formula (I) are prepared.

EXAMPLE 24

Biological Assays

ASK1 (Apoptosis Signal-Regulating Kinase 1) TR-FRET Kinase Assay (Biochemical $IC_{50}$)

The ability of compounds to inhibit ASK1 kinase activity was determined using a time resolved fluorescence resonance energy transfer [TR-FRET] assay utilizing biotinylated myelin basic protein [biotin-MBP] as the protein substrate. A Beckman Biomek FX liquid handling robot was utilized to spot 2 μL/well of compounds in 2.44% aqueous DMSO into low volume 384-well polypropylene plates [Nune, #267460] to give a final concentration of between 100 μM and 0.5 nM compound in the kinase assay. A Decrac Fluidics Equator was used to dispense 3 μL/well of 0.667 ng/μL [Upstate Biotechnologies, #14-606, or the equivalent protein prepared in-house] and 0.1665 ng/mL biotin-MBP [Upstate Biotechnologies, #13-111] in buffer (85 mM MOPS, pH 7.0, 8.5 mM Mg-acetate, 5% glycerol, 0.085% NP-40, 1.7 mM DTT and 1.7 mg/mL BSA) into the plates containing the spotted compounds. The enzyme was allowed to pre-incubate with compound for 20 minutes prior to initiating the kinase reaction with the addition of 5 μL/well 300 μM ATP in buffer (50 mM MOPS, pH 7.0, 5 mM Mg-acetate, 1 mM DTT, 5% DMSO) using the Decrac Fluidics Equator. The kinase reactions were allowed to proceed for 20 minutes at ambient temperature and were subsequently stopped with the addition of 5 μL/well 25 mM EDTA using the Deerac Fluidics Equator. The Biomek FX was then used to transfer 1 μL/well of each completed kinase reaction to the wells of an OptiPlate-1536 white polystyrene plate [PerkinElmer, #6004299] that contained 5 μL/well detection reagents (1.11 nM Eu-W1024 labeled anti-phosphothreonine antibody [PerkinElmer, #AD0094] and 55.56 nM streptavidin allophycocyanin [PerkinElmer, #CR130-100] in 1×LANCE detection buffer [PerkinElmer, #CR97-100]). The TR-FRET signal was then read on a Perkin. Elmer Envision plate reader after incubating the plates at ambient temperature for 2 hours. The 100% inhibition positive control wells were generated by switching the order of addition of the EDTA and ATP solutions described above. These wells and 0% inhibition wells containing spots of 2.44% DMSO at the beginning of the assay were used in calculating the % inhibition for the test compounds. When tested by the above method, the compounds of Formula (I) inhibited ASK1. For example;

| No. | Compound | $IC_{50}$ (nM) |
|---|---|---|
| 1 | 5-(2,5-difluorophenyl)-N-(3-(4-methyl-4H-1,2,4-triazol-3-yl)phenyl)nicotinamide | 39149 |
| 2 | N-(3-(4-methyl-4H-1,2,4-triazol-3-yl)phenyl)-5-phenylnicotinamide | 5587 |
| 3 | 2-hydroxy-N-(3-(4-methyl-4H-1,2,4-triazol-3-yl)phenyl)-6-phenylpyrimidine-4-carboxamide | |
| 4 | N-(3-(4-methyl-4H-1,2,4-triazol-3-yl)phenyl)-4-phenylpicolinamide | 701 |
| 5 | N-(3-(4-methyl-4H-1,2,4-triazol-3-yl)phenyl)-6-phenylpicolinamide | |
| 6 | N-(3-(4-methyl-4H-1,2,4-triazol-3-yl)phenyl)-2,3'-bipyridine-6-carboxamide | |
| 7 | N-(3-(4-methyl-4H-1,2,4-triazol-3-yl)phenyl)-6-(quinolin-6-yl)picolinamide | |
| 8 | N-(3-(4-methyl-4H-1,2,4-triazol-3-yl)phenyl)-3,3'-bipyridine-5-carboxamide | 220 |
| 9 | N-(3-(4-methyl-4H-1,2,4-triazol-3-yl)phenyl)-3,4'-bipyridine-2'-carboxamide | 42 |
| 10 | N-(3-(4-methyl-4H-1,2,4-triazol-3-yl)phenyl)-2-phenylisonicotinamide | 4821 |
| 11 | 5-methoxy-N-(3-(4-methyl-4H-1,2,4-triazol-3-yl)phenyl)-3,4'-bipyridine-2'-carboxamide | 40 |
| 12 | 5-acetamido-N-(3-(4-methyl-4H-1,2,4-triazol-3-yl)phenyl)-3,4'-bipyridine-2'-carboxamide | 101 |
| 13 | 4-(imidazo[1,2-a]pyridin-3-yl)-N-(3-(4-methyl-4H-1,2,4-triazol-3-yl)phenyl)picolinamide | 44 |
| 14 | N-(3-(4-cyclopropyl-4H-1,2,4-triazol-3-yl)phenyl)-4-phenylpicolinamide | 279 |
| 15 | N-(3-(4-cyclopropyl-4H-1,2,4-triazol-3-yl)phenyl)-3,4'-bipyridine-2'-carboxamide | 11 |
| 16 | N-(3-(4-(3-amino-3-oxopropyl)-4H-1,2,4-triazol-3-yl)phenyl)-3,4'-bipyridine-2'-carboxamide | 114 |
| 17 | N-(3-(4-(2-acetamidoethyl)-4H-1,2,4-triazol-3-yl)phenyl)-3,4'-bipyridine-2'-carboxamide | 73 |
| 18 | 4-(1-methyl-1H-imidazol-5-yl)-N-(3-(4-methyl-4H-1,2,4-triazol-3-yl)phenyl)picolinamide | 39 |
| 19 | (R)-N-(3-(4-(1-hydroxypropan-2-yl)-4H-1,2,4-triazol-3-yl)phenyl)-3,4'-bipyridine-2'-carboxamide | 9 |
| 20 | (S)-N-(3-(4-(1-hydroxypropan-2-yl)-4H-1,2,4-triazol-3-yl)phenyl)-3,4'-bipyridine-2'-carboxamide | 39 |

| No. | Compound | IC$_{50}$ (nM) |
|---|---|---|
| 21 | N-(3-(4-cyclopropyl-4H-1,2,4-triazol-3-yl)phenyl)-6-methoxy-3,4'-bipyridine-2'-carboxamide | 12 |
| 22 | 6-amino-N-(3-(4-cyclopropyl-4H-1,2,4-triazol-3-yl)phenyl)-3,4'-bipyridine-2'-carboxamide | 9 |
| 23 | methyl 2'-(3-(4-cyclopropyl-4H-1,2,4-triazol-3-yl)phenylcarbamoyl)-3,4'-bipyridin-6-ylcarbamate | 167 |
| 24 | N-(3-(4-cyclopropyl-4H-1,2,4-triazol-3-yl)phenyl)-4-(pyrimidin-5-yl)picolinamide | 21 |
| 25 | 4-(2-aminopyrimidin-5-yl)-N-(3-(4-cyclopropyl-4H-1,2,4-triazol-3-yl)phenyl)picolinamide | 13 |
| 26 | N-(3-(4-(tetrahydro-2H-pyran-4-yl)-4H-1,2,4-triazol-3-yl)phenyl)-3,4'-bipyridine-2'-carboxamide | 1967 |
| 27 | N-(3-(4-cyclopropyl-4H-1,2,4-triazol-3-yl)phenyl)-4-(1H-imidazol-1-yl)picolinamide | 11 |
| 28 | N-(3-(4-cyclopropyl-4H-1,2,4-triazol-3-yl)phenyl)-4-(1H-1,2,4-triazol-1-yl)picolinamide | 110 |
| 29 | N-(3-(4-methyl-4H-1,2,4-triazol-3-yl)phenyl)-4-(4-methylpiperazin-1-yl)picolinamide | 443 |
| 30 | N-(3-(4-methyl-4H-1,2,4-triazol-3-yl)phenyl)-4-morpholinopicolinamide | 335 |
| 31 | N-(3-(4-cyclopropyl-4H-1,2,4-triazol-3-yl)phenyl)-6-hydroxy-3,4'-bipyridine-2'-carboxamide | 63 |
| 32 | N-(3-(4-methyl-4H-1,2,4-triazol-3-yl)phenyl)-4-(3-oxopiperazin-1-yl)picolinamide | 569 |
| 33 | 4-(3-aminopyrrolidin-1-yl)-N-(3-(4-methyl-4H-1,2,4-triazol-3-yl)phenyl)picolinamide | 3483 |
| 34 | (R)-N-(3-(4-(2-hydroxypropyl)-4H-1,2,4-triazol-3-yl)phenyl)-3,4'-bipyridine-2'-carboxamide | 195 |
| 35 | (S)-N-(3-(4-(2-hydroxypropyl)-4H-1,2,4-triazol-3-yl)phenyl)-3,4'-bipyridine-2'-carboxamide | 87 |
| 36 | N-(3-(4-cyclopropyl-4H-1,2,4-triazol-3-yl)phenyl)-4-(1-methyl-1H-imidazol-5-yl)picolinamide | 18 |
| 37 | 4-(1H-benzo[d]imidazol-1-yl)-N-(3-(4-cyclopropyl-4H-1,2,4-triazol-3-yl)phenyl)picolinamide | 8 |
| 38 | N-(3-(4-cyclopropyl-4H-1,2,4-triazol-3-yl)phenyl)-4-(4-phenyl-1H-imidazol-1-yl)picolinamide | 17 |
| 39 | N-(3-(4-cyclobutyl-4H-1,2,4-triazol-3-yl)phenyl)-3,4'-bipyridine-2'-carboxamide | 63 |
| 40 | N-(3-(4-cyclopentyl-4H-1,2,4-triazol-3-yl)phenyl)-3,4'-bipyridine-2'-carboxamide | 75 |
| 41 | N-(3-(4-cyclopropyl-4H-1,2,4-triazol-3-yl)phenyl)-4-(2-methyl-1H-imidazol-1-yl)picolinamide | 48 |
| 42 | N-(3-(4-cyclopropyl-4H-1,2,4-triazol-3-yl)phenyl)-4-(4-methyl-1H-imidazol-1-yl)picolinamide | 11 |
| 43 | N-(3-(4-cyclopropyl-4H-1,2,4-triazol-3-yl)phenyl)-4-(4,5-dimethyl-1H-imidazol-1-yl)picolinamide | 8 |
| 44 | N-(3-(4-cyclopropyl-4H-1,2,4-triazol-3-yl)phenyl)-4-(4-(trifluoromethyl)-1H-imidazol-1-yl)picolinamide | 27 |
| 45 | N-(3-(4-cyclopropyl-4H-1,2,4-triazol-3-yl)phenyl)-4-(2-methoxypyrimidin-5-yl)picolinamide | 9 |
| 46 | 6'-methyl-N-(3-(4-methyl-4H-1,2,4-triazol-3-yl)phenyl)-3,4'-bipyridine-2'-carboxamide | 212 |
| 47 | N-(3-(4-cyclopropyl-4H-1,2,4-triazol-3-yl)phenyl)-6-(pyrrolidin-1-yl)-3,4'-bipyridine-2'-carboxamide | 32 |
| 48 | N-(3-(4-cyclopropyl-4H-1,2,4-triazol-3-yl)phenyl)-6-fluoro-5-methyl-3,4'-bipyridine-2'-carboxamide | 37 |
| 49 | N-(3-(4-cyclopropyl-4H-1,2,4-triazol-3-yl)phenyl)-4-(2,4-dimethoxypyrimidin-5-yl)picolinamide | 8 |
| 50 | 6-cyclopropyl-N-(3-(4-cyclopropyl-4H-1,2,4-triazol-3-yl)phenyl)-3,4'-bipyridine-2'-carboxamide | 8 |
| 51 | N2'-(3-(4-cyclopropyl-4H-1,2,4-triazol-3-yl)phenyl)-3,4'-bipyridine-2',6-dicarboxamide | 8 |
| 52 | N-(3-(4-cyclopropyl-4H-1,2,4-triazol-3-yl)phenyl)-6-(trifluoromethyl)-3,4'-bipyridine-2'-carboxamide | 12 |
| 53 | N-(3-(4-cyclopropyl-4H-1,2,4-triazol-3-yl)phenyl)-6-methyl-3,4'-bipyridine-2'-carboxamide | 11 |
| 54 | N-(6-(4-cyclopropyl-4H-1,2,4-triazol-3-yl)pyridin-2-yl)-3,4'-bipyridine-2'-carboxamide | 5 |
| 55 | N-(3-(4-((1S,2S)-2-methylcyclopropyl)-4H-1,2,4-triazol-3-yl)phenyl)-3,4'-bipyridine-2'-carboxamide | 24 |
| 56 | N-(3-(4-cyclopropyl-4H-1,2,4-triazol-3-yl)phenyl)-6-(2,2,2-trifluoroethoxy)-3,4'-bipyridine-2'-carboxamide | 69 |
| 57 | N-(3-(4-cyclopropyl-4H-1,2,4-triazol-3-yl)phenyl)-4-methyl-3,4'-bipyridine-2'-carboxamide | 244 |
| 58 | N-(3-(4-(2,2,2-trifluoroethyl)-4H-1,2,4-triazol-3-yl)phenyl)-3,4'-bipyridine-2'-carboxamide | 290 |
| 59 | N-(3-(4-cyclopropyl-4H-1,2,4-triazol-3-yl)phenyl)-5-(trifluoromethyl)-3,4'-bipyridine-2'-carboxamide | 44 |
| 60 | N-(3-(4-cyclopropyl-4H-1,2,4-triazol-3-yl)phenyl)-5-fluoro-3,4'-bipyridine-2'-carboxamide | 23 |
| 61 | N-(3-(4-((1-hydroxycyclopropyl)methyl)-4H-1,2,4-triazol-3-yl)phenyl)-3,4'-bipyridine-2'-carboxamide | 174 |
| 62 | (R)-N-(3-(4-(1,1,1-trifluoropropan-2-yl)-4H-1,2,4-triazol-3-yl)phenyl)-3,4'-bipyridine-2'-carboxamide | 1237 |
| 63 | (S)-N-(3-(4-(1,1,1-trifluoropropan-2-yl)-4H-1,2,4-triazol-3-yl)phenyl)-3,4'-bipyridine-2'-carboxamide | 21 |
| 64 | N2'-(3-(4-cyclopropyl-4H-1,2,4-triazol-3-yl)phenyl)-3,4'-bipyridine-2',5-dicarboxamide | 17 |
| 65 | 5-cyano-N-(3-(4-cyclopropyl-4H-1,2,4-triazol-3-yl)phenyl)-3,4'-bipyridine-2'-carboxamide | 30 |
| 66 | 2-amino-N-(3-(4-cyclopropyl-4H-1,2,4-triazol-3-yl)phenyl)-3,4'-bipyridine-2'-carboxamide | 86 |
| 67 | N-(3-(4-cyclopropyl-4H-1,2,4-triazol-3-yl)phenyl)-2-methoxy-3,4'-bipyridine-2'-carboxamide | 60 |
| 68 | N-(3-(4-cyclopropyl-4H-1,2,4-triazol-3-yl)phenyl)-4-(1-methyl-1H-pyrazol-4-yl)picolinamide | 39 |
| 69 | N-(3-(4-cyclopropyl-4H-1,2,4-triazol-3-yl)phenyl)-4-(imidazo[1,2-a]pyridin-3-yl)picolinamide | 11 |
| 70 | 6-Chloro-[3,2':5',4'']terpyridine-2''-carboxylic acid [3-(4-cyclopropyl-4H-[1,2,4]triazol-3-yl)-phenyl]-amide | 106 |
| 71 | N-(3-(4-cyclopropyl-4H-1,2,4-triazol-3-yl)phenyl)-5-methoxy-3,4'-bipyridine-2'-carboxamide | 17 |
| 72 | N-(3-(1-cyclopropyl-1H-imidazol-5-yl)phenyl)-3,4'-bipyridine-2'-carboxamide | 36 |
| 73 | N-(3-(4-cyclopropyl-4H-1,2,4-triazol-3-yl)phenyl)-4-(1,2-dimethyl-1H-imidazol-5-yl)picolinamide | 11 |
| 74 | N-(3-(4-cyclopropyl-4H-1,2,4-triazol-3-yl)phenyl)-2-methyl-3,4'-bipyridine-2'-carboxamide | 79 |
| 75 | N5-tert-butyl-N2'-(3-(4-cyclopropyl-4H-1,2,4-triazol-3-yl)phenyl)-3,4'-bipyridine-2',5-dicarboxamide | 10 |
| 76 | 5-chloro-N-(3-(4-cyclopropyl-4H-1,2,4-triazol-3-yl)phenyl)-3,4'-bipyridine-2'-carboxamide | 34 |
| 77 | N-(3-(4-cyclopropyl-4H-1,2,4-triazol-3-yl)phenyl)-4-(3-(methylsulfonyl)phenyl)picolinamide | 79 |
| 78 | N-(3-(4-cyclopropyl-4H-1,2,4-triazol-3-yl)phenyl)-4-(2-(methylsulfonyl)phenyl)picolinamide | 572 |
| 79 | N-(3-(4-cyclopropyl-4H-1,2,4-triazol-3-yl)phenyl)-4-(4-(methylsulfonyl)phenyl)picolinamide | 6 |
| 80 | N-(3-(4-cyclopropyl-4H-1,2,4-triazol-3-yl)phenyl)-4-(pyridin-3-yl)quinoline-2-carboxamide | 36 |
| 81 | N-(3-(4-cyclopropyl-4H-1,2,4-triazol-3-yl)phenyl)-4-(1H-imidazo[4,5-b]pyridin-1-yl)picolinamide | 16 |
| 82 | N-(3-(4-cyclopropyl-4H-1,2,4-triazol-3-yl)phenyl)-4-(3H-imidazo[4,5-b]pyridin-3-yl)picolinamide | 20 |
| 83 | N-(3-(4-cyclopropyl-4H-1,2,4-triazol-3-yl)phenyl)-4-(1H-imidazo[4,5-c]pyridin-1-yl)picolinamide | 53 |
| 84 | N-(3-(4-cyclopropyl-4H-1,2,4-triazol-3-yl)phenyl)-4-(quinolin-3-yl)picolinamide | 13 |
| 85 | 4-(1H-benzo[d][1,2,3]triazol-1-yl)-N-(3-(4-cyclopropyl-4H-1,2,4-triazol-3-yl)phenyl)picolinamide | 141 |
| 86 | N-(3-(4-cyclopropyl-4H-1,2,4-triazol-3-yl)phenyl)-4-(4,5,6,7-tetrahydro-1H-benzo[d]imidazol-1-yl)picolinamide | 9 |
| 87 | N-(3-(4-cyclopropyl-4H-1,2,4-triazol-3-yl)phenyl)-4-(pyrazin-2-yl)picolinamide | 69 |
| 88 | 4-(1H-benzo[d]imidazol-1-yl)-N-(3-(1-cyclopropyl-1H-imidazol-5-yl)phenyl)picolinamide | 35 |
| 89 | N-(3-(4-cyclopropyl-4H-1,2,4-triazol-3-yl)phenyl)-4-(isoquinolin-4-yl)picolinamide | 26 |
| 90 | N-(3-(4-cyclopropyl-4H-1,2,4-triazol-3-yl)phenyl)-4-(1,5-dimethyl-1H-pyrazol-4-yl)picolinamide | 38 |
| 91 | N-(3-(4-cyclopropyl-4H-1,2,4-triazol-3-yl)phenyl)-6-(dimethylamino)-3,4'-bipyridine-2'-carboxamide | 18 |
| 92 | N-(3-(4-cyclopropyl-4H-1,2,4-triazol-3-yl)phenyl)-4-(1H-pyrrolo[2,3-b]pyridin-5-yl)picolinamide | 13 |
| 93 | N-(3-(4-cyclopropyl-4H-1,2,4-triazol-3-yl)phenyl)-6-fluoro-3,4'-bipyridine-2'-carboxamide | 43 |
| 94 | N-(3-(4-cyclopropyl-4H-1,2,4-triazol-3-yl)phenyl)-6-isopropoxy-3,4'-bipyridine-2'-carboxamide | 61 |
| 95 | 6-cyclobutoxy-N-(3-(4-cyclopropyl-4H-1,2,4-triazol-3-yl)phenyl)-3,4'-bipyridine-2'-carboxamide | 31 |
| 96 | N-(3-(4-cyclopropyl-4H-1,2,4-triazol-3-yl)phenyl)-4-(4-(N-cyclopropylsulfamoyl)phenyl)picolinamide | 13 |

| No. | Compound | IC$_{50}$ (nM) |
|---|---|---|
| 97 | N-(3-(4-cyclopropyl-4H-1,2,4-triazol-3-yl)phenyl)-4-(4-sulfamoylphenyl)picolinamide | 81 |
| 98 | N-(3-(4-cyclopropyl-4H-1,2,4-triazol-3-yl)phenyl)-4-(4-(N-methylsulfamoyl)phenyl)picolinamide | 7 |
| 99 | N-(3-(4-cyclopropyl-4H-1,2,4-triazol-3-yl)phenyl)-4-(4-(N-isopropylsulfamoyl)phenyl)picolinamide | 17 |
| 100 | 6-cyclopropyl-N-(6-(4-cyclopropyl-4H-1,2,4-triazol-3-yl)pyridin-2-yl)-3,4'-bipyridine-2'-carboxamide | 6 |
| 101 | N-(6-(4-cyclopropyl-4H-1,2,4-triazol-3-yl)pyridin-2-yl)-4-(4-(methylsulfonyl)phenyl)picolinamide | 7 |
| 102 | N-(3-(4-cyclopropyl-4H-1,2,4-triazol-3-yl)phenyl)-6-isopropyl-3,4'-bipyridine-2'-carboxamide | 9 |
| 103 | 6-cyclobutyl-N-(3-(4-cyclopropyl-4H-1,2,4-triazol-3-yl)phenyl)-3,4'-bipyridine-2'-carboxamide | 11 |
| 104 | 6-cyclopropoxy-N-(3-(4-cyclopropyl-4H-1,2,4-triazol-3-yl)phenyl)-3,4'-bipyridine-2'-carboxamide | 12 |
| 105 | N-(3-(4-cyclopropyl-4H-1,2,4-triazol-3-yl)phenyl)-4-(4-(2-oxoimidazolidin-1-yl)phenyl)picolinamide | 15 |
| 106 | N-(3-(4-cyclopropyl-4H-1,2,4-triazol-3-yl)phenyl)-6-ethyl-3,4'-bipyridine-2'-carboxamide | 8 |
| 107 | 6-cyclopropyl-N-(3-(1-cyclopropyl-1H-imidazol-5-yl)phenyl)-3,4'-bipyridine-2'-carboxamide | 31 |
| 108 | N-(3-(1-cyclopropyl-1H-imidazol-5-yl)phenyl)-4-(quinolin-3-yl)picolinamide | 41 |
| 109 | 6-cyclopentyl-N-(3-(4-cyclopropyl-4H-1,2,4-triazol-3-yl)phenyl)-3,4'-bipyridine-2'-carboxamide | 21 |
| 110 | N-(3-(4-cyclopropyl-4H-1,2,4-triazol-3-yl)phenyl)-6-(1-methyl-2-oxopyrrolidin-3-yl)-3,4'-bipyridine-2'-carboxamide | 8 |
| 111 | N-(6-(4-cyclopropyl-4H-1,2,4-triazol-3-yl)pyridin-2-yl)-4-(4-(N-methylsulfamoyl)phenyl)picolinamide | 9 |
| 112 | N-(6-(4-cyclopropyl-4H-1,2,4-triazol-3-yl)pyridin-2-yl)-4-(quinolin-3-yl)picolinamide | 14 |
| 113 | N-(6-(4-cyclopropyl-4H-1,2,4-triazol-3-yl)pyridin-2-yl)-4-(4-phenyl-1H-imidazol-1-yl)picolinamide | 10 |
| 114 | N-(3-(4-cyclopropyl-4H-1,2,4-triazol-3-yl)phenyl)-6-propyl-3,4'-bipyridine-2'-carboxamide | 5 |
| 115 | N-(3-(4-cyclopropyl-4H-1,2,4-triazol-3-yl)phenyl)-6-neopentyl-3,4'-bipyridine-2'-carboxamide | 15 |
| 116 | N-(3-(4-cyclopropyl-4H-1,2,4-triazol-3-yl)phenyl)-4-(1-methyl-2-phenyl-1H-imidazol-5-yl)picolinamide | 23 |
| 117 | N-(3-(4-cyclopropyl-4H-1,2,4-triazol-3-yl)phenyl)-4-(4-(ethylsulfonyl)phenyl)picolinamide | 12 |
| 118 | N-(3-(4-cyclopropyl-4H-1,2,4-triazol-3-yl)phenyl)-4-(4-(isopropylsulfonyl)phenyl)picolinamide | 9 |
| 119 | N-(3-(4-cyclopropyl-4H-1,2,4-triazol-3-yl)phenyl)-6-(ethylamino)-3,4'-bipyridine-2'-carboxamide | 9 |
| 120 | N-(3-(4-cyclopropyl-4H-1,2,4-triazol-3-yl)phenyl)-6-(cyclopropylamino)-3,4'-bipyridine-2'-carboxamide | 6 |
| 121 | N-(3-(4-cyclopropyl-4H-1,2,4-triazol-3-yl)phenyl)-4-(imidazo[2,1-b][1,3,4]thiadiazol-5-yl)picolinamide | 47 |
| 122 | 4-chloro-1H-imidazol-1-yl)-N-(3-(4-cyclopropyl-4H-1,2,4-triazol-3-yl)phenyl)picolinamide | 17 |
| 123 | N-(3-(4-cyclopropyl-4H-1,2,4-triazol-3-yl)phenyl)-4-(2-cyclopropylpyrimidin-5-yl)picolinamide | 10 |
| 124 | N-(3-(4-cyclopropyl-4H-1,2,4-triazol-3-yl)phenyl)-6'-(trifluoromethyl)-3,4'-bipyridine-2'-carboxamide | 422 |
| 125 | N-(3-(4-cyclopropyl-4H-1,2,4-triazol-3-yl)phenyl)-4-(quinolin-3-yl)-6-(trifluoromethyl)picolinamide | 1453 |
| 126 | N-(6-(1-cyclopropyl-1H-imidazol-5-yl)pyridin-2-yl)-4-(quinolin-3-yl)picolinamide | 1038 |
| 127 | 6-cyclopropyl-N-(6-(1-cyclopropyl-1H-imidazol-5-yl)pyridin-2-yl)-3,4'-bipyridine-2'-carboxamide | 211 |
| 128 | N-(3-(4-cyclopropyl-4H-1,2,4-triazol-3-yl)phenyl)-4-(1H-pyrrolo[3,2-b]pyridin-6-yl)picolinamide | 6 |
| 129 | N-(3-(4-cyclopropyl-4H-1,2,4-triazol-3-yl)phenyl)-4-(4-cyclopropylphenyl)picolinamide | 22 |
| 130 | N-(6-(4-cyclopropyl-4H-1,2,4-triazol-3-yl)pyridin-2-yl)-3-(pyridin-3-yl)benzamide | 12 |
| 131 | N-(3-(4-cyclopropyl-4H-1,2,4-triazol-3-yl)phenyl)-6-(methylthio)-3,4'-bipyridine-2'-carboxamide | 11 |
| 132 | N-(3-(4-cyclopropyl-4H-1,2,4-triazol-3-yl)phenyl)-6-(isobutylthio)-3,4'-bipyridine-2'-carboxamide | 150 |
| 133 | N-(3-(4-cyclopropyl-4H-1,2,4-triazol-3-yl)phenyl)-4-(5-cyclopropylpyrazin-2-yl)picolinamide | 10 |
| 134 | 6-cyclopropyl-N-(3-(4-cyclopropyl-4H-1,2,4-triazol-3-yl)phenyl)-5-fluoro-3,4'-bipyridine-2'-carboxamide | 34 |
| 135 | 5-chloro-6-cyclopropyl-N-(3-(4-cyclopropyl-4H-1,2,4-triazol-3-yl)phenyl)-3,4'-bipyridine-2'-carboxamide | 131 |
| 136 | N-(3-(4-cyclopropyl-4H-1,2,4-triazol-3-yl)phenyl)-6-(2-methoxyethylamino)-3,4'-bipyridine-2'-carboxamide | 7 |
| 137 | N-(3-(4-cyclopropyl-4H-1,2,4-triazol-3-yl)phenyl)-4-(4-(methylsulfonyl)piperazin-1-yl)picolinamide | 31 |
| 138 | N-(3-(4-cyclopropyl-4H-1,2,4-triazol-3-yl)phenyl)-6-ethyl-5-fluoro-3,4'-bipyridine-2'-carboxamide | 8 |
| 139 | 5-chloro-N-(3-(4-cyclopropyl-4H-1,2,4-triazol-3-yl)phenyl)-6-ethyl-3,4'-bipyridine-2'-carboxamide | 16 |
| 140 | 4-(4-cyclopropyl-1H-imidazol-1-yl)-N-(3-(4-cyclopropyl-4H-1,2,4-triazol-3-yl)phenyl)picolinamide | 9 |
| 141 | N-(3-(4-cyclopropyl-4H-1,2,4-triazol-3-yl)phenyl)-5,6-diethyl-3,4'-bipyridine-2'-carboxamide | 13 |
| 142 | N-(3-(4-cyclopropyl-4H-1,2,4-triazol-3-yl)phenyl)-4-(furo[3,2-b]pyridin-6-yl)picolinamide | 11 |
| 143 | N-(3-(4-cyclopropyl-4H-1,2,4-triazol-3-yl)phenyl)-4-(3-methyl-3H-imidazo[4,5-b]pyridin-6-yl)picolinamide | 15 |
| 144 | N-(3-(4-cyclopropyl-4H-1,2,4-triazol-3-yl)phenyl)-6-(6-cyclopropylpyridin-3-yl)pyrimidine-4-carboxamide | 14 |
| 145 | N-(3-(4-cyclopropyl-4H-1,2,4-triazol-3-yl)phenyl)-4-(2-ethylpyrimidin-5-yl)picolinamide | 7 |
| 146 | N-(3-(4-cyclopropyl-4H-1,2,4-triazol-3-yl)phenyl)-5-ethyl-3,4'-bipyridine-2'-carboxamide | 8 |
| 147 | 6-cyclopropyl-N-(3-(4-cyclopropyl-4H-1,2,4-triazol-3-yl)-4-fluorophenyl)-3,4'-bipyridine-2'-carboxamide | 400 |
| 148 | N-(3-(4-cyclopropyl-4H-1,2,4-triazol-3-yl)-4-fluorophenyl)-6-ethyl-3,4'-bipyridine-2'-carboxamide | 56 |
| 149 | 6-tert-butyl-N-(3-(4-cyclopropyl-4H-1,2,4-triazol-3-yl)phenyl)-3,4'-bipyridine-2'-carboxamide | 25 |
| 150 | N-(6-(4-cyclopropyl-4H-1,2,4-triazol-3-yl)pyridin-2-yl)-3-(quinolin-3-yl)benzamide | 17 |
| 151 | N-(6-(4-cyclopropyl-4H-1,2,4-triazol-3-yl)pyridin-2-yl)-3-(6-cyclopropylpyridin-3-yl)benzamide | 8 |
| 152 | 6-cyclopropyl-N-(2-(4-cyclopropyl-4H-1,2,4-triazol-3-yl)pyridin-4-yl)-3,4'-bipyridine-2'-carboxamide | 286 |
| 153 | N-(2-(4-cyclopropyl-4H-1,2,4-triazol-3-yl)pyridin-4-yl)-4-(quinolin-3-yl)picolinamide | 409 |
| 154 | N-(3-(4-cyclopropyl-4H-1,2,4-triazol-3-yl)phenyl)-4-(5,6,7,8-tetrahydro-1,6-naphthyridin-3-yl)picolinamide | 34 |
| 155 | 6-cyclopropyl-N-(3-(4-cyclopropyl-4H-1,2,4-triazol-3-yl)-2-fluorophenyl)-3,4'-bipyridine-2'-carboxamide | 10 |
| 156 | 5-cyclopropyl-N-(3-(4-cyclopropyl-4H-1,2,4-triazol-3-yl)phenyl)-3,4'-bipyridine-2'-carboxamide | 11 |
| 157 | N-(3-(4-cyclopropyl-4H-1,2,4-triazol-3-yl)-2-fluorophenyl)-3,4'-bipyridine-2'-carboxamide | 38 |
| 158 | N-(3-(4-cyclopropyl-4H-1,2,4-triazol-3-yl)phenyl)-4-(4-ethyl-1H-imidazol-1-yl)picolinamide | 5 |
| 159 | N-(6-(4-cyclopropyl-4H-1,2,4-triazol-3-yl)pyridin-2-yl)-4-(4-methyl-1H-imidazol-1-yl)picolinamide | 3 |
| 160 | N-(6-(4-cyclopropyl-4H-1,2,4-triazol-3-yl)pyridin-2-yl)-4-(4,5-dimethyl-1H-imidazol-1-yl)picolinamide | 4 |
| 161 | N-(3-(4-cyclopropyl-4H-1,2,4-triazol-3-yl)phenyl)-4-(6-(2,2,2-trifluoroethyl)-5,6,7,8-tetrahydro-1,6-naphthyridin-3-yl)picolinamide | 9 |
| 162 | 6-cyclopropyl-N-(4-(4-cyclopropyl-4H-1,2,4-triazol-3-yl)pyridin-2-yl)-3,4'-bipyridine-2'-carboxamide | 5 |
| 163 | N-(3-(4-cyclopropyl-4H-1,2,4-triazol-3-yl)phenyl)-4-(4-isopropyl-1H-imidazol-1-yl)picolinamide | 4 |
| 164 | N-(4-(4-cyclopropyl-4H-1,2,4-triazol-3-yl)pyridin-2-yl)-3,4'-bipyridine-2'-carboxamide | 18 |
| 165 | N-(3-(4-cyclopropyl-4H-1,2,4-triazol-3-yl)phenyl)-6-(2-hydroxypropan-2-yl)-3,4'-bipyridine-2'-carboxamide | 5 |
| 166 | N-(6-(4-cyclopropyl-4H-1,2,4-triazol-3-yl)pyridin-2-yl)-6-(2-hydroxypropan-2-yl)-3,4'-bipyridine-2'-carboxamide | 5 |
| 167 | N-(6-(4-cyclopropyl-4H-1,2,4-triazol-3-yl)pyridin-2-yl)-4-(4-isopropyl-1H-imidazol-1-yl)picolinamide | 7 |
| 168 | 6-cyclopropyl-N-(3-(4-cyclopropyl-4H-1,2,4-triazol-3-yl)-5-fluorophenyl)-3,4'-bipyridine-2'-carboxamide | 143 |
| 169 | N-(3-(4-cyclopropyl-4H-1,2,4-triazol-3-yl)-5-fluorophenyl)-3,4'-bipyridine-2'-carboxamide | 157 |
| 170 | 4-(4-cyclopropyl-1H-imidazol-1-yl)-N-(6-(4-cyclopropyl-4H-1,2,4-triazol-3-yl)pyridin-2-yl)picolinamide | 7 |
| 171 | N-(3-(4-cyclopropyl-4H-1,2,4-triazol-3-yl)phenyl)-6-(2,2,2-trifluoroethyl)-3,4'-bipyridine-2'-carboxamide | 7 |

| No. | Compound | IC$_{50}$ (nM) |
| --- | --- | --- |
| 172 | N-(3-(4-cyclopropyl-4H-1,2,4-triazol-3-yl)phenyl)-4-(6-isopropyl-5,6,7,8-tetrahydro-1,6-naphthyridin-3-yl)picolinamide | 17 |
| 173 | N-(3-(4-cyclopropyl-4H-1,2,4-triazol-3-yl)phenyl)-4-(6-methyl-5,6,7,8-tetrahydro-1,6-naphthyridin-3-yl)picolinamide | 21 |
| 174 | N-(3-(4-cyclopropyl-4H-1,2,4-triazol-3-yl)phenyl)-4-(3-hydroxypiperidin-1-yl)picolinamide | 93 |
| 175 | N-(6-(4-cyclopropyl-4H-1,2,4-triazol-3-yl)pyridin-2-yl)-4-(3-hydroxypiperidin-1-yl)picolinamide | 10 |
| 176 | 6-cyclopropyl-N-(6-(4-isopropyl-4H-1,2,4-triazol-3-yl)pyridin-2-yl)-3,4'-bipyridine-2'-carboxamide | 13 |
| 177 | N-(3-(4-cyclopropyl-4H-1,2,4-triazol-3-yl)phenyl)-4-(4-ethyl-3-oxopiperazin-1-yl)picolinamide | 47 |
| 178 | N-(6-(4-cyclopropyl-4H-1,2,4-triazol-3-yl)pyridin-2-yl)-4-(4-ethyl-3-oxopiperazin-1-yl)picolinamide | 7 |
| 179 | (S)-6-cyclopropyl-N-(6-(4-(1,1,1-trifluoropropan-2-yl)-4H-1,2,4-triazol-3-yl)pyridin-2-yl)-3,4'-bipyridine-2'-carboxamide | 19 |
| 180 | N-(3-(4-isopropyl-4H-1,2,4-triazol-3-yl)phenyl)-3,4'-bipyridine-2'-carboxamide | 27 |
| 181 | N-(3-(4-(cyclopropylmethyl)-4H-1,2,4-triazol-3-yl)phenyl)-3,4'-bipyridine-2'-carboxamide | 131 |
| 182 | 4-(4-cyclopropyl-2-methyl-1H-imidazol-1-yl)-N-(3-(4-cyclopropyl-4H-1,2,4-triazol-3-yl)phenyl)picolinamide | 15 |
| 183 | 4-(4-cyclopropyl-2-methyl-1H-imidazol-1-yl)-N-(6-(4-cyclopropyl-4H-1,2,4-triazol-3-yl)pyridin-2-yl)picolinamide | 8 |
| 184 | 4-(4-cyclopropyl-1H-imidazol-1-yl)-N-(3-(4-isopropyl-4H-1,2,4-triazol-3-yl)phenyl)picolinamide | 20 |
| 185 | 4-(4-cyclopropyl-1H-imidazol-1-yl)-N-(3-(4-(cyclopropylmethyl)-4H-1,2,4-triazol-3-yl)phenyl)picolinamde | 34 |
| 186 | 4-(4-cyclopropyl-1H-imidazol-1-yl)-N-(3-(4-(1-phenylethyl)-4H-1,2,4-triazol-3-yl)phenyl)picolinamide | 30 |
| 187 | N-(6-(4-cyclopropyl-4H-1,2,4-triazol-3-yl)pyridin-2-yl)-4-(4,5,6,7-tetrahydro-1H-benzo[d]imidazol-1-yl)picolinamide | 4 |
| 188 | N-(6-(4-cyclopropyl-4H-1,2,4-triazol-3-yl)pyridin-2-yl)-4-(4-(trifluoromethyl)-1H-imidazol-1-yl)picolinamide | 6 |
| 189 | (S)-4-(4-cyclopropyl-1H-imidazol-1-yl)-N-(3-(4-(1,1,1-trifluoropropan-2-yl)-4H-1,2,4-triazol-3-yl)phenyl)picolinamide | 9 |
| 190 | N-(3-(4-cyclopropyl-4H-1,2,4-triazol-3-yl)phenyl)-4-(1,5-naphthyridin-3-yl)picolinamide | 13 |
| 191 | N-(6-(4-cyclopropyl-4H-1,2,4-triazol-3-yl)pyridin-2-yl)-3-(1,5-naphthyridin-3-yl)benzamide | 18 |
| 192 | 3-(4-cyclopropyl-1H-imidazol-1-yl)-N-(6-(4-cyclopropyl-4H-1,2,4-triazol-3-yl)pyridin-2-yl)benzamide | 7 |
| 193 | N-(6-(4-cyclopropyl-4H-1,2,4-triazol-3-yl)pyridin-2-yl)-3-(4-isopropyl-1H-imidazol-1-yl)benzamide | 5 |
| 194 | N-(3-(4-cyclopropyl-4H-1,2,4-triazol-3-yl)phenyl)-4-(4-(trifluoromethyl)-4,5,6,7-tetrahydro-1H-imidazo[4,5-c]pyridin-1-yl)picolinamide | 12 |
| 195 | N-(6-(4-cyclopropyl-4H-1,2,4-triazol-3-yl)pyridin-2-yl)-4-(4-(trifluoromethyl)-4,5,6,7-tetrahydro-1H-imidazo[4,5-c]pyridin-1-yl)picolinamide | 8 |
| 196 | 3-(4-cyclopropyl-1H-imidazol-1-yl)-N-(6-(4-cyclopropyl-4H-1,2,4-triazol-3-yl)pyridin-2-yl)-2-methylbenzamide | 1257 |
| 197 | 5-(4-cyclopropyl-1H-imidazol-1-yl)-N-(6-(4-cyclopropyl-4H-1,2,4-triazol-3-yl)pyridin-2-yl)-2-methylbenzamide | 47 |
| 198 | N-(3-(4-cyclopropyl-4H-1,2,4-triazol-3-yl)phenyl)-4-(4-(perfluoroethyl)-1H-imidazol-1-yl)picolinamide | 19 |
| 199 | N-(6-(4-cyclopropyl-4H-1,2,4-triazol-3-yl)pyridin-2-yl)-4-(4-(perfluoroethyl)-1H-imidazol-1-yl)picolinamide | 9 |
| 200 | 3-(4-cyclopropyl-1H-imidazol-1-yl)-N-(6-(4-cyclopropyl-4H-1,2,4-triazol-3-yl)pyridin-2-yl)-4-methylbenzamide | 11 |
| 201 | 4-(3-cyclopropyl-1H-1,2,4-triazol-1-yl)-N-(6-(4-cyclopropyl-4H-1,2,4-triazol-3-yl)pyridin-2-yl)picolinamide | 14 |
| 202 | 4-(3-cyclopropyl-1H-1,2,4-triazol-1-yl)-N-(3-(4-cyclopropyl-4H-1,2,4-triazol-3-yl)phenyl)picolinamide | 17 |
| 203 | 4-(5-cyclopropyl-1H-1,2,4-triazol-1-yl)-N-(3-(4-cyclopropyl-4H-1,2,4-triazol-3-yl)phenyl)picolinamide | 538 |
| 204 | N-(6-(4-cyclopropyl-4H-1,2,4-triazol-3-yl)pyridin-2-yl)-3-(6-(2-hydroxypropan-2-yl)pyridin-3-yl)benzamide | 17 |
| 205 | 3-(4-cyclopropyl-1H-imidazol-1-yl)-N-(6-(4-cyclopropyl-4H-1,2,4-triazol-3-yl)pyridin-2-yl)-5-fluorobenzamide | 9 |
| 206 | N-(3-(4-cyclopropyl-4H-1,2,4-triazol-3-yl)phenyl)-4-(4-(2,2,2-trifluoro-1-hydroxyethyl)-1H-imidazol-1-yl)picolinamide | 9 |
| 207 | N-(6-(4-cyclopropyl-4H-1,2,4-triazol-3-yl)pyridin-2-yl)-4-(4-(2,2,2-trifluoro-1-hydroxyethyl)-1H-imidazol-1-yl)picolinamide | 11 |
| 208 | N-(6-(4-cyclopropyl-4H-1,2,4-triazol-3-yl)pyridin-2-yl)-3-(4-(2,2,2-trifluoro-1-hydroxyethyl)-1H-imidazol-1-yl)benzamide | 5 |
| 209 | 3-(4-cyclopropyl-1H-imidazol-1-yl)-N-(6-(4-cyclopropyl-4H-1,2,4-triazol-3-yl)pyridin-2-yl)-5-methylbenzamide | 7 |
| 210 | 3-(4-cyclopropyl-1H-imidazol-1-yl)-N-(6-(4-cyclopropyl-4H-1,2,4-triazol-3-yl)pyridin-2-yl)-5-methylbenzamide | 7 |
| 211 | N-(6-(4-cyclopropyl-4H-1,2,4-triazol-3-yl)pyridin-2-yl)-3-(4,5-dimethyl-1H-imidazol-1-yl)benzamide | 9 |
| 212 | N-(6-(4-cyclopropyl-4H-1,2,4-triazol-3-yl)pyridin-2-yl)-3-(4,5,6,7-tetrahydro-1H-benzo[d]imidazol-1-yl)benzamide | 9 |
| 213 | 1-(3-(6-(4-cyclopropyl-4H-1,2,4-triazol-3-yl)pyridin-2-ylcarbamoyl)phenyl)-5-methyl-1H-imidazole-4-carboxylic acid | 11 |
| 214 | (S)-3-(4-cyclopropyl-1H-imidazol-1-yl)-N-(6-(4-(1-phenylethyl)-4H-1,2,4-triazol-3-yl)pyridin-2-yl)benzamide | 159 |
| 215 | 6-cyclopropyl-N-(6-(4-cyclopropyl-4H-1,2,4-triazol-3-yl)pyridin-2-yl)-5'-methyl-3,4'-bipyridine-2'-carboxamide | 30 |
| 216 | (S)-3-(4,5-dimethyl-1H-imidazol-1-yl)-N-(6-(4-(1,1,1-trifluoropropan-2-yl)-4H-1,2,4-triazol-3-yl)pyridin-2-yl)benzamide | 8 |
| 217 | (S)-3-(4-cyclopropyl-1H-imidazol-1-yl)-N-(6-(4-(1-phenylethyl)-4H-1,2,4-triazol-3-yl)pyridin-2-yl)benzamide | 14 |
| 218 | 3-(4-cyclopropyl-1H-imidazol-1-yl)-N-(6-(4-isopropyl-4H-1,2,4-triazol-3-yl)pyridin-2-yl)benzamide | 5 |
| 219 | 6-cyclopropyl-N-(3-(4-isopropyl-4H-1,2,4-triazol-3-yl)phenyl)-3,4'-bipyridine-2'-carboxamide | 16 |
| 220 | (S)-6-cyclopropyl-N-(3-(4-(1-phenylethyl)-4H-1,2,4-triazol-3-yl)phenyl)-3,4'-bipyridine-2'-carboxamide | 61 |
| 221 | N-(3-(4-cyclobutyl-4H-1,2,4-triazol-3-yl)phenyl)-6-cyclopropyl-3,4'-bipyridine-2'-carboxamide | 31 |
| 222 | (S)-tert-butyl 2-(3-(3-(6-cyclopropyl-3,4'-bipyridine-2'-carboxamido)phenyl)-4H-1,2,4-triazol-4-yl)propanoate | 79 |
| 223 | (S)-6-cyclopropyl-N-(3-(4-(1,1,1-trifluoropropan-2-yl)-4H-1,2,4-triazol-3-yl)phenyl)-3,4'-bipyridine-2'-carboxamide | 45 |
| 224 | N-(6-(4-cyclopropyl-4H-1,2,4-triazol-3-yl)pyridin-2-yl)-5-(6-cyclopropylpyridin-3-yl)-2-fluorobenzamide | 13 |
| 225 | N-(6-(4-cyclopropyl-4H-1,2,4-triazol-3-yl)pyridin-2-yl)-4-(6-cyclopropylpyridin-3-yl)quinoline-2-carboxamide | 103 |
| 226 | 4-(4-cyclopropyl-1H-imidazol-1-yl)-N-(6-(4-cyclopropyl-4H-1,2,4-triazol-3-yl)pyridin-2-yl)quinoline-2-carboxamide | 16 |
| 227 | 4-chloro-3-(4-cyclopropyl-1H-imidazol-1-yl)-N-(6-(4-cyclopropyl-4H-1,2,4-triazol-3-yl)pyridin-2-yl)benzamide | 8 |
| 228 | 3-(4-cyclopropyl-1H-imidazol-1-yl)-N-(6-(4-cyclopropyl-4H-1,2,4-triazol-3-yl)pyridin-2-yl)-4-methoxybenzamide | 7 |
| 229 | N-(3-(4-sec-butyl-4H-1,2,4-triazol-3-yl)phenyl)-6-cyclopropyl-3,4'-bipyridine-2'-carboxamide | 101 |
| 230 | (S)-6-cyclopropyl-N-(3-(4-(1-cyclopropylethyl)-4H-1,2,4-triazol-3-yl)phenyl)-3,4'-bipyridine-2'-carboxamide | 58 |
| 231 | 6-cyclopropyl-N-(3-(4-(pentan-3-yl)-4H-1,2,4-triazol-3-yl)phenyl)-3,4'-bipyridine-2'-carboxamide | 1423 |

-continued

| No. | Compound | IC$_{50}$ (nM) |
|---|---|---|
| 232 | (S)-6-cyclopropyl-N-(3-(4-(1-methoxypropan-2-yl)-4H-1,2,4-triazol-3-yl)phenyl)-3,4'-bipyridine-2'-carboxamide | 17 |
| 233 | 6-cyclopropyl-N-(6-(4-cyclopropyl-4H-1,2,4-triazol-3-yl)pyridin-2-yl)-6'-methyl-3,4'-bipyridine-2'-carboxamide | 14 |
| 234 | (S)-6-cyclopropyl-N-(6-(4-(1-methoxypropan-2-yl)-4H-1,2,4-triazol-3-yl)pyridin-2-yl)-3,4'-bipyridine-2'-carboxamide | 8 |
| 235 | N-(6-(4-cyclopropyl-4H-1,2,4-triazol-3-yl)pyridin-2-yl)-3-(4-(2,2,2-trifluoro-1-methoxyethyl)-1H-imidazol-1-yl)benzamide | 15 |
| 236 | N-(6-(4-cyclopropyl-4H-1,2,4-triazol-3-yl)pyridin-2-yl)-4-(6-cyclopropylpyridin-3-yl)-7,8-dimethylquinoline-2-carboxamide | 139 |
| 237 | (S)-N-(3-(4-sec-butyl-4H-1,2,4-triazol-3-yl)phenyl)-6-cyclopropyl-3,4'-bipyridine-2'-carboxamide | 38 |
| 238 | (S)-6-cyclopropyl-N-(3-(4-(3-methylbutan-2-yl)-4H-1,2,4-triazol-3-yl)phenyl)-3,4'-bipyridine-2'-carboxamide | 6 |
| 239 | (S)-6-cyclopropyl-N-(3-(4-(1-(2,6-dimethylphenoxy)propan-2-yl)-4H-1,2,4-triazol-3-yl)phenyl)-3,4'-bipyridine-2'-carboxamide | 10929 |
| 240 | N-(3-(4-cyclopropyl-4H-1,2,4-triazol-3-yl)phenyl)-4-(6-cyclopropylpyridin-3-yl)-7,8-dimethylquinoline-2-carboxamide | 222 |
| 241 | 6-cyclopropyl-N-(6-(4-(1-methylpiperidin-4-yl)-4H-1,2,4-triazol-3-yl)pyridin-2-yl)-3,4'-bipyridine-2'-carboxamide | 616 |
| 242 | (S)-6-cyclopropyl-N-(3-(4-(3,3-dimethylbutan-2-yl)-4H-1,2,4-triazol-3-yl)phenyl)-3,4'-bipyridine-2'-carboxamide | 1129 |
| 243 | N-(3-(4-cyclopropyl-4H-1,2,4-triazol-3-yl)phenyl)-4-(1-isopropyl-1H-pyrrolo[3,2-b]pyridin-6-yl)picolinamide | 15 |
| 244 | N-(3-(4-cyclopropyl-4H-1,2,4-triazol-3-yl)phenyl)-4-(1-(2,2,2-trifluoroethyl)-1H-pyrrolo[3,2-b]pyridin-6-yl)picolinamide | 25 |
| 245 | 6-cyclopropyl-N-(6-(4-(1-(pyrrolidin-1-yl)propan-2-yl)-4H-1,2,4-triazol-3-yl)pyridin-2-yl)-3,4'-bipyridine-2'-carboxamide | 36 |
| 246 | 6-cyclopropyl-N-(6-(4-((2S,3S)-3-hydroxybutan-2-yl)-4H-1,2,4-triazol-3-yl)pyridin-2-yl)-3,4'-bipyridine-2'-carboxamide | 6 |
| 247 | 6-cyclopropyl-N-(6-(4-((2S,3R)-3-hydroxybutan-2-yl)-4H-1,2,4-triazol-3-yl)pyridin-2-yl)-3,4'-bipyridine-2'-carboxamide | 10 |
| 248 | 6-cyclopropyl-N-(6-(4-((2R)-3-hydroxybutan-2-yl)-4H-1,2,4-triazol-3-yl)pyridin-2-yl)-3,4'-bipyridine-2'-carboxamide | 7 |
| 249 | 6-cyclopropyl-N-(3-(4-cyclopropyl-4H-1,2,4-triazol-3-yl)phenyl)-6'-methyl-3,4'-bipyridine-2'-carboxamide | 71 |
| 250 | 6-cyclopropyl-N-(3-(4-cyclopropyl-4H-1,2,4-triazol-3-yl)phenyl)-5'-methyl-3,4'-bipyridine-2'-carboxamide | 8 |
| 251 | N-(3-(4-cyclopropyl-4H-1,2,4-triazol-3-yl)phenyl)-4-(6-methoxyquinolin-3-yl)picolinamide | 7 |
| 252 | N-(3-(4-cyclopropyl-4H-1,2,4-triazol-3-yl)phenyl)-4-(5-(1-hydroxyethyl)-1,3,4-oxadiazol-2-yl)picolinamide | 3412 |
| 253 | N-(3-(4-cyclopropyl-4H-1,2,4-triazol-3-yl)phenyl)-4-(3-methyl-1,2,4-oxadiazol-5-yl)picolinamide | 3489 |
| 254 | 4-(3-cyclopropyl-1,2,4-oxadiazol-5-yl)-N-(3-(4-cyclopropyl-4H-1,2,4-triazol-3-yl)phenyl)picolinamide | 1269 |
| 255 | 4-(5-cyclopropyl-4-methyl-4H-1,2,4-triazol-3-yl)-N-(3-(4-cyclopropyl-4H-1,2,4-triazol-3-yl)phenyl)picolinamide | 685 |
| 256 | N-(6-(4-cyclopropyl-4H-1,2,4-triazol-3-yl)pyridin-2-yl)-4-(5-methyl-4-(trifluoromethyl)-4,5,6,7-tetrahydro-1H-imidazo[4,5-c]pyridin-1-yl)picolinamide | 4 |
| 257 | N-(3-(4-cyclopropyl-4H-1,2,4-triazol-3-yl)phenyl)-4-(5-methyl-4-(trifluoromethyl)-4,5,6,7-tetrahydro-1H-imidazo[4,5-c]pyridin-1-yl)picolinamide | 6 |
| 258 | 6'-cyclopropyl-N-(6-(4-cyclopropyl-4H-1,2,4-triazol-3-yl)pyridin-2-yl)-2,3'-bipyridine-6-carboxamide | 852 |
| 259 | 6'-cyclopropyl-N-(6-(4-cyclopropyl-4H-1,2,4-triazol-3-yl)pyridin-2-yl)-3,3'-bipyridine-5-carboxamide | 8 |
| 260 | 6'-cyclopropyl-N-(6-(4-cyclopropyl-4H-1,2,4-triazol-3-yl)pyridin-2-yl)-2,3'-bipyridine-4-carboxamide | 30 |
| 261 | N-(6-(4-cyclopropyl-4H-1,2,4-triarol-3-yl)pyridin-2-yl)-5-(6-cyclopropylpyridin-3-yl)-2,4-difluorobenzamide | |
| 262 | 6'-cyclopropyl-N-(3-(4-cyclopropyl-4H-1,2,4-triazol-3-yl)phenyl)-2,3'-bipyridine-4-carboxamide | |
| 263 | 6'-cyclopropyl-N-(3-(4-cyclopropyl-4H-1,2,4-triazol-3-yl)phenyl)-2,3'-bipyridine-6-carboxamide | 3600 |
| 264 | (S)-4-(4-cyclopropyl-1H-imidazol-1-yl)-N-(3-(4-(3-methylbutan-2-yl)-4H-1,2,4-triazol-3-yl)phenyl)picolinamide | 23 |
| 265 | 4-chloro-N-(6-(4-cyclopropyl-4H-1,2,4-triazol-3-yl)pyridin-2-yl)-5-(6-cyclopropylpyridin-3-yl)-2-fluorobenzamide | 27 |
| 266 | 6-cyclopropyl-N-(3-(4-(3-hydroxybutan-2-yl)-4H-1,2,4-triazol-3-yl)phenyl)-3,4'-bipyridine-2'-carboxamide | |
| 267 | 6-cyclopropyl-N-(3-(4-(2-phenylcyclopropyl)-4H-1,2,4-triazol-3-yl)phenyl)-3,4'-bipyridine-2'-carboxamide | 425 |
| 268 | N-(3-(4-cyclopropyl-4H-1,2,4-triazol-3-yl)phenyl)-6-(cyclopropylmethyl)-3,4'-bipyridine-2'-carboxamide | 13 |
| 269 | 3-(4-cyclopropyl-1H-1,2,3-triazol-1-yl)-N-(6-(4-cyclopropyl-4H-1,2,4-triazol-3-yl)pyridin-2-yl)benzamide | 23 |
| 270 | 4-(5-cyclopropyl-1,3,4-thiadiazol-2-yl)-N-(3-(4-cyclopropyl-4H-1,2,4-triazol-3-yl)phenyl)picolinamide | 107 |
| 271 | N-(3-(4-cyclopropyl-4H-1,2,4-triazol-3-yl)phenyl)-5-(6-cyclopropylpyridin-3-yl)-2-methoxybenzamide | 24 |
| 272 | 5-(4-cyclopropyl-1H-imidazol-1-yl)-N-(3-(4-cyclopropyl-4H-1,2,4-triazol-3-yl)phenyl)-2-methoxybenzamide | 11 |

What is claimed is:
1. A compound of formula (I)

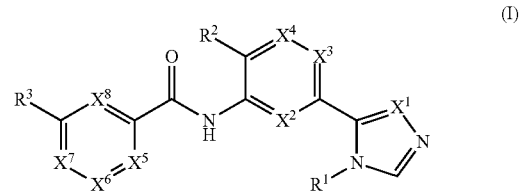

wherein:
R$^1$ is alkyl of 1-10 carbon atoms, cycloalkyl of 3-8 carbon atoms, alkenyl of 2-10 carbon atoms, alkynyl of 2-10 carbon atoms, aryl, heteroaryl or heterocyclyl, all of which are optionally
substituted with 1, 2, or 3 substituents selected from halo, oxo, alkyl of 1-6 carbon atoms, cycloalkyl of 3-8 carbon atoms, heterocyclyl, phenyl, phenoxy, halo, —CN, —O—R$^6$, —C(O)—R$^6$, —OC(O)—R$^6$, —C(O)—O—R$^6$, —N(R$^6$)—C(O)—O—R$^7$, —N(R$^6$)—C(O)—R$^7$, —N(R$^6$)—C(O)—N(R$^6$)(R$^7$), and —C(O)—N(R$^6$)(R$^7$), wherein alkyl, cycloalkyl, heterocyclyl, phenyl, and phenoxy are optionally substituted by 1, 2, or 3 substituents selected from alkyl of 1-6 carbon atoms, cycloalkyl of 3-8 carbon atoms, alkoxy of 1-6 carbon atoms, hydroxyl, and halo;
provided that R$^1$ is not methyl when R$^3$ is morpholinyl or furyl;
wherein R$^6$ and R$^7$ are independently selected from the group consisting of hydrogen, alkyl of 1-6 carbon atoms, or cycloalkyl of 3-8 carbon atoms; or
R$^6$ and R$^7$ when taken together with the nitrogen to which they are attached form a heterocycle;
R$^2$ is hydrogen, halo, cyano, alkoxy, or alkyl optionally substituted by halo;

R³ is aryl, heteroaryl, or heterocyclyl, all of which are optionally substituted with 1, 2 or 3 substituents selected from alkyl of 1-6 carbon atoms, alkoxy of 1-6 carbon atoms, cycloalkyl of 3-8 carbon atoms, cycloalkylalkyl, aryl, arylalkyl, heteroaryl, heteroarylalkyl, heterocyclyl, heterocyclylalkyl, halo, haloalkoxy, oxo, —CN, —O—R⁶, —O—C(O)—R⁶, —O—C(O)—N(R⁶)(R⁷), —S—R⁶, —N(R⁶)(R⁷), —S(=O)—R⁶, —S(=O)₂R⁶, —S(=O)₂—N(R⁶)(R⁷), —S(=O)₂—O—R⁶, —N(R⁶)—C(O)—R⁷, —N(R⁶)—C(O)—O—R⁷, —N(R⁶)—C(O)—N(R⁶)(R⁷), —C(O)—R⁶, —C(O)—O—R⁶, —C(O)—N(R⁶)(R⁷), and —N(R⁶)—S(=O)₂—R⁷, wherein the alkyl, alkoxy, cycloalkyl, aryl, heteroaryl or heterocyclyl is further optionally substituted with one or more substituents selected from halo, hydroxyl, oxo, —CN, and —O—R⁶;

with the proviso that the heteroaryl or heterocyclyl moiety includes at least one ring nitrogen atom; X¹ is C(R⁴), X² is N or C(R⁴), and X³, X⁴, X⁵, X⁶, X⁷ and X⁸ are each C(R⁴)

wherein each R⁴ is independently hydrogen, hydroxyl, halo, alkyl of 1-6 carbon atoms, alkoxy of 1-6 carbon atoms, or cycloalkyl of 3-8 carbon atoms, wherein the alkyl or cycloalkyl is further optionally substituted with one or more substituents selected from halo, hydroxyl, oxo, —CF₃, —O—CF₃, —N(R⁶)(R⁷), —C(O)—R⁶, —C(O)—O—R⁷, —C(O)—N(R⁶)(R⁷), —CN, and —O—R⁶; or X⁵ and X⁶ or X⁶ and X⁷ are joined to provide fused cycloalkyl, fused aryl, or fused heteroaryl, all of which are optionally substituted with alkyl of 1-6 carbon atoms, hydroxyl, or halo; or a pharmaceutically acceptable salt thereof.

2. The compound of claim 1, wherein R¹ is optionally substituted alkyl, optionally substituted cycloalkyl, or optionally substituted heterocyclyl.

3. The compound of claim 2, wherein alkyl, cycloalkyl, and heterocyclyl are optionally substituted by 1, 2, or 3 substituents chosen from hydroxyl, halo, or cycloalkyl.

4. The compound of claim 3, wherein R³ is optionally substituted aryl, optionally substituted heteroaryl or optionally substituted heterocyclyl, wherein the heteroaryl or heterocyclyl moieties contain 1, 2 or 3 ring nitrogen atoms.

5. The compound of claim 4, wherein the aryl, heteroaryl, and heterocyclyl moieties are optionally substituted by alkyl, cycloalkyl, halo, cyano, or —OR⁶, in which alkyl and cycloalkyl are optionally substituted by hydroxyl or halo.

6. The compound of claim 5, wherein R³ is selected from

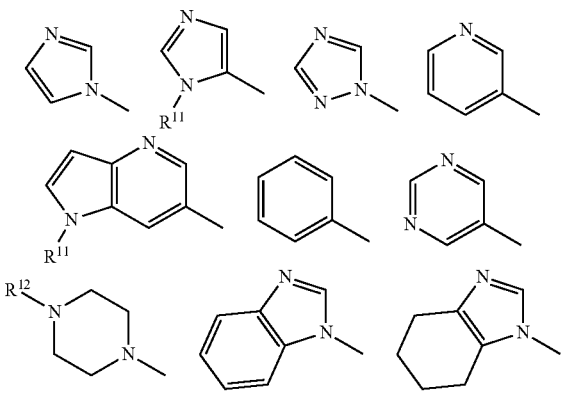

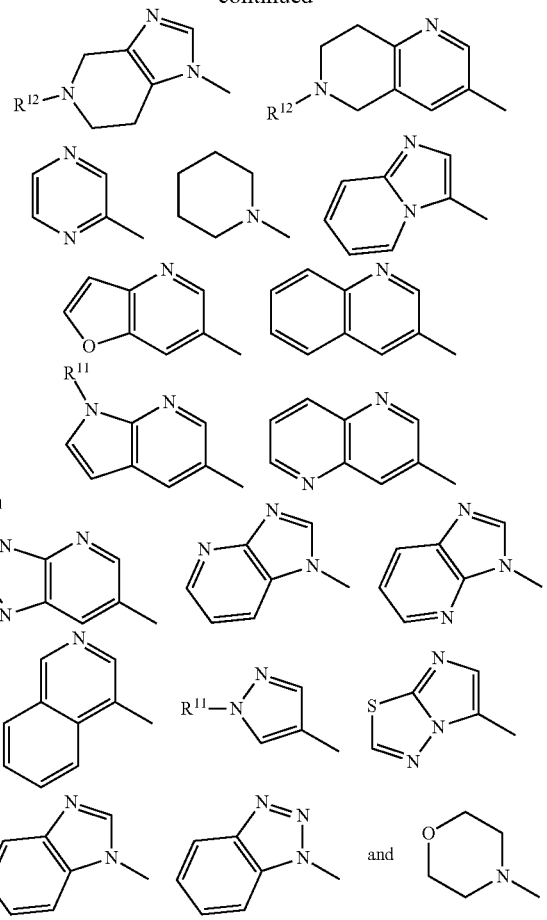

wherein:
R¹¹ is hydrogen, alkyl, or cycloalkyl, wherein alkyl and cycloalkyl are optionally substituted by hydroxyl or halo;
R¹² is hydrogen, alkyl, cycloalkyl, —S(=O)—R⁶ or —S(=O)₂R⁶, wherein alkyl and cycloalkyl are optionally substituted by hydroxyl or halo; and
wherein the R³ aryl, heteroaryl, and heterocyclyl moieties are optionally substituted by alkyl, cycloalkyl, halo, cyano, —OR⁶, in which alkyl and cycloalkyl are optionally substituted by hydroxyl or halo.

7. A compound selected from the group consisting of:
N-(6-(4-cyclopropyl-4H-1,2,4-triazol-3-yl)pyridin-2-yl)-3-(quinolin-3-yl)benzamide;
N-(6-(4-cyclopropyl-4H-1,2,4-triazol-3-yl)pyridin-2-yl)-5-(6-cyclopropylpyridin-3-yl)-2,4-difluorobenzamide;
4-chloro-N-(6-(4-cyclopropyl-4H-1,2,4-triazol-3-yl)pyridin-2-yl)-5-(6-cyclopropylpyridin-3-yl)-2-fluorobenzamide;
N-(6-(4-cyclopropyl-4H-1,2,4-triazol-3-yl)pyridin-2-yl)-3-(4-(2,2,2-trifluoro-1-methoxyethyl)-1H-imidazol-1-yl)benzamide;
3-(4-cyclopropyl-1H-imidazol-1-yl)-N-(6-(4-cyclopropyl-4H-1,2,4-triazol-3-yl)pyridin-2-yl)-4-methoxybenzamide;
4-chloro-3-(4-cyclopropyl-1H-imidazol-1-yl)-N-(6-(4-cyclopropyl-4H-1,2,4-triazol-3-yl)pyridin-2-yl)benzamide;
N-(6-(4-cyclopropyl-4H-1,2,4-triazol-3-yl)pyridin-2-yl)-5-(6-cyclopropylpyridin-3-yl)-2-fluorobenzamide;

3-(4-cyclopropyl-1H-imidazol-1-yl)-N-(6-(4-isopropyl-4H-1,2,4-triazol-3-yl)pyridin-2-yl)benzamide;

(S)-3-(4-cyclopropyl-1H-imidazol-1-yl)-N-(6-(4-(1-phenylethyl)-4H-1,2,4-triazol-3-yl)pyridin-2-yl)benzamide;

N-(6-(4-cyclopropyl-4H-1,2,4-triazol-3-yl)pyridin-2-yl)-3-(1,5-naphthyridin-3-yl)benzamide;

3-(4-cyclopropyl-1H-imidazol-1-yl)-N-(6-(4-cyclopropyl-4H-1,2,4-triazol-3-yl)pyridin-2-yl)benzamide;

N-(6-(4-cyclopropyl-4H-1,2,4-triazol-3-yl)pyridin-2-yl)-3-(4-isopropyl-1H-imidazol-1-yl)benzamide;

3-(4-cyclopropyl-1H-imidazol-1-yl)-N-(6-(4-cyclopropyl-4H-1,2,4-triazol-3-yl)pyridin-2-yl)-2-methylbenzamide;

5-(4-cyclopropyl-1H-imidazol-1-yl)-N-(6-(4-cyclopropyl-4H-1,2,4-triazol-3-yl)pyridin-2-yl)-2-methylbenzamide;

3-(4-cyclopropyl-1H-imidazol-1-yl)-N-(6-(4-cyclopropyl-4H-1,2,4-triazol-3-yl)pyridin-2-yl)-4-methylbenzamide;

N-(6-(4-cyclopropyl-4H-1,2,4-triazol-3-yl)pyridin-2-yl)-3-(6-(2-hydroxypropan-2-yl)pyridin-3-yl)benzamide;

3-(4-cyclopropyl-1H-imidazol-1-yl)-N-(6-(4-cyclopropyl-4H-1,2,4-triazol-3-yl)pyridin-2-yl)-5-fluorobenzamide;

N-(6-(4-cyclopropyl-4H-1,2,4-triazol-3-yl)pyridin-2-yl)-3-(4-(2,2,2-trifluoro-1-hydroxyethyl)-1H-imidazol-1-yl)benzamide;

3-(4-cyclopropyl-1H-imidazol-1-yl)-N-(6-(4-cyclopropyl-4H-1,2,4-triazol-3-yl)pyridin-2-yl)-5-methylbenzamide;

N-(6-(4-cyclopropyl-4H-1,2,4-triazol-3-yl)pyridin-2-yl)-3-(4,5-dimethyl-1H-imidazol-1-yl)benzamide;

N-(6-(4-cyclopropyl-4H-1,2,4-triazol-3-yl)pyridin-2-yl)-3-(4,5,6,7-tetrahydro-1H-benzo[d]imidazol-1-yl)benzamide;

1-(3-(6-(4-cyclopropyl-4H-1,2,4-triazol-3-yl)pyridin-2-ylcarbamoyl)phenyl)-5-methyl-1H-imidazole-4-carboxylic acid;

(S)-3-(4-cyclopropyl-1H-imidazol-1-yl)-N-(6-(4-(1-phenylethyl)-4H-1,2,4-triazol-3-yl)pyridin-2-yl)benzamide;

(S)-3-(4,5-dimethyl-1H-imidazol-1-yl)-N-(6-(4-(1,1,1-trifluoropropan-2-yl)-4H-1,2,4-triazol-3-yl)pyridin-2-yl)benzamide;

N-(6-(4-cyclopropyl-4H-1,2,4-triazol-3-yl)pyridin-2-yl)-3-(6-cyclopropylpyridin-3-yl)benzamide;

N-(6-(4-cyclopropyl-4H-1,2,4-triazol-3-yl)pyridin-2-yl)-3-(pyridin-3-yl)benzamide;

N-(6-(4-cyclopropyl-4H-1,2,4-triazol-3-yl)pyridin-2-yl)-5-(6-cyclopropylpyridin-3-yl)-2,4-difluorobenzamide;

4-chloro-N-(6-(4-cyclopropyl-4H-1,2,4-triazol-3-yl)pyridin-2-yl)-5-(6-cyclopropylpyridin-3-yl)-2-fluorobenzamide;

3-(4-cyclopropyl-1H-1,2,3-triazol-1-yl)-N-(6-(4-cyclopropyl-4H-1,2,4-triazol-3-yl)pyridin-2-yl)benzamide;

(S)-5-(4-tert-butyl-1H-imidazol-1-yl)-2-fluoro-4-methyl-N-(6-(4-(1,1,1-trifluoropropan-2-yl)-4H-1,2,4-triazol-3-yl)pyridin-2-yl)benzamide;

5-(4-tert-butyl-1H-imidazol-1-yl)-N-(6-(4-cyclopropyl-4H-1,2,4-triazol-3-yl)pyridin-2-yl)-2-fluoro-4-methylbenzamide;

(S)-5-(4-cyclopropyl-1H-imidazol-1-yl)-2,3-difluoro-N-(6-(4-(1,1,1-trifluoropropan-2-yl)-4H-1,2,4-triazol-3-yl)pyridin-2-yl)benzamide;

5-(4-cyclopropyl-1H-imidazol-1-yl)-N-(6-(4-cyclopropyl-4H-1,2,4-triazol-3-yl)pyridin-2-yl)-2,3-difluorobenzamide;

4-chloro-5-(4-cyclopropyl-1H-imidazol-1-yl)-N-(6-(4-cyclopropyl-4H-1,2,4-triazol-3-yl)pyridin-2-yl)-2-fluorobenzamide;

(S)-4-chloro-5-(4-cyclopropyl-1H-imidazol-1-yl)-2-fluoro-N-(6-(4-(1,1,1-trifluoropropan-2-yl)-4H-1,2,4-triazol-3-yl)pyridin-2-yl)benzamide;

5-(4-cyclopropyl-1H-imidazol-1-yl)-N-(6-(4-cyclopropyl-4H-1,2,4-triazol-3-yl)pyridin-2-yl)-2,4-difluorobenzamide;

(S)-3-(4-cyclopropyl-1H-imidazol-1-yl)-4-fluoro-N-(6-(4-(1,1,1-trifluoropropan-2-yl)-4H-1,2,4-triazol-3-yl)pyridin-2-yl)benzamide;

3-(4-cyclopropyl-1H-imidazol-1-yl)-N-(6-(4-cyclopropyl-4H-1,2,4-triazol-3-yl)pyridin-2-yl)-4-fluorobenzamide;

5-(4-cyclopropyl-1H-imidazol-1-yl)-N-(6-(4-cyclopropyl-4H-1,2,4-triazol-3-yl)pyridin-2-yl)-2-fluoro-4-methylbenzamide;

(S)-5-(4-cyclopropyl-1H-imidazol-1-yl)-2-fluoro-4-methyl-N-(6-(4-(1,1,1-trifluoropropan-2-yl)-4H-1,2,4-triazol-3-yl)pyridin-2-yl)benzamide;

5-(4-cyclopropyl-1H-imidazol-1-yl)-N-(6-(4-cyclopropyl-4H-1,2,4-triazol-3-yl)pyridin-2-yl)-2-fluorobenzamide; and (S)-3-(4-cyclopropyl-1H-imidazol-1-yl)-4-methyl-N-(6-(4-(1,1,1-trifluoropropan-2-yl)-4H-1,2,4-triazol-3-yl)pyridin-2-yl)benzamide; or a pharmaceutically acceptable salt thereof.

8. A compound selected from the group consisting of:

(S)-3-(4,5-dimethyl-1H-imidazol-1-yl)-N-(6-(4-(1,1,1-trifluoropropan-2-yl)-4H-1,2,4-triazol-3-yl)pyridin-2-yl)benzamide;

3-(4-cyclopropyl-1H-imidazol-1-yl)-N-(6-(4-isopropyl-4H-1,2,4-triazol-3-yl)pyridin-2-yl)benzamide;

5-(4-tert-butyl-1H-imidazol-1-yl)-4-chloro-N-(6-(4-cyclopropyl-4H-1,2,4-triazol-3-yl)pyridin-2-yl)-2-fluorobenzamide;

(S)-5-(4-tert-butyl-1H-imidazol-1-yl)-4-chloro-2-fluoro-N-(6-(4-(1,1,1-trifluoropropan-2-yl)-4H-1,2,4-triazol-3-yl)pyridin-2-yl)benzamide;

N-(6-(4-cyclopropyl-4H-1,2,4-triazol-3-yl)pyridin-2-yl)-2-fluoro-5-(4-(1-hydroxy-2-methylpropan-2-yl)-1H-imidazol-1-yl)-4-methylbenzamide;

N-(6-(4-cyclopropyl-4H-1,2,4-triazol-3-yl)pyridin-2-yl)-2-fluoro-4-methyl-5-(4-(1-methylcyclopropyl)-1H-imidazol-1-yl)benzamide;

(S)-2-fluoro-4-methyl-5-(4-(1-methylcyclopropyl)-1H-imidazol-1-yl)-N-(6-(4-(1,1,1-trifluoropropan-2-yl)-4H-1,2,4-triazol-3-yl)pyridin-2-yl)benzamide;

5-(4-cyclopropyl-1H-imidazol-1-yl)-2-fluoro-N-(6-(4-isopropyl-4H-1,2,4-triazol-3-yl)pyridin-2-yl)-4-methylbenzamide;

5-(4-cyclopropyl-1H-imidazol-1-yl)-2-fluoro-4-methyl-N-(6-(4-(1-methylcyclopropyl)-4H-1,2,4-triazol-3-yl)pyridin-2-yl)benzamide;

5-(4-cyclobutyl-1H-imidazol-1-yl)-N-(6-(4-cyclopropyl-4H-1,2,4-triazol-3-yl)pyridin-2-yl)-2-fluoro-4-methylbenzamide;

(S)-5-(4-cyclobutyl-1,4-imidazol-1-yl)-2-fluoro-4-methyl-N-(6-(4-(1,1,1-trifluoropropan-2-yl)-4H-1,2,4-triazol-3-yl)pyridin-2-yl)benzamide;

N-(6-(4-cyclobutyl-4H-1,2,4-triazol-3-yl)pyridin-2-yl)-5-(4-cyclopropyl-1H-imidazol-1-yl)-2-fluoro-4-methylbenzamide;

N-(6-(4-cyclopentyl-4H-1,2,4-triazol-3-yl)pyridin-2-yl)-5-(4-cyclopropyl-1H-imidazol-1-yl)-2-fluoro-4-methylbenzamide;

N-(6-(4-cyclohexyl-4H-1,2,4-triazol-3-yl)pyridin-2-yl)-5-(4-cyclopropyl-1H-imidazol-1-yl)-2-fluoro-4-methylbenzamide;

5-(4-cyclopropyl-1H-imidazol-1-yl)-N-(6-(4-(cyclopropylmethyl)-4H-1,2,4-triazol-3-yl)pyridin-2-yl)-2-fluoro-4-methylbenzamide;

(S)-5-(4-cyclopropyl-1H-imidazol-1-yl)-2-fluoro-N-(6-(4-(1-methoxypropan-2-yl)-4H-1,2,4-triazol-3-yl)pyridin-2-yl)-4-methylbenzamide;

N-(6-(4-tert-butyl-4H-1,2,4-triazol-3-yl)pyridin-2-yl)-5-(4-cyclopropyl-1H-imidazol-1-yl)-2-fluoro-4-methylbenzamide;

5-(4-cyclopropyl-1H-imidazol-1-yl)-2-fluoro-4-methyl-N-(6-(4-(tetrahydro-2H-pyran-4-yl)-4H-1,2,4-triazol-3-yl)pyridin-2-yl)benzamide;

5-(4-cyclopropyl-1H-imidazol-1-yl)-2-fluoro-4-methyl-N-(6-(4-(oxetan-3-ylmethyl)-4H-1,2,4-triazol-3-yl)pyridin-2-yl)benzamide;

N-(6-(4-(azetidin-3-ylmethyl)-4H-1,2,4-triazol-3-yl)pyridin-2-yl)-5-(4-cyclopropyl-1H-imidazol-1-yl)-2-fluoro-4-methylbenzamide;

5-(4-cyclopropyl-1H-imidazol-1-yl)-N-(6-(4-(2-(dimethylamino)ethyl)-4H-1,2,4-triazol-3-yl)pyridin-2-yl)-2-fluoro-4-methylbenzamide;

5-(4-cyclopropyl-1H-imidazol-1-yl)-2-fluoro-N-(6-(4-(2-methoxyethyl)-4H-1,2,4-triazol-3-yl)pyridin-2-yl)-4-methylbenzamide;

5-(4-cyclopropyl-1H-imidazol-1-yl)-2-fluoro-4-methyl-N-(6-(4-(2,2,2-trifluoroethyl)-4H-1,2,4-triazol-3-yl)pyridin-2-yl)benzamide;

5-(4-cyclopropyl-1H-imidazol-1-yl)-N-(6-(4-(2,2-difluoroethyl)-4H-1,2,4-triazol-3-yl)pyridin-2-yl)-2-fluoro-4-methylbenzamide;

5-(4-cyclopropyl-1H-imidazol-1-yl)-2-fluoro-4-methyl-N-(6-(4-(tetrahydrofuran-3-yl)-4H-1,2,4-triazol-3-yl)pyridin-2-yl)benzamide;

(S)-5-(4-cyclopropyl-1H-imidazol-1-yl)-2-fluoro-4-methyl-N-(6-(4-(pyrrolidin-3-yl)-4H-1,2,4-triazol-3-yl)pyridin-2-yl)benzamide;

N-(6-(4-cyclopropyl-4H-1,2,4-triazol-3-yl)pyridin-2-yl)-2-fluoro-5-(4-isopropyl-1H-imidazol-1-yl)-4-methylbenzamide;

(S)-2-fluoro-5-(4-isopropyl-1H-imidazol-1-yl)-4-methyl-N-(6-(4-(1,1,1-trifluoropropan-2-yl)-4H-1,2,4-triazol-3-yl)pyridin-2-yl)benzamide;

2-fluoro-5-(4-isopropyl-1H-imidazol-1-yl)-N-(6-(4-isopropyl-4H-1,2,4-triazol-3-yl)pyridin-2-yl)-4-methylbenzamide;

5-(4-cyclopropyl-1H-imidazol-1-yl)-2-fluoro-4-methyl-N-(6-(4-(1-(2,2,2-trifluoroethyl)azetidin-3-yl)-4H-1,2,4-triazol-3-yl)pyridin-2-yl)benzamide;

5-(4-cyclopropyl-1H-imidazol-1-yl)-N-(6-(4-(1-(2,2-difluoroethyl)azetidin-3-yl)-4H-1,2,4-triazol-3-yl)pyridin-2-yl)-2-fluoro-4-methylbenzamide;

N-(6-(4-(1-acetylazetidin-3-yl)-4H-1,2,4-triazol-3-yl)pyridin-2-yl)-5-(4-cyclopropyl-1H-imidazol-1-yl)-2-fluoro-4-methylbenzamide;

5-(4-cyclopropyl-1H-imidazol-1-yl)-N-(6-(4-(3,3-difluorocyclobutyl)-4H-1,2,4-triazol-3-yl)pyridin-2-yl)-2-fluoro-4-methylbenzamide;

5-(4-cyclopropyl-1H-imidazol-1-yl)-2-fluoro-4-methyl-N-(6-(4-(3-methyloxetan-3-yl)-4H-1,2,4-triazol-3-yl)pyridin-2-yl)benzamide; and 5-(4-cyclopropyl-1H-imidazol-1-yl)-2-fluoro-4-methyl-N-(6-(4-(1-methylpiperidin-4-yl)-4H-1,2,4-triazol-3-yl)pyridin-2yl)benzamide; or a pharmaceutically acceptable salt thereof.

9. A compound selected from the group consisting of:

N-(3-(4-methyl-4H-1,2,4-triazol-3-yl)phenyl)-3,3'-bipyridine-5-carboxamide;

N-(3-(4-methyl-4H-1,2,4-triazol-3-yl)phenyl)-5-phenylnicotinamide;

N-(3-(4-methyl-4H-1,2,4-triazol-3-yl)phenyl)-2-phenylisonicotinamide;

6'-cyclopropyl-N-(3-(4-cyclopropyl-4H-1,2,4-triazol-3-yl)phenyl)-2,3'-bipyridine-4-carboxamide;

5-(2,5-difluorophenyl)-N-(3-(4-methyl-4H-1,2,4-triazol-3-yl)phenyl)nicotinamide;

N-(3-(4-cyclopropyl-4H-1,2,4-triazol-3-yl)phenyl)-6-(6-cyclopropylpyridin-3-yl)pyrimidine-4-carboxamide;

6'-cyclopropyl-N-(6-(4-cyclopropyl-4H-1,2,4-triazol-3-yl)pyridin-2-yl)-2,3'-bipyridine-4-carboxamide; and 2-hydroxy-N-(3-(4-methyl-4H-1,2,4-triazol-3-yl)phenyl)-6-phenylpyrimidine-4-carboxamide; or a pharmaceutically acceptable salt thereof.

10. A pharmaceutical composition comprising one or more compounds according to claim 1 and a pharmaceutically acceptable carrier.

* * * * *

UNITED STATES PATENT AND TRADEMARK OFFICE
CERTIFICATE OF CORRECTION

| | |
|---|---|
| PATENT NO. | : 8,552,196 B2 |
| APPLICATION NO. | : 13/615259 |
| DATED | : October 8, 2013 |
| INVENTOR(S) | : Britton Corkey et al. |

It is certified that error appears in the above-identified patent and that said Letters Patent is hereby corrected as shown below:

In the Claims

In claim 1, at Column 163, lines 18-21, please replace the existing paragraph;

"With the proviso that the heteroaryl or heterocyclyl moiety includes at least one ring nitrogen atoms; $X^1$ is $C(R^4)$, $X^2$ is N or $C(R^4)$, and $X^3$, $X^4$, $X^5$, $X^6$, $X^7$ and $X^8$ are each $C(R^4)$"

With the below paragraph:–

"With the proviso that the heteroaryl or heterocyclyl moiety includes at least one ring nitrogen atoms; $X^1$ is N, $X^2$ is N or $C(R^4)$, and $X^3$, $X^4$, $X^5$, $X^6$, $X^7$ and $X^8$ are each $C(R^4)$"

Signed and Sealed this
Fourteenth Day of July, 2015

Michelle K. Lee
*Director of the United States Patent and Trademark Office*